US012378576B2

(12) United States Patent
Keravala et al.

(10) Patent No.: US 12,378,576 B2
(45) Date of Patent: Aug. 5, 2025

(54) GENE THERAPY FOR CNS DEGENERATION

(71) Applicant: Spacecraft Seven, LLC, Cranbury, NJ (US)

(72) Inventors: Annahita Keravala, New York, NY (US); Paven Battiprolu, New York, NY (US); Raj Prabhakar, New York, NY (US); Roderick Wong, New York, NY (US); Piratip Pratumsuwan, New York, NY (US); Naveen Yalamanchi, New York, NY (US)

(73) Assignee: Spacecraft Seven, LLC, Cranbury, NJ (US)

( * ) Notice: Subject to any disclaimer, the term of this patent is extended or adjusted under 35 U.S.C. 154(b) by 1139 days.

(21) Appl. No.: 17/050,784

(22) PCT Filed: Apr. 29, 2019

(86) PCT No.: PCT/US2019/029744

§ 371 (c)(1),
(2) Date: Oct. 26, 2020

(87) PCT Pub. No.: WO2019/210325

PCT Pub. Date: Oct. 31, 2019

(65) Prior Publication Data

US 2021/0230631 A1 Jul. 29, 2021

Related U.S. Application Data

(60) Provisional application No. 62/664,006, filed on Apr. 27, 2018.

(51) Int. Cl.

| | |
|---|---|
| ***C12N 15/86*** | (2006.01) |
| ***A61K 9/00*** | (2006.01) |
| ***A61K 48/00*** | (2006.01) |
| ***A61P 25/16*** | (2006.01) |
| ***C12N 9/10*** | (2006.01) |
| ***C12N 9/22*** | (2006.01) |
| ***C12N 15/11*** | (2006.01) |
| ***C12N 15/90*** | (2006.01) |

(52) U.S. Cl.

CPC ............ *C12N 15/86* (2013.01); *A61K 9/0085* (2013.01); *A61P 25/16* (2018.01); *C12N 9/104* (2013.01); *C12N 9/22* (2013.01); *C12N 15/11* (2013.01); *C12N 15/907* (2013.01); *C12Y 203/02* (2013.01); *A61K 48/00* (2013.01); *C12N 2310/20* (2017.05); *C12N 2750/14143* (2013.01); *C12N 2800/22* (2013.01); *C12N 2800/80* (2013.01)

(58) Field of Classification Search

None

See application file for complete search history.

(56) References Cited

U.S. PATENT DOCUMENTS

| | | | |
|---|---|---|---|
| 4,861,719 | A | 8/1989 | Miller |
| 5,126,260 | A | 6/1992 | Tuan et al. |
| 5,139,941 | A | 8/1992 | Muzyczka et al. |
| 5,173,414 | A | 12/1992 | Lebkowski et al. |
| 5,278,056 | A | 1/1994 | Bank et al. |
| 5,356,802 | A | 10/1994 | Chandrasegaran |
| 5,436,150 | A | 7/1995 | Chandrasegaran |
| 5,487,994 | A | 1/1996 | Chandrasegaran |
| 5,882,877 | A | 3/1999 | Gregory et al. |
| 6,004,797 | A | 12/1999 | Colosi |
| 6,013,516 | A | 1/2000 | Verma et al. |
| 6,027,721 | A | 2/2000 | Hammang et al. |
| 6,136,597 | A | 10/2000 | Hope et al. |
| 6,180,613 | B1 | 1/2001 | Kaplitt et al. |
| 6,453,242 | B1 | 9/2002 | Eisenberg et al. |
| 7,094,604 | B2 | 8/2006 | Snyder et al. |
| 7,198,950 | B2 | 4/2007 | Trono et al. |
| 7,575,924 | B2 | 8/2009 | Trono et al. |
| 7,588,772 | B2 | 9/2009 | Kay et al. |
| 7,629,153 | B2 | 12/2009 | Trono et al. |
| 7,867,484 | B2 | 1/2011 | Samulski et al. |
| 7,906,111 | B2 | 3/2011 | Wilson et al. |
| 8,093,042 | B2 | 1/2012 | Charneau et al. |
| 8,329,462 | B2 | 12/2012 | Trono et al. |

(Continued)

FOREIGN PATENT DOCUMENTS

| | | |
|---|---|---|
| JP | 2006524051 A | 10/2006 |
| JP | 2007054069 A | 3/2007 |

(Continued)

OTHER PUBLICATIONS

Mochizuki et al. Advances in Gene Therapy for Movement Disorders (2008) Neurotherapeutics, 5, pp. 260-269. (Year: 2008).*
Manfredsson et al. rAAV-mediated nigral human parkin over-expression partially ameliorates motor deficits via enhanced dopamine neurotransmission in a rat model of Parkinson's disease (2007) Experimental Neurology, 207, pp. 289-301. (Year: 2007).*
Blast Alignment SEQ ID No. 60, Chicken beta actin promoter. Accessed on Jun. 22, 2024. (Year: 2024).*

(Continued)

*Primary Examiner* — Peter Paras, Jr.
*Assistant Examiner* — Maytee Marie Contes De Jesus
(74) *Attorney, Agent, or Firm* — Finnegan, Henderson, Farabow, Garrett & Dunner, LLP

(57) ABSTRACT

The present disclosure relates generally to compositions and methods for treating, preventing, inhibiting, or delaying central nervous system degeneration. The disclosure relates to a recombinant gene therapy vector comprising a PARK2, PINK1, DJ-1, LRRK2, SCNA, c-Rel, ATG7, VMAT2, or GBA gene, or functional fragment or variant thereof. The disclosure also relates to CRISPR/Cas-based gene editing systems for treating, preventing, inhibiting, or delaying central nervous system degeneration.

12 Claims, 23 Drawing Sheets

Specification includes a Sequence Listing.

(56) References Cited

U.S. PATENT DOCUMENTS

| | | | |
|---|---|---|---|
| 8,524,446 | B2 | 9/2013 | Gao et al. |
| 8,748,169 | B2 | 6/2014 | Trono et al. |
| 8,900,858 | B2 | 12/2014 | Trono et al. |
| 9,109,012 | B2 | 8/2015 | Williams |
| 9,175,077 | B2 | 11/2015 | Gallo et al. |
| 9,340,798 | B2 | 5/2016 | Trono et al. |
| 9,434,928 | B2 | 9/2016 | Mendell et al. |
| 9,737,620 | B2 | 8/2017 | Williams |
| 9,782,437 | B2 | 10/2017 | Holmes et al. |
| 10,363,269 | B2 | 7/2019 | Tareen |
| 2002/0065236 | A1 | 5/2002 | Yew et al. |
| 2004/0053870 | A1 | 3/2004 | Yew et al. |
| 2006/0171935 | A1 | 8/2006 | Abeliovich et al. |
| 2006/0200869 | A1 | 9/2006 | Naldini et al. |
| 2009/0111106 | A1 | 4/2009 | Mitrophanous et al. |
| 2010/0284990 | A1 | 11/2010 | Kaemmerer et al. |
| 2012/0071859 | A1 | 3/2012 | Morgan et al. |
| 2012/0082650 | A1 | 4/2012 | Bartus et al. |
| 2012/0172418 | A1 | 7/2012 | Schambach et al. |
| 2012/0277286 | A1 | 11/2012 | Youle et al. |
| 2014/0010861 | A1 | 1/2014 | Bancel et al. |
| 2014/0220678 | A1 | 8/2014 | Trono et al. |
| 2015/0111955 | A1 | 4/2015 | High et al. |
| 2015/0291966 | A1 | 10/2015 | Zhang et al. |
| 2016/0108430 | A1 | 4/2016 | Carrier et al. |
| 2017/0029798 | A1 | 2/2017 | Jo et al. |
| 2017/0218395 | A1 | 8/2017 | Byrne et al. |
| 2018/0086807 | A1 | 3/2018 | Bancel et al. |
| 2018/0326022 | A1 | 11/2018 | Prosser et al. |
| 2018/0360992 | A1 | 12/2018 | Patel et al. |
| 2019/0000998 | A1 | 1/2019 | Mendell et al. |
| 2019/0038773 | A1 | 2/2019 | Esteves et al. |
| 2022/0143215 | A1 | 5/2022 | Keravala et al. |
| 2023/0174994 | A1 | 6/2023 | Sacramento et al. |

FOREIGN PATENT DOCUMENTS

| | | | |
|---|---|---|---|
| JP | 2015523065 | A | 8/2015 |
| RU | 2233333 | C2 | 7/2004 |
| RU | 2280074 | C2 | 7/2006 |
| WO | WO-9201070 | A1 | 1/1992 |
| WO | WO-9303769 | A1 | 3/1993 |
| WO | WO-9419478 | A1 | 9/1994 |
| WO | WO-9514785 | A1 | 6/1995 |
| WO | WO-9622378 | A1 | 7/1996 |
| WO | WO-01/83692 | A2 | 11/2001 |
| WO | WO-01/83692 | A3 | 11/2001 |
| WO | WO-03042397 | A2 | 5/2003 |
| WO | WO-2003/092612 | A2 | 11/2003 |
| WO | WO-2003/092612 | A3 | 11/2003 |
| WO | WO-2004015106 | A1 | 2/2004 |
| WO | WO-2006/083797 | A2 | 8/2006 |
| WO | WO-2006/083797 | A3 | 8/2006 |
| WO | WO-2009012176 | A2 | 1/2009 |
| WO | WO-2009026116 | A2 | 2/2009 |
| WO | WO-2012067970 | A2 | 5/2012 |
| WO | WO-2013078316 | A1 | 5/2013 |
| WO | WO-2015038958 | A1 | 3/2015 |
| WO | WO-2015056014 | A1 | 4/2015 |
| WO | WO-2015060722 | A1 | 4/2015 |
| WO | WO-2015/071474 | A2 | 5/2015 |
| WO | WO-2015/071474 | A3 | 5/2015 |
| WO | WO-2015/161276 | A2 | 10/2015 |
| WO | WO-2015/161276 | A3 | 10/2015 |
| WO | WO-2015168547 | A2 | 11/2015 |
| WO | WO-2015168666 | A2 | 11/2015 |
| WO | WO-2015188191 | A1 | 12/2015 |
| WO | WO-2016118780 | A1 | 7/2016 |
| WO | WO-2016145217 | A1 | 9/2016 |
| WO | WO-2016200543 | A2 | 12/2016 |
| WO | WO-2017100671 | A1 | 6/2017 |
| WO | WO-2017127565 | A1 | 7/2017 |
| WO | WO-2017184903 | A1 | 10/2017 |
| WO | WO-2018/002938 | A1 | 1/2018 |
| WO | WO-2018049273 | A1 | 3/2018 |
| WO | WO-2018060097 | A1 | 4/2018 |
| WO | WO-2018201065 | A1 | 11/2018 |
| WO | WO-2019079338 | A1 | 4/2019 |
| WO | WO-2019200167 | A1 | 10/2019 |
| WO | WO-2019207132 | A1 | 10/2019 |
| WO | WO-2019210325 | A1 | 10/2019 |
| WO | WO-2020014523 | A1 | 1/2020 |
| WO | WO-2020028430 | A1 | 2/2020 |
| WO | WO-2020033842 | A1 | 2/2020 |
| WO | WO-2020037249 | A1 | 2/2020 |
| WO | WO-2020167996 | A1 | 8/2020 |
| WO | WO-2020237219 | A1 | 11/2020 |
| WO | WO-2021216456 | A2 | 10/2021 |
| WO | WO-2021236981 | A2 | 11/2021 |
| WO | WO-2021237158 | A1 | 11/2021 |
| WO | WO-2022017630 | A1 | 1/2022 |
| WO | WO-2022018171 | A1 | 1/2022 |
| WO | WO-2022031756 | A1 | 2/2022 |
| WO | WO-2022031760 | A1 | 2/2022 |
| WO | WO-2022032226 | A1 | 2/2022 |
| WO | WO-2022125489 | A1 | 6/2022 |
| WO | WO-2023/154763 | A2 | 8/2023 |

OTHER PUBLICATIONS

Blast Alignment SEQ ID No. 75, WPRE(r). Accessed on Jun. 22, 2024. (Year: 2024).*

Alcalay, R.N. et al. (2010). "Frequency of known mutations in early onset PD; implication for genetic counseling: the CORE-PD study," Arch. Neurol. 67:1116-1122.

Beerli, R.R. et al. (2002). "Engineering polydactyl zinc-finger transcription factors," Nature Biotechnol. 20:135-141.

Belfort, M. et al. (1997). "Homing endonucleases: keeping the house in order," Nucleic Acids Res. 25:3379-3388.

Berns, K.I. (1990). Parvoviridae and their replication, Virology, pp. 1743-1764.

Bitinaite, J. et al. (1998). "FokI dimerization is required for DNA cleavage," PNAS 95:10570-10575.

Blacklowe, N.R. (1988). Chapter 11 in Parvoviruses and Human Disease, pp. 165-174.

Blesa, J. et al. (2014). "Parkinson's disease: Animal models and dopaminergic cell vulnerability," Front. Neuroanat. 8:1-12.

Carter, B.J. et al. (1989). Chapter 11 in Handbook of Parvoviruses, vol. I, CRC Press, Inc., pp. 169-226.

Cermak, T. et al. (2011). "Efficient design and assembly of custom TALEN and other TAL effector-based constructs for DNA targeting," Nucleic Acids Research 39:12, e82.

Choo, Y. et al. (2000). "Advances in zinc finger engineering," Curr. Opin. Struct. Biol. 10:411-416.

Chylinski, K. et al. (2013). "The tracrRNA and Cas9 families of type II CRISPR-Cas immunity systems," RNA Biology 10:5, 726-737.

Creed, R.B. et al. (2018). "New Developments in Genetic Rat Models of Parkinson's Disease," Mov. Disord. 33:717-729.

De, B.P. et al. (2006). "High Levels of Persistent Expression of A1-Antitrypsin Mediated by the Nonhuman Primate Serotype rh.10 Adeno-associated Virus Despite Preexisting Immunity to Common Human Adeno-associated Viruses," Mol. Ther. 13:67-76.

Deveau, H. et al. (2008). "Phage Response to CRISPR-Encoded Resistance in *Streptococcus thermophiles*," J Bacteriol 190:1390-1400.

Esvelt, K.M. et al. (2011). "A System for the Continuous Directed Evolution of Biomolecules," Nature 472:499-503.

Esvelt, K.M. (2013). "Orthogonal Cas9 Proteins for RNA-Guided Gene Regulation and Editing," Nat Methods. 10:1116-1121.

Gao, G. et al. (2004). "Clades of Adeno-Associated Viruses Are Widely Disseminated in Human Tissues," J. Virol. 78:6381-6388.

GenBank Accession No. AX753246.1 (2003). "Sequence 1 from patent EP1310571," 2 total pages.

GenBank Accession No. AF085716.1 (1999). "Adeno-associated virus 5 DNA binding trs helicase (Rep22) and capsid protein (VP1) genes,complete cds," 2 total pages.

GenBank Accession No. NC_002077.1 (2018). "Adeno-associated virus—1, complete genome," 3 total pages.

(56) References Cited

OTHER PUBLICATIONS

GenBank Accession No. NC_001401.2 (2018). "Adeno-associated virus—2, complete genome," 5 total pages.
GenBank Accession No. NC_001829.1 (2018). "Adeno-associated virus—4, complete genome," 3 total pages.
GenBank Accession No. NC_001862.1 (2004). "Adeno-associated virus—6, complete genome," 3 total pages.
GenBank Accession No. AX753249.1 (2003). "Sequence 4 from patent EP1310571," 2 total pages.
Horvath, P. et al. (2010). "CRISPR/Cas, the immune system of bacteria and archaea," Science 327:167-170.
Hou, Z. et al. (2013). "Efficient genome engineering in human pluripotent stem cells using Cas9 from Neisseria meningitides," PNAS 110:15644-15649.
International Search Report mailed on Sep. 10, 2019, for PCT Application No. PCT/US2019/029744, filed on Apr. 29, 2019, 6 pages.
Isalan, M. et al. (2001). "A rapid, generally applicable method to engineer zinc fingers illustrated by targeting the HIV-1 promoter," Nature Biotechnol. 19:656-660.
Jiang, Y. et al. (2008). "Extracellular dopamine induces the oxidative toxicity of SH-SY5Y cells," Synapse. 62:797-803.
Kim, Y.G. et al. (1994). "Chimeric restriction endonuclease," PNAS 91:883-887.
Kim, Y-G. et al. (1994). "Insertion and deletion mutants of Fokl restriction endonuclease," J. Biol. Chem. 269:31978-31982.
Li, L. et al. (1992). "Functional domains in Fok I restriction endonuclease," PNAS 89:4275-4279.
Li, L. et al. (1993). "Alteration of the cleavage distance of Fok I restriction endonuclease by insertion mutagenesis," PNAS 90:2764-2768.
Mali, P. et al. (2013). "RNA-Guided Human Genome Engineering via Cas9," Science 339:823-826.
Marsic, D. et al. (2014). "Vector Design Tour de Force: Integrating Combinatorial and Rational Approaches to Derive Novel Adeno-associated Virus Variants," Molecular Therapy 22:1900-1909.
McCarty, D. et al. (2001). "Self-complementary recombinant adeno-associated virus (scAAV) vectors promote efficient transduction independently of DNA synthesis," Gene Therapy. 8:1248-1254.
Miller, J. et al. (1985). "Repetitive zinc-binding domains in the protein transcription factor IIIA from Xenopus oocytes," EMBO J. 4:16010-1714.
Mori, S. et al. (2004). "Two novel adeno-associated viruses from cynomolgus monkey: Pseudotyping characterization of capsid protein," Virology 330:375-383.
Muzyczka, N. (1992). "Use of adeno-associated virus as a general transduction vector for mammalian cells," Current Topics in Microbiology and Immunology 158:97-129.
Pabo, C.O. et al. (2001). "Design and selection of novel Cys2His2 zinc finger proteins," Ann. Rev. Biochem. 70:313-340.
Rhodes, D. et al. (1993). "Zinc fingers," Scientific American 268:56-59, 62-65.
Rose, J.A. (1974). Chapter 1: Parvovirus reproduction, Comprehensive Virology, pp. 1-61.
Schlabach, M.R. et al. (2010). "Synthetic design of strong promoters," PNAS 107:2538-2543.
Segal, D.J. et al. (2001). "Custom DNA-binding proteins come of age: Polydactyl zinc-finger proteins," Curr. Opin. Biotechnol. 12:632-637.
Srivastava, A. et al. (1983). "Nucleotide Sequence and Organization of the Adeno-Associated Virus 2 Genome," J. Virol. 45:555-564.
Wang, L. et al. (2017). "Single stranded adeno-associated virus achieves efficient gene transfer to anterior segment in the mouse eye," PLoS One 12:e0182473, 12 total pages.
Written Opinion of the International Searching Authority mailed on Sep. 10, 2019, for PCT Application No. PCT/US2019/029744, filed on Apr. 29, 2019, 8 pages.
Zhang, Y. et al. (2014). "Comparison of non-canonical PAMs for CRISPR/Cas9-mediated DNA cleavage in human cells," Sci Rep. 4:5405.
Albert, K et al., "AAV Vector-Mediated Gene Delivery to Substantia Nigra Dopamine Neurons: Implications for Gene Therapy and Disease Models," Genes, Feb. 8, 2017, vol. 8, No. 63, Feb. 8, 2017, 15 pages.
Albrechtsen, B. et al., (1991). "Transcriptional termination sequence at the end of the *Escherichia coli* ribosomal RNA G operon: Complex terminators and antitermination" Nucl. Acids Res. 19:1845-1852.
Almarza, E. et al. (2011). "Correction of SCID-X1 using an enhancerless Vav promoter," Hum. Gene Ther. 22:263-270.
Altschul, S.F., et al., "Basic local alignment search tool," J. Mol. Biol. 215:403-410 (Oct. 5, 1990).
Avazzadeh et al., "Modelling Parkinson's Disease: iPSCs towards Better Understanding of Human Pathology," Brain Sci. 2021, vol. 11, No. 373, pp. 1-26.
Bass-Stringer et al., "Adeno-Associated Virus Gene Therapy: Translational Progress and Future Prospects in the Treatment of Heart Failure" Heart Lung Circ. Nov. 2018;27(11):1285-1300.
Benskey et al., "The Role of Parkin in the Differential Susceptibility of Tuberoinfundibular and Nigrostriatal Dopamine Neurons to Acute Toxicant Exposure," Neurotoxicology, Jan. 2015, vol. 46, pp. 1-11, doi: 10.1016/j.neuro.2014.11.004.
Bouchard, M.J. et al. (2004). The Enigmatic X Gene Of Hepatitis B Virus, J. Virol. 78:12725-12734.
Brown, H.C. et al. (2018). "Target-cell directed bioengineering approaches for gene therapy of Hemophilia A," Mol. Ther. Methods Clin. Dev. 9:57-69.
Burger, C. et al. (2004). "Recombinant AAV Viral vectors pseudotyped with viral capsids from serotypes 1, 2, and 5 display differential efficiency and cell tropism alter delivery to different regions of the central nervous system." Mol. Ther. 10:302-317.
Cearley, C.N. et al. (Oct. 2008). "Expanded repertoire of AAV vector serotypes mediate unique patterns of transduction in mouse brain," Mol. Ther. 16:1710-1718.
Chandler et al., "Systemic AAV9 gene therapy improves the lifespan of mice with Niemann-Pick disease, type C1," Human Molecular Genetics 26(1):52-64 (Jan. 1, 2017).
Cid-Arregui, et al., "A Synthetic E7 Gene of Human Papillomavirus Type 16 That Yields Enhanced Expression of the Protein in Mammalian Cells and Is Useful for DNA Immunization Studies". J Virol. (Apr. 2003); 77(8): 4928-4937.
Colella et, al., "Emerging Issues in AAV-Mediated In Vivo Gene Therapy" Methods & Clinical Development, Molecular Therapy, Dec. 1, 2017, vol. 8, pp. 87-104.
Deyle and Russell, "Adeno-associated virus vector integration." Curr. Opin. Mol. Therapy (2009); 11 (4): 442-447.
Donello, J.E. et al., (1998). "Woodchuck hepatitis virus contains a tripartite posttranscriptional regulatory element," J. Virol. 72:5085-5092.
Du, F et al., "PINK1 signaling rescues amyloid pathology and mitochondrial dysfunction in Alzheimer's disease," Brain, Dec. 1, 2017, vol. 140, No. 12, pp. 3233-3251.
Duan et al., "Expanding AAV Packaging Capacity with Trans-splicing or Overlapping Vectors: A Quantitative Comparison," Molecular Therapy, vol. 4, No. 4, Oct. 2001, pp. 383-391.
Extended European Search Report in European Application No. 19792202.4, mailed Jul. 15, 2022, 22 pages.
Ferrari et al., "From cell lines to pluripotent stem cells for modelling Parkinson's Disease," J. Neuroscience Methods, 2020, vol. 340, No. 108741, 11 pages.
Fiesel et al., "Structural and Functional Impact of Parkinson Disease-Associated Mutations in the E3 Ubiquitin Ligase Parkin," Hum Mutat. Aug. 2015, vol. 36, No. 8, pp. 774-786.
Fu, H. et al., (2011). "Correction of neurological disease of Mucopolysaccharidosis IIIB in adult mice by rAAV9 trans-blood-brain barrier gene delivery," Mol. Therapy 19:1025-1033.
Galibert, F et al., "Woodchuck Hepatitis Virus, complete genome" GenBank: J02442.1, publication date: Aug. 3, 1993.
GenBank Accession No. AAH22014.1 (2005). "PARK2 protein [*Homo sapiens*]," 2 total pages.
GenBank Accession No. AAM21457.1 (2002). "parkin isoform [*Homo sapiens*]," 2 total pages.

(56) References Cited

OTHER PUBLICATIONS

GenBank Accession No. AAM21459.1 (2002). "parkin isoform [*Homo sapiens*]," 2 total pages.
GenBank Accession No. ABN46990.1 (2007). "parkin 2 [*Homo sapiens*]," 2 total pages.
GenBank Accession No. ADB90269.1 (2010). "truncated parkin variant SV4DEL [*Homo sapiens*]," 2 total pages.
GenBank Accession No. ADB90270.1 (2010). "parkin variant SV5DEL [*Homo sapiens*]," 2 total pages.
GenBank Accession No. ADB90271.1 (2010). "parkin variant SV9DEL [*Homo sapiens*]," 2 total pages.
GenBank Accession No. ADB91978.1 (2010). "truncated parkin variant SV4,8DEL [*Homo sapiens*]," 2 total pages.
GenBank Accession No. ADB91979.1 (2010). "parkin variant SV5,9DEL [*Homo sapiens*]," 2 total pages.
GenBank Accession No. ADB91980.1 (2010). "truncated parkin variant SV3,8,9DEL [*Homo sapiens*]," 1 total page.
GenBank Accession No. ADB91981.1 (2010). "truncated parkin variant SV1bINS [*Homo sapiens*]," 1 total page.
GenBank Accession No. AGH62056.1 (2013). PARK2 splice variant [*Homo sapiens*], 1 total page.
GenBank Accession No. AGH62057.1 (2013). "PARK2 splice variant [*Homo sapiens*]," 2 total pages.
GenBank Accession No. AGP25366.1 (2013). "E3 ubiquitin-protein ligase parkin isoform [*Homo sapiens*]," 2 total pages.
GenBank Accession No. BAA25751.1 (2011). "Parkin [*Homo sapiens*]," 2 total pages.
GenBank Accession No. BAF43729.1 (2007). "parkin 2 [*Homo sapiens*]," 2 total pages.
GenBank Accession No. BAF85279.1 (2008). "unnamed protein product [*Homo sapiens*]," 2 total pages.
GenBank Accession No. BAG57845.1 (2008). "unnamed protein product [*Homo sapiens*]," 2 total pages.
GenBank Accession No. NP 004553.2 (2023). "E3 ubiquitin-protein ligase parkin isoform 1 [*Homo sapiens*]," 4 total pages.
GenBank Accession No. NP 054642.2 (2023). "E3 ubiquitin-protein ligase parkin isoform 2 [*Homo sapiens*]," 4 total pages.
GenBank Accession No. NP 054643.2 (2023). "E3 ubiquitin-protein ligase parkin isoform 3 [*Homo sapiens*]," 3 total pages.
Gibbs A. R. et al., "Evolutionary and Biomedical Insights from the Rhesus Macaque Genome," Science, 2007, vol. 316, pp. 222-234.
Gray, S.J. et al. (2011). "Preclinical differences of intravascular AAV9 delivery to neurons and glia: A comparative study of adult mice and nonhuman primates," Mol. Therapy 19:1058-1069.
Grimm, D. et al., (2003). From virus evolution to vector revolution use of naturally occurring serotypes of adeno-associated virus (AAV) as novel vectors for human gene therapy, Curr. Gene Ther. 3:281-304.
Gupta et al., "There Is a Positive Dose-Dependent Association between Low-Dose Oral Minoxidil and Its Efficacy for Androgenetic Alopecia: Findings from a Systematic Review with Meta-Regression Analyses," Skin Appendage Disord., 2022, vol. 8, 5, pp. 355-361.
Hanrott et al., "6-Hydroxydopamine-induced Apoptosis Is Mediated via Extracellular Auto-oxidation and Caspase 3-dependent Activation of Protein Kinase Cδ*," J. Biol. Chem., Mar. 2006, vol. 281, Issue 9, pp. 5373-5382.
Hlavaty, et al., "Effect of posttranscriptional regulatory elements on transgene expression and virus production in the context of retroviral vectors", Virology (2005), 341: 1-11.
Inagaki, K. et al., (2006). "Robust systemic transduction with AAV9 vectors in mice: Efficient global cardiac gene transfer superior to that of AAV8," Mol. Therapy 14:45-53.
International Preliminary Report on Patentability for PCT Application No. PCT/US2019/029744, mailed on Oct. 27, 2020, 9 pages.
International Preliminary Report on Patentability for PCT Application No. PCT/US2021/033491, mailed Nov. 17, 2022, 9 pages.
International Search Report and Written Opinion for International Application No. PCT/US2021/033491 dated Dec. 29, 2021, 19 pages.
Jackson, K.L. et al., (2016). "Corrigendum: Better targeting, better efficiency for wide-scale neuronal transduction with the Synapsin promoter and AAV-PHP.B," Front. Mol. Neurosci. 9:1.
Jonquieres von G. et al., "Uncoupling N acetylaspartate from brain pathology: implications for Canavan disease gene therapy," Acta Neuropathol, 2018, vol. 135, pp. 95-113.
Kingsman, S.M. et al., (2005). "Potential oncogene activity of the Woodchuck Hepatitis posttranscriptional regulatory element (WPRE)" Gene Ther. 12:3-4.
Klein et al., "Parkin is protective for substantia nigra dopamine neurons in a tau gene transfer neurodegeneration model," Neurosci Lett. Jun. 19, 2006; 401(1-2): 130-135, 10 pages total.
Kwon, et al.; "Designer gene delivery vectors: molecular engineering and evolution of adeno-associated viral vectors for enhanced gene transfer"; Pharmaceutical Research; vol. 25, No. 3, pp. 489-499 (Mar. 2008).
Lee, Y et al., "PINK1 Primes Parkin-Mediated Ubiquitination of PARIS in Dopaminergic Neuronal Survival," Cell Reports, vol. 18, No. 4, Jan. 24, 2017, pp. 918-932.
Lesage S. et al., "Parkinson's disease: from monogenic forms to genetic susceptibility factors," Human Molecular Genetics, 2009, vol. 18, pp. 48-59.
Manfredsson, F. et al., "rAAV-mediated nigral human parkin over-expression partially ameliorates motor deficits via enhanced dopamine neurotransmission in a rat model of Parkinson's disease," Experimental Neurology, Elsevier, Amsterdam, NL, Sep. 22, 2007, vol. 207, No. 2, pp. 289-301.
Matrai, J. et al., (2010). "Preclinical and clinical progress in hemophilia gene therapy" Curr Opin Hematol. 17:387-392.
Milanowski, L., May 26. 2020). "PARK2, PINK1, and DJ1 in EOPD in four European countries," poster AAN 2020, 6 total pages, located at https://cslide-us.ctimeetingtech.com/aan2020/attendee/eposter/poster/2671?q=milanowski.
Mochizuki, H., "Parkin Gene Therapy for a-synucleinopathy: A rat model of Parkinson's disease," Parkinsonism and Related Disorders, 2006, vol. 12, pp. S107- S109.
Naldini, L. (2011). "Ex vivo gene transfer and correction for cell-based therapies" Nature Reviews Genetics 12:301-315.
Office Action and Search Report in Russian Application No. 2020134965, mailed Oct. 26, 2022, 11 pages.
Oh et al., "Combined Nurr1 and Foxa2 roles in the therapy of Parkinson's disease," EMBO Mol. Med., 2015, vol. 7, No. 5, pp. 510-525.
Olanow, C. et al., "Gene delivery of neurturin to putamen and substantia nigra in Parkinson disease: A double-blind, randomized, controlled trial," Ann. Neurol., Aug. 2015, vol. 78, No. 2, pp. 248-257.
Orr, A L et al., "Long-term oral kinetin does not protect against [alpha]-synuclein-induced neurodegeneration in rodent models of Parkinson's disease," Neurochemistry International, Apr. 20, 2017, vol. 109, pp. 106-116.
Paltsev, M.A., "Neurodegenerative diseases: molecular basis of pathogenesis, lifelong personalized diagnostics and targeted pharmacotherapy," St. Petersburg: Eco-Vector, 2019, p. 138-146, 13 pages.
Parret et al., "Critical reflections on synthetic gene design for recombinant protein expression" Current Opinion in Structural Biology 38 (2016): 155-162.
Partial Supplementary European Search Report in European application No. 19792202.4, mailed Feb. 16, 2022, 18 pages.
Paterna, J. et al., "DJ-1 and Parkin Modulate Dopamine-dependent Behavior and Inhibit MPTP-induced Nigral Dopamine Neuron Loss in Mice," Molecular Therapy, Apr. 1, 2007, vol. 15, No. 4, pp. 698-704.
Pellagatti A., et al., "Application of CRISPR/Cas9 genome editing to the study and treatment of disease," Archives of Toxicology, 2015, vol. 89, pp. 1023-1024.
Pfeifer G.P et al., "*Homo sapiens* phosphoglycerate kinase 1 (PGK1) gene, partial cds" GenBank: M60581.1, publication date: Jul. 26, 2016.
Powell, S.K., et al., "Viral expression cassette elements to enhance transgene target specificity and expression in gene therapy," Discovery Medicine, Jan. 2015, vol. 19(102), pp. 49-57.

(56) References Cited

OTHER PUBLICATIONS

Ran, F.A., et al., "Double nicking by RNA-guided CRISPR Cas9 for enhanced genome editing specificity," Cell, 2013, vol. 154, No. 6, pp. 1380-1389.
Ruzo, A. et al., (2012). "Correction of pathological accumulation of glycosaminoglycans in central nervous system and peripheral tissues of MPSIIIA mice through systemic AAV9 gene transfer," Human Gene Ther. 23:1237-1246.
Salva et al., "Design of tissue-specific regulatory cassettes for high-level rAAV-mediated expression in skeletal and cardiac muscle" Mol Ther. Feb. 2007; 15(2):320-329.
Schambach, A. et al., (2006). Woodchuck hepatitis virus post-transcriptional regulatory element deleted from X protein and promoter sequences enhances retroviral vector titer and expression, Gene Ther. 13:641-645.
Scuderi et al., "Alternative Splicing Generates Different Parkin Protein Isoforms: Evidences in Human, Rat, and Mouse Brain," BioMed Res. Int'l., 2014, vol. 2014, Article 690796, 14 pages.
Shevtsova, Z. et al., "Promoters and serotypes: targeting of adeno-associated virus vectors for gene transfer in the rat central nervous system in vitro and in vivo," Experimental Physiology, Cambridge University Press, Cambridge, GB, Jan. 1, 2005, vol. 90, No. 1, pp. 53-59.
Simola et al., "The 6-hydroxydopamine model of Parkinson's disease," Neurotox Res., Apr. 2007, vol. 11(3-4), pp. 151-167.
Takeshita, F. et al. "Muscle creatine kinase/SV40 hybrid promoter for muscle-targeted long-term transgene expression." International Journal of Molecular Medicine, vol. 19.2 (2007): pp. 309-315, 7 pages.
Weismann, C.M. et al., (2015). "Systemic AAV9 gene transfer in adult GM1 gangliosidosis mice reduces lysosomal storage in CNS and extends lifespan," Human Molecular Genetics 24:4353-4364.
Werfel, S. et al., "Rapid and highly efficient inducible cardiac gene knockout in adult mice using AAV-mediated expression of Cre recombinase," Cardiovascular Research, 104(1):15-23 (2014).
Wu et al., "Adena-associated virus serotypes: vector toolkit for human gene therapy," Molecular Therapy 14(3):316-327 (2006).
Yasuda et al., "Parkin-Mediated Protection of Dopaminergic Neurons in a Chronic MPTP-Minipump Mouse Model of Parkinson Disease," J. Neuropath Exp Neurol, 2011, vol. 70, No. 8, pp. 686-697.
Zanta-Boussif, M.A. et al. (2009). "Validation of a mutated PRE sequence allowing high and sustained transgene expression while abrogating WHV-X protein synthesis: Application to the gene therapy of WAS" Gene Ther. 16:605-619.
Zufferey et al., "Woodchuck Hepatitis Virus Posttranscriptional Regulatory Element Enhances Expression of Transgenes Delivered by Retroviral Vectors." J. Virol. (1999); 73(4): 2886-2892.
Zychlinski, D., et al., "Physiological Promoters Reduce the Genotoxic Risk of Integrating Gene Vectors," Molecular Therapy, 2008, vol. 16, pp. 718-725.

* cited by examiner

SEQUENCE LISTING

```
<160> NUMBER OF SEQ ID NOS: 81

<210> SEQ ID NO 1
<211> LENGTH: 465
<212> TYPE: PRT
<213> ORGANISM: Homo sapiens

<400> SEQUENCE: 1

Met Ile Val Phe Val Arg Phe Asn Ser Ser His Gly Phe Pro Val Glu
1               5                   10                  15

Val Asp Ser Asp Thr Ser Ile Phe Gln Leu Lys Glu Val Val Ala Lys
            20                  25                  30

Arg Gln Gly Val Pro Ala Asp Gln Leu Arg Val Ile Phe Ala Gly Lys
        35                  40                  45

Glu Leu Arg Asn Asp Trp Thr Val Gln Asn Cys Asp Leu Asp Gln Gln
    50                  55                  60

Ser Ile Val His Ile Val Gln Arg Pro Trp Arg Lys Gly Gln Glu Met
65                  70                  75                  80
```

-continued

```
Asn Ala Thr Gly Gly Asp Asp Pro Arg Asn Ala Ala Gly Gly Cys Glu
                85                  90                  95

Arg Glu Pro Gln Ser Leu Thr Arg Val Asp Leu Ser Ser Ser Val Leu
            100                 105                 110

Pro Gly Asp Ser Val Gly Leu Ala Val Ile Leu His Thr Asp Ser Arg
        115                 120                 125

Lys Asp Ser Pro Pro Ala Gly Ser Pro Ala Gly Arg Ser Ile Tyr Asn
    130                 135                 140

Ser Phe Tyr Val Tyr Cys Lys Gly Pro Cys Gln Arg Val Gln Pro Gly
145                 150                 155                 160

Lys Leu Arg Val Gln Cys Ser Thr Cys Arg Gln Ala Thr Leu Thr Leu
                165                 170                 175

Thr Gln Gly Pro Ser Cys Trp Asp Asp Val Leu Ile Pro Asn Arg Met
            180                 185                 190

Ser Gly Glu Cys Gln Ser Pro His Cys Pro Gly Thr Ser Ala Glu Phe
        195                 200                 205

Phe Phe Lys Cys Gly Ala His Pro Thr Ser Asp Lys Glu Thr Ser Val
    210                 215                 220

Ala Leu His Leu Ile Ala Thr Asn Ser Arg Asn Ile Thr Cys Ile Thr
225                 230                 235                 240

Cys Thr Asp Val Arg Ser Pro Val Leu Val Phe Gln Cys Asn Ser Arg
                245                 250                 255

His Val Ile Cys Leu Asp Cys Phe His Leu Tyr Cys Val Thr Arg Leu
            260                 265                 270

Asn Asp Arg Gln Phe Val His Asp Pro Gln Leu Gly Tyr Ser Leu Pro
        275                 280                 285

Cys Val Ala Gly Cys Pro Asn Ser Leu Ile Lys Glu Leu His His Phe
    290                 295                 300

Arg Ile Leu Gly Glu Glu Gln Tyr Asn Arg Tyr Gln Gln Tyr Gly Ala
305                 310                 315                 320

Glu Glu Cys Val Leu Gln Met Gly Gly Val Leu Cys Pro Arg Pro Gly
                325                 330                 335

Cys Gly Ala Gly Leu Leu Pro Glu Pro Asp Gln Arg Lys Val Thr Cys
            340                 345                 350

Glu Gly Gly Asn Gly Leu Gly Cys Gly Phe Ala Phe Cys Arg Glu Cys
        355                 360                 365

Lys Glu Ala Tyr His Glu Gly Glu Cys Ser Ala Val Phe Glu Ala Ser
    370                 375                 380

Gly Thr Thr Thr Gln Ala Tyr Arg Val Asp Glu Arg Ala Ala Glu Gln
385                 390                 395                 400

Ala Arg Trp Glu Ala Ala Ser Lys Glu Thr Ile Lys Lys Thr Thr Lys
                405                 410                 415

Pro Cys Pro Arg Cys His Val Pro Val Glu Lys Asn Gly Gly Cys Met
            420                 425                 430

His Met Lys Cys Pro Gln Pro Gln Cys Arg Leu Glu Trp Cys Trp Asn
        435                 440                 445

Cys Gly Cys Glu Trp Asn Arg Val Cys Met Gly Asp His Trp Phe Asp
    450                 455                 460

Val
465
```

<210> SEQ ID NO 2
<211> LENGTH: 581
<212> TYPE: PRT

<213> ORGANISM: Homo sapiens

<400> SEQUENCE: 2

```
Met Ala Val Arg Gln Ala Leu Gly Arg Gly Leu Gln Leu Gly Arg Ala
1               5                   10                  15

Leu Leu Leu Arg Phe Thr Gly Lys Pro Gly Arg Ala Tyr Gly Leu Gly
            20                  25                  30

Arg Pro Gly Pro Ala Ala Gly Cys Val Arg Gly Glu Arg Pro Gly Trp
        35                  40                  45

Ala Ala Gly Pro Gly Ala Glu Pro Arg Arg Val Gly Leu Gly Leu Pro
    50                  55                  60

Asn Arg Leu Arg Phe Phe Arg Gln Ser Val Ala Gly Leu Ala Ala Arg
65                  70                  75                  80

Leu Gln Arg Gln Phe Val Val Arg Ala Trp Gly Cys Ala Gly Pro Cys
                85                  90                  95

Gly Arg Ala Val Phe Leu Ala Phe Gly Leu Gly Leu Gly Leu Ile Glu
            100                 105                 110

Glu Lys Gln Ala Glu Ser Arg Arg Ala Val Ser Ala Cys Gln Glu Ile
        115                 120                 125

Gln Ala Ile Phe Thr Gln Lys Ser Lys Pro Gly Pro Asp Pro Leu Asp
    130                 135                 140

Thr Arg Arg Leu Gln Gly Phe Arg Leu Glu Glu Tyr Leu Ile Gly Gln
145                 150                 155                 160

Ser Ile Gly Lys Gly Cys Ser Ala Ala Val Tyr Glu Ala Thr Met Pro
                165                 170                 175

Thr Leu Pro Gln Asn Leu Glu Val Thr Lys Ser Thr Gly Leu Leu Pro
            180                 185                 190

Gly Arg Gly Pro Gly Thr Ser Ala Pro Gly Glu Gly Gln Glu Arg Ala
        195                 200                 205

Pro Gly Ala Pro Ala Phe Pro Leu Ala Ile Lys Met Met Trp Asn Ile
    210                 215                 220

Ser Ala Gly Ser Ser Ser Glu Ala Ile Leu Asn Thr Met Ser Gln Glu
225                 230                 235                 240

Leu Val Pro Ala Ser Arg Val Ala Leu Ala Gly Glu Tyr Gly Ala Val
                245                 250                 255

Thr Tyr Arg Lys Ser Lys Arg Gly Pro Lys Gln Leu Ala Pro His Pro
            260                 265                 270

Asn Ile Ile Arg Val Leu Arg Ala Phe Thr Ser Ser Val Pro Leu Leu
        275                 280                 285

Pro Gly Ala Leu Val Asp Tyr Pro Asp Val Leu Pro Ser Arg Leu His
    290                 295                 300

Pro Glu Gly Leu Gly His Gly Arg Thr Leu Phe Leu Val Met Lys Asn
305                 310                 315                 320

Tyr Pro Cys Thr Leu Arg Gln Tyr Leu Cys Val Asn Thr Pro Ser Pro
                325                 330                 335

Arg Leu Ala Ala Met Met Leu Leu Gln Leu Leu Glu Gly Val Asp His
            340                 345                 350

Leu Val Gln Gln Gly Ile Ala His Arg Asp Leu Lys Ser Asp Asn Ile
        355                 360                 365

Leu Val Glu Leu Asp Pro Asp Gly Cys Pro Trp Leu Val Ile Ala Asp
    370                 375                 380

Phe Gly Cys Cys Leu Ala Asp Glu Ser Ile Gly Leu Gln Leu Pro Phe
385                 390                 395                 400
```

-continued

```
Ser Ser Trp Tyr Val Asp Arg Gly Gly Asn Gly Cys Leu Met Ala Pro
                405                 410                 415

Glu Val Ser Thr Ala Arg Pro Gly Pro Arg Ala Val Ile Asp Tyr Ser
            420                 425                 430

Lys Ala Asp Ala Trp Ala Val Gly Ala Ile Ala Tyr Glu Ile Phe Gly
        435                 440                 445

Leu Val Asn Pro Phe Tyr Gly Gln Gly Lys Ala His Leu Glu Ser Arg
    450                 455                 460

Ser Tyr Gln Glu Ala Gln Leu Pro Ala Leu Pro Glu Ser Val Pro Pro
465                 470                 475                 480

Asp Val Arg Gln Leu Val Arg Ala Leu Leu Gln Arg Glu Ala Ser Lys
                485                 490                 495

Arg Pro Ser Ala Arg Val Ala Ala Asn Val Leu His Leu Ser Leu Trp
            500                 505                 510

Gly Glu His Ile Leu Ala Leu Lys Asn Leu Lys Leu Asp Lys Met Val
        515                 520                 525

Gly Trp Leu Leu Gln Gln Ser Ala Ala Thr Leu Leu Ala Asn Arg Leu
    530                 535                 540

Thr Glu Lys Cys Cys Val Glu Thr Lys Met Lys Met Leu Phe Leu Ala
545                 550                 555                 560

Asn Leu Glu Cys Glu Thr Leu Cys Gln Ala Ala Leu Leu Leu Cys Ser
                565                 570                 575

Trp Arg Ala Ala Leu
            580


<210> SEQ ID NO 3
<211> LENGTH: 189
<212> TYPE: PRT
<213> ORGANISM: Homo sapiens

<400> SEQUENCE: 3

Met Ala Ser Lys Arg Ala Leu Val Ile Leu Ala Lys Gly Ala Glu Glu
1               5                   10                  15

Met Glu Thr Val Ile Pro Val Asp Val Met Arg Arg Ala Gly Ile Lys
            20                  25                  30

Val Thr Val Ala Gly Leu Ala Gly Lys Asp Pro Val Gln Cys Ser Arg
        35                  40                  45

Asp Val Val Ile Cys Pro Asp Ala Ser Leu Glu Asp Ala Lys Lys Glu
    50                  55                  60

Gly Pro Tyr Asp Val Val Val Leu Pro Gly Gly Asn Leu Gly Ala Gln
65                  70                  75                  80

Asn Leu Ser Glu Ser Ala Ala Val Lys Glu Ile Leu Lys Glu Gln Glu
                85                  90                  95

Asn Arg Lys Gly Leu Ile Ala Ala Ile Cys Ala Gly Pro Thr Ala Leu
            100                 105                 110

Leu Ala His Glu Ile Gly Phe Gly Ser Lys Val Thr Thr His Pro Leu
        115                 120                 125

Ala Lys Asp Lys Met Met Asn Gly Gly His Tyr Thr Tyr Ser Glu Asn
    130                 135                 140

Arg Val Glu Lys Asp Gly Leu Ile Leu Thr Ser Arg Gly Pro Gly Thr
145                 150                 155                 160

Ser Phe Glu Phe Ala Leu Ala Ile Val Glu Ala Leu Asn Gly Lys Glu
                165                 170                 175

Val Ala Ala Gln Val Lys Ala Pro Leu Val Leu Lys Asp
            180                 185
```

<210> SEQ ID NO 4
<211> LENGTH: 2527
<212> TYPE: PRT
<213> ORGANISM: Homo sapiens

<400> SEQUENCE: 4

```
Met Ala Ser Gly Ser Cys Gln Gly Cys Glu Glu Asp Glu Glu Thr Leu
1               5                   10                  15

Lys Lys Leu Ile Val Arg Leu Asn Asn Val Gln Glu Gly Lys Gln Ile
            20                  25                  30

Glu Thr Leu Val Gln Ile Leu Glu Asp Leu Leu Val Phe Thr Tyr Ser
        35                  40                  45

Glu Arg Ala Ser Lys Leu Phe Gln Gly Lys Asn Ile His Val Pro Leu
    50                  55                  60

Leu Ile Val Leu Asp Ser Tyr Met Arg Val Ala Ser Val Gln Gln Val
65                  70                  75                  80

Gly Trp Ser Leu Leu Cys Lys Leu Ile Glu Val Cys Pro Gly Thr Met
                85                  90                  95

Gln Ser Leu Met Gly Pro Gln Asp Val Gly Asn Asp Trp Glu Val Leu
            100                 105                 110

Gly Val His Gln Leu Ile Leu Lys Met Leu Thr Val His Asn Ala Ser
        115                 120                 125

Val Asn Leu Ser Val Ile Gly Leu Lys Thr Leu Asp Leu Leu Leu Thr
    130                 135                 140

Ser Gly Lys Ile Thr Leu Leu Ile Leu Asp Glu Glu Ser Asp Ile Phe
145                 150                 155                 160

Met Leu Ile Phe Asp Ala Met His Ser Phe Pro Ala Asn Asp Glu Val
                165                 170                 175

Gln Lys Leu Gly Cys Lys Ala Leu His Val Leu Phe Glu Arg Val Ser
            180                 185                 190

Glu Glu Gln Leu Thr Glu Phe Val Glu Asn Lys Asp Tyr Met Ile Leu
        195                 200                 205

Leu Ser Ala Leu Thr Asn Phe Lys Asp Glu Glu Glu Ile Val Leu His
    210                 215                 220

Val Leu His Cys Leu His Ser Leu Ala Ile Pro Cys Asn Asn Val Glu
225                 230                 235                 240

Val Leu Met Ser Gly Asn Val Arg Cys Tyr Asn Ile Val Val Glu Ala
                245                 250                 255

Met Lys Ala Phe Pro Met Ser Glu Arg Ile Gln Glu Val Ser Cys Cys
            260                 265                 270

Leu Leu His Arg Leu Thr Leu Gly Asn Phe Phe Asn Ile Leu Val Leu
        275                 280                 285

Asn Glu Val His Glu Phe Val Val Lys Ala Val Gln Gln Tyr Pro Glu
    290                 295                 300

Asn Ala Ala Leu Gln Ile Ser Ala Leu Ser Cys Leu Ala Leu Leu Thr
305                 310                 315                 320

Glu Thr Ile Phe Leu Asn Gln Asp Leu Glu Glu Lys Asn Glu Asn Gln
                325                 330                 335

Glu Asn Asp Asp Glu Gly Glu Glu Asp Lys Leu Phe Trp Leu Glu Ala
            340                 345                 350

Cys Tyr Lys Ala Leu Thr Trp His Arg Lys Asn Lys His Val Gln Glu
        355                 360                 365

Ala Ala Cys Trp Ala Leu Asn Asn Leu Leu Met Tyr Gln Asn Ser Leu
```

-continued

```
    370                 375                 380

His Glu Lys Ile Gly Asp Glu Asp Gly His Phe Pro Ala His Arg Glu
385                 390                 395                 400

Val Met Leu Ser Met Leu Met His Ser Ser Ser Lys Glu Val Phe Gln
                405                 410                 415

Ala Ser Ala Asn Ala Leu Ser Thr Leu Leu Glu Gln Asn Val Asn Phe
            420                 425                 430

Arg Lys Ile Leu Leu Ser Lys Gly Ile His Leu Asn Val Leu Glu Leu
        435                 440                 445

Met Gln Lys His Ile His Ser Pro Glu Val Ala Glu Ser Gly Cys Lys
    450                 455                 460

Met Leu Asn His Leu Phe Glu Gly Ser Asn Thr Ser Leu Asp Ile Met
465                 470                 475                 480

Ala Ala Val Val Pro Lys Ile Leu Thr Val Met Lys Arg His Glu Thr
                485                 490                 495

Ser Leu Pro Val Gln Leu Glu Ala Leu Arg Ala Ile Leu His Phe Ile
            500                 505                 510

Val Pro Gly Met Pro Glu Glu Ser Arg Glu Asp Thr Glu Phe His His
        515                 520                 525

Lys Leu Asn Met Val Lys Lys Gln Cys Phe Lys Asn Asp Ile His Lys
    530                 535                 540

Leu Val Leu Ala Ala Leu Asn Arg Phe Ile Gly Asn Pro Gly Ile Gln
545                 550                 555                 560

Lys Cys Gly Leu Lys Val Ile Ser Ser Ile Val His Phe Pro Asp Ala
                565                 570                 575

Leu Glu Met Leu Ser Leu Glu Gly Ala Met Asp Ser Val Leu His Thr
            580                 585                 590

Leu Gln Met Tyr Pro Asp Asp Gln Glu Ile Gln Cys Leu Gly Leu Ser
        595                 600                 605

Leu Ile Gly Tyr Leu Ile Thr Lys Lys Asn Val Phe Ile Gly Thr Gly
    610                 615                 620

His Leu Leu Ala Lys Ile Leu Val Ser Ser Leu Tyr Arg Phe Lys Asp
625                 630                 635                 640

Val Ala Glu Ile Gln Thr Lys Gly Phe Gln Thr Ile Leu Ala Ile Leu
                645                 650                 655

Lys Leu Ser Ala Ser Phe Ser Lys Leu Leu Val His His Ser Phe Asp
            660                 665                 670

Leu Val Ile Phe His Gln Met Ser Ser Asn Ile Met Glu Gln Lys Asp
        675                 680                 685

Gln Gln Phe Leu Asn Leu Cys Cys Lys Cys Phe Ala Lys Val Ala Met
    690                 695                 700

Asp Asp Tyr Leu Lys Asn Val Met Leu Glu Arg Ala Cys Asp Gln Asn
705                 710                 715                 720

Asn Ser Ile Met Val Glu Cys Leu Leu Leu Leu Gly Ala Asp Ala Asn
                725                 730                 735

Gln Ala Lys Glu Gly Ser Ser Leu Ile Cys Gln Val Cys Glu Lys Glu
            740                 745                 750

Ser Ser Pro Lys Leu Val Glu Leu Leu Leu Asn Ser Gly Ser Arg Glu
        755                 760                 765

Gln Asp Val Arg Lys Ala Leu Thr Ile Ser Ile Gly Lys Gly Asp Ser
    770                 775                 780

Gln Ile Ile Ser Leu Leu Leu Arg Arg Leu Ala Leu Asp Val Ala Asn
785                 790                 795                 800
```

```
Asn Ser Ile Cys Leu Gly Gly Phe Cys Ile Gly Lys Val Glu Pro Ser
                805                 810                 815

Trp Leu Gly Pro Leu Phe Pro Asp Lys Thr Ser Asn Leu Arg Lys Gln
            820                 825                 830

Thr Asn Ile Ala Ser Thr Leu Ala Arg Met Val Ile Arg Tyr Gln Met
        835                 840                 845

Lys Ser Ala Val Glu Glu Gly Thr Ala Ser Gly Ser Asp Gly Asn Phe
    850                 855                 860

Ser Glu Asp Val Leu Ser Lys Phe Asp Glu Trp Thr Phe Ile Pro Asp
865                 870                 875                 880

Ser Ser Met Asp Ser Val Phe Ala Gln Ser Asp Asp Leu Asp Ser Glu
                885                 890                 895

Gly Ser Glu Gly Ser Phe Leu Val Lys Lys Lys Ser Asn Ser Ile Ser
            900                 905                 910

Val Gly Glu Phe Tyr Arg Asp Ala Val Leu Gln Arg Cys Ser Pro Asn
        915                 920                 925

Leu Gln Arg His Ser Asn Ser Leu Gly Pro Ile Phe Asp His Glu Asp
    930                 935                 940

Leu Leu Lys Arg Lys Arg Lys Ile Leu Ser Ser Asp Asp Ser Leu Arg
945                 950                 955                 960

Ser Ser Lys Leu Gln Ser His Met Arg His Ser Asp Ser Ile Ser Ser
                965                 970                 975

Leu Ala Ser Glu Arg Glu Tyr Ile Thr Ser Leu Asp Leu Ser Ala Asn
            980                 985                 990

Glu Leu Arg Asp Ile Asp Ala Leu  Ser Gln Lys Cys Cys  Ile Ser Val
        995                 1000                1005

His Leu  Glu His Leu Glu Lys  Leu Glu Leu His Gln  Asn Ala Leu
    1010                1015                1020

Thr Ser  Phe Pro Gln Gln Leu  Cys Glu Thr Leu Lys  Ser Leu Thr
    1025                1030                1035

His Leu  Asp Leu His Ser Asn  Lys Phe Thr Ser Phe  Pro Ser Tyr
    1040                1045                1050

Leu Leu  Lys Met Ser Cys Ile  Ala Asn Leu Asp Val  Ser Arg Asn
    1055                1060                1065

Asp Ile  Gly Pro Ser Val Val  Leu Asp Pro Thr Val  Lys Cys Pro
    1070                1075                1080

Thr Leu  Lys Gln Phe Asn Leu  Ser Tyr Asn Gln Leu  Ser Phe Val
    1085                1090                1095

Pro Glu  Asn Leu Thr Asp Val  Val Glu Lys Leu Glu  Gln Leu Ile
    1100                1105                1110

Leu Glu  Gly Asn Lys Ile Ser  Gly Ile Cys Ser Pro  Leu Arg Leu
    1115                1120                1125

Lys Glu  Leu Lys Ile Leu Asn  Leu Ser Lys Asn His  Ile Ser Ser
    1130                1135                1140

Leu Ser  Glu Asn Phe Leu Glu  Ala Cys Pro Lys Val  Glu Ser Phe
    1145                1150                1155

Ser Ala  Arg Met Asn Phe Leu  Ala Ala Met Pro Phe  Leu Pro Pro
    1160                1165                1170

Ser Met  Thr Ile Leu Lys Leu  Ser Gln Asn Lys Phe  Ser Cys Ile
    1175                1180                1185

Pro Glu  Ala Ile Leu Asn Leu  Pro His Leu Arg Ser  Leu Asp Met
    1190                1195                1200
```

-continued

```
Ser Ser  Asn Asp Ile Gln Tyr  Leu Pro Gly Pro Ala  His Trp Lys
    1205                 1210                 1215

Ser Leu  Asn Leu Arg Glu Leu  Leu Phe Ser His Asn  Gln Ile Ser
    1220                 1225                 1230

Ile Leu  Asp Leu Ser Glu Lys  Ala Tyr Leu Trp Ser  Arg Val Glu
    1235                 1240                 1245

Lys Leu  His Leu Ser His Asn  Lys Leu Lys Glu Ile  Pro Pro Glu
    1250                 1255                 1260

Ile Gly  Cys Leu Glu Asn Leu  Thr Ser Leu Asp Val  Ser Tyr Asn
    1265                 1270                 1275

Leu Glu  Leu Arg Ser Phe Pro  Asn Glu Met Gly Lys  Leu Ser Lys
    1280                 1285                 1290

Ile Trp  Asp Leu Pro Leu Asp  Glu Leu His Leu Asn  Phe Asp Phe
    1295                 1300                 1305

Lys His  Ile Gly Cys Lys Ala  Lys Asp Ile Ile Arg  Phe Leu Gln
    1310                 1315                 1320

Gln Arg  Leu Lys Lys Ala Val  Pro Tyr Asn Arg Met  Lys Leu Met
    1325                 1330                 1335

Ile Val  Gly Asn Thr Gly Ser  Gly Lys Thr Thr Leu  Leu Gln Gln
    1340                 1345                 1350

Leu Met  Lys Thr Lys Lys Ser  Asp Leu Gly Met Gln  Ser Ala Thr
    1355                 1360                 1365

Val Gly  Ile Asp Val Lys Asp  Trp Pro Ile Gln Ile  Arg Asp Lys
    1370                 1375                 1380

Arg Lys  Arg Asp Leu Val Leu  Asn Val Trp Asp Phe  Ala Gly Arg
    1385                 1390                 1395

Glu Glu  Phe Tyr Ser Thr His  Pro His Phe Met Thr  Gln Arg Ala
    1400                 1405                 1410

Leu Tyr  Leu Ala Val Tyr Asp  Leu Ser Lys Gly Gln  Ala Glu Val
    1415                 1420                 1425

Asp Ala  Met Lys Pro Trp Leu  Phe Asn Ile Lys Ala  Arg Ala Ser
    1430                 1435                 1440

Ser Ser  Pro Val Ile Leu Val  Gly Thr His Leu Asp  Val Ser Asp
    1445                 1450                 1455

Glu Lys  Gln Arg Lys Ala Cys  Met Ser Lys Ile Thr  Lys Glu Leu
    1460                 1465                 1470

Leu Asn  Lys Arg Gly Phe Pro  Ala Ile Arg Asp Tyr  His Phe Val
    1475                 1480                 1485

Asn Ala  Thr Glu Glu Ser Asp  Ala Leu Ala Lys Leu  Arg Lys Thr
    1490                 1495                 1500

Ile Ile  Asn Glu Ser Leu Asn  Phe Lys Ile Arg Asp  Gln Leu Val
    1505                 1510                 1515

Val Gly  Gln Leu Ile Pro Asp  Cys Tyr Val Glu Leu  Glu Lys Ile
    1520                 1525                 1530

Ile Leu  Ser Glu Arg Lys Asn  Val Pro Ile Glu Phe  Pro Val Ile
    1535                 1540                 1545

Asp Arg  Lys Arg Leu Leu Gln  Leu Val Arg Glu Asn  Gln Leu Gln
    1550                 1555                 1560

Leu Asp  Glu Asn Glu Leu Pro  His Ala Val His Phe  Leu Asn Glu
    1565                 1570                 1575

Ser Gly  Val Leu Leu His Phe  Gln Asp Pro Ala Leu  Gln Leu Ser
    1580                 1585                 1590

Asp Leu  Tyr Phe Val Glu Pro  Lys Trp Leu Cys Lys  Ile Met Ala
```

-continued

```
    1595                1600                1605

Gln Ile  Leu Thr Val Lys Val  Glu Gly Cys Pro Lys  His Pro Lys
    1610                1615                1620

Gly Ile  Ile Ser Arg Arg Asp  Val Glu Lys Phe Leu  Ser Lys Lys
    1625                1630                1635

Arg Lys  Phe Pro Lys Asn Tyr  Met Ser Gln Tyr Phe  Lys Leu Leu
    1640                1645                1650

Glu Lys  Phe Gln Ile Ala Leu  Pro Ile Gly Glu Glu  Tyr Leu Leu
    1655                1660                1665

Val Pro  Ser Ser Leu Ser Asp  His Arg Pro Val Ile  Glu Leu Pro
    1670                1675                1680

His Cys  Glu Asn Ser Glu Ile  Ile Ile Arg Leu Tyr  Glu Met Pro
    1685                1690                1695

Tyr Phe  Pro Met Gly Phe Trp  Ser Arg Leu Ile Asn  Arg Leu Leu
    1700                1705                1710

Glu Ile  Ser Pro Tyr Met Leu  Ser Gly Arg Glu Arg  Ala Leu Arg
    1715                1720                1725

Pro Asn  Arg Met Tyr Trp Arg  Gln Gly Ile Tyr Leu  Asn Trp Ser
    1730                1735                1740

Pro Glu  Ala Tyr Cys Leu Val  Gly Ser Glu Val Leu  Asp Asn His
    1745                1750                1755

Pro Glu  Ser Phe Leu Lys Ile  Thr Val Pro Ser Cys  Arg Lys Gly
    1760                1765                1770

Cys Ile  Leu Leu Gly Gln Val  Val Asp His Ile Asp  Ser Leu Met
    1775                1780                1785

Glu Glu  Trp Phe Pro Gly Leu  Leu Glu Ile Asp Ile  Cys Gly Glu
    1790                1795                1800

Gly Glu  Thr Leu Leu Lys Lys  Trp Ala Leu Tyr Ser  Phe Asn Asp
    1805                1810                1815

Gly Glu  Glu His Gln Lys Ile  Leu Leu Asp Asp Leu  Met Lys Lys
    1820                1825                1830

Ala Glu  Glu Gly Asp Leu Leu  Val Asn Pro Asp Gln  Pro Arg Leu
    1835                1840                1845

Thr Ile  Pro Ile Ser Gln Ile  Ala Pro Asp Leu Ile  Leu Ala Asp
    1850                1855                1860

Leu Pro  Arg Asn Ile Met Leu  Asn Asn Asp Glu Leu  Glu Phe Glu
    1865                1870                1875

Gln Ala  Pro Glu Phe Leu Leu  Gly Asp Gly Ser Phe  Gly Ser Val
    1880                1885                1890

Tyr Arg  Ala Ala Tyr Glu Gly  Glu Glu Val Ala Val  Lys Ile Phe
    1895                1900                1905

Asn Lys  His Thr Ser Leu Arg  Leu Leu Arg Gln Glu  Leu Val Val
    1910                1915                1920

Leu Cys  His Leu His His Pro  Ser Leu Ile Ser Leu  Leu Ala Ala
    1925                1930                1935

Gly Ile  Arg Pro Arg Met Leu  Val Met Glu Leu Ala  Ser Lys Gly
    1940                1945                1950

Ser Leu  Asp Arg Leu Leu Gln  Gln Asp Lys Ala Ser  Leu Thr Arg
    1955                1960                1965

Thr Leu  Gln His Arg Ile Ala  Leu His Val Ala Asp  Gly Leu Arg
    1970                1975                1980

Tyr Leu  His Ser Ala Met Ile  Ile Tyr Arg Asp Leu  Lys Pro His
    1985                1990                1995
```

-continued

Asn Val Leu Leu Phe Thr Leu Tyr Pro Asn Ala Ala Ile Ile Ala
2000 2005 2010

Lys Ile Ala Asp Tyr Gly Ile Ala Gln Tyr Cys Cys Arg Met Gly
2015 2020 2025

Ile Lys Thr Ser Glu Gly Thr Pro Gly Phe Arg Ala Pro Glu Val
2030 2035 2040

Ala Arg Gly Asn Val Ile Tyr Asn Gln Gln Ala Asp Val Tyr Ser
2045 2050 2055

Phe Gly Leu Leu Leu Tyr Asp Ile Leu Thr Thr Gly Gly Arg Ile
2060 2065 2070

Val Glu Gly Leu Lys Phe Pro Asn Glu Phe Asp Glu Leu Glu Ile
2075 2080 2085

Gln Gly Lys Leu Pro Asp Pro Val Lys Glu Tyr Gly Cys Ala Pro
2090 2095 2100

Trp Pro Met Val Glu Lys Leu Ile Lys Gln Cys Leu Lys Glu Asn
2105 2110 2115

Pro Gln Glu Arg Pro Thr Ser Ala Gln Val Phe Asp Ile Leu Asn
2120 2125 2130

Ser Ala Glu Leu Val Cys Leu Thr Arg Arg Ile Leu Leu Pro Lys
2135 2140 2145

Asn Val Ile Val Glu Cys Met Val Ala Thr His His Asn Ser Arg
2150 2155 2160

Asn Ala Ser Ile Trp Leu Gly Cys Gly His Thr Asp Arg Gly Gln
2165 2170 2175

Leu Ser Phe Leu Asp Leu Asn Thr Glu Gly Tyr Thr Ser Glu Glu
2180 2185 2190

Val Ala Asp Ser Arg Ile Leu Cys Leu Ala Leu Val His Leu Pro
2195 2200 2205

Val Glu Lys Glu Ser Trp Ile Val Ser Gly Thr Gln Ser Gly Thr
2210 2215 2220

Leu Leu Val Ile Asn Thr Glu Asp Gly Lys Lys Arg His Thr Leu
2225 2230 2235

Glu Lys Met Thr Asp Ser Val Thr Cys Leu Tyr Cys Asn Ser Phe
2240 2245 2250

Ser Lys Gln Ser Lys Gln Lys Asn Phe Leu Leu Val Gly Thr Ala
2255 2260 2265

Asp Gly Lys Leu Ala Ile Phe Glu Asp Lys Thr Val Lys Leu Lys
2270 2275 2280

Gly Ala Ala Pro Leu Lys Ile Leu Asn Ile Gly Asn Val Ser Thr
2285 2290 2295

Pro Leu Met Cys Leu Ser Glu Ser Thr Asn Ser Thr Glu Arg Asn
2300 2305 2310

Val Met Trp Gly Gly Cys Gly Thr Lys Ile Phe Ser Phe Ser Asn
2315 2320 2325

Asp Phe Thr Ile Gln Lys Leu Ile Glu Thr Arg Thr Ser Gln Leu
2330 2335 2340

Phe Ser Tyr Ala Ala Phe Ser Asp Ser Asn Ile Ile Thr Val Val
2345 2350 2355

Val Asp Thr Ala Leu Tyr Ile Ala Lys Gln Asn Ser Pro Val Val
2360 2365 2370

Glu Val Trp Asp Lys Lys Thr Glu Lys Leu Cys Gly Leu Ile Asp
2375 2380 2385

-continued

```
Cys Val  His Phe Leu Arg Glu  Val Met Val Lys Glu  Asn Lys Glu
    2390                 2395                 2400

Ser Lys  His Lys Met Ser Tyr  Ser Gly Arg Val Lys  Thr Leu Cys
    2405                 2410                 2415

Leu Gln  Lys Asn Thr Ala Leu  Trp Ile Gly Thr Gly  Gly Gly His
    2420                 2425                 2430

Ile Leu  Leu Leu Asp Leu Ser  Thr Arg Arg Leu Ile  Arg Val Ile
    2435                 2440                 2445

Tyr Asn  Phe Cys Asn Ser Val  Arg Val Met Met Thr  Ala Gln Leu
    2450                 2455                 2460

Gly Ser  Leu Lys Asn Val Met  Leu Val Leu Gly Tyr  Asn Arg Lys
    2465                 2470                 2475

Asn Thr  Glu Gly Thr Gln Lys  Gln Lys Glu Ile Gln  Ser Cys Leu
    2480                 2485                 2490

Thr Val  Trp Asp Ile Asn Leu  Pro His Glu Val Gln  Asn Leu Glu
    2495                 2500                 2505

Lys His  Ile Glu Val Arg Lys  Glu Leu Ala Glu Lys  Met Arg Arg
    2510                 2515                 2520

Thr Ser  Val Glu
    2525


<210> SEQ ID NO 5
<211> LENGTH: 140
<212> TYPE: PRT
<213> ORGANISM: Homo sapiens

<400> SEQUENCE: 5

Met Asp Val Phe Met Lys Gly Leu Ser Lys Ala Lys Glu Gly Val Val
1               5                   10                  15

Ala Ala Ala Glu Lys Thr Lys Gln Gly Val Ala Glu Ala Ala Gly Lys
            20                  25                  30

Thr Lys Glu Gly Val Leu Tyr Val Gly Ser Lys Thr Lys Glu Gly Val
        35                  40                  45

Val His Gly Val Ala Thr Val Ala Glu Lys Thr Lys Glu Gln Val Thr
    50                  55                  60

Asn Val Gly Gly Ala Val Val Thr Gly Val Thr Ala Val Ala Gln Lys
65                  70                  75                  80

Thr Val Glu Gly Ala Gly Ser Ile Ala Ala Ala Thr Gly Phe Val Lys
                85                  90                  95

Lys Asp Gln Leu Gly Lys Asn Glu Glu Gly Ala Pro Gln Glu Gly Ile
            100                 105                 110

Leu Glu Asp Met Pro Val Asp Pro Asp Asn Glu Ala Tyr Glu Met Pro
        115                 120                 125

Ser Glu Glu Gly Tyr Gln Asp Tyr Glu Pro Glu Ala
    130                 135                 140


<210> SEQ ID NO 6
<211> LENGTH: 619
<212> TYPE: PRT
<213> ORGANISM: Homo sapiens

<400> SEQUENCE: 6

Met Ala Ser Gly Ala Tyr Asn Pro Tyr Ile Glu Ile Ile Glu Gln Pro
1               5                   10                  15

Arg Gln Arg Gly Met Arg Phe Arg Tyr Lys Cys Glu Gly Arg Ser Ala
            20                  25                  30
```

-continued

```
Gly Ser Ile Pro Gly Glu His Ser Thr Asp Asn Asn Arg Thr Tyr Pro
        35                  40                  45

Ser Ile Gln Ile Met Asn Tyr Tyr Gly Lys Gly Lys Val Arg Ile Thr
    50                  55                  60

Leu Val Thr Lys Asn Asp Pro Tyr Lys Pro His Pro His Asp Leu Val
65                  70                  75                  80

Gly Lys Asp Cys Arg Asp Gly Tyr Tyr Glu Ala Glu Phe Gly Gln Glu
                85                  90                  95

Arg Arg Pro Leu Phe Phe Gln Asn Leu Gly Ile Arg Cys Val Lys Lys
            100                 105                 110

Lys Glu Val Lys Glu Ala Ile Ile Thr Arg Ile Lys Ala Gly Ile Asn
        115                 120                 125

Pro Phe Asn Val Pro Glu Lys Gln Leu Asn Asp Ile Glu Asp Cys Asp
    130                 135                 140

Leu Asn Val Val Arg Leu Cys Phe Gln Val Phe Leu Pro Asp Glu His
145                 150                 155                 160

Gly Asn Leu Thr Thr Ala Leu Pro Pro Val Val Ser Asn Pro Ile Tyr
                165                 170                 175

Asp Asn Arg Ala Pro Asn Thr Ala Glu Leu Arg Ile Cys Arg Val Asn
            180                 185                 190

Lys Asn Cys Gly Ser Val Arg Gly Gly Asp Glu Ile Phe Leu Leu Cys
        195                 200                 205

Asp Lys Val Gln Lys Asp Asp Ile Glu Val Arg Phe Val Leu Asn Asp
    210                 215                 220

Trp Glu Ala Lys Gly Ile Phe Ser Gln Ala Asp Val His Arg Gln Val
225                 230                 235                 240

Ala Ile Val Phe Lys Thr Pro Pro Tyr Cys Lys Ala Ile Thr Glu Pro
                245                 250                 255

Val Thr Val Lys Met Gln Leu Arg Arg Pro Ser Asp Gln Glu Val Ser
            260                 265                 270

Glu Ser Met Asp Phe Arg Tyr Leu Pro Asp Glu Lys Asp Thr Tyr Gly
        275                 280                 285

Asn Lys Ala Lys Lys Gln Lys Thr Thr Leu Leu Phe Gln Lys Leu Cys
    290                 295                 300

Gln Asp His Val Glu Thr Gly Phe Arg His Val Asp Gln Asp Gly Leu
305                 310                 315                 320

Glu Leu Leu Thr Ser Gly Asp Pro Pro Thr Leu Ala Ser Gln Ser Ala
                325                 330                 335

Gly Ile Thr Val Asn Phe Pro Glu Arg Pro Arg Pro Gly Leu Leu Gly
            340                 345                 350

Ser Ile Gly Glu Gly Arg Tyr Phe Lys Lys Glu Pro Asn Leu Phe Ser
        355                 360                 365

His Asp Ala Val Val Arg Glu Met Pro Thr Gly Val Ser Ser Gln Ala
    370                 375                 380

Glu Ser Tyr Tyr Pro Ser Pro Gly Pro Ile Ser Ser Gly Leu Ser His
385                 390                 395                 400

His Ala Ser Met Ala Pro Leu Pro Ser Ser Ser Trp Ser Ser Val Ala
                405                 410                 415

His Pro Thr Pro Arg Ser Gly Asn Thr Asn Pro Leu Ser Ser Phe Ser
            420                 425                 430

Thr Arg Thr Leu Pro Ser Asn Ser Gln Gly Ile Pro Pro Phe Leu Arg
        435                 440                 445

Ile Pro Val Gly Asn Asp Leu Asn Ala Ser Asn Ala Cys Ile Tyr Asn
```

```
    450                 455                 460

Asn Ala Asp Asp Ile Val Gly Met Glu Ala Ser Ser Met Pro Ser Ala
465                 470                 475                 480

Asp Leu Tyr Gly Ile Ser Asp Pro Asn Met Leu Ser Asn Cys Ser Val
                485                 490                 495

Asn Met Met Thr Thr Ser Ser Asp Ser Met Gly Glu Thr Asp Asn Pro
            500                 505                 510

Arg Leu Leu Ser Met Asn Leu Glu Asn Pro Ser Cys Asn Ser Val Leu
        515                 520                 525

Asp Pro Arg Asp Leu Arg Gln Leu His Gln Met Ser Ser Ser Ser Met
    530                 535                 540

Ser Ala Gly Ala Asn Ser Asn Thr Thr Val Phe Val Ser Gln Ser Asp
545                 550                 555                 560

Ala Phe Glu Gly Ser Asp Phe Ser Cys Ala Asp Asn Ser Met Ile Asn
                565                 570                 575

Glu Ser Gly Pro Ser Asn Ser Thr Asn Pro Asn Ser His Gly Phe Val
            580                 585                 590

Gln Asp Ser Gln Tyr Ser Gly Ile Gly Ser Met Gln Asn Glu Gln Leu
        595                 600                 605

Ser Asp Ser Phe Pro Tyr Glu Phe Phe Gln Val
    610                 615
```

<210> SEQ ID NO 7
<211> LENGTH: 698
<212> TYPE: PRT
<213> ORGANISM: Homo sapiens

<400> SEQUENCE: 7

```
Met Gly Asp Pro Gly Leu Ala Lys Leu Gln Phe Ala Pro Phe Asn Ser
1               5                   10                  15

Ala Leu Asp Val Gly Phe Trp His Glu Leu Thr Gln Lys Lys Leu Asn
            20                  25                  30

Glu Tyr Arg Leu Asp Glu Ala Pro Lys Asp Ile Lys Gly Tyr Tyr Tyr
        35                  40                  45

Asn Gly Asp Ser Ala Gly Leu Pro Thr Arg Leu Thr Leu Glu Phe Ser
    50                  55                  60

Ala Phe Asp Met Ser Ala Ser Thr Pro Ala His Cys Cys Pro Ala Met
65                  70                  75                  80

Gly Thr Leu His Asn Thr Asn Thr Leu Glu Ala Phe Lys Thr Ala Asp
                85                  90                  95

Lys Lys Leu Leu Leu Glu Gln Ser Ala Asn Glu Ile Trp Glu Ala Ile
            100                 105                 110

Lys Ser Gly Ala Ala Leu Glu Asn Pro Met Leu Leu Asn Lys Phe Leu
        115                 120                 125

Leu Leu Thr Phe Ala Asp Leu Lys Lys Tyr His Phe Tyr Tyr Trp Phe
    130                 135                 140

Cys Cys Pro Ala Leu Cys Leu Pro Glu Ser Ile Pro Leu Ile Arg Gly
145                 150                 155                 160

Pro Val Ser Leu Asp Gln Arg Leu Ser Pro Lys Gln Ile Gln Ala Leu
                165                 170                 175

Glu His Ala Tyr Asp Asp Leu Cys Arg Ala Glu Gly Val Thr Ala Leu
            180                 185                 190

Pro Tyr Phe Leu Phe Lys Tyr Asp Asp Asp Thr Val Leu Val Ser Leu
        195                 200                 205
```

-continued

```
Leu Lys His Tyr Ser Asp Phe Phe Gln Gly Gln Arg Thr Lys Ile Thr
    210                 215                 220

Val Gly Val Tyr Asp Pro Cys Asn Leu Ala Gln Tyr Pro Gly Trp Pro
225                 230                 235                 240

Leu Arg Asn Phe Leu Val Leu Ala Ala His Arg Trp Ser Gly Ser Phe
                245                 250                 255

Gln Ser Val Glu Val Leu Cys Phe Arg Asp Arg Thr Met Gln Gly Ala
            260                 265                 270

Arg Asp Val Thr His Ser Ile Ile Phe Glu Val Lys Leu Pro Glu Met
        275                 280                 285

Ala Phe Ser Pro Asp Cys Pro Lys Ala Val Gly Trp Glu Lys Asn Gln
    290                 295                 300

Lys Gly Gly Met Gly Pro Arg Met Val Asn Leu Ser Gly Cys Met Asp
305                 310                 315                 320

Pro Lys Arg Leu Ala Glu Ser Ser Val Asp Leu Asn Leu Lys Leu Met
                325                 330                 335

Cys Trp Arg Leu Val Pro Thr Leu Asp Leu Asp Lys Val Val Ser Val
            340                 345                 350

Lys Cys Leu Leu Leu Gly Ala Gly Thr Leu Gly Cys Asn Val Ala Arg
        355                 360                 365

Thr Leu Met Gly Trp Gly Val Arg His Val Thr Phe Val Asp Asn Ala
    370                 375                 380

Lys Ile Ser Tyr Ser Asn Pro Val Arg Gln Pro Leu Tyr Glu Phe Glu
385                 390                 395                 400

Asp Cys Leu Gly Gly Gly Lys Pro Lys Ala Leu Ala Ala Ala Glu Arg
                405                 410                 415

Leu Gln Lys Ile Phe Pro Gly Val Asn Ala Arg Gly Phe Asn Met Ser
            420                 425                 430

Ile Pro Met Pro Gly His Pro Val Asn Phe Ser Asp Val Thr Met Glu
        435                 440                 445

Gln Ala Arg Arg Asp Val Glu Gln Leu Glu Gln Leu Ile Asp Asn His
    450                 455                 460

Asp Val Ile Phe Leu Leu Met Asp Thr Arg Glu Ser Arg Trp Leu Pro
465                 470                 475                 480

Thr Val Ile Ala Ala Ser Lys Arg Lys Leu Val Ile Asn Ala Ala Leu
                485                 490                 495

Gly Phe Asp Thr Phe Val Val Met Arg His Gly Leu Lys Lys Pro Lys
            500                 505                 510

Gln Gln Gly Ala Gly Asp Leu Cys Pro Ser His Leu Val Ala Pro Ala
        515                 520                 525

Asp Leu Gly Ser Ser Leu Phe Ala Asn Ile Pro Gly Tyr Lys Leu Gly
    530                 535                 540

Cys Tyr Phe Cys Asn Asp Val Val Ala Pro Gly Asp Ser Thr Arg Asp
545                 550                 555                 560

Arg Thr Leu Asp Gln Gln Cys Thr Val Ser Arg Pro Gly Leu Ala Val
                565                 570                 575

Ile Ala Gly Ala Leu Ala Val Glu Leu Met Val Ser Val Leu Gln His
            580                 585                 590

Pro Glu Gly Gly Tyr Ala Ile Ala Ser Ser Ser Asp Asp Arg Met Asn
        595                 600                 605

Glu Pro Pro Thr Ser Leu Gly Leu Val Pro His Gln Ile Arg Gly Phe
    610                 615                 620

Leu Ser Arg Phe Asp Asn Val Leu Pro Val Ser Leu Ala Phe Asp Lys
```

```
625                 630                 635                 640

Cys Thr Ala Cys Ser Pro Lys Val Leu Asp Gln Tyr Glu Arg Glu Gly
                645                 650                 655

Phe Thr Phe Leu Ala Lys Val Phe Asn Ser Ser His Ser Phe Leu Glu
            660                 665                 670

Asp Leu Thr Gly Leu Thr Leu Leu His Gln Glu Thr Gln Ala Ala Glu
        675                 680                 685

Ile Trp Asp Met Ser Asp Glu Glu Thr Val
    690                 695


<210> SEQ ID NO 8
<211> LENGTH: 514
<212> TYPE: PRT
<213> ORGANISM: Homo sapiens

<400> SEQUENCE: 8

Met Ala Leu Ser Glu Leu Ala Leu Val Arg Trp Leu Gln Glu Ser Arg
1               5                   10                  15

Arg Ser Arg Lys Leu Ile Leu Phe Ile Val Phe Leu Ala Leu Leu Leu
            20                  25                  30

Asp Asn Met Leu Leu Thr Val Val Val Pro Ile Ile Pro Ser Tyr Leu
        35                  40                  45

Tyr Ser Ile Lys His Glu Lys Asn Ala Thr Glu Ile Gln Thr Ala Arg
    50                  55                  60

Pro Val His Thr Ala Ser Ile Ser Asp Ser Phe Gln Ser Ile Phe Ser
65                  70                  75                  80

Tyr Tyr Asp Asn Ser Thr Met Val Thr Gly Asn Ala Thr Arg Asp Leu
                85                  90                  95

Thr Leu His Gln Thr Ala Thr Gln His Met Val Thr Asn Ala Ser Ala
            100                 105                 110

Val Pro Ser Asp Cys Pro Ser Glu Asp Lys Asp Leu Leu Asn Glu Asn
        115                 120                 125

Val Gln Val Gly Leu Leu Phe Ala Ser Lys Ala Thr Val Gln Leu Ile
    130                 135                 140

Thr Asn Pro Phe Ile Gly Leu Leu Thr Asn Arg Ile Gly Tyr Pro Ile
145                 150                 155                 160

Pro Ile Phe Ala Gly Phe Cys Ile Met Phe Val Ser Thr Ile Met Phe
                165                 170                 175

Ala Phe Ser Ser Ser Tyr Ala Phe Leu Leu Ile Ala Arg Ser Leu Gln
            180                 185                 190

Gly Ile Gly Ser Ser Cys Ser Ser Val Ala Gly Met Gly Met Leu Ala
        195                 200                 205

Ser Val Tyr Thr Asp Asp Glu Glu Arg Gly Asn Val Met Gly Ile Ala
    210                 215                 220

Leu Gly Gly Leu Ala Met Gly Val Leu Val Gly Pro Pro Phe Gly Ser
225                 230                 235                 240

Val Leu Tyr Glu Phe Val Gly Lys Thr Ala Pro Phe Leu Val Leu Ala
                245                 250                 255

Ala Leu Val Leu Leu Asp Gly Ala Ile Gln Leu Phe Val Leu Gln Pro
            260                 265                 270

Ser Arg Val Gln Pro Glu Ser Gln Lys Gly Thr Pro Leu Thr Thr Leu
        275                 280                 285

Leu Lys Asp Pro Tyr Ile Leu Ile Ala Ala Gly Ser Ile Cys Phe Ala
    290                 295                 300
```

```
Asn Met Gly Ile Ala Met Leu Glu Pro Ala Leu Pro Ile Trp Met Met
305                 310                 315                 320

Glu Thr Met Cys Ser Arg Lys Trp Gln Leu Gly Val Ala Phe Leu Pro
                325                 330                 335

Ala Ser Ile Ser Tyr Leu Ile Gly Thr Asn Ile Phe Gly Ile Leu Ala
            340                 345                 350

His Lys Met Gly Arg Trp Leu Cys Ala Leu Leu Gly Met Ile Ile Val
        355                 360                 365

Gly Val Ser Ile Leu Cys Ile Pro Phe Ala Lys Asn Ile Tyr Gly Leu
    370                 375                 380

Ile Ala Pro Asn Phe Gly Val Gly Phe Ala Ile Gly Met Val Asp Ser
385                 390                 395                 400

Ser Met Met Pro Ile Met Gly Tyr Leu Val Asp Leu Arg His Val Ser
                405                 410                 415

Val Tyr Gly Ser Val Tyr Ala Ile Ala Asp Val Ala Phe Cys Met Gly
            420                 425                 430

Tyr Ala Ile Gly Pro Ser Ala Gly Gly Ala Ile Ala Lys Ala Ile Gly
        435                 440                 445

Phe Pro Trp Leu Met Thr Ile Ile Gly Ile Ile Asp Ile Leu Phe Ala
    450                 455                 460

Pro Leu Cys Phe Phe Leu Arg Ser Pro Pro Ala Lys Glu Glu Lys Met
465                 470                 475                 480

Ala Ile Leu Met Asp His Asn Cys Pro Ile Lys Thr Lys Met Tyr Thr
                485                 490                 495

Gln Asn Asn Ile Gln Ser Tyr Pro Ile Gly Glu Asp Glu Glu Ser Glu
            500                 505                 510

Ser Asp
```

<210> SEQ ID NO 9
<211> LENGTH: 536
<212> TYPE: PRT
<213> ORGANISM: Homo sapiens

<400> SEQUENCE: 9

```
Met Glu Phe Ser Ser Pro Ser Arg Glu Glu Cys Pro Lys Pro Leu Ser
1               5                   10                  15

Arg Val Ser Ile Met Ala Gly Ser Leu Thr Gly Leu Leu Leu Leu Gln
            20                  25                  30

Ala Val Ser Trp Ala Ser Gly Ala Arg Pro Cys Ile Pro Lys Ser Phe
        35                  40                  45

Gly Tyr Ser Ser Val Val Cys Val Cys Asn Ala Thr Tyr Cys Asp Ser
    50                  55                  60

Phe Asp Pro Pro Thr Phe Pro Ala Leu Gly Thr Phe Ser Arg Tyr Glu
65                  70                  75                  80

Ser Thr Arg Ser Gly Arg Arg Met Glu Leu Ser Met Gly Pro Ile Gln
                85                  90                  95

Ala Asn His Thr Gly Thr Gly Leu Leu Leu Thr Leu Gln Pro Glu Gln
            100                 105                 110

Lys Phe Gln Lys Val Lys Gly Phe Gly Gly Ala Met Thr Asp Ala Ala
        115                 120                 125

Ala Leu Asn Ile Leu Ala Leu Ser Pro Pro Ala Gln Asn Leu Leu Leu
    130                 135                 140

Lys Ser Tyr Phe Ser Glu Glu Gly Ile Gly Tyr Asn Ile Ile Arg Val
145                 150                 155                 160
```

```
Pro Met Ala Ser Cys Asp Phe Ser Ile Arg Thr Tyr Thr Tyr Ala Asp
                165                 170                 175

Thr Pro Asp Asp Phe Gln Leu His Asn Phe Ser Leu Pro Glu Glu Asp
            180                 185                 190

Thr Lys Leu Lys Ile Pro Leu Ile His Arg Ala Leu Gln Leu Ala Gln
        195                 200                 205

Arg Pro Val Ser Leu Leu Ala Ser Pro Trp Thr Ser Pro Thr Trp Leu
    210                 215                 220

Lys Thr Asn Gly Ala Val Asn Gly Lys Gly Ser Leu Lys Gly Gln Pro
225                 230                 235                 240

Gly Asp Ile Tyr His Gln Thr Trp Ala Arg Tyr Phe Val Lys Phe Leu
                245                 250                 255

Asp Ala Tyr Ala Glu His Lys Leu Gln Phe Trp Ala Val Thr Ala Glu
            260                 265                 270

Asn Glu Pro Ser Ala Gly Leu Leu Ser Gly Tyr Pro Phe Gln Cys Leu
        275                 280                 285

Gly Phe Thr Pro Glu His Gln Arg Asp Phe Ile Ala Arg Asp Leu Gly
    290                 295                 300

Pro Thr Leu Ala Asn Ser Thr His His Asn Val Arg Leu Leu Met Leu
305                 310                 315                 320

Asp Asp Gln Arg Leu Leu Leu Pro His Trp Ala Lys Val Val Leu Thr
                325                 330                 335

Asp Pro Glu Ala Ala Lys Tyr Val His Gly Ile Ala Val His Trp Tyr
            340                 345                 350

Leu Asp Phe Leu Ala Pro Ala Lys Ala Thr Leu Gly Glu Thr His Arg
        355                 360                 365

Leu Phe Pro Asn Thr Met Leu Phe Ala Ser Glu Ala Cys Val Gly Ser
    370                 375                 380

Lys Phe Trp Glu Gln Ser Val Arg Leu Gly Ser Trp Asp Arg Gly Met
385                 390                 395                 400

Gln Tyr Ser His Ser Ile Ile Thr Asn Leu Leu Tyr His Val Val Gly
                405                 410                 415

Trp Thr Asp Trp Asn Leu Ala Leu Asn Pro Glu Gly Gly Pro Asn Trp
            420                 425                 430

Val Arg Asn Phe Val Asp Ser Pro Ile Ile Val Asp Ile Thr Lys Asp
        435                 440                 445

Thr Phe Tyr Lys Gln Pro Met Phe Tyr His Leu Gly His Phe Ser Lys
    450                 455                 460

Phe Ile Pro Glu Gly Ser Gln Arg Val Gly Leu Val Ala Ser Gln Lys
465                 470                 475                 480

Asn Asp Leu Asp Ala Val Ala Leu Met His Pro Asp Gly Ser Ala Val
                485                 490                 495

Val Val Val Leu Asn Arg Ser Ser Lys Asp Val Pro Leu Thr Ile Lys
            500                 505                 510

Asp Pro Ala Val Gly Phe Leu Glu Thr Ile Ser Pro Gly Tyr Ser Ile
        515                 520                 525

His Thr Tyr Leu Trp Arg Arg Gln
    530                 535
```

<210> SEQ ID NO 10
<211> LENGTH: 464
<212> TYPE: PRT
<213> ORGANISM: Homo sapiens

<400> SEQUENCE: 10

-continued

```
Ile Val Phe Val Arg Phe Asn Ser Ser His Gly Phe Pro Val Glu Val
1               5                   10                  15

Asp Ser Asp Thr Ser Ile Phe Gln Leu Lys Glu Val Val Ala Lys Arg
            20                  25                  30

Gln Gly Val Pro Ala Asp Gln Leu Arg Val Ile Phe Ala Gly Lys Glu
        35                  40                  45

Leu Arg Asn Asp Trp Thr Val Gln Asn Cys Asp Leu Asp Gln Gln Ser
    50                  55                  60

Ile Val His Ile Val Gln Arg Pro Trp Arg Lys Gly Gln Glu Met Asn
65                  70                  75                  80

Ala Thr Gly Gly Asp Asp Pro Arg Asn Ala Ala Gly Gly Cys Glu Arg
                85                  90                  95

Glu Pro Gln Ser Leu Thr Arg Val Asp Leu Ser Ser Ser Val Leu Pro
            100                 105                 110

Gly Asp Ser Val Gly Leu Ala Val Ile Leu His Thr Asp Ser Arg Lys
        115                 120                 125

Asp Ser Pro Pro Ala Gly Ser Pro Ala Gly Arg Ser Ile Tyr Asn Ser
    130                 135                 140

Phe Tyr Val Tyr Cys Lys Gly Pro Cys Gln Arg Val Gln Pro Gly Lys
145                 150                 155                 160

Leu Arg Val Gln Cys Ser Thr Cys Arg Gln Ala Thr Leu Thr Leu Thr
                165                 170                 175

Gln Gly Pro Ser Cys Trp Asp Asp Val Leu Ile Pro Asn Arg Met Ser
            180                 185                 190

Gly Glu Cys Gln Ser Pro His Cys Pro Gly Thr Ser Ala Glu Phe Phe
        195                 200                 205

Phe Lys Cys Gly Ala His Pro Thr Ser Asp Lys Glu Thr Ser Val Ala
    210                 215                 220

Leu His Leu Ile Ala Thr Asn Ser Arg Asn Ile Thr Cys Ile Thr Cys
225                 230                 235                 240

Thr Asp Val Arg Ser Pro Val Leu Val Phe Gln Cys Asn Ser Arg His
                245                 250                 255

Val Ile Cys Leu Asp Cys Phe His Leu Tyr Cys Val Thr Arg Leu Asn
            260                 265                 270

Asp Arg Gln Phe Val His Asp Pro Gln Leu Gly Tyr Ser Leu Pro Cys
        275                 280                 285

Val Ala Gly Cys Pro Asn Ser Leu Ile Lys Glu Leu His His Phe Arg
    290                 295                 300

Ile Leu Gly Glu Glu Gln Tyr Asn Arg Tyr Gln Gln Tyr Gly Ala Glu
305                 310                 315                 320

Glu Cys Val Leu Gln Met Gly Gly Val Leu Cys Pro Arg Pro Gly Cys
                325                 330                 335

Gly Ala Gly Leu Leu Pro Glu Pro Asp Gln Arg Lys Val Thr Cys Glu
            340                 345                 350

Gly Gly Asn Gly Leu Gly Cys Gly Phe Ala Phe Cys Arg Glu Cys Lys
        355                 360                 365

Glu Ala Tyr His Glu Gly Glu Cys Ser Ala Val Phe Glu Ala Ser Gly
    370                 375                 380

Thr Thr Thr Gln Ala Tyr Arg Val Asp Glu Arg Ala Ala Glu Gln Ala
385                 390                 395                 400

Arg Trp Glu Ala Ala Ser Lys Glu Thr Ile Lys Lys Thr Thr Lys Pro
                405                 410                 415
```

```
Cys Pro Arg Cys His Val Pro Val Glu Lys Asn Gly Gly Cys Met His
            420                 425                 430

Met Lys Cys Pro Gln Pro Gln Cys Arg Leu Glu Trp Cys Trp Asn Cys
        435                 440                 445

Gly Cys Glu Trp Asn Arg Val Cys Met Gly Asp His Trp Phe Asp Val
    450                 455                 460


<210> SEQ ID NO 11
<211> LENGTH: 437
<212> TYPE: PRT
<213> ORGANISM: Homo sapiens

<400> SEQUENCE: 11

Met Ile Val Phe Val Arg Phe Asn Ser Ser His Gly Phe Pro Val Glu
1               5                   10                  15

Val Asp Ser Asp Thr Ser Ile Phe Gln Leu Lys Glu Val Val Ala Lys
            20                  25                  30

Arg Gln Gly Val Pro Ala Asp Gln Leu Arg Val Ile Phe Ala Gly Lys
        35                  40                  45

Glu Leu Arg Asn Asp Trp Thr Val Gln Asn Cys Asp Leu Asp Gln Gln
    50                  55                  60

Ser Ile Val His Ile Val Gln Arg Pro Trp Arg Lys Gly Gln Glu Met
65                  70                  75                  80

Asn Ala Thr Gly Gly Asp Asp Pro Arg Asn Ala Ala Gly Gly Cys Glu
                85                  90                  95

Arg Glu Pro Gln Ser Leu Thr Arg Val Asp Leu Ser Ser Ser Val Leu
            100                 105                 110

Pro Gly Asp Ser Val Gly Leu Ala Val Ile Leu His Thr Asp Ser Arg
        115                 120                 125

Lys Asp Ser Pro Pro Ala Gly Ser Pro Ala Gly Arg Ser Ile Tyr Asn
    130                 135                 140

Ser Phe Tyr Val Tyr Cys Lys Gly Pro Cys Gln Arg Val Gln Pro Gly
145                 150                 155                 160

Lys Leu Arg Val Gln Cys Ser Thr Cys Arg Gln Ala Thr Leu Thr Leu
                165                 170                 175

Thr Gln Glu Phe Phe Phe Lys Cys Gly Ala His Pro Thr Ser Asp Lys
            180                 185                 190

Glu Thr Ser Val Ala Leu His Leu Ile Ala Thr Asn Ser Arg Asn Ile
        195                 200                 205

Thr Cys Ile Thr Cys Thr Asp Val Arg Ser Pro Val Leu Val Phe Gln
    210                 215                 220

Cys Asn Ser Arg His Val Ile Cys Leu Asp Cys Phe His Leu Tyr Cys
225                 230                 235                 240

Val Thr Arg Leu Asn Asp Arg Gln Phe Val His Asp Pro Gln Leu Gly
                245                 250                 255

Tyr Ser Leu Pro Cys Val Ala Gly Cys Pro Asn Ser Leu Ile Lys Glu
            260                 265                 270

Leu His His Phe Arg Ile Leu Gly Glu Glu Gln Tyr Asn Arg Tyr Gln
        275                 280                 285

Gln Tyr Gly Ala Glu Glu Cys Val Leu Gln Met Gly Gly Val Leu Cys
    290                 295                 300

Pro Arg Pro Gly Cys Gly Ala Gly Leu Leu Pro Glu Pro Asp Gln Arg
305                 310                 315                 320

Lys Val Thr Cys Glu Gly Gly Asn Gly Leu Gly Cys Gly Phe Ala Phe
                325                 330                 335
```

Cys Arg Glu Cys Lys Glu Ala Tyr His Glu Gly Glu Cys Ser Ala Val
340 345 350

Phe Glu Ala Ser Gly Thr Thr Thr Gln Ala Tyr Arg Val Asp Glu Arg
355 360 365

Ala Ala Glu Gln Ala Arg Trp Glu Ala Ala Ser Lys Glu Thr Ile Lys
370 375 380

Lys Thr Thr Lys Pro Cys Pro Arg Cys His Val Pro Val Glu Lys Asn
385 390 395 400

Gly Gly Cys Met His Met Lys Cys Pro Gln Pro Gln Cys Arg Leu Glu
405 410 415

Trp Cys Trp Asn Cys Gly Cys Glu Trp Asn Arg Val Cys Met Gly Asp
420 425 430

His Trp Phe Asp Val
435

<210> SEQ ID NO 12
<211> LENGTH: 218
<212> TYPE: PRT
<213> ORGANISM: Homo sapiens

<400> SEQUENCE: 12

Met Asn Ala Thr Gly Gly Asp Asp Pro Arg Asn Ala Ala Gly Gly Cys
1 5 10 15

Glu Arg Glu Pro Gln Ser Leu Thr Arg Val Asp Leu Ser Ser Ser Val
20 25 30

Leu Pro Gly Asp Ser Val Gly Leu Ala Val Ile Leu His Thr Asp Ser
35 40 45

Arg Lys Asp Ser Pro Pro Ala Gly Ser Pro Ala Gly Arg Ser Ile Tyr
50 55 60

Asn Ser Phe Tyr Val Tyr Cys Lys Gly Pro Cys Gln Arg Val Gln Pro
65 70 75 80

Gly Lys Leu Arg Val Gln Cys Ser Thr Cys Arg Gln Ala Thr Leu Thr
85 90 95

Leu Thr Gln Gly Pro Ser Cys Trp Asp Asp Val Leu Ile Pro Asn Arg
100 105 110

Met Ser Gly Glu Cys Gln Ser Pro His Cys Pro Gly Thr Ser Ala Glu
115 120 125

Phe Phe Phe Lys Cys Gly Ala His Pro Thr Ser Asp Lys Glu Thr Ser
130 135 140

Val Ala Leu His Leu Ile Ala Thr Asn Ser Arg Asn Ile Thr Cys Ile
145 150 155 160

Thr Cys Thr Asp Val Arg Ser Pro Val Leu Val Phe Gln Cys Asn Ser
165 170 175

Arg His Val Ile Cys Leu Asp Cys Phe His Leu Tyr Cys Val Thr Arg
180 185 190

Leu Asn Asp Arg Gln Phe Val His Asp Pro Gln Leu Gly Tyr Ser Leu
195 200 205

Pro Cys Val Val Cys Leu Leu Pro Gly Met
210 215

<210> SEQ ID NO 13
<211> LENGTH: 274
<212> TYPE: PRT
<213> ORGANISM: Homo sapiens

<400> SEQUENCE: 13

-continued

Met Ser Gly Glu Cys Gln Ser Pro His Cys Pro Gly Thr Ser Ala Glu
1               5                   10                  15

Phe Phe Phe Lys Cys Gly Ala His Pro Thr Ser Asp Lys Glu Thr Ser
            20                  25                  30

Val Ala Leu His Leu Ile Ala Thr Asn Ser Arg Asn Ile Thr Cys Ile
        35                  40                  45

Thr Cys Thr Asp Val Arg Ser Pro Val Leu Val Phe Gln Cys Asn Ser
    50                  55                  60

Arg His Val Ile Cys Leu Asp Cys Phe His Leu Tyr Cys Val Thr Arg
65                  70                  75                  80

Leu Asn Asp Arg Gln Phe Val His Asp Pro Gln Leu Gly Tyr Ser Leu
                85                  90                  95

Pro Cys Val Ala Gly Cys Pro Asn Ser Leu Ile Lys Glu Leu His His
            100                 105                 110

Phe Arg Ile Leu Gly Glu Glu Gln Tyr Asn Arg Tyr Gln Gln Tyr Gly
        115                 120                 125

Ala Glu Glu Cys Val Leu Gln Met Gly Gly Val Leu Cys Pro Arg Pro
    130                 135                 140

Gly Cys Gly Ala Gly Leu Leu Pro Glu Pro Asp Gln Arg Lys Val Thr
145                 150                 155                 160

Cys Glu Gly Gly Asn Gly Leu Gly Cys Gly Phe Ala Phe Cys Arg Glu
                165                 170                 175

Cys Lys Glu Ala Tyr His Glu Gly Glu Cys Ser Ala Val Phe Glu Ala
            180                 185                 190

Ser Gly Thr Thr Thr Gln Ala Tyr Arg Val Asp Glu Arg Ala Ala Glu
        195                 200                 205

Gln Ala Arg Trp Glu Ala Ala Ser Lys Glu Thr Ile Lys Lys Thr Thr
    210                 215                 220

Lys Pro Cys Pro Arg Cys His Val Pro Val Glu Lys Asn Gly Gly Cys
225                 230                 235                 240

Met His Met Lys Cys Pro Gln Pro Gln Cys Arg Leu Glu Trp Cys Trp
                245                 250                 255

Asn Cys Gly Cys Glu Trp Asn Arg Val Cys Met Gly Asp His Trp Phe
            260                 265                 270

Asp Val

<210> SEQ ID NO 14
<211> LENGTH: 387
<212> TYPE: PRT
<213> ORGANISM: Homo sapiens

<400> SEQUENCE: 14

Met Ile Val Phe Val Arg Phe Asn Ser Ser His Gly Phe Pro Val Glu
1               5                   10                  15

Val Asp Ser Asp Thr Ser Ile Phe Gln Leu Lys Glu Val Val Ala Lys
            20                  25                  30

Arg Gln Gly Val Pro Ala Asp Gln Leu Arg Val Ile Phe Ala Gly Lys
        35                  40                  45

Glu Leu Arg Asn Asp Trp Thr Val Gln Asn Cys Asp Leu Asp Gln Gln
    50                  55                  60

Ser Ile Val His Ile Val Gln Arg Pro Trp Arg Lys Gly Gln Glu Met
65                  70                  75                  80

Asn Ala Thr Gly Gly Asp Asp Pro Arg Asn Ala Ala Gly Gly Cys Glu
                85                  90                  95

Arg Glu Pro Gln Ser Leu Thr Arg Val Asp Leu Ser Ser Ser Val Leu
100 105 110

Pro Gly Asp Ser Val Gly Leu Ala Val Ile Leu His Thr Asp Ser Arg
115 120 125

Lys Asp Ser Pro Pro Ala Gly Ser Pro Ala Gly Arg Ser Ile Tyr Asn
130 135 140

Ser Phe Tyr Val Tyr Cys Lys Gly Pro Cys Gln Arg Val Gln Pro Gly
145 150 155 160

Lys Leu Arg Val Gln Cys Ser Thr Cys Arg Gln Ala Thr Leu Thr Leu
165 170 175

Thr Gln Gly Pro Ser Cys Trp Asp Asp Val Leu Ile Pro Asn Arg Met
180 185 190

Ser Gly Glu Cys Gln Ser Pro His Cys Pro Gly Thr Ser Ala Glu Phe
195 200 205

Phe Phe Lys Cys Gly Ala His Pro Thr Ser Asp Lys Glu Thr Ser Val
210 215 220

Ala Leu His Leu Ile Ala Thr Asn Ser Arg Asn Ile Thr Cys Ile Thr
225 230 235 240

Cys Thr Asp Val Arg Ser Pro Val Leu Val Phe Gln Cys Asn Ser Arg
245 250 255

His Val Ile Cys Leu Asp Cys Phe His Leu Tyr Cys Val Thr Arg Leu
260 265 270

Asn Asp Arg Gln Phe Val His Asp Pro Gln Leu Gly Tyr Ser Leu Pro
275 280 285

Cys Val Gly Thr Gly Asp Thr Val Val Leu Arg Gly Ala Leu Gly Gly
290 295 300

Phe Arg Arg Gly Val Ala Gly Cys Pro Asn Ser Leu Ile Lys Glu Leu
305 310 315 320

His His Phe Arg Ile Leu Gly Glu Glu Gln Tyr Asn Arg Tyr Gln Gln
325 330 335

Tyr Gly Ala Glu Glu Cys Val Leu Gln Met Gly Gly Val Leu Cys Pro
340 345 350

Arg Pro Gly Cys Gly Ala Gly Leu Leu Pro Glu Pro Asp Gln Arg Lys
355 360 365

Val Thr Cys Glu Gly Gly Asn Gly Leu Gly Cys Gly Tyr Gly Gln Arg
370 375 380

Arg Thr Lys
385

<210> SEQ ID NO 15
<211> LENGTH: 316
<212> TYPE: PRT
<213> ORGANISM: Homo sapiens

<400> SEQUENCE: 15

Met Ile Val Phe Val Arg Phe Asn Ser Ser His Gly Phe Pro Val Glu
1 5 10 15

Val Asp Ser Asp Thr Ser Ile Phe Gln Leu Lys Glu Val Val Ala Lys
20 25 30

Arg Gln Gly Val Pro Ala Asp Gln Leu Arg Val Ile Phe Ala Gly Lys
35 40 45

Glu Leu Arg Asn Asp Trp Thr Val Gln Glu Phe Phe Phe Lys Cys Gly
50 55 60

Ala His Pro Thr Ser Asp Lys Glu Thr Ser Val Ala Leu His Leu Ile

```
65                  70                  75                  80

Ala Thr Asn Ser Arg Asn Ile Thr Cys Ile Thr Cys Thr Asp Val Arg
                85                  90                  95

Ser Pro Val Leu Val Phe Gln Cys Asn Ser Arg His Val Ile Cys Leu
            100                 105                 110

Asp Cys Phe His Leu Tyr Cys Val Thr Arg Leu Asn Asp Arg Gln Phe
        115                 120                 125

Val His Asp Pro Gln Leu Gly Tyr Ser Leu Pro Cys Val Ala Gly Cys
    130                 135                 140

Pro Asn Ser Leu Ile Lys Glu Leu His His Phe Arg Ile Leu Gly Glu
145                 150                 155                 160

Glu Gln Tyr Asn Arg Tyr Gln Gln Tyr Gly Ala Glu Glu Cys Val Leu
                165                 170                 175

Gln Met Gly Gly Val Leu Cys Pro Arg Pro Gly Cys Gly Ala Gly Leu
            180                 185                 190

Leu Pro Glu Pro Asp Gln Arg Lys Val Thr Cys Glu Gly Gly Asn Gly
        195                 200                 205

Leu Gly Cys Gly Phe Ala Phe Cys Arg Glu Cys Lys Glu Ala Tyr His
    210                 215                 220

Glu Gly Glu Cys Ser Ala Val Phe Glu Ala Ser Gly Thr Thr Thr Gln
225                 230                 235                 240

Ala Tyr Arg Val Asp Glu Arg Ala Ala Glu Gln Ala Arg Trp Glu Ala
                245                 250                 255

Ala Ser Lys Glu Thr Ile Lys Lys Thr Thr Lys Pro Cys Pro Arg Cys
            260                 265                 270

His Val Pro Val Glu Lys Asn Gly Gly Cys Met His Met Lys Cys Pro
        275                 280                 285

Gln Pro Gln Cys Arg Leu Glu Trp Cys Trp Asn Cys Gly Cys Glu Trp
    290                 295                 300

Asn Arg Val Cys Met Gly Asp His Trp Phe Asp Val
305                 310                 315


<210> SEQ ID NO 16
<211> LENGTH: 387
<212> TYPE: PRT
<213> ORGANISM: Homo sapiens

<400> SEQUENCE: 16

Met Ile Val Phe Val Arg Phe Asn Ser Ser His Gly Phe Pro Val Glu
1               5                   10                  15

Val Asp Ser Asp Thr Ser Ile Phe Gln Leu Lys Glu Val Val Ala Lys
            20                  25                  30

Arg Gln Gly Val Pro Ala Asp Gln Leu Arg Val Ile Phe Ala Gly Lys
        35                  40                  45

Glu Leu Arg Asn Asp Trp Thr Val Gln Asn Cys Asp Leu Asp Gln Gln
    50                  55                  60

Ser Ile Val His Ile Val Gln Arg Pro Trp Arg Lys Gly Gln Glu Met
65                  70                  75                  80

Asn Ala Thr Gly Gly Asp Asp Pro Arg Asn Ala Ala Gly Gly Cys Glu
                85                  90                  95

Arg Glu Pro Gln Ser Leu Thr Arg Val Asp Leu Ser Ser Ser Val Leu
            100                 105                 110

Pro Gly Asp Ser Val Gly Leu Ala Val Ile Leu His Thr Asp Ser Arg
        115                 120                 125
```

Lys Asp Ser Pro Pro Ala Gly Ser Pro Ala Gly Arg Ser Ile Tyr Asn
130 135 140

Ser Phe Tyr Val Tyr Cys Lys Gly Pro Cys Gln Arg Val Gln Pro Gly
145 150 155 160

Lys Leu Arg Val Gln Cys Ser Thr Cys Arg Gln Ala Thr Leu Thr Leu
165 170 175

Thr Gln Glu Phe Phe Phe Lys Cys Gly Ala His Pro Thr Ser Asp Lys
180 185 190

Glu Thr Ser Val Ala Leu His Leu Ile Ala Thr Asn Ser Arg Asn Ile
195 200 205

Thr Cys Ile Thr Cys Thr Asp Val Arg Ser Pro Val Leu Val Phe Gln
210 215 220

Cys Asn Ser Arg His Val Ile Cys Leu Asp Cys Phe His Leu Tyr Cys
225 230 235 240

Val Thr Arg Leu Asn Asp Arg Gln Phe Val His Asp Pro Gln Leu Gly
245 250 255

Tyr Ser Leu Pro Cys Val Ala Gly Cys Pro Asn Ser Leu Ile Lys Glu
260 265 270

Leu His His Phe Arg Ile Leu Gly Glu Glu Gln Phe Ala Phe Cys Arg
275 280 285

Glu Cys Lys Glu Ala Tyr His Glu Gly Glu Cys Ser Ala Val Phe Glu
290 295 300

Ala Ser Gly Thr Thr Thr Gln Ala Tyr Arg Val Asp Glu Arg Ala Ala
305 310 315 320

Glu Gln Ala Arg Trp Glu Ala Ala Ser Lys Glu Thr Ile Lys Lys Thr
325 330 335

Thr Lys Pro Cys Pro Arg Cys His Val Pro Val Glu Lys Asn Gly Gly
340 345 350

Cys Met His Met Lys Cys Pro Gln Pro Gln Cys Arg Leu Glu Trp Cys
355 360 365

Trp Asn Cys Gly Cys Glu Trp Asn Arg Val Cys Met Gly Asp His Trp
370 375 380

Phe Asp Val
385

<210> SEQ ID NO 17
<211> LENGTH: 415
<212> TYPE: PRT
<213> ORGANISM: Homo sapiens

<400> SEQUENCE: 17

Met Ile Val Phe Val Arg Phe Asn Ser Ser His Gly Phe Pro Val Glu
1 5 10 15

Val Asp Ser Asp Thr Ser Ile Phe Gln Leu Lys Glu Val Val Ala Lys
20 25 30

Arg Gln Gly Val Pro Ala Asp Gln Leu Arg Val Ile Phe Ala Gly Lys
35 40 45

Glu Leu Arg Asn Asp Trp Thr Val Gln Asn Cys Asp Leu Asp Gln Gln
50 55 60

Ser Ile Val His Ile Val Gln Arg Pro Trp Arg Lys Gly Gln Glu Met
65 70 75 80

Asn Ala Thr Gly Gly Asp Asp Pro Arg Asn Ala Ala Gly Gly Cys Glu
85 90 95

Arg Glu Pro Gln Ser Leu Thr Arg Val Asp Leu Ser Ser Ser Val Leu
100 105 110

-continued

Pro Gly Asp Ser Val Gly Leu Ala Val Ile Leu His Thr Asp Ser Arg
115 120 125

Lys Asp Ser Pro Pro Ala Gly Ser Pro Ala Gly Arg Ser Ile Tyr Asn
130 135 140

Ser Phe Tyr Val Tyr Cys Lys Gly Pro Cys Gln Arg Val Gln Pro Gly
145 150 155 160

Lys Leu Arg Val Gln Cys Ser Thr Cys Arg Gln Ala Thr Leu Thr Leu
165 170 175

Thr Gln Gly Pro Ser Cys Trp Asp Asp Val Leu Ile Pro Asn Arg Met
180 185 190

Ser Gly Glu Cys Gln Ser Pro His Cys Pro Gly Thr Ser Ala Glu Phe
195 200 205

Phe Phe Lys Cys Gly Ala His Pro Thr Ser Asp Lys Glu Thr Ser Val
210 215 220

Ala Leu His Leu Ile Ala Thr Asn Ser Arg Asn Ile Thr Cys Ile Thr
225 230 235 240

Cys Thr Asp Val Arg Ser Pro Val Leu Val Phe Gln Cys Asn Ser Arg
245 250 255

His Val Ile Cys Leu Asp Cys Phe His Leu Tyr Cys Val Thr Arg Leu
260 265 270

Asn Asp Arg Gln Phe Val His Asp Pro Gln Leu Gly Tyr Ser Leu Pro
275 280 285

Cys Val Ala Gly Cys Pro Asn Ser Leu Ile Lys Glu Leu His His Phe
290 295 300

Arg Ile Leu Gly Glu Glu Gln Phe Ala Phe Cys Arg Glu Cys Lys Glu
305 310 315 320

Ala Tyr His Glu Gly Glu Cys Ser Ala Val Phe Glu Ala Ser Gly Thr
325 330 335

Thr Thr Gln Ala Tyr Arg Val Asp Glu Arg Ala Ala Glu Gln Ala Arg
340 345 350

Trp Glu Ala Ala Ser Lys Glu Thr Ile Lys Lys Thr Thr Lys Pro Cys
355 360 365

Pro Arg Cys His Val Pro Val Glu Lys Asn Gly Gly Cys Met His Met
370 375 380

Lys Cys Pro Gln Pro Gln Cys Arg Leu Glu Trp Cys Trp Asn Cys Gly
385 390 395 400

Cys Glu Trp Asn Arg Val Cys Met Gly Asp His Trp Phe Asp Val
405 410 415

<210> SEQ ID NO 18
<211> LENGTH: 1398
<212> TYPE: DNA
<213> ORGANISM: Homo sapiens

<400> SEQUENCE: 18
atgatagtgt ttgtcaggtt caactccagc catggtttcc cagtggaggt cgattctgac 60
accagcatct tccagctcaa ggaggtggtt gctaagcgac agggggttcc ggctgaccag 120
ttgcgtgtga ttttcgcagg gaaggagctg aggaatgact ggactgtgca gaattgtgac 180
ctggatcagc agagcattgt tcacattgtg cagagaccgt ggagaaaagg tcaagaaatg 240
aatgcaactg gaggcgacga ccccagaaac gcggcgggag gctgtgagcg ggagccccag 300
agcttgactc gggtggacct cagcagctca gtcctcccag gagactctgt ggggctggct 360
gtcattctgc acactgacag caggaaggac tcaccaccag ctggaagtcc agcaggtaga 420

```
tcaatctaca acagctttta tgtgtattgc aaaggcccct gtcaaagagt gcagccggga    480
aaactcaggg tacagtgcag cacctgcagg caggcaacgc tcaccttgac ccagggtcca    540
tcttgctggg atgatgtttt aattccaaac cggatgagtg gtgaatgcca atccccacac    600
tgccctggga ctagtgcaga atttttcttt aaatgtggag cacaccccac ctctgacaag    660
gaaacatcag tagctttgca cctgatcgca acaaatagtc ggaacatcac ttgcattacg    720
tgcacagacg tcaggagccc cgtcctggtt ttccagtgca actcccgcca cgtgatttgc    780
ttagactgtt tccacttata ctgtgtgaca agactcaatg atcggcagtt tgttcacgac    840
cctcaacttg gctactccct gccttgtgtg gctggctgtc ccaactcctt gattaaagag    900
ctccatcact tcaggattct gggagaagag cagtacaacc ggtaccagca gtatggtgca    960
gaggagtgtg tcctgcagat ggggggcgtg ttatgccccc gccctggctg tggagcgggg   1020
ctgctgccgg agcctgacca gaggaaagtc acctgcgaag gggggcaatgg cctgggctgt   1080
gggtttgcct tctgccggga atgtaaagaa gcgtaccatg aaggggagtg cagtgccgta   1140
tttgaagcct caggaacaac tactcaggcc tacagagtcg atgaaagagc cgccgagcag   1200
gctcgttggg aagcagcctc caaagaaacc atcaagaaaa ccaccaagcc ctgtccccgc   1260
tgccatgtac cagtggaaaa aaatggaggc tgcatgcaca tgaagtgtcc gcagccccag   1320
tgcaggctcg agtggtgctg gaactgtggc tgcgagtgga accgcgtctg catgggggac   1380
cactggttcg acgtgtag                                                 1398
```

<210> SEQ ID NO 19
<211> LENGTH: 1746
<212> TYPE: DNA
<213> ORGANISM: Homo sapiens

<400> SEQUENCE: 19

```
atggcggtgc gacaggcgct gggccgcggc ctgcagctgg gtcgagcgct gctgctgcgc     60
ttcacgggca agcccggccg ggcctacggc ttggggcggc cgggcccggc ggcgggctgt    120
gtccgcgggg agcgtccagg ctgggccgca ggaccgggcg cggagcctcg cagggtcggg    180
ctcgggctcc ctaaccgtct ccgcttcttc cgccagtcgg tggccgggct ggcggcgcgg    240
ttgcagcggc agttcgtggt gcgggcctgg ggctgcgcgg gcccttgcgg ccgggcagtc    300
tttctggcct tcgggctagg gctgggcctc atcgaggaaa aacaggcgga gagccggcgg    360
gcggtctcgg cctgtcagga gatccaggca atttttaccc agaaaagcaa gccggggcct    420
gacccgttgg acacgagacg cttgcagggc tttcggctgg aggagtatct gatagggcag    480
tccattggta agggctgcag tgctgctgtg tatgaagcca ccatgcctac attgccccag    540
aacctggagg tgacaaagag caccgggttg cttccaggga gaggcccagg taccagtgca    600
ccaggagaag ggcaggagcg agctccgggg gcccctgcct tccccttggc catcaagatg    660
atgtggaaca tctcggcagg ttcctccagc gaagccatct tgaacacaat gagccaggag    720
ctggtcccag cgagccgagt ggccttggct ggggagtatg gagcagtcac ttacagaaaa    780
tccaagagag gtcccaagca actagcccct caccccaaca tcatccgggt tctccgcgcc    840
ttcacctctt ccgtgccgct gctgccaggg gccctggtcg actaccctga tgtgctgccc    900
tcacgcctcc accctgaagg cctgggccat ggccggacgc tgttcctcgt tatgaagaac    960
tatccctgta ccctgcgcca gtacctttgt gtgaacacac ccagcccccg cctcgccgcc   1020
atgatgctgc tgcagctgct ggaaggcgtg gaccatctgg ttcaacaggg catcgcgcac   1080
```

agagacctga aatccgacaa catccttgtg gagctggacc cagacggctg cccctggctg 1140
gtgatcgcag attttggctg ctgcctggct gatgagagca tcggcctgca gttgcccttc 1200
agcagctggt acgtggatcg ggcggaaac ggctgtctga tggccccaga ggtgtccacg 1260
gcccgtcctg gccccagggc agtgattgac tacagcaagg ctgatgcctg ggcagtggga 1320
gccatcgcct atgaaatctt cgggcttgtc aatcccttct acggccaggg caaggcccac 1380
cttgaaagcc gcagctacca agaggctcag ctacctgcac tgcccgagtc agtgcctcca 1440
gacgtgagac agttggtgag ggcactgctc cagcgagagg ccagcaagag accatctgcc 1500
cgagtagccg caaatgtgct tcatctaagc ctctggggtg aacatattct agccctgaag 1560
aatctgaagt tagacaagat ggttggctgg ctcctccaac aatcggccgc cactttgttg 1620
gccaacaggc tcacagagaa gtgttgtgtg gaaacaaaaa tgaagatgct ctttctggct 1680
aacctggagt gtgaaacgct ctgccaggca gccctcctcc tctgctcatg gagggcagcc 1740
ctgtga 1746

<210> SEQ ID NO 20
<211> LENGTH: 570
<212> TYPE: DNA
<213> ORGANISM: Homo sapiens

<400> SEQUENCE: 20
atggcttcca aaagagctct ggtcatcctg gctaaaggag cagaggaaat ggagacggtc 60
atccctgtag atgtcatgag gcgagctggg attaaggtca ccgttgcagg cctggctgga 120
aaagacccag tacagtgtag ccgtgatgtg gtcatttgtc ctgatgccag ccttgaagat 180
gcaaaaaaag agggaccata tgatgtggtg gttctaccag gaggtaatct gggcgcacag 240
aatttatctg agtctgctgc tgtgaaggag atactgaagg agcaggaaaa ccggaagggc 300
ctgatagccg ccatctgtgc aggtcctact gctctgttgg ctcatgaaat aggttttgga 360
agtaaagtta caacacaccc tcttgctaaa gacaaaatga tgaatggagg tcattacacc 420
tactctgaga atcgtgtgga aaaagacggc ctgattctta caagccgggg gcctgggacc 480
agcttcgagt ttgcgcttgc aattgttgaa gccctgaatg gcaaggaggt ggcggctcaa 540
gtgaaggctc cacttgttct taaagactag 570

<210> SEQ ID NO 21
<211> LENGTH: 7583
<212> TYPE: DNA
<213> ORGANISM: Homo sapiens

<400> SEQUENCE: 21
atggctagtg gcagctgtca ggggtgcgaa gaggacgagg aaactctgaa gaagttgata 60
gtcaggctga acaatgtcca ggaaggaaaa cagatagaaa cgctggtcca aatcctggag 120
gatctgctgg tgttcacgta ctccgagcac gcctccaagt tatttcaagg caaaaatatc 180
catgtgcctc tgttgatcgt cttggactcc tatatgagag tcgcgagtgt gcagcaggtg 240
ggttggtcac ttctgtgcaa attaatagaa gtctgtccag gtacaatgca aagcttaatg 300
ggaccccagg atgttggaaa tgattgggaa gtccttggtg ttcaccaatt gattcttaaa 360
atgctaacag ttcataatgc cagtgtaaac ttgtcagtga ttggactgaa gaccttagat 420
ctcctcctaa cttcaggtaa aatcaccttg ctgatattgg atgaagaaag tgatattttc 480
atgttaattt ttgatgccat gcactcattt ccagccaatg atgaagtcca gaaacttgga 540
tgcaaagctt tacatgtgct gtttgagaga gtctcagagg agcaactgac tgaatttgtt 600

-continued

```
gagaacaaag attatatgat attgttaagt gcgttaacaa attttaaaga tgaagaggaa    660
attgtgcttc atgtgctgca ttgtttacat tccctagcga ttccttgcaa taatgtggaa    720
gtcctcatga gtggcaatgt caggtgttat aatattgtgg tggaagctat gaaagcattc    780
cctatgagtg aaagaattca agaagtgagt tgctgtttgc tccataggct tacattaggt    840
aatttttttca atatcctggt attaaacgaa gtccatgagt ttgtggtgaa agctgtgcag    900
cagtacccag agaatgcagc attgcagatc tcagcgctca gctgtttggc cctcctcact    960
gagactattt tcttaaatca agatttagag gaaaagaatg agaatcaaga gaatgatgat   1020
gagggggaag aagataaatt gttttggctg gaagcctgtt acaaagcatt aacgtggcat   1080
agaaagaaca agcacgtgca ggaggccgca tgctgggcac taaataatct ccttatgtac   1140
caaaacagtt tacatgagaa gattggagat gaagatggcc atttcccagc tcatagggaa   1200
gtgatgctct ccatgctgat gcattcttca tcaaaggaag ttttccaggc atctgcgaat   1260
gcattgtcaa ctctcttaga acaaaatgtt aatttcagaa aaatactgtt atcaaaagga   1320
atacacctga atgttttgga gttaatgcag aagcatatac attctcctga agtggctgaa   1380
agtggctgta aaatgctaaa tcatcttttt gaaggaagca acacttccct ggatataatg   1440
gcagcagtgg tccccaaaat actaacagtt atgaaacgtc atgagacatc attaccagtg   1500
cagctggagg cgcttcgagc tattttacat tttatagtgc ctggcatgcc agaagaatcc   1560
agggaggata cagaatttca tcataagcta aatatggtta aaaaacagtg tttcaagaat   1620
gatattcaca aactggtcct agcagctttg aacaggttca ttggaaatcc tgggattcag   1680
aaatgtggat taaaagtaat ttcttctatt gtacattttc ctgatgcatt agagatgtta   1740
tccctggaag gtgctatgga ttcagtgctt cacacactgc agatgtatcc agatgaccaa   1800
gaaattcagt gtctgggttt aagtcttata ggatacttga ttacaaagaa gaatgtgttc   1860
ataggaactg gacatctgct ggcaaaaatt ctggtttcca gcttataccg atttaaggat   1920
gttgctgaaa tacagactaa aggatttcag acaatcttag caatcctcaa attgtcagca   1980
tctttttcta agctgctggt gcatcattca tttgacttag taatattcca tcaaatgtct   2040
tccaatatca tggaacaaaa ggatcaacag tttctaaacc tctgttgcaa gtgttttgca   2100
aaagtagcta tggatgattc ttaaaaaatg tgatgctaga gagagcgtgt gatcagaata   2160
acagcatcat ggttgaatgc ttgcttctat tgggagcaga tgccaatcaa gcaaaggagg   2220
gatcttcttt aatttgtcag gtatgtgaga aagagagcag tcccaaattg gtggaactct   2280
tactgaatag tggatctcgt gaacaagatg tacgaaaagc gttgacgata agcattggga   2340
aaggtgacag ccagatcatc agcttgctct taaggaggct ggccctggat gtggccaaca   2400
atagcatttg ccttggagga ttttgtatag gaaaagttga accttcttgg cttggtcctt   2460
tatttccaga taagacttct aatttaagga aacaaacaaa tatagcatct acactagcaa   2520
gaatggtgat cagatatcag atgaaaagtg ctgtggaaga aggaacagcc tcaggcagcg   2580
atggaaattt ttctgaagat gtgctgtcta aatttgatga atggaccttt attcctgact   2640
cttctatgga cagtgtgttt gctcaaagtg atgacctgga tagtgaagga agtgaaggct   2700
catttcttgt gaaaaagaaa tctaattcaa ttagtgtagg agaattttac cgagatgccg   2760
tattacagcg ttgctcacca aatttgcaaa gacattccaa ttccttgggg cccatttttg   2820
atcatgaaga tttactgaag cgaaaaagaa aaatattatc ttcagatgat tcactcaggt   2880
catcaaaact tcaatcccat atgaggcatt cagacagcat ttcttctctg gcttctgaga   2940
```

-continued

```
gagaatatat tacatcacta gacctttcag caaatgaact aagagatatt gatgccctaa   3000
gccagaaatg ctgtataagt gttcatttgg agcatcttga aaagctggag cttcaccaga   3060
atgcactcac gagctttcca caacagctat gtgaaactct gaagagtttg acacatttgg   3120
acttgcacag taataaattt acatcatttc cttcttattt gttgaaaatg agttgtattg   3180
ctaatcttga tgtctctcga aatgacattg gaccctcagt ggttttagat cctacagtga   3240
aatgtccaac tctgaaacag tttaacctgt catataacca gctgtctttt gtacctgaga   3300
acctcactga tgtggtagag aaactggagc agctcatttt agaaggaaat aaaatatcag   3360
ggatatgctc cccccttgaga ctgaaggaac tgaagatttt aaaccttagt aagaaccaca   3420
tttcatccct atcagagaac tttcttgagg cttgtcctaa agtggagagt ttcagtgcca   3480
gaatgaattt tcttgctgct atgcctttct tgcctccttc tatgacaatc ctaaaattat   3540
ctcagaacaa attttcctgt attccagaag caattttaaa tcttccacac ttgcggtctt   3600
tagatatgag cagcaatgat attcagtacc taccaggtcc cgcacactgg aaatctttga   3660
acttaaggga actcttattt agccataatc agatcagcat cttggacttg agtgaaaaag   3720
catatttatg gtctagagta gagaaactgc atctttctca caataaactg aaagagattc   3780
ctcctgagat tggctgtctt gaaaatctga catctctgga tgtcagttac aacttggaac   3840
taagatcctt tcccaatgaa atggggaaat taagcaaaat atgggatctt cctttggatg   3900
aactgcatct taactttgat tttaaacata taggatgtaa agccaaagac atcataaggt   3960
ttcttcaaca gcgattaaaa aaggctgtgc cttataaccg aatgaaactt atgattgtgg   4020
gaaatactgg gagtggtaaa accaccttat tgcagcaatt aatgaaaacc aagaaatcag   4080
atcttggaat gcaaagtgcc acagttggca tagatgtgaa agactggcct atccaaataa   4140
gagacaaaag aaagagagat ctcgtcctaa atgtgtggga ttttgcaggt cgtgaggaat   4200
tctatagtac tcatccccat tttatgacgc agcgagcatt gtaccttgct gtctatgacc   4260
tcagcaaggg acaggctgaa gttgatgcca tgaagccttg gctcttcaat ataaaggctc   4320
gcgcttcttc ttcccctgtg attctcgttg gcacacattt ggatgtttct gatgagaagc   4380
aacgcaaagc ctgcatgagt aaaatcacca aggaactcct gaataagcga gggttccctg   4440
ccatacgaga ttaccacttt gtgaatgcca ccgaggaatc tgatgctttg gcaaaacttc   4500
ggaaaaccat cataaacgag agccttaatt tcaagatccg agatcagctt gttgttggac   4560
agctgattcc agactgctat gtagaacttg aaaaaatcat tttatcggag cgtaaaaatg   4620
tgccaattga atttcccgta attgaccgga aacgattatt acaactagtg agagaaaatc   4680
agctgcagtt agatgaaaat gagcttcctc acgcagttca ctttctaaat gaatcaggag   4740
tccttcttca ttttcaagac ccagcactgc agttaagtga cttgtacttt gtggaaccca   4800
agtggctttg taaaatcatg gcacagattt tgacagtgaa agtggaaggt tgtccaaaac   4860
accctaaggg cattatttcg cgtagagatg tggaaaaatt tctttcaaaa aaaaggaaat   4920
ttccaaagaa ctacatgtca cagtatttta agctcctaga aaaattccag attgctttgc   4980
caataggaga agaatatttg ctggttccaa gcagtttgtc tgaccacagg cctgtgatag   5040
agcttcccca ttgtgagaac tctgaaatta tcatccgact atatgaaatg ccttattttc   5100
caatgggatt ttggtcaaga ttaatcaatc gattacttga gatttcacct tacatgcttt   5160
cagggagaga acgagcactt cgcccaaaca gaatgtattg gcgacaaggc atttacttaa   5220
attggtctcc tgaagcttat tgtctggtag gatctgaagt cttagacaat catccagaga   5280
gtttcttaaa aattacagtt ccttcttgta gaaaaggctg tattcttttg ggccaagttg   5340
```

```
tggaccacat tgattctctc atggaagaat ggtttcctgg gttgctggag attgatattt   5400
gtggtgaagg agaaactctg ttgaagaaat gggcattata tagttttaat gatggtgaag   5460
aacatcaaaa aatcttactt gatgacttga tgaagaaagc agaggaagga gatctcttag   5520
taaatccaga tcaaccaagg ctcaccattc caatatctca gattgcccct gacttgattt   5580
tggctgacct gcctagaaat attatgttga ataatgatga gttggaattt gaacaagctc   5640
cagagtttct cctaggtgat ggcagttttg gatcagttta ccgagcagcc tatgaaggag   5700
aagaagtggc tgtgaagatt tttaataaac atacatcact caggctgtta agacaagagc   5760
ttgtggtgct ttgccacctc caccacccca gtttgatatc tttgctggca gctgggattc   5820
gtccccggat gttggtgatg gagttagcct ccaagggttc cttggatcgc ctgcttcagc   5880
aggacaaagc cagcctcact agaaccctac agcacaggat tgcactccac gtagctgatg   5940
gtttgagata cctccactca gccatgatta tataccgaga cctgaaaccc cacaatgtgc   6000
tgcttttcac actgtatccc aatgctgcca tcattgcaaa gattgctgac tacggcattg   6060
ctcagtactg ctgtagaatg gggataaaaa catcagaggg cacaccaggg tttcgtgcac   6120
ctgaagttgc cagaggaaat gtcatttata accaacaggc tgatgtttat tcatttggtt   6180
tactactcta tgacattttg acaactggag gtagaatagt agagggtttg aagtttccaa   6240
atgagtttga tgaattagaa atacaaggaa aattacctga tccagttaaa gaatatggtt   6300
gtgccccatg gcctatggtt gagaaattaa ttaaacagtg tttgaaagaa aatcctcaag   6360
aaaggcctac ttctgcccag gtctttgaca ttttgaattc agctgaatta gtctgtctga   6420
cgagacgcat tttattacct aaaaacgtaa ttgttgaatg catggttgct acacatcaca   6480
acagcaggaa tgcaagcatt tggctgggct gtgggcacac cgacagagga cagctctcat   6540
ttcttgactt aaatactgaa ggatacactt ctgaggaagt tgctgatagt agaatattgt   6600
gcttagcctt ggtgcatctt cctgttgaaa aggaaagctg gattgtgtct gggacacagt   6660
ctggtactct cctggtcatc aataccgaag atgggaaaaa gagacatacc ctagaaaaga   6720
tgactgattc tgtcacttgt ttgtattgca attccttttc caagcaaagc aaacaaaaaa   6780
attttctttt ggttggaacc gctgatggca agttagcaat ttttgaagat aagactgtta   6840
agcttaaagg agctgctcct ttgaagatac taaatatagg aaatgtcagt actccattga   6900
tgtgtttgag tgaatccaca aattcaacgg aaagaaatgt aatgtgggga ggatgtggca   6960
caaagatttt ctccttttct aatgatttca ccattcagaa actcattgag acaagaacaa   7020
gccaactgtt ttcttatgca gctttcagtg attccaacat cataacagtg gtggtagaca   7080
ctgctctcta tattgctaag caaaatagcc ctgttgtgga agtgtgggat aagaaaactg   7140
aaaaactctg tggactaata gactgcgtgc actttttaag ggaggtaatg gtaaaagaaa   7200
acaaggaatc aaaacacaaa atgtcttatt ctgggagagt gaaaaccctc tgccttcaga   7260
agaacactgc tctttggata ggaactggag gaggccatat tttactcctg gatctttcaa   7320
ctcgtcgact tatacgtgta atttacaact tttgtaattc ggtcagagtc atgatgacag   7380
cacagctagg aagccttaaa aatgtcatgc tggtattggg ctacaaccgg aaaaatactg   7440
aaggtacaca aaagcagaaa gagatacaat cttgcttgac cgtttgggac atcaatcttc   7500
cacatgaagt gcaaaattta gaaaaacaca ttgaagtgag aaaagaatta gctgaaaaaa   7560
tgagacgaac atctgttgag taa                                           7583
```

<210> SEQ ID NO 22

<211> LENGTH: 423
<212> TYPE: DNA
<213> ORGANISM: Homo sapiens

<400> SEQUENCE: 22
atggatgtat tcatgaaagg actttcaaag gccaaggagg gagttgtggc tgctgctgag 60
aaaaccaaac agggtgtggc agaagcagca ggaaagacaa aagagggtgt tctctatgta 120
ggctccaaaa ccaaggaggg agtggtgcat ggtgtggcaa cagtggctga gaagaccaaa 180
gagcaagtga caaatgttgg aggagcagtg gtgacgggtg tgacagcagt agcccagaag 240
acagtggagg gagcagggag cattgcagca gccactggct ttgtcaaaaa ggaccagttg 300
ggcaagaatg aagaaggagc cccacaggaa ggaattctgg aagatatgcc tgtggatcct 360
gacaatgagg cttatgaaat gccttctgag gaagggtatc aagactacga acctgaagcc 420
taa 423

<210> SEQ ID NO 23
<211> LENGTH: 1860
<212> TYPE: DNA
<213> ORGANISM: Homo sapiens

<400> SEQUENCE: 23
atggcctccg gtgcgtataa cccgtatata gagataattg aacaacccag gcagagggga 60
atgcgtttta gatacaaatg tgaagggcga tcagcaggca gcattccagg ggagcacagc 120
acagacaaca accgaacata cccttctatc cagattatga actattatgg aaaaggaaaa 180
gtgagaatta cattagtaac aaagaatgac ccatataaac ctcatcctca tgatttagtt 240
ggaaaagact gcagagacgg ctactatgaa gcagaatttg gacaagaacg cagacctttg 300
tttttccaaa atttgggtat tcgatgtgtg aagaaaaaag aagtaaaaga agctattatt 360
acaagaataa aggcaggaat caatccattc aatgtccctg aaaaacagct gaatgatatt 420
gaagattgtg acctcaatgt ggtgagactg tgttttcaag tttttctccc tgatgaacat 480
ggtaatttga cgactgctct tcctcctgtt gtctcgaacc caatttatga caaccgtgct 540
ccaaatactg cagaattaag gatttgtcgt gtaaacaaga attgtggaag tgtcagagga 600
ggagatgaaa tatttctact ttgtgacaaa gttcagaaag atgacataga agttcgtttt 660
gtgttgaacg attgggaagc aaaaggcatc ttttcacaag ctgatgtaca ccgtcaagta 720
gccattgttt tcaaaactcc accatattgc aaagctatca cagaacccgt aacagtaaaa 780
atgcagttgc ggagaccttc tgaccaggaa gttagtgaat ctatggattt tagatatctg 840
ccagatgaaa aagatactta cggcaataaa gcaaagaaac aaaagacaac tctgcttttc 900
cagaaactgt gccaggatca cgtagaaaca gggtttcgcc atgttgacca ggatggtctt 960
gaactcctga catcaggtga tccacccacc ttggcctccc aaagtgctgg gattacagtt 1020
aattttcctg agagaccaag acctggtctc ctcggttcaa ttggagaagg aagatacttc 1080
aaaaaagaac caaacttgtt ttctcatgat gcagttgtga gagaaatgcc tacaggggtt 1140
tcaagtcaag cagaatccta ctatccctca cctgggccca tctcaagtgg attgtcacat 1200
catgcctcaa tggcacctct gccttcttca agctggtcat cagtggccca ccccaccccca 1260 cgctcaggca atacaaaccc actgagtagt tttcaacaa ggacacttcc ttctaattcg 1320
caaggtatcc caccattcct gagaatacct gttgggaatg atttaaatgc ttctaatgct 1380
tgcatttaca acaatgccga tgacatagtc ggaatggaag cgtcatccat gccatcagca 1440
gatttatatg gtatttctga tcccaacatg ctgtctaatt gttctgtgaa tatgatgaca 1500
accagcagtg acagcatggg agagactgat aatccaagac ttctgagcat gaatcttgaa 1560
aacccctcat gtaattcagt gttagaccca agagacttga gacagctcca tcagatgtcc 1620
tcttccagta tgtcagcagg cgccaattcc aatactactg tttttgtttc acaatcagat 1680
gcatttgagg gatctgactt cagttgtgca gataacagca tgataaatga gtcgggacca 1740
tcaaacagta ctaatccaaa cagtcatggt tttgttcaag atagtcagta ttcaggtatt 1800
ggcagtatgc aaaatgagca attgagtgac tcctttccat atgaattttt tcaagtataa 1860

<210> SEQ ID NO 24
<211> LENGTH: 2097
<212> TYPE: DNA
<213> ORGANISM: Homo sapiens

<400> SEQUENCE: 24
atgggggacc ctggactggc caagttgcag ttcgcccccct ttaatagtgc cctggacgtt 60
ggcttctggc acgaactgac ccagaagaag ttgaacgagt accgcctgga cgaggcaccc 120
aaagacatca agggctatta ctacaatggt gactctgctg gtctgcccac ccgcttgacg 180
ttggagttca gtgcttttga catgagtgcc tccacgcctg cccactgctg cccggccatg 240
ggaaccctgc acaacaccaa cacacttgag gcttttaaga cagcagacaa gaagctcctt 300
ctggagcagt cagcaaatga gatctgggaa gccataaagt caggtgctgc tctcgaaaac 360
cccatgctcc tcaacaagtt tctgctcctg accttcgcgg acctaaagaa gtaccacttc 420
tactactggt tttgctgccc cgccctctgt cttcctgaga gcatccctct aatccgggga 480
cctgtgagct tggatcaaag gctttcacca aaacagatcc aggccctgga gcatgcctat 540
gatgatctgt gtcgagccga aggcgtcacg gccctgccct acttcttatt caagtacgat 600
gacgacactg ttctggtctc cttgctcaaa cactacagtg atttcttcca aggtcaaagg 660
acaaagataa cagttggtgt gtacgatccc tgtaacctag cccagtaccc tggatggcct 720
ttgaggaatt ttttggtcct ggcagcccac agatggagcg gcagtttcca gtccgttgaa 780
gtcctctgct ttcgggaccg caccatgcag ggagctagag acgtgacaca tagcatcatc 840
tttgaagtga aacttccaga aatggcattt agcccagatt gtcctaaagc tgttggctgg 900
gagaagaacc agaaaggagg catgggtccg aggatggtga acctcagtgg atgtatggac 960
cccaaaaggc tggctgagtc atctgtggat ctgaatctca agctgatgtg ctggcgattg 1020
gtccccacct tggacttgga caaggtcgtg tctgtcaagt gcctgctgct gggagctggt 1080
accttggggt gtaatgtggc taggacactg atgggctggg gcgtcagaca tgtcaccttt 1140
gtggataacg ccaagatctc ctactccaat cccgtgaggc agcctctgta tgaatttgaa 1200
gattgtctag gggtggcaa gcccaaggcc ctggctgcag cagagcggct acagaaaata 1260
tttcccggag tgaatgccag agggttcaac atgagcatcc ccatgccagg acaccctgtg 1320
aacttctctg acgtcacgat ggagcaggcc cgcagagatg tggagcagct ggagcagctc 1380
attgataacc atgatgtcat cttcctgcta atggacacca gggagagccg gtggcttcct 1440
actgttattg cagccagcaa gcgaaagctg gtcatcaacg ctgccttggg gtttgatacc 1500
tttgttgtca tgagacatgg cctgaagaaa cccaagcagc agggagccgg agacctctgc 1560
ccaagccatc ttgtagcacc tgctgacctg ggctcctcac tttttgccaa catccctgga 1620
tacaagcttg gctgctactt ctgcaatgat gtggtggctc caggagattc aaccagagac 1680
cggactctgg accagcagtg cacagtgagc cgcccaggcc tggccgtgat tgcaggtgcc 1740

-continued

```
ctggctgtgg agctgatggt ctctgtcctg cagcatcctg aggggggcta cgccatcgcc   1800

agcagcagtg atgaccgcat gaatgagcct cccacctcgc tgggacttgt gcctcaccag   1860

atccggggtt ttctgtcacg gttcgataat gttcttcctg tcagcctggc atttgataaa   1920

tgtacagcct gttcacccaa agttcttgat cagtacgagc gagaaggatt caccttccta   1980

gcgaaggttt ttaactcctc acattccttc ttagaagact tgaccggtct taccctgctc   2040

catcaagaga cccaagctgc tgagatctgg gacatgagtg acgaggagac tgtctga      2097
```

<210> SEQ ID NO 25
<211> LENGTH: 1545
<212> TYPE: DNA
<213> ORGANISM: Homo sapiens

<400> SEQUENCE: 25

```
atggccctga gcgagctggc gctggtccgc tggctgcagg agagccgccg ctcgcggaag     60

ctcatcctgt tcatcgtgtt cctggcgctg ctgctggaca acatgctgct cactgtcgtg    120

gtccccatca tcccaagtta tctgtacagc attaagcatg agaagaatgc tacagaaatc    180

cagacggcca ggccagtgca cactgcctcc atctcagaca gcttccagag catcttctcc    240

tattatgata actcgactat ggtcaccggg aatgctacca gagacctgac acttcatcag    300

accgccacac agcacatggt gaccaacgcg tccgctgttc cttccgactg tcccagtgaa    360

gacaaagacc tcctgaatga aaacgtgcaa gttggtctgt tgtttgcctc gaaagccacc    420

gtccagctca tcaccaaccc tttcatagga ctactgacca acagaattgg ctatccaatt    480

cccatatttg cgggattctg catcatgttt gtctcaacaa ttatgtttgc cttctccagc    540

agctatgcct tcctgctgat tgccaggtcg ctgcagggca tcggctcgtc ctgctcctct    600

gtggctggga tgggcatgct tgccagtgtc tacacagatg atgaagagag aggcaacgtc    660

atgggaatcg ccttgggagg cctggccatg ggggtcttag tgggcccccc cttcgggagt    720

gtgctctatg agtttgtggg gaagacggct ccgttcctgg tgctggccgc cctggtactc    780

ttggatggag ctattcagct ctttgtgctc cagccgtccc gggtgcagcc agagagtcag    840

aaggggacac ccctaaccac gctgctgaag gacccgtaca tcctcattgc tgcaggctcc    900

atctgctttg caaacatggg catcgccatg ctggagccag ccctgcccat ctggatgatg    960

gagaccatgt gttcccgaaa gtggcagctg ggcgttgcct tcttgccagc tagtatctct   1020

tatctcattg gaaccaatat ttttgggata cttgcacaca aaatggggag gtggctttgt   1080

gctcttctgg gaatgataat tgttggagtc agcattttat gtattccatt tgcaaaaaac   1140

atttatggac tcatagctcc gaactttgga gttggttttg caattggaat ggtggattcg   1200

tcaatgatgc ctatcatggg ctacctcgta gacctgcggc acgtgtccgt ctatgggagt   1260

gtgtacgcca ttgcggatgt ggcattttgt atggggtatg ctataggtcc ttctgctggt   1320

ggtgctattg caaaggcaat tggatttcca tggctcatga caattattgg gataattgat   1380

attctttttg cccctctctg ctttttttctt cgaagtccac ctgccaaaga agaaaaaatg   1440

gctattctca tggatcacaa ctgccctatt aaaacaaaaa tgtacactca gaataatatc   1500

cagtcatatc cgataggtga agatgaagaa tctgaaagtg actga                   1545
```

<210> SEQ ID NO 26
<211> LENGTH: 2324
<212> TYPE: DNA
<213> ORGANISM: Homo sapiens

<400> SEQUENCE: 26

```
atcacatgac ccatccacat cgggaagccg gaattacttg cagggctaac ctagtgccta     60
tagctaaggc aggtacctgc atccttgttt ttgtttagtg gatcctctat ccttcagaga    120
ctctggaacc cctgtggtct tctcttcatc taatgaccct gaggggatgg agttttcaag    180
tccttccaga gaggaatgtc ccaagccttt gagtagggta agcatcatgg ctggcagcct    240
cacaggattg cttctacttc aggcagtgtc gtgggcatca ggtgcccgcc cctgcatccc    300
taaaagcttc ggctacagct cggtggtgtg tgtctgcaat gccacatact gtgactcctt    360
tgaccccccg acctttcctg cccttggtac cttcagccgc tatgagagta cacgcagtgg    420
gcgacggatg gagctgagta tggggcccat ccaggctaat cacacgggca caggcctgct    480
actgaccctg cagccagaac agaagttcca gaaagtgaag ggatttggag gggccatgac    540
agatgctgct gctctcaaca tccttgccct gtcacccccct gcccaaaatt tgctacttaa    600
atcgtacttc tctgaagaag gaatcggata taacatcatc cgggtaccca tggccagctg    660
tgacttctcc atccgcacct acacctatgc agacacccct gatgatttcc agttgcacaa    720
cttcagcctc ccagaggaag ataccaagct caagataccc ctgattcacc gagccctgca    780
gttggcccag cgtcccgttt cactccttgc cagcccctgg acatcaccca cttggctcaa    840
gaccaatgga gcggtgaatg ggaaggggtc actcaaggga cagcccggag acatctacca    900
ccagacctgg gccagatact ttgtgaagtt cctggatgcc tatgctgagc acaagttaca    960
gttctgggca gtgacagctg aaaatgagcc ttctgctggg ctgttgagtg gataccccctt   1020
ccagtgcctg ggcttcaccc ctgaacatca gcgagacttc attgcccgtg acctaggtcc   1080
taccctcgcc aacagtactc accacaatgt ccgcctactc atgctggatg accaacgctt   1140
gctgctgccc cactgggcaa aggtggtact gacagaccca gaagcagcta aatatgttca   1200
tggcattgct gtacattggt acctggactt tctggctcca gccaaagcca ccctagggga   1260
gacacaccgc ctgttcccca acaccatgct ctttgcctca gaggcctgtg tgggctccaa   1320
gttctgggag cagagtgtgc ggctaggctc ctgggatcga gggatgcagt acagccacag   1380
catcatcacg aacctcctgt accatgtggt cggctggacc gactggaacc ttgccctgaa   1440
ccccgaagga ggacccaatt gggtgcgtaa ctttgtcgac agtcccatca ttgtagacat   1500
caccaaggac acgttttaca aacagcccat gttctaccac cttggccact tcagcaagtt   1560
cattcctgag ggctcccaga gagtggggct ggttgccagt cagaagaacg acctggacgc   1620
agtggcactg atgcatcccg atggctctgc tgttgtggtc gtgctaaacc gctcctctaa   1680
ggatgtgcct cttaccatca aggatcctgc tgtgggcttc ctggagacaa tctcacctgg   1740
ctactccatt cacacctacc tgtggcgtcg ccagtgatgg agcagatact caaggaggca   1800
ctgggctcag cctgggcatt aaagggacag agtcagctca cacgctgtct gtgactaaag   1860
agggcacagc agggccagtg tgagcttaca gcgacgtaag cccaggggca atggtttggg   1920
tgactcactt tcccctctag gtggtgccag gggctggagg cccctagaaa aagatcagta   1980
agccccagtg tccccccagc cccatgctt atgtgaacat gcgctgtgtg ctgcttgctt   2040
tggaaactgg gcctgggtcc aggcctaggg tgagctcact gtccgtacaa acacaagatc   2100
agggctgagg gtaaggaaaa gaagagacta ggaaagctgg gcccaaaact ggagactgtt   2160
tgtctttcct ggagatgcag aactgggccc gtggagcagc agtgtcagca tcagggcgga   2220
agccttaaag cagcagcggg tgtgcccagg cacccagatg attcctatgg caccagccag   2280
gaaaaatggc agctcttaaa ggagaaaatg tttgagccca gtca                    2324
```

<210> SEQ ID NO 27
<211> LENGTH: 1398
<212> TYPE: DNA
<213> ORGANISM: Homo sapiens

<400> SEQUENCE: 27
atgatagtgt ttgtcaggtt caactccagc catggtttcc cagtggaggt cgattctgac 60
accagcatct tccagctcaa ggaggtggtt gctaagcgac agggggttcc ggctgaccag 120
ttgcgtgtga ttttcgcagg gaaggagctg aggaatgact ggactgtgca gaattgtgac 180
ctggatcagc agagcattgt tcacattgtg cagagaccgt ggagaaaagg tcaagaaatg 240
aatgcaactg gaggcgacga ccccagaaac gcggcgggag gctgtgagcg ggagccccag 300
agcttgactc gggtggacct cagcagctca gtcctcccag gagactctgt ggggctggct 360
gtcattctgc acactgacag caggaaggac tcaccaccag ctggaagtcc agcaggtaga 420
tcaatctaca acagctttta tgtgtattgc aaaggcccct gtcaaagagt gcagccggga 480
aaactcaggg tacagtgcag cacctgcagg caggcaacgc tcaccttgac ccagggtcca 540
tcttgctggg atgatgtttt aattccaaac cggatgagtg gtgaatgcca atccccacac 600
tgccctggga ctagtgcaga atttttcttt aaatgtggag cacaccccac ctctgacaag 660
gaaacatcag tagctttgca cctgatcgca acaaatagtc ggaacatcac ttgcattacg 720
tgcacagacg tcaggagccc cgtcctggtt ttccagtgca actcccgcca cgtgatttgc 780
ttagactgtt tccacttata ctgtgtgaca agactcaatg atcggcagtt tgttcacgac 840
cctcaacttg gctactccct gccttgtgtg gctggctgtc ccaactcctt gattaaagag 900
ctccatcact tcaggattct gggagaagag cagtacaacc ggtaccagca gtatggtgca 960
gaggagtgtg tcctgcagat gggggggcgtg ttatgccccc gccctggctg tggagcgggg 1020
ctgctgccgg agcctgacca gaggaaagtc acctgcgaag gggggcaatgg cctgggctgt 1080 gggtttgcct tctgccggga atgtaaagaa gcgtaccatg aaggggagtg cagtgccgta 1140
tttgaagcct caggaacaac tactcaggcc tacagagtcg atgaaagagc cgccgagcag 1200
gctcgttggg aagcagcctc caaagaaacc atcaagaaaa ccaccaagcc ctgtccccgc 1260
tgccatgtac cagtggaaaa aaatggaggc tgcatgcaca tgaagtgtcc gcagccccag 1320
tgcaggctcg agtggtgctg gaactgtggc tgcgagtgga accgcgtctg catgggggac 1380
cactggttcg acgtgtag 1398

<210> SEQ ID NO 28
<211> LENGTH: 1314
<212> TYPE: DNA
<213> ORGANISM: Homo sapiens

<400> SEQUENCE: 28
atgatagtgt ttgtcaggtt caactccagc catggtttcc cagtggaggt cgattctgac 60
accagcatct tccagctcaa ggaggtggtt gctaagcgac agggggttcc ggctgaccag 120
ttgcgtgtga ttttcgcagg gaaggagctg aggaatgact ggactgtgca gaattgtgac 180
ctggatcagc agagcattgt tcacattgtg cagagaccgt ggagaaaagg tcaagaaatg 240
aatgcaactg gaggcgacga ccccagaaac gcggcgggag gctgtgagcg ggagccccag 300
agcttgactc gggtggacct cagcagctca gtcctcccag gagactctgt ggggctggct 360
gtcattctgc acactgacag caggaaggac tcaccaccag ctggaagtcc agcaggtaga 420
tcaatctaca acagctttta tgtgtattgc aaaggcccct gtcaaagagt gcagccggga 480

-continued

```
aaactcaggg tacagtgcag cacctgcagg caggcaacgc tcaccttgac ccaggaattt     540
ttctttaaat gtggagcaca ccccacctct gacaaggaaa catcagtagc tttgcacctg     600
atcgcaacaa atagtcggaa catcacttgc attacgtgca cagacgtcag gagccccgtc     660
ctggttttcc agtgcaactc ccgccacgtg atttgcttag actgtttcca cttatactgt     720
gtgacaagac tcaatgatcg gcagtttgtt cacgaccctc aacttggcta ctccctgcct     780
tgtgtggctg gctgtcccaa ctccttgatt aaagagctcc atcacttcag gattctggga     840
gaagagcagt acaaccggta ccagcagtat ggtgcagagg agtgtgtcct gcagatgggg     900
ggcgtgttat gcccccgccc tggctgtgga gcggggctgc tgccggagcc tgaccagagg     960
aaagtcacct gcgaaggggg caatggcctg ggctgtgggt ttgccttctg ccgggaatgt    1020
aaagaagcgt accatgaagg ggagtgcagt gccgtatttg aagcctcagg aacaactact    1080
caggcctaca gagtcgatga aagagccgcc gagcaggctc gttgggaagc agcctccaaa    1140
gaaaccatca agaaaaccac caagccctgt ccccgctgcc atgtaccagt ggaaaaaaat    1200
ggaggctgca tgcacatgaa gtgtccgcag ccccagtgca ggctcgagtg gtgctggaac    1260
tgtggctgcg agtggaaccg cgtctgcatg gggaccact ggttcgacgt gtag           1314
```

<210> SEQ ID NO 29
<211> LENGTH: 657
<212> TYPE: DNA
<213> ORGANISM: Homo sapiens

<400> SEQUENCE: 29

```
atgaatgcaa ctggaggcga cgaccccaga aacgcggcgg gaggctgtga gcgggagccc      60
cagagcttga ctcgggtgga cctcagcagc tcagtcctcc caggagactc tgtggggctg     120
gctgtcattc tgcacactga cagcaggaag gactcaccac cagctggaag tccagcaggt     180
agatcaatct acaacagctt ttatgtgtat tgcaaaggcc cctgtcaaag agtgcagccg     240
ggaaaactca gggtacagtg cagcacctgc aggcaggcaa cgctcacctt gacccagggt     300
ccatcttgct gggatgatgt tttaattcca aaccggatga gtggtgaatg ccaatcccca     360
cactgccctg ggactagtgc agaatttttc tttaaatgtg gagcacaccc cacctctgac     420
aaggaaacat cagtagcttt gcacctgatc gcaacaaata gtcggaacat cacttgcatt     480
acgtgcacag acgtcaggag ccccgtcctg gttttccagt gcaactcccg ccacgtgatt     540
tgcttagact gtttccactt atactgtgtg acaagactca atgatcggca gtttgttcac     600
gaccctcaac ttggctactc cctgccttgt gtggtttgcc ttctgccggg aatgtaa        657
```

<210> SEQ ID NO 30
<211> LENGTH: 825
<212> TYPE: DNA
<213> ORGANISM: Homo sapiens

<400> SEQUENCE: 30

```
atgagtggtg aatgccaatc cccacactgc cctgggacta gtgcagaatt tttctttaaa      60
tgtggagcac accccacctc tgacaaggaa acatcagtag ctttgcacct gatcgcaaca     120
aatagtcgga acatcacttg cattacgtgc acagacgtca ggagccccgt cctggttttc     180
cagtgcaact cccgccacgt gatttgctta gactgtttcc acttatactg tgtgacaaga     240
ctcaatgatc ggcagtttgt tcacgaccct caacttggct actccctgcc ttgtgtggct     300
ggctgtccca actccttgat taaagagctc catcacttca ggattctggg agaagagcag     360
```

-continued

```
tacaaccggt accagcagta tggtgcagag gagtgtgtcc tgcagatggg gggcgtgtta    420

tgcccccgcc ctggctgtgg agcggggctg ctgccggagc ctgaccagag gaaagtcacc    480

tgcgaagggg gcaatggcct gggctgtggg tttgccttct gccgggaatg taaagaagcg    540

taccatgaag ggagtgcag tgccgtattt gaagcctcag gaacaactac tcaggcctac    600

agagtcgatg aaagagccgc cgagcaggct cgttgggaag cagcctccaa agaaaccatc    660

aagaaaacca ccaagccctg tccccgctgc catgtaccag tggaaaaaaa tggaggctgc    720

atgcacatga agtgtccgca gccccagtgc aggctcgagt ggtgctggaa ctgtggctgc    780

gagtggaacc gcgtctgcat gggggaccac tggttcgacg tgtag                    825
```

<210> SEQ ID NO 31
<211> LENGTH: 1161
<212> TYPE: DNA
<213> ORGANISM: Homo sapiens

<400> SEQUENCE: 31

```
atgatagtgt ttgtcaggtt caactccagc catggtttcc cagtggaggt cgattctgac     60

accagcatct tccagctcaa ggaggtggtt gctaagcgac agggggttcc ggctgaccag    120

ttgcgtgtga ttttcgcagg gaaggagctg aggaatgact ggactgtgca gaattgtgac    180

ctggatcagc agagcattgt tcacattgtg cagagaccgt ggagaaaagg tcaagaaatg    240

aatgcaactg gaggcgacga ccccagaaac gcggcgggag gctgtgagcg ggagccccag    300

agcttgactc gggtggacct cagcagctca gtcctcccag gagactctgt ggggctggct    360

gtcattctgc acactgacag caggaaggac tcaccaccag ctggaagtcc agcaggtaga    420

tcaatctaca acagctttta tgtgtattgc aaaggcccct gtcaaagagt gcagccggga    480

aaactcaggg tacagtgcag cacctgcagg caggcaacgc tcaccttgac ccagggtcca    540

tcttgctggg atgatgtttt aattccaaac cggatgagtg gtgaatgcca atccccacac    600

tgccctggga ctagtgcaga atttttcttt aaatgtggag cacaccccac ctctgacaag    660

gaaacatcag tagctttgca cctgatcgca acaaatagtc ggaacatcac ttgcattacg    720

tgcacagacg tcaggagccc cgtcctggtt ttccagtgca actcccgcca cgtgatttgc    780

ttagactgtt tccacttata ctgtgtgaca agactcaatg atcggcagtt tgttcacgac    840

cctcaacttg gctactccct gccttgtgtg ggaactggag acacagtggt gcttagagga    900

gctctggggg gattcaggag aggagtcgct ggctgtccca actccttgat taaagagctc    960

catcacttca ggattctggg agaagagcag tacaaccggt accagcagta tggtgcagag   1020

gagtgtgtcc tgcagatggg gggcgtgtta tgcccccgcc ctggctgtgg agcggggctg   1080

ctgccggagc ctgaccagag gaaagtcacc tgcgaagggg gcaatggcct gggctgtggg   1140

tatggacaac gaagaacaaa a                                             1161
```

<210> SEQ ID NO 32
<211> LENGTH: 951
<212> TYPE: DNA
<213> ORGANISM: Homo sapiens

<400> SEQUENCE: 32

```
atgatagtgt ttgtcaggtt caactccagc catggtttcc cagtggaggt cgattctgac     60

accagcatct tccagctcaa ggaggtggtt gctaagcgac agggggttcc ggctgaccag    120

ttgcgtgtga ttttcgcagg gaaggagctg aggaatgact ggactgtgca ggaatttttc    180

tttaaatgtg gagcacaccc cacctctgac aaggaaacat cagtagcttt gcacctgatc    240
```

```
gcaacaaata gtcggaacat cacttgcatt acgtgcacag acgtcaggag ccccgtcctg    300

gttttccagt gcaactcccg ccacgtgatt tgcttagact gtttccactt atactgtgtg    360

acaagactca atgatcggca gtttgttcac gaccctcaac ttggctactc cctgccttgt    420

gtggctggct gtcccaactc cttgattaaa gagctccatc acttcaggat tctgggagaa    480

gagcagtaca accggtacca gcagtatggt gcagaggagt gtgtcctgca gatggggggc    540

gtgttatgcc cccgccctgg ctgtggagcg gggctgctgc cggagcctga ccagaggaaa    600

gtcacctgcg aagggggcaa tggcctgggc tgtgggtttg ccttctgccg ggaatgtaaa    660

gaagcgtacc atgaagggga gtgcagtgcc gtatttgaag cctcaggaac aactactcag    720

gcctacagag tcgatgaaag agccgccgag caggctcgtt gggaagcagc ctccaaagaa    780

accatcaaga aaaccaccaa gccctgtccc cgctgccatg taccagtgga aaaaaatgga    840

ggctgcatgc acatgaagtg tccgcagccc cagtgcaggc tcgagtggtg ctggaactgt    900

ggctgcgagt ggaaccgcgt ctgcatgggg gaccactggt tcgacgtgta g             951
```

```
<210> SEQ ID NO 33
<211> LENGTH: 1164
<212> TYPE: DNA
<213> ORGANISM: Homo sapiens

<400> SEQUENCE: 33

atgatagtgt ttgtcaggtt caactccagc catggtttcc cagtggaggt cgattctgac     60

accagcatct tccagctcaa ggaggtggtt gctaagcgac agggggttcc ggctgaccag    120

ttgcgtgtga ttttcgcagg gaaggagctg aggaatgact ggactgtgca gaattgtgac    180

ctggatcagc agagcattgt tcacattgtg cagagaccgt ggagaaaagg tcaagaaatg    240

aatgcaactg gaggcgacga ccccagaaac gcggcgggag gctgtgagcg ggagccccag    300

agcttgactc gggtggacct cagcagctca gtcctcccag gagactctgt ggggctggct    360

gtcattctgc acactgacag caggaaggac tcaccaccag ctggaagtcc agcaggtaga    420

tcaatctaca acagctttta tgtgtattgc aaaggcccct gtcaaagagt gcagccggga    480

aaactcaggg tacagtgcag cacctgcagg caggcaacgc tcaccttgac ccaggaattt    540

ttctttaaat gtggagcaca ccccacctct gacaaggaaa catcagtagc tttgcacctg    600

atcgcaacaa atagtcggaa catcacttgc attacgtgca cagacgtcag gagccccgtc    660

ctggttttcc agtgcaactc ccgccacgtg atttgcttag actgtttcca cttatactgt    720

gtgacaagac tcaatgatcg gcagtttgtt cacgaccctc aacttggcta ctccctgcct    780

tgtgtggctg gctgtcccaa ctccttgatt aaagagctcc atcacttcag gattctggga    840

gaagagcagt ttgccttctg ccgggaatgt aaagaagcgt accatgaagg ggagtgcagt    900

gccgtatttg aagcctcagg aacaactact caggcctaca gagtcgatga aagagccgcc    960

gagcaggctc gttgggaagc agcctccaaa gaaaccatca agaaaaccac caagccctgt   1020

ccccgctgcc atgtaccagt ggaaaaaaat ggaggctgca tgcacatgaa gtgtccgcag   1080

ccccagtgca ggctcgagtg gtgctggaac tgtggctgcg agtggaaccg cgtctgcatg   1140

ggggaccact ggttcgacgt gtag                                          1164
```

```
<210> SEQ ID NO 34
<211> LENGTH: 1248
<212> TYPE: DNA
<213> ORGANISM: Homo sapiens
```

<400> SEQUENCE: 34
atgatagtgt ttgtcaggtt caactccagc catggtttcc cagtggaggt cgattctgac 60
accagcatct tccagctcaa ggaggtggtt gctaagcgac agggggttcc ggctgaccag 120
ttgcgtgtga ttttcgcagg gaaggagctg aggaatgact ggactgtgca gaattgtgac 180
ctggatcagc agagcattgt tcacattgtg cagagaccgt ggagaaaagg tcaagaaatg 240
aatgcaactg gaggcgacga ccccagaaac gcggcgggag gctgtgagcg ggagccccag 300
agcttgactc gggtggacct cagcagctca gtcctcccag gagactctgt ggggctggct 360
gtcattctgc acactgacag caggaaggac tcaccaccag ctggaagtcc agcaggtaga 420
tcaatctaca acagctttta tgtgtattgc aaaggcccct gtcaaagagt gcagccggga 480
aaactcaggg tacagtgcag cacctgcagg caggcaacgc tcaccttgac ccagggtcca 540
tcttgctggg atgatgtttt aattccaaac cggatgagtg gtgaatgcca atccccacac 600
tgccctggga ctagtgcaga atttttcttt aaatgtggag cacaccccac ctctgacaag 660
gaaacatcag tagctttgca cctgatcgca acaaatagtc ggaacatcac ttgcattacg 720
tgcacagacg tcaggagccc cgtcctggtt ttccagtgca actcccgcca cgtgatttgc 780
ttagactgtt tccacttata ctgtgtgaca agactcaatg atcggcagtt tgttcacgac 840
cctcaacttg gctactccct gccttgtgtg gctggctgtc ccaactcctt gattaaagag 900
ctccatcact tcaggattct gggagaagag cagtttgcct tctgccggga atgtaaagaa 960
gcgtaccatg aaggggagtg cagtgccgta tttgaagcct caggaacaac tactcaggcc 1020
tacagagtcg atgaaagagc cgccgagcag gctcgttggg aagcagcctc caaagaaacc 1080
atcaagaaaa ccaccaagcc ctgtccccgc tgccatgtac cagtggaaaa aaatggaggc 1140
tgcatgcaca tgaagtgtcc gcagccccag tgcaggctcg agtggtgctg gaactgtggc 1200
tgcgagtgga accgcgtctg catgggggac cactggttcg acgtgtag 1248

<210> SEQ ID NO 35
<211> LENGTH: 1398
<212> TYPE: DNA
<213> ORGANISM: Artificial Sequence
<220> FEATURE:
<223> OTHER INFORMATION: Made in Lab - Codon optimized PRKN variant CO1

<400> SEQUENCE: 35
atgattgtgt ttgtcagatt caactcctcc catggcttcc ctgtggaagt ggactcagat 60
acctccatct tccaactgaa ggaggtggtg gccaagagac agggggtgcc tgcagatcag 120
cttagggtca tctttgctgg aaaggagctg agaaatgact ggactgtgca gaactgtgac 180
ctggaccagc agagcatagt gcacattgtc caacggccct ggaggaaagg acaggagatg 240
aatgccactg gaggagatga cccccgcaat gctgcgggtg gctgtgaaag agaacctcag 300
tccctgacca gagtggacct gtccagctca gtgctcccag gagactcagt ggggcttgct 360
gtgattctgc acactgactc caggaaggac tccccccctg ctggaagccc agcgggcaga 420
agcatctaca actccttcta tgtgtactgc aagggcccct gccagagagt gcagcctgga 480
aagctgaggg tgcagtgctc cacctgtcgc caagccactc tcaccctgac ccagggccca 540
tcctgctggg atgatgtctt gatccccaac aggatgtcgg gagaatgtca gtcaccacac 600
tgccctggaa cctcggcaga gttcttcttc aaatgtggtg cccaccctac ctccgacaag 660
gaaacctcag tggccctgca tctcattgcc accaacagca ggaacatcac ctgtatcact 720
tgcactgatg tcaggtcacc tgtgctggtg ttccagtgca actccagaca tgtgatctgc 780
ctggactgct tccacctgta ctgtgtgact aggctcaatg acagacaatt tgtccatgac 840
ccccagctgg gctactccct gccctgtgtg gctggatgcc ctaactccct gatcaaggaa 900
ctccaccact tccgcatcct gggagaagaa cagtacaaca ggtaccagca gtacggtgca 960
gaagagtgtg tgctccaaat gggggagtg ctgtgccccc ggccgggctg tggagctggc 1020
ctgctgcctg aacctgatca gagaaaggtc acttgcgagg gtggaaacgg tcttggttgt 1080
gggtttgcct tctgccggga gtgcaaggag gcctaccacg aaggagagtg ctctgcagtg 1140
ttcgaggcct ctggcactac cacccaagcc tatagagtgg atgagcgggc agcagaacag 1200
gccagatggg aagctgccag caaggaaacc attaagaaaa ccaccaagcc atgcccccgg 1260
tgccacgtgc cagtggagaa gaatggaggg tgcatgcaca tgaagtgccc ccagccccag 1320
tgccgcttgg agtggtgctg gaactgtggt tgtgaatgga acagggtctg tatgggggac 1380
cactggtttg atgtgtaa 1398

<210> SEQ ID NO 36
<211> LENGTH: 1398
<212> TYPE: DNA
<213> ORGANISM: Artificial Sequence
<220> FEATURE:
<223> OTHER INFORMATION: Made in Lab - Codon optimized PRKN variant CO2

<400> SEQUENCE: 36
atgattgtgt ttgtcagatt caactcctcc catggcttcc ctgtggaagt ggactcggac 60
accagcatct tccagctgaa ggaagtggtg gccaagagac agggagtgcc agcagatcag 120
ctccgggtca tttttgctgg aaaggaactg aggaatgact ggactgtcca gaactgtgac 180
ctggaccagc agtccattgt ccacattgtg cagaggcctt ggaggaaggg ccaagagatg 240
aatgccactg ggggggatga ccctagaaat gcggctggag gctgtgaacg ggagcctcag 300
tccctcacta gagtggacct gagctcctca gtcctccctg gagactcagt gggcctggct 360
gtgatcctcc acactgactc ccgcaaggac agcccccag cgggcagccc tgcaggccgg 420
tccatctaca actccttcta tgtgtactgc aagggaccct gccagagagt ccagcctggc 480
aaactgaggg tgcagtgctc cacctgtcgc caagccaccc tgaccctgac ccaaggaccc 540
tcctgctggg atgatgtgct gatccccaac cggatgtcag gagaatgtca aagcccgcat 600
tgcccaggga cctctgcaga gttcttcttc aagtgtggag cccaccccac ctcggacaag 660
gaaacctcag tggccctgca cctgattgcc acaaactccc ggaacatcac ctgtatcacc 720
tgtactgatg tgcgctcacc agtgctggtg ttccagtgca actcccgcca tgtgatctgc 780
ctggattgct tccacttgta ctgtgtgact agactgaatg acaggcagtt tgtgcatgat 840
ccccagctgg gttacagctt gccctgtgtg gctggttgcc ccaactccct gatcaaggag 900
ctgcaccact tccgcatttt gggggaggag caatacaaca gataccagca gtatggagca 960
gaagaatgtg tgctgcagat gggggggtg ctctgcccga ggccaggatg tggtgcaggc 1020
ctgctccctg aacctgacca gagaaaagtg acctgtgaag gggcaacgg acttggttgt 1080 ggatttgcct tctgccggga gtgcaaggag gcctaccacg agggagaatg ctctgctgtc 1140
tttgaggcct caggaaccac tacccaggcc tacagagtgg atgaaagggc tgctgagcaa 1200
gccagatggg aagcagcctc caaggaaacc atcaagaaaa ccactaagcc ctgcccccgc 1260
tgccatgtgc ctgtggagaa gaatggtgga tgcatgcaca tgaagtgccc ccaacctcag 1320
tgcaggcttg aatggtgctg gaactgtggc tgtgaatgga acagagtctg catgggggac 1380

```
cactggtttg atgtctaa                                                1398


<210> SEQ ID NO 37
<211> LENGTH: 1398
<212> TYPE: DNA
<213> ORGANISM: Artificial Sequence
<220> FEATURE:
<223> OTHER INFORMATION: Made in Lab - Codon optimized PRKN variant CO3

<400> SEQUENCE: 37

atgattgtgt ttgtgagatt caactcctcc catggcttcc cagtggaagt ggattctgac     60

acctccatct tccaattaaa ggaggtggtg gccaagcgtc agggagtccc agcagaccag    120

ctgagggtga tctttgctgg caaagaactt agaaatgact ggactgtgca gaactgtgac    180

ctggaccagc agagcattgt gcatattgtc caacggccct ggcggaaggg ccaggagatg    240

aatgccactg gggggggatga cccccggaat gccgcggggg gctgtgagag ggaacctcaa    300

tccctgacca gagtggacct gagctcctcg gtgttgccag gagacagcgt gggcctggct    360

gtgatcctgc acactgactc caggaaggac agcccccctg ctggaagccc agctggccgc    420

tccatctaca actccttcta tgtctactgc aagggcccct gccagagagt gcagcctgga    480

aagctgagag tgcagtgctc cacctgtcgc caggccaccc tgaccctgac ccaaggaccg    540

tcctgctggg atgatgtcct catccccaac aggatgtcag gagaatgcca atccccccac    600

tgtcctggca cttcagcgga gttcttcttc aagtgtggag ctcaccccac ttctgacaag    660

gaaacctcag tggccctcca cctgattgcc accaactcca gaaacatcac atgcattact    720

tgcactgatg tcaggtcccc tgtgttggtg ttccagtgca actcaagaca tgtgatctgc    780

ctggactgct tccatctcta ctgtgtgact agacttaacg acagacagtt tgtccatgac    840

ccacagcttg gatacagcct cccctgtgtg gctgggtgcc ccaactccct gattaaggaa    900

ctgcaccact tcaggatcct gggagaggaa cagtacaaca ggtaccagca atatggggct    960

gaggagtgtg tgctccagat gggggggagtc ctgtgccccc ggccgggatg tggtgcaggc   1020

ctgctccctg agcctgacca gcgcaaagtg acctgtgaag gtggcaacgg tctgggttgt   1080

ggttttgcct tctgccggga gtgcaaggaa gcctaccacg aaggggaatg ctcagctgtg   1140

tttgaggcct caggaaccac cacccaggcc tacagggtgg atgagcgagc agcagagcag   1200

gccagatggg aggcagcctc caaggaaacc atcaagaaaa ccactaagcc ttgccctcgg   1260

tgccatgtgc ctgtggagaa gaatggaggg tgcatgcaca tgaagtgccc ccagcctcag   1320

tgcaggctgg aatggtgctg gaactgtggc tgtgaatgga acagggtctg catgggagat   1380

cactggtttg atgtctaa                                                1398


<210> SEQ ID NO 38
<211> LENGTH: 1398
<212> TYPE: DNA
<213> ORGANISM: Artificial Sequence
<220> FEATURE:
<223> OTHER INFORMATION: Made in Lab - Codon optimized PRKN variant CO4

<400> SEQUENCE: 38

atgattgtgt ttgtccggtt caactcctcc catggtttcc cggtggaagt ggactcagac     60

accagcatct tccaactgaa ggaagtggtg gccaagcgtc agggggtccc ggcagaccag    120

ttgagagtga tcttcgctgg aaaggaactg agaaacgact ggactgtgca gaactgtgac    180

ctggaccaac agtccattgt gcacattgtc cagcggcctt ggcggaaagg tcaagagatg    240

aacgccactg gtggagatga ccccaggaat gcagctgggg gctgtgaacg ggaacctcag    300
```

agcctgacca gagtggacct cagctcctct gtcctcccgg gagactccgt gggactggca 360
gtcattctgc acactgacag ccgcaaggat tcccccccctg cgggttcacc agctggacgg 420
tccatctaca actccttcta tgtgtactgc aagggaccct gccagagggt gcagccggga 480
aagctcagag tgcagtgcag cacttgcaga caagccaccc tgaccctgac ccagggccca 540
tcctgctggg atgatgtcct gatccccaac cggatgtcag gggaatgcca aagccctcac 600
tgccctggaa cctcggccga gttcttcttc aaatgtggag cccaccccac ctcggacaag 660
gaaacctcgg tggcccttca cctcattgcc accaactccc gcaacatcac ctgtatcact 720
tgcactgatg ttcgctctcc ggtgctggtg ttccagtgca actcccgaca cgtgatctgc 780
ctggactgct tccacctgta ctgtgtgacc agactgaatg acaggcagtt tgtccacgac 840
ccccaactgg gctactcctt gccttgtgtg gctggctgcc ccaactccct gatcaaggag 900
ttgcaccact tccggatcct gggagaggaa cagtacaaca gataccagca gtacggggca 960
gaggaatgtg tcctccaaat gggggggagtg ctgtgccccc ggcctggttg tggagctggc 1020
ctcctgccgg aacctgacca gcggaaggtc acttgcgagg gtggaaacgg cctgggctgt 1080
ggcttcgcct tctgtcggga gtgcaaggag gcctaccacg aaggagaatg ctccgcggtg 1140
tttgaagcct cagggaccac cacacaagcc tacagagtgg atgagagggc agcggagcag 1200
gcccgctggg aagcggcctc caaggagact atcaagaaaa ccaccaagcc atgccctagg 1260
tgccatgtgc ctgtggaaaa gaatggaggc tgcatgcaca tgaagtgccc ccagccacag 1320
tgccgccttg aatggtgctg gaactgtggc tgcgagtgga acagagtgtg tatgggggac 1380
cactggtttg atgtgtga 1398

<210> SEQ ID NO 39
<211> LENGTH: 4187
<212> TYPE: DNA
<213> ORGANISM: Artificial Sequence
<220> FEATURE:
<223> OTHER INFORMATION: Made in Lab - AAV expression cassette construct

<400> SEQUENCE: 39
ctctggagac gcgttacata acttacggta aatggcccgc ctggctgacc gcccaacgac 60
ccccgcccat tgacgtcaat aatgacgtat gttcccatag taacgccaat agggactttc 120
cattgacgtc aatgggtgga gtatttacgg taaactgccc acttggcagt acatcaagtg 180
tatcatatgc caagtacgcc ccctattgac gtcaatgacg gtaaatggcc cgcctggcat 240
tatgcccagt acatgacctt atgggacttt cctacttggc agtacatcta cgtattagtc 300
atcgctatta ccagcccagc accccaaggc ggccaacgcc aaaactctcc ctcctcctct 360
tcctcaatct cgctctcgct cttttttttt ttcgcaaaag gaggggagag ggggtaaaaa 420
aatgctgcac tgtgcggcga agccggtgag tgagcggcgc ggggccaatc agcgtgcgcc 480
gttccgaaag ttgcctttta tggctcgagc ggccgcggcg gcgccctata aaacccagcg 540
gcgcgacgcg ccaccaccgc cgagtccgcg tccgcccgcg agcacagagc ctcgcctttg 600
ccgatccgcc gcccgtccac acccgccgcc aggtaagccc ggccagccga ccggggcatg 660
cggccgcggc ccttcgcccg tgcagagccg ccgtctgggc cgcagcgggg ggcgcatggg 720
gcggaaccgg accgccgtgg ggggcgcggg agaagcccct gggcctccgg agatggggga 780
caccccacgc cagttcgcag gcgcgaggcc gcgctcgggc gggcgcgctc cgggggtgcc 840
gctctcgggg cgggggcaac cggcggggtc tttgtctgag ccgggctctt gccaatgggg 900

-continued

```
atcgcacggt gggcgcggcg tagcccccgt caggcccggt gggggctggg gcgccatgcg    960
cgtgcgcgct ggtcctttgg gcgctaactg cgtgcgcgct gggaattggc gctaattgcg   1020
cgtgcgcgct gggactcaat ggcgctaatc gcgcgtgcgt tctggggccc gggcgcttgc   1080
gccacttcct gcccgagccg ctggcgcccg agggtgtggc cgctgcgtgc gcgcgcgcga   1140
cccggtcgct gtttgaaccg ggcggaggcg gggctggcgc ccggttggga gggggttggg   1200
gcctggcttc ctgccgcgcg ccgcggggac gcctccgacc agtgtttgcc ttttatggta   1260
ataacgcggc cggcccggct tcctttgtcc ccaatctggg cgcgcgccgg cgccccctgg   1320
cggcctaagg actcggcgcg ccggaagtgg ccagggcggc agcggctgct cttggcggcc   1380
ccgaggtgac tatagccttc ttttgtgtct tgatagttcg ccagcctctg ctaaccatgt   1440
tcatgccttc ttcttttcc tacagctcct gggcaacgtg ctggttattg tgctgtctca   1500
tcattttggc aaagaattcg gcttgatcga agccgtctca ggggaattca aagcaagccg   1560
ccaccatgat tgtgtttgtc cggttcaact cctcccatgg tttcccggtg gaagtggact   1620
cagacaccag catcttccaa ctgaaggaag tggtggccaa gcgtcagggg gtcccggcag   1680
accagttgag agtgatcttc gctggaaagg aactgagaaa cgactggact gtgcagaact   1740
gtgacctgga ccaacagtcc attgtgcaca ttgtccagcg gccttggcgg aaaggtcaag   1800
agatgaacgc cactggtgga gatgacccca ggaatgcagc tgggggctgt gaacgggaac   1860
ctcagagcct gaccagagtg gacctcagct cctctgtcct cccgggagac tccgtgggac   1920
tggcagtcat tctgcacact gacagccgca aggattcccc ccctgcgggt tcaccagctg   1980
gacggtccat ctacaactcc ttctatgtgt actgcaaggg accctgccag agggtgcagc   2040
cgggaaagct cagagtgcag tgcagcactt gcagacaagc caccctgacc ctgacccagg   2100
gcccatcctg ctgggatgat gtcctgatcc ccaaccggat gtcaggggaa tgccaaagcc   2160
ctcactgccc tggaacctcg gccgagttct tcttcaaatg tggagcccac cccacctcgg   2220
acaaggaaac ctcggtggcc cttcacctca ttgccaccaa ctcccgcaac atcacctgta   2280
tcacttgcac tgatgttcgc tctccggtgc tggtgttcca gtgcaactcc cgacacgtga   2340
tctgcctgga ctgcttccac ctgtactgtg tgaccagact gaatgacagg cagtttgtcc   2400
acgaccccca actgggctac tccttgcctt gtgtggctgg ctgccccaac tccctgatca   2460
aggagttgca ccacttccgg atcctgggag aggaacagta caacagatac cagcagtacg   2520
gggcagagga atgtgtcctc caaatggggg gagtgctgtg cccccggcct ggttgtggag   2580
ctggcctcct gccggaacct gaccagcgga aggtcacttg cgagggtgga aacggcctgg   2640
gctgtggctt cgccttctgt cgggagtgca aggaggccta ccacgaagga gaatgctccg   2700
cggtgtttga agcctcaggg accaccacac aagcctacag agtggatgag agggcagcgg   2760
agcaggcccg ctgggaagcg gcctccaagg agactatcaa gaaaaccacc aagccatgcc   2820
ctaggtgcca tgtgcctgtg gaaaagaatg gaggctgcat gcacatgaag tgcccccagc   2880
cacagtgccg ccttgaatgg tgctggaact gtggctgcga gtggaacaga gtgtgtatgg   2940
gggaccactg gtttgatgtg tgataatgga ttcctgttaa tcaacctctg gattacaaaa   3000
tttgtgaaag attgactggt attcttaact atgttgctcc ttttacgcta tgtggatacg   3060
ctgctttaat gcctttgtat catgctattg cttcccgtat ggctttcatt ttctcctcct   3120
tgtataaatc ctggttgctg tctctttatg aggagttgtg gcccgttgtc aggcaacgtg   3180
gcgtggtgtg cactgtgttt gctgacgcaa cccccactgg ttggggcatt gccaccacct   3240
gtcagctcct ttccgggact ttcgctttcc ccctccctat tgccacggcg gaactcatcg   3300
```

```
ccgcctgcct tgcccgctgc tggacagggg ctcggctgtt gggcactgac aattccgtgg   3360

tgttgtcggg gaagctgacg tcctttccgc ggctgctcgc ctgtgttgcc acctggattc   3420

tgcgcgggac gtccttctgc tacgtccctt cggccctcaa tccagcggac cttccttccc   3480

gcggcctgct gccggctctg cggcctcttc cgcctcttcg ccttcgccct cagacgagtc   3540

ggatctccct ttgggccgcc tccccgccca tgtatctttt tcacctgtgc cttgtttttg   3600

cctgtgttcc gcgtcctact tttcaagcct ccaagctgtg ccttgggcgg ctttggggca   3660

tggacataga tccctataaa gaatttggtt catcttatca gttgttgaat tttcttcctt   3720

tggactggct aataaaggaa atttattttc attgcaatag tgtgttggaa ttttttgtgt   3780

ctctcactcg gaagaacata tgggagggca aatcatttaa aacatcagaa tgagtatttg   3840

gtttagagtt tggcaacata tgcccatatg ctggctgcca tgaacaaagg ttggctataa   3900

agaggtcatc agtatatgaa acagcccct gctgtccatt ccttattcca tagaaaagcc   3960

ttgacttgag gttagatttt ttttatattt tgttttgtgt tatttttttc tttaacatcc   4020

ctaaaatttt ccttacatgt tttactagcc agatttttcc tcctctcctg actactccca   4080

gtcatagctg tccctcttct cttatggaga tcgttaccca ggctggagtg cagtggcaca   4140

tttctgctca ctgcaacctc ctcctccctg ggttcaagca atttcag                 4187
```

<210> SEQ ID NO 40
<211> LENGTH: 4166
<212> TYPE: DNA
<213> ORGANISM: Artificial Sequence
<220> FEATURE:
<223> OTHER INFORMATION: Made in Lab - AAV expression cassette construct

<400> SEQUENCE: 40

```
ctctgggctc tggagacgac ttacggtaaa tggcccgcct ggctgaccgc ccaacgaccc     60

ccgcccattg acgtcaataa tgacgtatgt tcccatagta acgccaatag ggactttcca    120

ttgacgtcaa tgggtggagt atttacggta aactgcccac ttggcagtac atcaagtgta    180

tcatatgcca agtccgcccc ctattgacgt caatgacggt aaatggcccg cctggcatta    240

tgcccagtac atgaccttac gggactttcc tacttggcag tacatctacg tattagtcat    300

cgctattacc atggtgatgc ggttttggca gtacaccaat gggcgtggat agcggtttga    360

ctcacgggga tttccaagtc tccaccccat tgacgtcaat gggagtttgt tttggcacca    420

aaatcaacgg gactttccaa aatgtcgtaa taaccccgcc ccgttgacgc aaatgggcgg    480

taggcgtgta cggtgggagg tctatataag cagagctcgt ttagtgaacc gtcagatcgc    540

ctggagaggc catccacgct gttttgacct ccatagtgga caccgggacc gatccagcct    600

ccgcggccgg gaacggtgca ttggaacgcg gattccccgt gccaagagtg actcagatcc    660

tcactctctt ccgcatcgct gtctgcgagg gccagctgtt gggctcgcgg ttgaggacaa    720

actcttcgcg gtctttccag tactcttgga tcggaaaccc gtcggcctcc gaacggtact    780

ccgccaccga gggacctgag cgagtccgca tcgaccggat cggaaaacct ctcgagaaag    840

gcgtctaacc agtcacagtc gcaaggtagg ctgagcaccg tggcgggcgg cagcgggtgg    900

cggtcggggt tgtttctggc ggaggtgctg ctgatgatgt aattaaagta ggcggtcttg    960

agacggcgga tggtcgaggt gaggtgtggc aggcttgaga tccagctgtt ggggtgagta   1020

ctccctctca aaagcgggca ttacttctgc gctaagattg tcagtttcca aaaacgagga   1080

ggatttgata ttcacctggc ccgatctggc catacacttg agtgacaatg acatccactt   1140
```

-continued

```
tgcctttctc tccacaggtg tccactccca ggtccaagtt taaacgccgc cacccaccat   1200
gattgtgttt gtccggttca actcctccca tggtttcccg gtggaagtgg actcagacac   1260
cagcatcttc caactgaagg aagtggtggc caagcgtcag gggtcccgg cagaccagtt    1320
gagagtgatc ttcgctggaa aggaactgag aaacgactgg actgtgcaga actgtgacct   1380
ggaccaacag tccattgtgc acattgtcca gcggccttgg cggaaaggtc aagagatgaa   1440
cgccactggt ggagatgacc ccaggaatgc agctgggggc tgtgaacggg aacctcagag   1500
cctgaccaga gtggacctca gctcctctgt cctcccggga gactccgtgg gactggcagt   1560
cattctgcac actgacagcc gcaaggattc ccccccctgcg ggttcaccag ctggacggtc   1620
catctacaac tccttctatg tgtactgcaa gggaccctgc cagagggtgc agccgggaaa   1680
gctcagagtg cagtgcagca cttgcagaca agccaccctg accctgaccc agggcccatc   1740
ctgctgggat gatgtcctga tccccaaccg gatgtcaggg gaatgccaaa gccctcactg   1800
ccctggaacc tcggccgagt tcttcttcaa atgtggagcc caccccacct cggacaagga   1860
aacctcggtg gcccttcacc tcattgccac caactcccgc aacatcacct gtatcacttg   1920
cactgatgtt cgctctccgg tgctggtgtt ccagtgcaac tcccgacacg tgatctgcct   1980
ggactgcttc cacctgtact gtgtgaccag actgaatgac aggcagtttg tccacgaccc   2040
ccaactgggc tactccttgc cttgtgtggc tggctgcccc aactccctga tcaaggagtt   2100
gcaccacttc cggatcctgg gagaggaaca gtacaacaga taccagcagt acggggcaga   2160
ggaatgtgtc ctccaaatgg ggggagtgct gtgcccccgg cctggttgtg gagctggcct   2220
cctgccggaa cctgaccagc ggaaggtcac ttgcgagggt ggaaacggcc tgggctgtgg   2280
cttcgccttc tgtcgggagt gcaaggaggc ctaccacgaa ggagagaatgct ccgcggtgtt 2340
tgaagcctca gggaccacca cacaagccta cagagtggat gagagggcag cggagcaggc   2400
ccgctgggaa gcggcctcca aggagactat caagaaaacc accaagccat gccctaggtg   2460
ccatgtgcct gtggaaaaga atggaggctg catgcacatg aagtgccccc agccacagtg   2520
ccgccttgaa tggtgctgga actgtggctg cgagtggaac agagtgtgta tgggggacca   2580
ctggtttgat gtgtgataat ggattcctgt taatcaacct ctggattaca aaatttgtga   2640
aagattgact ggtattctta actatgttgc tccttttacg ctatgtggat acgctgcttt   2700
aatgcctttg tatcatgcta ttgcttcccg tatggctttc attttctcct ccttgtataa   2760
atcctggttg ctgtctcttt atgaggagtt gtggcccgtt gtcaggcaac gtggcgtggt   2820
gtgcactgtg tttgctgacg caacccccac tggttggggc attgccacca cctgtcagct   2880
cctttccggg actttcgctt tccccctccc tattgccacg gcggaactca tcgccgcctg   2940
ccttgcccgc tgctggacag gggctcggct gttgggcact gacaattccg tggtgttgtc   3000
ggggaagctg acgtcctttc cgcggctgct cgcctgtgtt gccacctgga ttctgcgcgg   3060
gacgtccttc tgctacgtcc cttcggccct caatccagcg gaccttcctt cccgcggcct   3120
gctgccggct ctgcggcctc ttccgcctct tcgccttcgc cctcagacga gtcggatctc   3180
cctttgggcc gcctccccgc ccatgtatct tttcacctg tgccttgttt ttgcctgtgt    3240
tccgcgtcct acttttcaag cctccaagct gtgccttggg cggctttggg gcatggacat   3300
agatccctat aaagaatttg gttcatctta tcagttgttg aattttcttc ctttggacgc   3360
tggagcctcg gtagccgttc ctcctgcccg ctgggcctcc caacgggccc tcctcccctc   3420
cttgcaccgg cccttcctgg tctttgaata aattcattgc tggctaataa aggaaattta   3480
ttttcattgc aatagtgtgt tggaattttt tgtgtctctc actcggaaga acatatggga   3540
```

gggcaaatca tttaaaacat cagaatgagt atttggttta gagtttggca acatatgccc 3600
atatgctggc tgccatgaac aaaggttggc tataaagagg tcatcagtat atgaaacagc 3660
cccctgctgt ccattcctta ttccatagaa aagccttgac ttgaggttag attttttta 3720 tattttgttt tgtgttattt ttttctttaa catccctaaa attttcctta catgttttac 3780
tagccagatt tttcctcctc tcctgactac tcccagtcat agctgtccct cttctcttat 3840
ggagatcgtt acccaggctg gagtgcagtg gcacatttct gctcactgca acctcctcct 3900
ccctgggttc aagcaattct cctgcctcag cctcccaagt agctgtgatt ataggtgcac 3960
accaccaagc ctggctaatt tttatatctt tagtagagac gggagtctca ccatgttggc 4020
caggctagtc tctggcaagc catggtaaaa tgtaactatt taaggctgct ttaaattaga 4080
ctaatagcag agtggtcaga ctatactgaa agcttggtga atcacaatta agtacctcaa 4140
agaactattc ttgtttgcct tatcag 4166

<210> SEQ ID NO 41
<211> LENGTH: 4198
<212> TYPE: DNA
<213> ORGANISM: Artificial Sequence
<220> FEATURE:
<223> OTHER INFORMATION: Made in Lab - AAV expression cassette construct

<400> SEQUENCE: 41
ctctggagac gcgttacata acttacggta aatggcccgc ctggctgacc gcccaacgac 60
ccccgcccat tgacgtcaat aatgacgtat gttcccatag taacgccaat agggactttc 120
cattgacgtc aatgggtgga gtatttacgg taaactgccc acttggcagt acatcaagtg 180
tatcatatgc caagtacgcc ccctattgac gtcaatgacg gtaaatggcc cgcctggcat 240
tatgcccagt acatgacctt atgggacttt cctacttggc agtacatcta cgtattagtc 300
atcgctatta ccactgcaga gggccctgcg tatgagtgca agtgggtttt aggaccagga 360
tgaggcgggg tgggggtgcc tacctgacga ccgaccccga cccactggac aagcacccaa 420
cccccattcc ccaaattgcg catcccctat cagagagggg gaggggaaac aggatgcggc 480
gaggcgcgtg cgcactgcca gcttcagcac cgcggacagt gccttcgccc ccgcctggcg 540
gcgcgcgcca ccgccgcctc agcactgaag gcgcgctgac gtcactcgcc ggtcccccgc 600
aaactcccct tcccggccac cttggtcgcg tccgcgccgc cgccggccca gccggaccgc 660
accacgcgag gcgcgagata ggggggcacg ggcgcgacca tctgcgctgc ggcgccggcg 720
actcagcgct gcctcagtct gcggtgggca gcggaggagt cgtgtcgtgc ctgagagcgc 780
agctgtgctc ctgggcaccg cgcagtccgc ccccgcggct cctggccaga ccacccctag 840 gacccctgc cccaagtcgc aggggaattc aaagcaagcc gccaccatga ttgtgtttgt 900
ccggttcaac tcctcccatg gtttcccggt ggaagtggac tcagacacca gcatcttcca 960
actgaaggaa gtggtggcca agcgtcaggg ggtcccggca gaccagttga gagtgatctt 1020
cgctggaaag gaactgagaa acgactggac tgtgcagaac tgtgacctgg accaacagtc 1080
cattgtgcac attgtccagc ggccttggcg gaaaggtcaa gagatgaacg ccactggtgg 1140
agatgacccc aggaatgcag ctgggggctg tgaacgggaa cctcagagcc tgaccagagt 1200
ggacctcagc tcctctgtcc tcccgggaga ctccgtggga ctggcagtca ttctgcacac 1260
tgacagccgc aaggattccc cccctgcggg ttcaccagct ggacggtcca tctacaactc 1320
cttctatgtg tactgcaagg gaccctgcca gagggtgcag ccgggaaagc tcagagtgca 1380

-continued

```
gtgcagcact tgcagacaag ccaccctgac cctgacccag ggcccatcct gctgggatga   1440
tgtcctgatc cccaaccgga tgtcagggga atgccaaagc cctcactgcc ctggaacctc   1500
ggccgagttc ttcttcaaat gtggagccca ccccacctcg gacaaggaaa cctcggtggc   1560
ccttcacctc attgccacca actcccgcaa catcacctgt atcacttgca ctgatgttcg   1620
ctctccggtg ctggtgttcc agtgcaactc ccgacacgtg atctgcctgg actgcttcca   1680
cctgtactgt gtgaccagac tgaatgacag gcagtttgtc cacgaccccc aactgggcta   1740
ctccttgcct tgtgtggctg gctgccccaa ctccctgatc aaggagttgc accacttccg   1800
gatcctggga gaggaacagt acaacagata ccagcagtac ggggcagagg aatgtgtcct   1860
ccaaatgggg ggagtgctgt gcccccggcc tggttgtgga gctggcctcc tgccggaacc   1920
tgaccagcgg aaggtcactt gcgagggtgg aaacggcctg ggctgtggct tcgccttctg   1980
tcgggagtgc aaggaggcct accacgaagg agaatgctcc gcggtgtttg aagcctcagg   2040
gaccaccaca caagcctaca gagtggatga gagggcagcg gagcaggccc gctgggaagc   2100
ggcctccaag gagactatca agaaaaccac caagccatgc cctaggtgcc atgtgcctgt   2160
ggaaaagaat ggaggctgca tgcacatgaa gtgcccccag ccacagtgcc gccttgaatg   2220
gtgctggaac tgtggctgcg agtggaacag agtgtgtatg gggaccact ggtttgatgt    2280
gtgataatgg actattcgag catcttaccg ccatttattc ccatatttgt tctgtttttc   2340
ttgatttggg tatacattta aatgttaata aaacaaaatg gtggggcaat catttacatt   2400
tttagggata tgtaattact agttcaggtg tattgccaca agacaaacat gttaagaaac   2460
tttcccgtta tttacgctct gttcctgtta atcaacctct ggattacaaa atttgtgaaa   2520
gattgactga tattcttaac tatgttgctc cttttacgct gtgtggatat gctgctttaa   2580
tgcctctgta tcatgctatt gcttcccgta cggctttcgt tttctcctcc ttgtataaat   2640
cctggttgct gtctctttat gaggagttgt ggcccgttgt ccgtcaacgt ggcgtggtgt   2700
gctctgtgtt tgctgacgca acccccactg gctggggcat tgccaccacc tgtcaactcc   2760
tttctgggac tttcgctttc cccctcccga tcgccacggc agaactcatc gccgcctgcc   2820
ttgcccgctg ctggacaggg gctaggttgc tgggcactga taattccgtg gtgttgtcgg   2880
ggaagggcct ttaattaggc tggagcctcg gtagccgttc ctcctgcccg ctgggcctcc   2940
caacgggccc tcctcccctc cttgcaccgg cccttcctgg tctttgaata aattatctta   3000
gcttattgcc agccatctgt tgtttgcccc tcccccgtgc cttccttgac cctggaaggt   3060
gccactccca ctgtcctttc ctaataaaat gaggaaattg catcgcattg tctgagtagg   3120
tgtcattcta ttctgggggg tggggtgggg caggacagca agggggagga ttgggaatac   3180
aatagcaggc atgctgggga tgcggtgggc tctatgggta cccaggtgct gaagaattga   3240
cccggttcct cctggggtta cccaggctgg agtgcagtgg cacaattctg ctcactgcaa   3300
cctcctcctc cctgggttca agcaattctc ctgcctcagc ctcccaagta gctgtgatta   3360
taggtgcaca ccaccaagcc tggctaattt ttatatcttt agtagagacg ggagtctcac   3420
catgttggcc aggctagtct ctggcaagcc atggtaaaat gtaactattt aaggctgctt   3480
taaattagac taatagcaga gtggtcagac tatactgaaa gcttggtgaa tcacaattaa   3540
gtacctcaaa gaactattct tgtttgcctt attcctatgt aaataactga aatctttgtt   3600
tttcttccta aaaggggtca tgttgatttt tacttacaat gtattttaag tttgtcactc   3660
taaatggtta tgagcaagtt taagaaaaat cttcagcaaa tactacctta gattatgacc   3720
ccaaaacaca tttacttatg attatgttga aaacataggg tctggggaaa aaggatttta   3780
```

aaataagaag aaaaagaaga cttgggactt aaaaagtctt ttagaggcca gctcaccaac 3840
attcagaaca cccagtctgt gttgcacaat atgttactta ggtataaatc aaggattcat 3900
gtaattttgt cattccttgc gtgatatttt aaaaaacatt ctgtgtaagg tatttataaa 3960
gctctcttct aaaaatacaa aaatttgtgg ggccttgtag tcccagctac ttgggaggct 4020
gaggcaggag gatttcttga actgggaggc agagcttgca gtgagcccac tgcactccag 4080
cctgggcaac agagtagaac tcctctcaaa aaaaaaaaaa aaaaagaaag aaagaaaaaa 4140
aagtggactg tgaaaactga aaggactaga aaaactacac tacaaagata cagatcag 4198

<210> SEQ ID NO 42
<211> LENGTH: 4198
<212> TYPE: DNA
<213> ORGANISM: Artificial Sequence
<220> FEATURE:
<223> OTHER INFORMATION: Made in Lab - AAV expression cassette construct

<400> SEQUENCE: 42
ctctggagac gcgttacata acttacggta aatggcccgc ctggctgacc gcccaacgac 60
ccccgcccat tgacgtcaat aatgacgtat gttcccatag taacgccaat agggactttc 120
cattgacgtc aatgggtgga gtatttacgg taaactgccc acttggcagt acatcaagtg 180
tatcatatgc caagtacgcc ccctattgac gtcaatgacg gtaaatggcc cgcctggcat 240
tatgcccagt acatgacctt atgggacttt cctacttggc agtacatcta cgtattagtc 300
atcgctatta ccatggtcga ggtgagcccc acgttctgct tcactctccc catctccccc 360
ccctccccac ccccaatttt gtatttattt atttttaat tattttgtgc agcgatgggg 420
gcgggggggg ggggggcgcg cgccaggcgg ggcggggcgg ggcgaggggc ggggcggggc 480
gaggcggaga ggtgcggcgg cagccaatca gagcggcgcg ctccgaaagt ttccttttat 540
ggcgaggcgg cggcggcggc ggccctataa aaagcgaagc gcgcggcggg cgggagtcgc 600
tgcgcgctgc cttcgccccg tgccccgctc cgccgccgcc tcgcgccgcc cgccccggct 660
ctgactgacc gcgttactcc cacaggtgag cgggcgggac ggcccttctc ctccgggctg 720
taattagcgc ttggtttaat gacggcttgt ttcttttctg tggctgcgtg aaagccttga 780
ggggctccgg gagggccctt tgtgcggggg gagcggctcg gggggtgcgt gcgtgtgtgt 840
gtgcgtgggg agcgccgcgt gcggctccgc gctgcccggc ggctgtgagc gctgcgggcg 900
cggcgcgggg ctttgtgcgc tccgcagtgt gcgcgagggg agcgcggccg gggcggtgc 960 cccgcggtgc ggggggggct gcgaggggaa caaaggctgc gtgcggggtg tgtgcgtggg 1020
ggggtgagca gggggtgtgg gcgcgtcggt cgggctgcaa ccccccctgc acccccctcc 1080
ccgagttgct gagcacggcc cggcttcggg tgcggggctc cgtacggggc gtggcgcggg 1140
gctcgccgtg ccgggcgggg ggtggcggca ggtgggggtg ccgggcgggg cggggccgcc 1200
tcgggccggg gagggctcgg gggaggggcg cggcggcccc cggagcgccg gcggctgtcg 1260
aggcgcggcg agccgcagcc attgcctttt atggtaatcg tgcgagaggg cgcagggact 1320
tcctttgtcc caaatctgtg cggagccgaa atctgggagg cgccgccgca ccccctctag 1380
cgggcgcggg gcgaagcggt gcggcgccgg caggaaggaa atgggcgggg agggccttcg 1440
tgcgtcgccg cgccgccgtc cccttctccc tctccagcct cggggctgtc cgcgggggga 1500
cggctgcctt cggggggac ggggcagggc ggggttcggc ttctggcgtg tgaccggcgg 1560
ctctagagcc tctgctaacc atgttcatgc cttcttcttt ttcctacagc tcctgggcaa 1620

-continued

```
cgtgctggtt attgtgctgt ctcatcattt tggcaaagaa ttcggcttga tcgaagccgt   1680
ctcaggggaa ttcaaagcaa gccgccacca tgattgtgtt tgtccggttc aactcctccc   1740
atggtttccc ggtggaagtg gactcagaca ccagcatctt ccaactgaag gaagtggtgg   1800
ccaagcgtca gggggtcccg gcagaccagt tgagagtgat cttcgctgga aaggaactga   1860
gaaacgactg gactgtgcag aactgtgacc tggaccaaca gtccattgtg cacattgtcc   1920
agcggccttg gcggaaaggt caagagatga acgccactgg tggagatgac cccaggaatg   1980
cagctggggg ctgtgaacgg gaacctcaga gcctgaccag agtggacctc agctcctctg   2040
tcctcccggg agactccgtg ggactggcag tcattctgca cactgacagc cgcaaggatt   2100
ccccccctgc gggttcacca gctggacggt ccatctacaa ctccttctat gtgtactgca   2160
agggaccctg ccagagggtg cagccgggaa agctcagagt gcagtgcagc acttgcagac   2220
aagccaccct gaccctgacc cagggcccat cctgctggga tgatgtcctg atccccaacc   2280
ggatgtcagg ggaatgccaa agccctcact gccctggaac ctcggccgag ttcttcttca   2340
aatgtggagc ccaccccacc tcggacaagg aaacctcggt ggcccttcac ctcattgcca   2400
ccaactcccg caacatcacc tgtatcactt gcactgatgt tcgctctccg gtgctggtgt   2460
tccagtgcaa ctcccgacac gtgatctgcc tggactgctt ccacctgtac tgtgtgacca   2520
gactgaatga caggcagttt gtccacgacc cccaactggg ctactccttg ccttgtgtgg   2580
ctggctgccc caactccctg atcaaggagt tgcaccactt ccggatcctg ggagaggaac   2640
agtacaacag ataccagcag tacggggcag aggaatgtgt cctccaaatg gggggagtgc   2700
tgtgcccccg gcctggttgt ggagctggcc tcctgccgga acctgaccag cggaaggtca   2760
cttgcgaggg tggaaacggc ctgggctgtg gcttcgcctt ctgtcgggag tgcaaggagg   2820
cctaccacga aggagaatgc tccgcggtgt ttgaagcctc agggaccacc acacaagcct   2880
acagagtgga tgagagggca gcggagcagg cccgctggga agcggcctcc aaggagacta   2940
tcaagaaaac caccaagcca tgccctaggt gccatgtgcc tgtggaaaag aatggaggct   3000
gcatgcacat gaagtgcccc cagccacagt gccgccttga atggtgctgg aactgtggct   3060
gcgagtggaa cagagtgtgt atgggggacc actggtttga tgtgtgataa tggattaatc   3120
aattattgcc agccatctgt tgtttgcccc tcccccgtgc cttccttgac cctggaaggt   3180
gccactccca ctgtcctttc ctaataaaat gaggaaattg catcgcattg tctgagtagg   3240
tgtcattcta ttctgggggg tggggtgggg caggacagca agggggagga ttgggaatac   3300
aatagcaggc atgctgggga tgcggtgggc tctatgggta cccaggtgct gaagaattga   3360
cccggttcct cctggggtta cccaggctgg agtgcagtgg cacatttctg ctcactgcaa   3420
cctcctcctc cctgggttca agcaattctc ctgcctcagc ctcccaagta gctgtgatta   3480
taggtgcaca ccaccaagcc tggctaattt ttatatcttt agtagagacg ggagtctcac   3540
catgttggcc aggctagtct ctggcaagcc atggtaaaat gtaactattt aaggctgctt   3600
taaattagac taatagcaga gtggtcagac tatactgaaa gcttggtgaa tcacaattaa   3660
gtacctcaaa gaactattct tgtttgcctt attcctatgt aaataactga aatctttgtt   3720
tttcttccta aaaggggtca tgttgatttt tacttacaat gtattttaag tttgtcactc   3780
taaatggtta tgagcaagtt taagaaaaat cttcagcaaa tactacctta gattatgacc   3840
ccaaaacaca tttacttatg attatgttga aaacataggg tctggggaaa aagggattta   3900
aaataagaag aaaaagaaga cttgggactt aaaaagtctt ttagaggcca gctcaccaac   3960
attcagaaca cccagtctgt gttgcacaat atgttactta ggtataaatc aaggattcat   4020
```

gtaattttgt cattccttgc gtgatatttt aaaaaacatt ctgtgtaagg tatttataaa 4080
gctctcttct aaaaatacaa aaatttgtgg ggccttgtag tcccagctac ttgggaggct 4140
gaggcaggag gatttcttga actgggaggc agagcttgca gtgagcccac tgcatcag 4198

<210> SEQ ID NO 43
<211> LENGTH: 4166
<212> TYPE: DNA
<213> ORGANISM: Artificial Sequence
<220> FEATURE:
<223> OTHER INFORMATION: Made in Lab - AAV expression cassette construct

<400> SEQUENCE: 43
ctctggagac gcaacctttg gagctaagcc agcaatggta gagggaagat tctgcacgtc 60
ccttccaggc ggcctccccg tcaccacccc ccccaacccg ccccgaccgg agctgagagt 120
aattcataca aaaggactcg cccctgcctt ggggaatccc agggaccgtc gttaaactcc 180
cactaacgta gaacccagag atcgctgcgt tcccgccccc tcacccgccc gctctcgtca 240
tcactgaggt ggagaatagc atgcgtgagg ctccggtgcc cgtcagtggg cagagcgcac 300
atcgcccaca gtccccgaga agttgggggg aggggtcggc aattgaacgg gtgcctagag 360
aaggtggcgc ggggtaaact gggaaagtga tgtcgtgtac tggctccgcc tttttcccga 420
gggtggggga gaaccgtata taagtgcagt agtcgccgtg aacgttcttt ttcgcaacgg 480
gtttgccgcc agaacacagg taagtgccgt gtgtggttcc cgcgggcctg gcctctttac 540
gggttatggc ccttgcgtgc cttgaattac ttccacctgg ctccagtacg tgattcttga 600
tcccgagctg gagccagggg cgggccttgc gctttaggag ccccttcgcc tcgtgcttga 660
gttgaggcct ggcctgggcg ctggggccgc cgcgtgcgaa tctggtggca ccttcgcgcc 720
tgtctcgctg ctttcgataa gtctctagcc atttaaaatt tttgatgacg tgctgcgacg 780
ctttttttct ggcaagatag tcttgtaaat gcgggccagg atctgcacac tggtatttcg 840
gtttttgggc ccgcggccgg cgacggggcc cgtgcgtccc agcgcacatg ttcggcgagg 900
cggggcctgc gagcgcggcc accgagaatc ggacgggggt agtctcaagc tggccggcct 960
gctctggtgc ctggcctcgc gccgccgtgt atcgccccgc cctgggcggc aaggctggcc 1020
cggtcggcac cagttgcgtg agcggaaaga tggccgcttc ccggccctgc tccagggggc 1080
tcaaaatgga ggacgcggcg ctcgggagag cgggcgggtg agtcacccac acaaaggaaa 1140
agggcctttc cgtcctcagc cgtcgcttca tgtgactcca cggagtaccg ggcgccgtcc 1200
aggcacctcg attagttctg gagcttttgg agtacgtcgt ctttaggttg gggggagggg 1260
ttttatgcga tggagtttcc ccacactgag tgggtggaga ctgaagttag gccagcttgg 1320
cacttgatgt aattctcctt ggaatttggc ctttttgagt ttggatcttg gttcattctc 1380
aagcctcaga cagtggttca aagttttttt cttccatttc aggtgtcgtg aacacgtctc 1440
aggggaattc aaagcaagcc gccaccatga ttgtgtttgt ccggttcaac tcctcccatg 1500
gtttcccggt ggaagtggac tcagacacca gcatcttcca actgaaggaa gtggtggcca 1560
agcgtcaggg ggtcccggca gaccagttga gagtgatctt cgctggaaag gaactgagaa 1620
acgactggac tgtgcagaac tgtgacctgg accaacagtc cattgtgcac attgtccagc 1680
ggccttggcg gaaaggtcaa gagatgaacg ccactggtgg agatgacccc aggaatgcag 1740
ctgggggctg tgaacgggaa cctcagagcc tgaccagagt ggacctcagc tcctctgtcc 1800
tcccgggaga ctccgtggga ctggcagtca ttctgcacac tgacagccgc aaggattccc 1860

-continued

```
ccccctgcggg ttcaccagct ggacggtcca tctacaactc cttctatgtg tactgcaagg   1920
gaccctgcca gagggtgcag ccgggaaagc tcagagtgca gtgcagcact tgcagacaag   1980
ccaccctgac cctgacccag ggcccatcct gctgggatga tgtcctgatc cccaaccgga   2040
tgtcagggga atgccaaagc cctcactgcc ctggaacctc ggccgagttc ttcttcaaat   2100
gtggagccca ccccacctcg gacaaggaaa cctcggtggc ccttcacctc attgccacca   2160
actcccgcaa catcacctgt atcacttgca ctgatgttcg ctctccggtg ctggtgttcc   2220
agtgcaactc ccgacacgtg atctgcctgg actgcttcca cctgtactgt gtgaccagac   2280
tgaatgacag gcagtttgtc cacgaccccc aactgggcta ctccttgcct tgtgtggctg   2340
gctgccccaa ctccctgatc aaggagttgc accacttccg gatcctggga gaggaacagt   2400
acaacagata ccagcagtac ggggcagagg aatgtgtcct ccaaatgggg ggagtgctgt   2460
gcccccggcc tggttgtgga gctggcctcc tgccggaacc tgaccagcgg aaggtcactt   2520
gcgagggtgg aaacggcctg ggctgtggct tcgccttctg tcgggagtgc aaggaggcct   2580
accacgaagg agaatgctcc gcggtgtttg aagcctcagg gaccaccaca caagcctaca   2640
gagtggatga gagggcagcg gagcaggccc gctgggaagc ggcctccaag gagactatca   2700
agaaaaccac caagccatgc cctaggtgcc atgtgcctgt ggaaaagaat ggaggctgca   2760
tgcacatgaa gtgcccccag ccacagtgcc gccttgaatg gtgctggaac tgtggctgcg   2820
agtggaacag agtgtgtatg gggaccact ggtttgatgt gtgataatgg agctggagcc   2880
tcggtagccg ttcctcctgc ccgctgggcc tcccaacggg ccctcctccc ctccttgcac   2940
cggcccttcc tggtctttga ataaattcat tgctggctaa taaaggaaat ttattttcat   3000
tgcaatagtg tgttggaatt ttttgtgtct ctcactcgga agaacatatg ggagggcaaa   3060
tcatttaaaa catcagaatg agtatttggt ttagagtttg gcaacatatg cccatatgct   3120
ggctgccatg aacaaaggtt ggctataaag aggtcatcag tatatgaaac agccccctgc   3180
tgtccattcc ttattccata gaaaagcctt gacttgaggt tagatttttt ttatattttg   3240
ttttgtgtta tttttttctt taacatccct aaaatttcc ttacatgttt tactagccag   3300
atttttcctc ctctcctgac tactcccagt catagctgtc cctcttctct tatggagatc   3360
gttacccagg ctggagtgca gtggcacatt tctgctcact gcaacctcct cctccctggg   3420
ttcaagcaat tctcctgcct cagcctccca agtagctgtg attataggtg cacaccacca   3480
agcctggcta atttttatat ctttagtaga gacgggagtc tcaccatgtt ggccaggcta   3540
gtctctggca agccatggta aaatgtaact atttaaggct gctttaaatt agactaatag   3600
cagagtggtc agactatact gaaagcttgg tgaatcacaa ttaagtacct caaagaacta   3660
ttcttgtttg ccttattcct atgtaaataa ctgaaatctt tgtttttctt cctaaaaggg   3720
gtcatgttga tttttactta caatgtattt taagtttgtc actctaaatg gttatgagca   3780
agtttaagaa aaatcttcag caaatactac cttagattat gaccccaaaa cacatttact   3840
tatgattatg ttgaaaacat agggtctggg gaaaaaggga tttaaaataa gaagaaaaag   3900
aagacttggg acttaaaaag tcttttagag gccagctcac caacattcag aacacccagt   3960
ctgtgttgca caatatgtta cttaggtata aatcaaggat tcatgtaatt ttgtcattcc   4020
ttgcgtgata ttttaaaaaa cattctgtgt aaggtattta taaagctctc ttctaaaaat   4080
acaaaaattt gtggggcctt gtagtcccag ctacttggga ggctgaggca ggaggatttc   4140
ttgaactggg aggcagagct tgtcag                                         4166
```

<210> SEQ ID NO 44
<211> LENGTH: 4173
<212> TYPE: DNA
<213> ORGANISM: Artificial Sequence
<220> FEATURE:
<223> OTHER INFORMATION: Made in Lab - AAV expression cassette construct

<400> SEQUENCE: 44
ctctggagac gcgttacata acttacggta aatggcccgc ctggctgacc gcccaacgac 60
ccccgcccat tgacgtcaat aatgacgtat gttcccatag taacgccaat agggactttc 120
cattgacgtc aatgggtgga gtatttacgg taaactgccc acttggcagt acatcaagtg 180
tatcatatgc caagtacgcc ccctattgac gtcaatgacg gtaaatggcc cgcctggcat 240
tatgcccagt acatgacctt atgggacttt cctacttggc agtacatcta cgtattagtc 300
atcgctatta ccagcccagc accccaaggc ggccaacgcc aaaactctcc ctcctcctct 360
tcctcaatct cgctctcgct cttttttttt ttcgcaaaag gaggggagag gggtaaaaa 420 aatgctgcac tgtgcggcga agccggtgag tgagcggcgc ggggccaatc agcgtgcgcc 480
gttccgaaag ttgcctttta tggctcgagc ggccgcggcg gcgccctata aaacccagcg 540
gcgcgacgcg ccaccaccgc cgagtccgcg tccgcccgcg agcacagagc ctcgcctttg 600
ccgatccgcc gcccgtccac acccgccgcc aggtaagccc ggccagccga ccggggcatg 660
cggccgcggc ccttcgcccg tgcagagccg ccgtctgggc cgcagcgggg ggcgcatggg 720
gcggaaccgg accgccgtgg ggggcgcggg agaagcccct gggcctccgg agatggggga 780
caccccacgc cagttcgcag gcgcgaggcc gcgctcgggc gggcgcgctc cgggggtgcc 840
gctctcgggg cgggggcaac cggcggggtc tttgtctgag ccgggctctt gccaatgggg 900
atcgcacggt gggcgcggcg tagcccccgt caggcccggt gggggctggg gcgccatgcg 960
cgtgcgcgct ggtcctttgg gcgctaactg cgtgcgcgct gggaattggc gctaattgcg 1020
cgtgcgcgct gggactcaat ggcgctaatc gcgcgtgcgt tctggggccc gggcgcttgc 1080
gccacttcct gcccgagccg ctggcgcccg agggtgtggc cgctgcgtgc gcgcgcgcga 1140
cccggtcgct gtttgaaccg ggcggaggcg gggctggcgc ccggttggga gggggttggg 1200
gcctggcttc ctgccgcgcg ccgcggggac gcctccgacc agtgtttgcc ttttatggta 1260
ataacgcggc cggcccggct tcctttgtcc ccaatctggg cgcgcgccgg cgccccctgg 1320
cggcctaagg actcggcgcg ccggaagtgg ccagggcggc agcggctgct cttggcggcc 1380
ccgaggtgac tatagccttc ttttgtgtct tgatagttcg ccagcctctg ctaaccatgt 1440
tcatgccttc ttctttttcc tacagctcct gggcaacgtg ctggttattg tgctgtctca 1500
tcattttggc aaagaattcg gcttgatcga agccgtctca ggggaattca aagcaagccg 1560
ccaccatgat tgtgtttgtc cggttcaact cctcccatgg tttcccggtg gaagtggact 1620
cagacaccag catcttccaa ctgaaggaag tggtggccaa gcgtcagggg gtcccggcag 1680
accagttgag agtgatcttc gctggaaagg aactgagaaa cgactggact gtgcagaact 1740
gtgacctgga ccaacagtcc attgtgcaca ttgtccagcg gccttggcgg aaaggtcaag 1800
agatgaacgc cactggtgga gatgacccca ggaatgcagc tgggggctgt gaacgggaac 1860
ctcagagcct gaccagagtg gacctcagct cctctgtcct cccgggagac tccgtgggac 1920
tggcagtcat tctgcacact gacagccgca aggattcccc ccctgcgggt tcaccagctg 1980
gacggtccat ctacaactcc ttctatgtgt actgcaaggg accctgccag agggtgcagc 2040
cgggaaagct cagagtgcag tgcagcactt gcagacaagc caccctgacc ctgacccagg 2100

-continued

```
gcccatcctg ctgggatgat gtcctgatcc ccaaccggat gtcaggggaa tgccaaagcc   2160
ctcactgccc tggaacctcg gccgagttct tcttcaaatg tggagcccac cccacctcgg   2220
acaaggaaac ctcggtggcc cttcacctca ttgccaccaa ctcccgcaac atcacctgta   2280
tcacttgcac tgatgttcgc tctccggtgc tggtgttcca gtgcaactcc cgacacgtga   2340
tctgcctgga ctgcttccac ctgtactgtg tgaccagact gaatgacagg cagtttgtcc   2400
acgaccccca actgggctac tccttgcctt gtgtggctgg ctgccccaac tccctgatca   2460
aggagttgca ccacttccgg atcctgggag aggaacagta caacagatac cagcagtacg   2520
gggcagagga atgtgtcctc caaatggggg gagtgctgtg cccccggcct ggttgtggag   2580
ctggcctcct gccggaacct gaccagcgga aggtcacttg cgagggtgga aacggcctgg   2640
gctgtggctt cgccttctgt cgggagtgca aggaggccta ccacgaagga gaatgctccg   2700
cggtgtttga agcctcaggg accaccacac aagcctacag agtggatgag agggcagcgg   2760
agcaggcccg ctgggaagcg gcctccaagg agactatcaa gaaaaccacc aagccatgcc   2820
ctaggtgcca tgtgcctgtg gaaaagaatg gaggctgcat gcacatgaag tgcccccagc   2880
cacagtgccg ccttgaatgg tgctggaact gtggctgcga gtggaacaga gtgtgtatgg   2940
gggaccactg gtttgatgtg tgataatgga ttcctgtaaa caggcctatt gattggaaag   3000
tttgtcaacg aattgtgggt cttttggggt ttgctgcccc ttttacgcaa tgtggatatc   3060
ctgctttaat gcctttatat gcatgtatac aagcaaaaca ggcttttact ttctcgccaa   3120
cttacaaggc ctttctcagt aaacagtata tgaccctta ccccgttgct cggcaacggc   3180
ctggtctgtg ccaagtgttt gctgacgcaa cccccactgg ttggggcttg gccataggcc   3240
atcagcgcat gcgtggaacc tttgtgtctc ctctgccgat ccatactgcg gaactcctag   3300
ccgcttgttt tgctcgcagc tggactggag caaacctcat cgggaccgac aattctgtcg   3360
tactctcccg caagcactca ccgtttccgc ggctgctcgc ctgtgttgcc acctggattc   3420
tgcgcgggac gtccttctgc tacgtccctt cggccctcaa tccagcggac cttccttccc   3480
gcggcctgct gccggctctg cggcctcttc cgcctcttcg ccttcgccct cagacgagtc   3540
ggatctccct ttgggccgcc tccccgccca tgtatctttt tcacctgtgc cttgtttttg   3600
cctgtgttcc gcgtcctact tttcaagcct ccaagctgtg ccttgggcgg ctttggggca   3660
tggacataga tccctataaa gaatttggtt catcttatca gttgttgaat tttcttcctt   3720
tggacgctgg agcctcggta gccgttcctc ctgcccgctg ggcctcccaa cgggccctcc   3780
tcccctcctt gcaccggccc ttcctggtct ttgaataaat tcattgcttg ccagccatct   3840
gttgtttgcc cctcccccgt gccttccttg accctggaag gtgccactcc cactgtcctt   3900
tcctaataaa atgaggaaat tgcatcgcat tgtctgagta ggtgtcattc tattctgggg   3960
ggtggggtgg ggcaggacag caagggggag gattgggaat acaatagcag gcatgctggg   4020
gatgcggtgg gctctatggg tacccaggtg ctgaagaatt gacccggttc ctcctggggt   4080
tacccaggct ggagtgcagt ggcacatttc tgctcactgc aacctcctcc tccctgggtt   4140
caagcaattc tcctgcctca gcctcccaat cag                                4173
```

```
<210> SEQ ID NO 45
<211> LENGTH: 4172
<212> TYPE: DNA
<213> ORGANISM: Artificial Sequence
<220> FEATURE:
<223> OTHER INFORMATION: Made in Lab - AAV expression cassette construct

<400> SEQUENCE: 45
```

```
ctctggagac gcgttacata acttacggta aatggcccgc ctggctgacc gcccaacgac     60
ccccgcccat tgacgtcaat aatgacgtat gttcccatag taacgccaat agggactttc    120
cattgacgtc aatgggtgga gtatttacgg taaactgccc acttggcagt acatcaagtg    180
tatcatatgc caagtacgcc ccctattgac gtcaatgacg gtaaatggcc cgcctggcat    240
tatgcccagt acatgacctt atgggacttt cctacttggc agtacatcta cgtattagtc    300
atcgctatta ccactgcaga gggccctgcg tatgagtgca agtgggtttt aggaccagga    360
tgaggcgggg tgggggtgcc tacctgacga ccgaccccga cccactggac aagcacccaa    420
cccccattcc ccaaattgcg catcccctat cagagagggg gaggggaaac aggatgcggc    480
gaggcgcgtg cgcactgcca gcttcagcac cgcggacagt gccttcgccc ccgcctggcg    540
gcgcgcgcca ccgccgcctc agcactgaag gcgcgctgac gtcactcgcc ggtcccccgc    600
aaactcccct tcccggccac cttggtcgcg tccgcgccgc cgccggccca gccggaccgc    660
accacgcgag gcgcgagata gggggcacg ggcgcgacca tctgcgctgc ggcgccggcg     720
actcagcgct gcctcagtct gcggtgggca gcggaggagt cgtgtcgtgc ctgagagcgc    780
agctgtgctc ctgggcaccg cgcagtccgc ccccgcggct cctggccaga ccacccctag    840
gacccctgc cccaagtcgc aggggaattc aaagcaagcc gccaccatga ttgtgtttgt     900
ccggttcaac tcctcccatg gtttcccggt ggaagtggac tcagacacca gcatcttcca    960
actgaaggaa gtggtggcca agcgtcaggg ggtcccggca gaccagttga gagtgatctt   1020
cgctggaaag gaactgagaa acgactggac tgtgcagaac tgtgacctgg accaacagtc   1080
cattgtgcac attgtccagc ggccttggcg gaaaggtcaa gagatgaacg ccactggtgg   1140
agatgacccc aggaatgcag ctgggggctg tgaacgggaa cctcagagcc tgaccagagt   1200
ggacctcagc tcctctgtcc tcccgggaga ctccgtggga ctggcagtca ttctgcacac   1260
tgacagccgc aaggattccc cccctgcggg ttcaccagct ggacggtcca tctacaactc   1320
cttctatgtg tactgcaagg gaccctgcca gagggtgcag ccgggaaagc tcagagtgca   1380
gtgcagcact tgcagacaag ccaccctgac cctgacccag ggcccatcct gctgggatga   1440
tgtcctgatc cccaaccgga tgtcagggga atgccaaagc cctcactgcc ctggaacctc   1500
ggccgagttc ttcttcaaat gtggagccca ccccacctcg gacaaggaaa cctcggtggc   1560
ccttcacctc attgccacca actcccgcaa catcacctgt atcacttgca ctgatgttcg   1620
ctctccggtg ctggtgttcc agtgcaactc ccgacacgtg atctgcctgg actgcttcca   1680
cctgtactgt gtgaccagac tgaatgacag gcagtttgtc cacgaccccc aactgggcta   1740
ctccttgcct tgtgtggctg gctgccccaa ctccctgatc aaggagttgc accacttccg   1800
gatcctggga gaggaacagt acaacagata ccagcagtac ggggcagagg aatgtgtcct   1860
ccaaatgggg ggagtgctgt gcccccggcc tggttgtgga gctggcctcc tgccggaacc   1920
tgaccagcgg aaggtcactt gcgagggtgg aaacggcctg ggctgtggct tcgccttctg   1980
tcgggagtgc aaggaggcct accacgaagg agaatgctcc gcggtgtttg aagcctcagg   2040
gaccaccaca caagcctaca gagtggatga gagggcagcg gagcaggccc gctgggaagc   2100
ggcctccaag gagactatca agaaaaccac caagccatgc cctaggtgcc atgtgcctgt   2160
ggaaaagaat ggaggctgca tgcacatgaa gtgcccccag ccacagtgcc gccttgaatg   2220
gtgctggaac tgtggctgcg agtggaacag agtgtgtatg gggaccact ggtttgatgt    2280
gtgataatgg attcctgtta atcaacctct ggattacaaa atttgtgaaa gattgactgg   2340
```

tattcttaac tatgttgctc cttttacgct atgtggatac gctgctttaa tgcctttgta 2400
tcatgctatt gcttcccgta tggctttcat tttctcctcc ttgtataaat cctggttgct 2460
gtctctttat gaggagttgt ggcccgttgt caggcaacgt ggcgtggtgt gcactgtgtt 2520
tgctgacgca acccccactg gttggggcat tgccaccacc tgtcagctcc tttccgggac 2580
tttcgctttc cccctcccta ttgccacggc ggaactcatc gccgcctgcc ttgcccgctg 2640
ctggacaggg gctcggctgt tgggcactga caattccgtg gtgttgtcgg ggaagctgac 2700
gtcctttccg cggctgctcg cctgtgttgc cacctggatt ctgcgcggga cgtccttctg 2760
ctacgtccct tcggccctca atccagcgga ccttccttcc cgcggcctgc tgccggctct 2820
gcggcctctt ccgcctcttc gccttcgccc tcagacgagt cggatctccc tttgggccgc 2880
ctccccgccc atgtatcttt ttcacctgtg ccttgttttt gcctgtgttc cgcgtcctac 2940
ttttcaagcc tccaagctgt gccttgggcg gctttggggc atggacatag atccctataa 3000
agaatttggt tcatcttatc agttgttgaa ttttcttcct ttggacgctg gagcctcggt 3060
agccgttcct cctgcccgct gggcctccca acgggccctc ctcccctcct tgcaccggcc 3120
cttcctggtc tttgaataaa ttcattgcct gcccgggtgg catccctgtg accccteccc 3180 agtgcctctc ctggccctgg aagttgccac tccagtgccc accagccttg tcctaataaa 3240
attaagttgc atcattttgt ctgactaggt gtccttctat aatattatgg ggtggagggg 3300
ggtggtatgg agcaaggggc ccaagttggg aagaaacctg tagggcctgc gttacccagg 3360
ctggagtgca gtggcacatt tctgctcact gcaacctcct cctccctggg ttcaagcaat 3420
tctcctgcct cagcctccca agtagctgtg attataggtg cacaccacca agcctggcta 3480
atttttatat ctttagtaga gacgggagtc tcaccatgtt ggccaggcta gtctctggca 3540
agccatggta aaatgtaact atttaaggct gctttaaatt agactaatag cagagtggtc 3600
agactatact gaaagcttgg tgaatcacaa ttaagtacct caaagaacta ttcttgtttg 3660
ccttattcct atgtaaataa ctgaaatctt tgtttttctt cctaaaaggg gtcatgttga 3720
tttttactta caatgtattt taagtttgtc actctaaatg gttatgagca agtttaagaa 3780
aaatcttcag caaatactac cttagattat gaccccaaaa cacatttact tatgattatg 3840
ttgaaaacat agggtctggg gaaaaaggga tttaaaataa gaagaaaaag aagacttggg 3900
acttaaaaag tcttttagag gccagctcac caacattcag aacacccagt ctgtgttgca 3960
caatatgtta cttaggtata aatcaaggat tcatgtaatt ttgtcattcc ttgcgtgata 4020
ttttaaaaaa cattctgtgt aaggtattta taaagctctc ttctaaaaat acaaaaattt 4080
gtggggcctt gtagtcccag ctacttggga ggctgaggca ggaggatttc ttgaactggg 4140
aggcagagct tgcagtgagc ccactgcatc ag 4172

<210> SEQ ID NO 46
<211> LENGTH: 4166
<212> TYPE: DNA
<213> ORGANISM: Artificial Sequence
<220> FEATURE:
<223> OTHER INFORMATION: Made in Lab - AAV expression cassette construct

<400> SEQUENCE: 46
ctctggagac gcgttacata acttacggta aatggcccgc ctggctgacc gcccaacgac 60
ccccgcccat tgacgtcaat aatgacgtat gttcccatag taacgccaat agggactttc 120
cattgacgtc aatgggtgga gtatttacgg taaactgccc acttggcagt acatcaagtg 180
tatcatatgc caagtacgcc ccctattgac gtcaatgacg gtaaatggcc cgcctggcat 240

```
tatgcccagt acatgacctt atgggacttt cctacttggc agtacatcta cgtattagtc    300
atcgctatta ccaacttgtg gacaaagttt gctctattcc acctcctcca ggccctcctt    360
gggtccatca ccccaggggt gctgggtcca tcccaccccc aggcccacac aggcttgcag    420
tattgtgtgc ggtatggtca gggcgtccga gagcaggttt cgcagtggaa ggcaggcagg    480
tgttggggag gcagttaccg gggcaacggg aacagggcgt tttggaggtg gttgccatgg    540
ggacctggat gctgacgaag gctcgcgagg ctgtgagcag ccacagtgcc ctgctcagaa    600
gccccgggct cgtcagtcaa accggttctc tgtttgcact cggcagcacg ggcaggcaag    660
tggtccctag gttcggggaa ttcaaagcaa gccgccacca tgattgtgtt tgtccggttc    720
aactcctccc atggtttccc ggtggaagtg gactcagaca ccagcatctt ccaactgaag    780
gaagtggtgg ccaagcgtca gggggtcccg gcagaccagt tgagagtgat cttcgctgga    840
aaggaactga gaaacgactg gactgtgcag aactgtgacc tggaccaaca gtccattgtg    900
cacattgtcc agcggccttg gcggaaaggt caagagatga acgccactgg tggagatgac    960
cccaggaatg cagctggggg ctgtgaacgg gaacctcaga gcctgaccag agtggacctc   1020
agctcctctg tcctcccggg agactccgtg ggactggcag tcattctgca cactgacagc   1080
cgcaaggatt cccccccctgc gggttcacca gctggacggt ccatctacaa ctccttctat   1140
gtgtactgca agggaccctg ccagagggtg cagccgggaa agctcagagt gcagtgcagc   1200
acttgcagac aagccaccct gaccctgacc cagggcccat cctgctggga tgatgtcctg   1260
atccccaacc ggatgtcagg ggaatgccaa agccctcact gccctggaac ctcggccgag   1320
ttcttcttca aatgtggagc ccaccccacc tcggacaagg aaacctcggt ggcccttcac   1380
ctcattgcca ccaactcccg caacatcacc tgtatcactt gcactgatgt tcgctctccg   1440
gtgctggtgt tccagtgcaa ctcccgacac gtgatctgcc tggactgctt ccacctgtac   1500
tgtgtgacca gactgaatga caggcagttt gtccacgacc cccaactggg ctactccttg   1560
ccttgtgtgg ctggctgccc caactccctg atcaaggagt tgcaccactt ccggatcctg   1620
ggagaggaac agtacaacag ataccagcag tacggggcag aggaatgtgt cctccaaatg   1680
gggggagtgc tgtgcccccg gcctggttgt ggagctggcc tcctgccgga acctgaccag   1740
cggaaggtca cttgcgaggg tggaaacggc ctgggctgtg gcttcgcctt ctgtcgggag   1800
tgcaaggagg cctaccacga aggagaatgc tccgcggtgt ttgaagcctc agggaccacc   1860
acacaagcct acagagtgga tgagagggca gcggagcagg cccgctggga agcggcctcc   1920
aaggagacta tcaagaaaac caccaagcca tgccctaggt gccatgtgcc tgtggaaaag   1980
aatggaggct gcatgcacat gaagtgcccc cagccacagt gccgccttga atggtgctgg   2040
aactgtggct gcgagtggaa cagagtgtgt atgggggacc actggtttga tgtgtgataa   2100
tggattcctg ttaatcaacc tctggattac aaaatttgtg aaagattgac tggtattctt   2160
aactatgttg ctccttttac gctatgtgga tacgctgctt taatgccttt gtatcatgct   2220
attgcttccc gtatggcttt cattttctcc tccttgtata aatcctggtt gctgtctctt   2280
tatgaggagt tgtggcccgt tgtcaggcaa cgtggcgtgg tgtgcactgt gtttgctgac   2340
gcaaccccca ctggttgggg cattgccacc acctgtcagc tcctttccgg gactttcgct   2400
ttccccctcc ctattgccac ggcggaactc atcgccgcct gccttgcccg ctgctggaca   2460
ggggctcggc tgttgggcac tgacaattcc gtggtgttgt cggggaagct gacgtccttt   2520
ccgcggctgc tcgcctgtgt tgccacctgg attctgcgcg ggacgtcctt ctgctacgtc   2580
```

```
ccttcggccc tcaatccagc ggaccttcct tcccgcggcc tgctgccggc tctgcggcct   2640

cttccgcctc ttcgccttcg ccctcagacg agtcggatct ccctttgggc cgcctccccg   2700

cccatgtatc tttttcacct gtgccttgtt tttgcctgtg ttccgcgtcc tacttttcaa   2760

gcctccaagc tgtgccttgg gcggctttgg ggcatggaca tagatcccta taaagaattt   2820

ggttcatctt atcagttgtt gaattttctt cctttggacc tgcccgggtg gcatccctgt   2880

gacccctccc cagtgcctct cctggccctg gaagttgcca ctccagtgcc caccagcctt   2940

gtcctaataa aattaagttg catcattttg tctgactagg tgtccttcta taatattatg   3000

gggtggaggg gggtggtatg gagcaagggg cccaagttgg gaagaaacct gtagggcctg   3060

cgttacccag gctggagtgc agtggcacat ttctgctcac tgcaacctcc tcctccctgg   3120

gttcaagcaa ttctcctgcc tcagcctccc aagtagctgt gattataggt gcacaccacc   3180

aagcctggct aatttttata tctttagtag agacgggagt ctcaccatgt tggccaggct   3240

agtctctggc aagccatggt aaaatgtaac tatttaaggc tgctttaaat tagactaata   3300

gcagagtggt cagactatac tgaaagcttg gtgaatcaca attaagtacc tcaaagaact   3360

attcttgttt gccttattcc tatgtaaata actgaaatct ttgtttttct tcctaaaagg   3420

ggtcatgttg atttttactt acaatgtatt ttaagtttgt cactctaaat ggttatgagc   3480

aagtttaaga aaaatcttca gcaaatacta ccttagatta tgaccccaaa acacatttac   3540

ttatgattat gttgaaaaca tagggtctgg ggaaaaaggg atttaaaata agaagaaaaa   3600

gaagacttgg gacttaaaaa gtcttttaga ggccagctca ccaacattca gaacacccag   3660

tctgtgttgc acaatatgtt acttaggtat aaatcaagga ttcatgtaat tttgtcattc   3720

cttgcgtgat attttaaaaa acattctgtg taaggtattt ataaagctct cttctaaaaa   3780

tacaaaaatt tgtggggcct tgtagtccca gctacttggg aggctgaggc aggaggattt   3840

cttgaactgg gaggcagagc ttgcagtgag cccactgcac tccagcctgg gcaacagagt   3900

agaactcctc tcaaaaaaaa aaaaaaaaaa gaaagaaaga aaaaaaagtg gactgtgaaa   3960

actgaaagga ctagaaaaac tacactacaa agatacagaa accaagaaag caccaaaggt   4020

ttgccttcaa ctgcttccca acttgttttc ctcttccaat ttgattgtgg tttcctctcc   4080

agaaggaact ccacagtact tagcgttggt cacatagtag gttctcaaat acttgttaat   4140

aaataagttt gttcgagaag cttcag                                        4166
```

<210> SEQ ID NO 47
<211> LENGTH: 4155
<212> TYPE: DNA
<213> ORGANISM: Artificial Sequence
<220> FEATURE:
<223> OTHER INFORMATION: Made in Lab - AAV expression cassette construct

<400> SEQUENCE: 47

```
ctctgggctc tggagacgac ttacggtaaa tggcccgcct ggctgaccgc ccaacgaccc     60

ccgcccattg acgtcaataa tgacgtatgt tcccatagta acgccaatag ggactttcca    120

ttgacgtcaa tgggtggagt atttacggta aactgcccac ttggcagtac atcaagtgta    180

tcatatgcca agtccgcccc ctattgacgt caatgacggt aaatggcccg cctggcatta    240

tgcccagtac atgaccttac gggactttcc tacttggcag tacatctacg tattagtcat    300

cgctattacc atggtgatgc ggttttggca gtacaccaat gggcgtggat agcggtttga    360

ctcacgggga tttccaagtc tccaccccat tgacgtcaat gggagtttgt tttggcacca    420

aaatcaacgg gactttccaa aatgtcgtaa taaccccgcc ccgttgacgc aaatgggcgg    480
```

```
taggcgtgta cggtgggagg tctatataag cagagctcgt ttagtgaacc gtcagatcgc    540
ctggagaggc catccacgct gttttgacct ccatagtgga caccgggacc gatccagcct    600
ccgcggccgg gaacggtgca ttggaacgcg gattccccgt gccaagagtg actcagatcc    660
tcactctctt ccgcatcgct gtctgcgagg gccagctgtt gggctcgcgg ttgaggacaa    720
actcttcgcg gtctttccag tactcttgga tcggaaaccc gtcggcctcc gaacggtact    780
ccgccaccga gggacctgag cgagtccgca tcgaccggat cggaaaacct ctcgagaaag    840
gcgtctaacc agtcacagtc gcaaggtagg ctgagcaccg tggcgggcgg cagcgggtgg    900
cggtcggggt tgtttctggc ggaggtgctg ctgatgatgt aattaaagta ggcggtcttg    960
agacggcgga tggtcgaggt gaggtgtggc aggcttgaga tccagctgtt ggggtgagta   1020
ctccctctca aaagcgggca ttacttctgc gctaagattg tcagtttcca aaaacgagga   1080
ggatttgata ttcacctggc ccgatctggc catacacttg agtgacaatg acatccactt   1140
tgcctttctc tccacaggtg tccactccca ggtccaagtt taaacgccgc cacccaccat   1200
gattgtgttt gtccggttca actcctccca tggtttcccg gtggaagtgg actcagacac   1260
cagcatcttc caactgaagg aagtggtggc caagcgtcag ggggtcccgg cagaccagtt   1320
gagagtgatc ttcgctggaa aggaactgag aaacgactgg actgtgcaga actgtgacct   1380
ggaccaacag tccattgtgc acattgtcca gcggccttgg cggaaaggtc aagagatgaa   1440
cgccactggt ggagatgacc ccaggaatgc agctgggggc tgtgaacggg aacctcagag   1500
cctgaccaga gtggacctca gctcctctgt cctcccggga gactccgtgg gactggcagt   1560
cattctgcac actgacagcc gcaaggattc ccccccctgcg ggttcaccag ctggacggtc   1620
catctacaac tccttctatg tgtactgcaa gggaccctgc cagagggtgc agccgggaaa   1680
gctcagagtg cagtgcagca cttgcagaca agccaccctg accctgaccc agggcccatc   1740
ctgctgggat gatgtcctga tccccaaccg gatgtcaggg gaatgccaaa gccctcactg   1800
ccctggaacc tcggccgagt tcttcttcaa atgtggagcc caccccacct cggacaagga   1860
aacctcggtg gcccttcacc tcattgccac caactcccgc aacatcacct gtatcacttg   1920
cactgatgtt cgctctccgg tgctggtgtt ccagtgcaac tcccgacacg tgatctgcct   1980
ggactgcttc cacctgtact gtgtgaccag actgaatgac aggcagtttg tccacgaccc   2040
ccaactgggc tactccttgc cttgtgtggc tggctgcccc aactccctga tcaaggagtt   2100
gcaccacttc cggatcctgg gagaggaaca gtacaacaga taccagcagt acggggcaga   2160
ggaatgtgtc ctccaaatgg ggggagtgct gtgcccccgg cctggttgtg gagctggcct   2220
cctgccggaa cctgaccagc ggaaggtcac ttgcgagggt ggaaacggcc tgggctgtgg   2280
cttcgccttc tgtcgggagt gcaaggaggc ctaccacgaa ggagaatgct ccgcggtgtt   2340
tgaagcctca gggaccacca cacaagccta cagagtggat gagagggcag cggagcaggc   2400
ccgctgggaa gcggcctcca aggagactat caagaaaacc accaagccat gccctaggtg   2460
ccatgtgcct gtggaaaaga atggaggctg catgcacatg aagtgccccc agccacagtg   2520
ccgccttgaa tggtgctgga actgtggctg cgagtggaac agagtgtgta tgggggacca   2580
ctggtttgat gtgtgataat ggactaatta aattcgagca tcttaccgcc atttattccc   2640
atatttgttc tgtttttctt gatttgggta tacatttaaa tgttaataaa acaaaatggt   2700
ggggcaatca tttacatttt tagggatatg taattactag ttcaggtgta ttgccacaag   2760
acaaacatgt taagaaactt tcccgttatt tacgctctgt tcctgttaat caacctctgg   2820
```

-continued

```
attacaaaat ttgtgaaaga ttgactgata ttcttaacta tgttgctcct tttacgctgt   2880

gtggatatgc tgctttaatg cctctgtatc atgctattgc ttcccgtacg gctttcgttt   2940

tctcctcctt gtataaatcc tggttgctgt ctctttatga ggagttgtgg cccgttgtcc   3000

gtcaacgtgg cgtggtgtgc tctgtgtttg ctgacgcaac ccccactggc tggggcattg   3060

ccaccacctg tcaactcctt tctgggactt tcgctttccc cctcccgatc gccacggcag   3120

aactcatcgc cgcctgcctt gcccgctgct ggacaggggc taggttgctg ggcactgata   3180

attccgtggt gttgtcgggg aagggccttt aattagctgc ccgggtggca tccctgtgac   3240

ccctccccag tgcctctcct ggccctggaa gttgccactc cagtgcccac cagccttgtc   3300

ctaataaaat taagttgcat cattttgtct gactaggtgt ccttctataa tattatgggg   3360

tggagggggg tggtatggag caaggggccc aagttgggaa gaaacctgta gggcctgcgt   3420

tacccaggct ggagtgcagt ggcacatttc tgctcactgc aacctcctcc tccctgggtt   3480

caagcaattc tcctgcctca gcctcccaag tagctgtgat tataggtgca caccaccaag   3540

cctggctaat ttttatatct ttagtagaga cgggagtctc accatgttgg ccaggctagt   3600

ctctggcaag ccatggtaaa atgtaactat ttaaggctgc tttaaattag actaatagca   3660

gagtggtcag actatactga aagcttggtg aatcacaatt aagtacctca aagaactatt   3720

cttgtttgcc ttattcctat gtaaataact gaaatctttg tttttcttcc taaaaggggt   3780

catgttgatt tttacttaca atgtatttta agtttgtcac tctaaatggt tatgagcaag   3840

tttaagaaaa atcttcagca aatactacct tagattatga ccccaaaaca catttactta   3900

tgattatgtt gaaaacatag ggtctgggga aaaagggatt taaaataaga agaaaaagaa   3960

gacttgggac ttaaaaagtc ttttagaggc cagctcacca acattcagaa cacccagtct   4020

gtgttgcaca atatgttact taggtataaa tcaaggattc atgtaatttt gtcattcctt   4080

gcgtgatatt ttaaaaaaca ttctgtgtaa ggtatttata aagctctctt ctaaaaatac   4140

aaaaatttgt gtcag                                                     4155
```

<210> SEQ ID NO 48
<211> LENGTH: 4166
<212> TYPE: DNA
<213> ORGANISM: Artificial Sequence
<220> FEATURE:
<223> OTHER INFORMATION: Made in Lab - AAV expression cassette construct

<400> SEQUENCE: 48

```
ctctggagac gcgttacata acttacggta aatggcccgc ctggctgacc gcccaacgac     60

ccccgcccat tgacgtcaat aatgacgtat gttcccatag taacgccaat agggactttc    120

cattgacgtc aatgggtgga gtatttacgg taaactgccc acttggcagt acatcaagtg    180

tatcatatgc caagtacgcc ccctattgac gtcaatgacg gtaaatggcc cgcctggcat    240

tatgcccagt acatgacctt atgggacttt cctacttggc agtacatcta cgtattagtc    300

atcgctatta ccagcccagc accccaaggc ggccaacgcc aaaactctcc ctcctcctct    360

tcctcaatct cgctctcgct cttttttttt ttcgcaaaag gaggggagag ggggtaaaaa    420

aatgctgcac tgtgcggcga agccggtgag tgagcggcgc ggggccaatc agcgtgcgcc    480

gttccgaaag ttgcctttta tggctcgagc ggccgcggcg gcgccctata aaacccagcg    540

gcgcgacgcg ccaccaccgc cgagtccgcg tccgcccgcg agcacagagc ctcgcctttg    600

ccgatccgcc gcccgtccac acccgccgcc aggtaagccc ggccagccga ccggggcatg    660

cggccgcggc ccttcgcccg tgcagagccg ccgtctgggc cgcagcgggg ggcgcatggg    720
```

-continued

```
gcggaaccgg accgccgtgg ggggcgcggg agaagcccct gggcctccgg agatggggga    780
caccccacgc cagttcgcag gcgcgaggcc gcgctcgggc gggcgcgctc cgggggtgcc    840
gctctcgggg cgggggcaac cggcggggtc tttgtctgag ccgggctctt gccaatgggg    900
atcgcacggt gggcgcggcg tagcccccgt caggcccggt gggggctggg gcgccatgcg    960
cgtgcgcgct ggtcctttgg gcgctaactg cgtgcgcgct gggaattggc gctaattgcg   1020
cgtgcgcgct gggactcaat ggcgctaatc gcgcgtgcgt tctggggccc gggcgcttgc   1080
gccacttcct gcccgagccg ctggcgcccg agggtgtggc cgctgcgtgc gcgcgcgcga   1140
cccggtcgct gtttgaaccg ggcggaggcg gggctggcgc ccggttggga gggggttggg   1200
gcctggcttc ctgccgcgcg ccgcggggac gcctccgacc agtgtttgcc ttttatggta   1260
ataacgcggc cggcccggct tcctttgtcc ccaatctggg cgcgcgccgg cgccccctgg   1320
cggcctaagg actcggcgcg ccggaagtgg ccagggcggc agcggctgct cttggcggcc   1380
ccgaggtgac tatagccttc ttttgtgtct tgatagttcg ccagcctctg ctaaccatgt   1440
tcatgccttc ttctttttcc tacagctcct gggcaacgtg ctggttattg tgctgtctca   1500
tcattttggc aaagaattcg gcttgatcga agccgtctca ggggaattca aagcaagccg   1560
ccaccatgat tgtgtttgtc cggttcaact cctcccatgg tttcccggtg gaagtggact   1620
cagacaccag catcttccaa ctgaaggaag tggtggccaa gcgtcagggg gtcccggcag   1680
accagttgag agtgatcttc gctggaaagg aactgagaaa cgactggact gtgcagaact   1740
gtgacctgga ccaacagtcc attgtgcaca ttgtccagcg gccttggcgg aaaggtcaag   1800
agatgaacgc cactggtgga gatgacccca ggaatgcagc tgggggctgt gaacgggaac   1860
ctcagagcct gaccagagtg gacctcagct cctctgtcct cccgggagac tccgtgggac   1920
tggcagtcat tctgcacact gacagccgca aggattcccc ccctgcgggt tcaccagctg   1980
gacggtccat ctacaactcc ttctatgtgt actgcaaggg accctgccag agggtgcagc   2040
cgggaaagct cagagtgcag tgcagcactt gcagacaagc caccctgacc ctgacccagg   2100
gcccatcctg ctgggatgat gtcctgatcc ccaaccggat gtcaggggaa tgccaaagcc   2160
ctcactgccc tggaacctcg gccgagttct tcttcaaatg tggagcccac cccacctcgg   2220
acaaggaaac ctcggtggcc cttcacctca ttgccaccaa ctcccgcaac atcacctgta   2280
tcacttgcac tgatgttcgc tctccggtgc tggtgttcca gtgcaactcc cgacacgtga   2340
tctgcctgga ctgcttccac ctgtactgtg tgaccagact gaatgacagg cagtttgtcc   2400
acgaccccca actgggctac tccttgcctt gtgtggctgg ctgccccaac tccctgatca   2460
aggagttgca ccacttccgg atcctgggag aggaacagta caacagatac cagcagtacg   2520
gggcagagga atgtgtcctc caaatggggg gagtgctgtg cccccggcct ggttgtggag   2580
ctggcctcct gccggaacct gaccagcgga aggtcacttg cgagggtgga aacggcctgg   2640
gctgtggctt cgccttctgt cgggagtgca aggaggccta ccacgaagga gaatgctccg   2700
cggtgtttga agcctcaggg accaccacac aagcctacag agtggatgag agggcagcgg   2760
agcaggcccg ctgggaagcg gcctccaagg agactatcaa gaaaaccacc aagccatgcc   2820
ctaggtgcca tgtgcctgtg gaaaagaatg gaggctgcat gcacatgaag tgcccccagc   2880
cacagtgccg ccttgaatgg tgctggaact gtggctgcga gtggaacaga gtgtgtatgg   2940
gggaccactg gtttgatgtg tgataatgga ctgcccgggt ggcatccctg tgacccctcc   3000
ccagtgcctc tcctggccct ggaagttgcc actccagtgc ccaccagcct tgtcctaata   3060
```

-continued

```
aaattaagtt gcatcatttt gtctgactag gtgtccttct ataatattat ggggtggagg   3120
ggggtggtat ggagcaaggg gcccaagttg ggaagaaacc tgtagggcct gcgttaccca   3180
ggctggagtg cagtggcaca tttctgctca ctgcaacctc ctcctccctg ggttcaagca   3240
attctcctgc ctcagcctcc caagtagctg tgattatagg tgcacaccac caagcctggc   3300
taatttttat atctttagta gagacgggag tctcaccatg ttggccaggc tagtctctgg   3360
caagccatgg taaaatgtaa ctatttaagg ctgctttaaa ttagactaat agcagagtgg   3420
tcagactata ctgaaagctt ggtgaatcac aattaagtac ctcaaagaac tattcttgtt   3480
tgccttattc ctatgtaaat aactgaaatc tttgtttttc ttcctaaaag ggtcatgtt    3540
gatttttact tacaatgtat tttaagtttg tcactctaaa tggttatgag caagtttaag   3600
aaaaatcttc agcaaatact accttagatt atgaccccaa aacacattta cttatgatta   3660
tgttgaaaac atagggtctg ggaaaaaagg gatttaaaat aagaagaaaa agaagacttg   3720
ggacttaaaa agtcttttag aggccagctc accaacattc agaacaccca gtctgtgttg   3780
cacaatatgt tacttaggta taaatcaagg attcatgtaa ttttgtcatt ccttgcgtga   3840
tattttaaaa aacattctgt gtaaggtatt tataaagctc tcttctaaaa atacaaaaat   3900
ttgtggggcc ttgtagtccc agctacttgg gaggctgagg caggaggatt tcttgaactg   3960
ggaggcagag cttgcagtga gcccactgca ctccagcctg ggcaacagag tagaactcct   4020
ctcaaaaaaa aaaaaaaaaa agaaagaaag aaaaaaaagt ggactgtgaa aactgaaagg   4080
actagaaaaa ctacactaca aagatacaga aaccaagaaa gcaccaaagg tttgccttca   4140
actgcttccc aacttgtttt cctcag                                         4166
```

<210> SEQ ID NO 49
<211> LENGTH: 4166
<212> TYPE: DNA
<213> ORGANISM: Artificial Sequence
<220> FEATURE:
<223> OTHER INFORMATION: Made in Lab - AAV expression cassette construct

<400> SEQUENCE: 49

```
ctctgggctc tggagacgac ttacggtaaa tggcccgcct ggctgaccgc ccaacgaccc     60
ccgcccattg acgtcaataa tgacgtatgt tcccatagta acgccaatag ggactttcca    120
ttgacgtcaa tgggtggagt atttacggta aactgcccac ttggcagtac atcaagtgta    180
tcatatgcca agtccgcccc ctattgacgt caatgacggt aaatggcccg cctggcatta    240
tgcccagtac atgaccttac gggactttcc tacttggcag tacatctacg tattagtcat    300
cgctattacc atggtgatgc ggttttggca gtacaccaat gggcgtggat agcggtttga    360
ctcacgggga tttccaagtc tccaccccat tgacgtcaat gggagtttgt tttggcacca    420
aaatcaacgg gactttccaa aatgtcgtaa taaccccgcc ccgttgacgc aaatgggcgg    480
taggcgtgta cggtgggagg tctatataag cagagctcgt ttagtgaacc gtcagatcgc    540
ctggagaggc catccacgct gttttgacct ccatagtgga caccgggacc gatccagcct    600
ccgcggccgg gaacggtgca ttggaacgcg gattccccgt gccaagagtg actcagatcc    660
tcactctctt ccgcatcgct gtctgcgagg gccagctgtt gggctcgcgg ttgaggacaa    720
actcttcgcg gtctttccag tactcttgga tcggaaaccc gtcggcctcc gaacggtact    780
ccgccaccga gggacctgag cgagtccgca tcgaccggat cggaaaacct ctcgagaaag    840
gcgtctaacc agtcacagtc gcaaggtagg ctgagcaccg tggcgggcgg cagcgggtgg    900
cggtcggggt tgtttctggc ggaggtgctg ctgatgatgt aattaaagta ggcggtcttg    960
```

```
agacggcgga tggtcgaggt gaggtgtggc aggcttgaga tccagctgtt ggggtgagta   1020
ctccctctca aaagcgggca ttacttctgc gctaagattg tcagtttcca aaaacgagga   1080
ggatttgata ttcacctggc ccgatctggc catacacttg agtgacaatg acatccactt   1140
tgcctttctc tccacaggtg tccactccca ggtccaagtt taaacgccgc cacccaccat   1200
gattgtgttt gtccggttca actcctccca tggtttcccg gtggaagtgg actcagacac   1260
cagcatcttc caactgaagg aagtggtggc caagcgtcag gggtcccgg cagaccagtt    1320
gagagtgatc ttcgctggaa aggaactgag aaacgactgg actgtgcaga actgtgacct   1380
ggaccaacag tccattgtgc acattgtcca gcggccttgg cggaaaggtc aagagatgaa   1440
cgccactggt ggagatgacc ccaggaatgc agctgggggc tgtgaacggg aacctcagag   1500
cctgaccaga gtggacctca gctcctctgt cctcccggga gactccgtgg gactggcagt   1560
cattctgcac actgacagcc gcaaggattc ccccctgcg ggttcaccag ctggacggtc    1620
catctacaac tccttctatg tgtactgcaa gggaccctgc cagagggtgc agccgggaaa   1680
gctcagagtg cagtgcagca cttgcagaca agccaccctg accctgaccc agggcccatc   1740
ctgctgggat gatgtcctga tccccaaccg gatgtcaggg gaatgccaaa gccctcactg   1800
ccctggaacc tcggccgagt tcttcttcaa atgtggagcc caccccacct cggacaagga   1860
aacctcggtg gcccttcacc tcattgccac caactcccgc aacatcacct gtatcacttg   1920
cactgatgtt cgctctccgg tgctggtgtt ccagtgcaac tcccgacacg tgatctgcct   1980
ggactgcttc cacctgtact gtgtgaccag actgaatgac aggcagtttg tccacgaccc   2040
ccaactgggc tactccttgc cttgtgtggc tggctgcccc aactccctga tcaaggagtt   2100
gcaccacttc cggatcctgg gagaggaaca gtacaacaga taccagcagt acggggcaga   2160
ggaatgtgtc ctccaaatgg ggggagtgct gtgcccccgg cctggttgtg gagctggcct   2220
cctgccggaa cctgaccagc ggaaggtcac ttgcgagggt ggaaacggcc tgggctgtgg   2280
cttcgccttc tgtcgggagt gcaaggaggc ctaccacgaa ggagaatgct ccgcggtgtt   2340
tgaagcctca gggaccacca cacaagccta cagagtggat gagagggcag cggagcaggc   2400
ccgctgggaa gcggcctcca aggagactat caagaaaacc accaagccat gccctaggtg   2460
ccatgtgcct gtggaaaaga atggaggctg catgcacatg aagtgccccc agccacagtg   2520
ccgccttgaa tggtgctgga actgtggctg cgagtggaac agagtgtgta tgggggacca   2580
ctggtttgat gtgtgataat ggattcctgt aaacaggcct attgattgga aagtttgtca   2640
acgaattgtg ggtcttttgg ggtttgctgc cccttttacg caatgtggat atcctgcttt   2700
aatgccttta tatgcatgta tacaagcaaa acaggctttt actttctcgc caacttacaa   2760
ggcctttctc agtaaacagt atatgaccct ttaccccgtt gctcggcaac ggcctggtct   2820
gtgccaagtg tttgctgacg caacccccac tggttggggc ttggccatag gccatcagcg   2880
catgcgtgga acctttgtgt ctcctctgcc gatccatact gcggaactcc tagccgcttg   2940
ttttgctcgc agctggactg gagcaaacct catcgggacc gacaattctg tcgtactctc   3000
ccgcaagcac tcaccgtttc cgcggctgct cgcctgtgtt gccacctgga ttctgcgcgg   3060
gacgtccttc tgctacgtcc cttcggccct caatccagcg gaccttcctt cccgcggcct   3120
gctgccggct ctgcggcctc ttccgcctct tcgccttcgc cctcagacga gtcggatctc   3180
cctttgggcc gcctccccgc ccatgtatct ttttcacctg tgccttgttt ttgcctgtgt   3240
tccgcgtcct acttttcaag cctccaagct gtgccttggg cggctttggg gcatggacat   3300
```

-continued

```
agatccctat aaagaatttg gttcatctta tcagttgttg aattttcttc ctttggacgc   3360

tggagcctcg gtagccgttc ctcctgcccg ctgggcctcc caacgggccc tcctcccctc   3420

cttgcaccgg cccttcctgg tctttgaata aattcattgc ttgccagcca tctgttgttt   3480

gcccctcccc cgtgccttcc ttgaccctgg aaggtgccac tcccactgtc ctttcctaat   3540

aaaatgagga aattgcatcg cattgtctga gtaggtgtca ttctattctg gggggtgggg   3600

tggggcagga cagcaagggg gaggattggg aatacaatag caggcatgct ggggatgcgg   3660

tgggctctat gggtacccag gtgctgaaga attgacccgg ttcctcctgg ggttacccag   3720

gctggagtgc agtggcacat ttctgctcac tgcaacctcc tcctccctgg gttcaagcaa   3780

ttctcctgcc tcagcctccc aagtagctgt gattataggt gcacaccacc aagcctggct   3840

aatttttata tctttagtag agacgggagt ctcaccatgt tggccaggct agtctctggc   3900

aagccatggt aaaatgtaac tatttaaggc tgctttaaat tagactaata gcagagtggt   3960

cagactatac tgaaagcttg gtgaatcaca attaagtacc tcaaagaact attcttgttt   4020

gccttattcc tatgtaaata actgaaatct ttgtttttct tcctaaaagg ggtcatgttg   4080

atttttactt acaatgtatt ttaagtttgt cactctaaat ggttatgagc aagtttaaga   4140

aaaatcttca gcaaatacta cctcag                                        4166
```

<210> SEQ ID NO 50
<211> LENGTH: 4166
<212> TYPE: DNA
<213> ORGANISM: Artificial Sequence
<220> FEATURE:
<223> OTHER INFORMATION: Made in Lab - AAV expression cassette construct

<400> SEQUENCE: 50

```
ctctggagac gcaacctttg gagctaagcc agcaatggta gagggaagat tctgcacgtc     60

ccttccaggc ggcctccccg tcaccacccc ccccaacccg ccccgaccgg agctgagagt    120

aattcataca aaaggactcg cccctgcctt ggggaatccc agggaccgtc gttaaactcc    180

cactaacgta gaacccagag atcgctgcgt tcccgccccc tcacccgccc gctctcgtca    240

tcactgaggt ggagaatagc atgcgtgagg ctccggtgcc cgtcagtggg cagagcgcac    300

atcgcccaca gtccccgaga agttgggggg aggggtcggc aattgaacgg gtgcctagag    360

aaggtggcgc ggggtaaact gggaaagtga tgtcgtgtac tggctccgcc tttttcccga    420

gggtggggga gaaccgtata taagtgcagt agtcgccgtg aacgttcttt ttcgcaacgg    480

gtttgccgcc agaacacagg taagtgccgt gtgtggttcc cgcgggcctg gcctctttac    540

gggttatggc ccttgcgtgc cttgaattac ttccacctgg ctccagtacg tgattcttga    600

tcccgagctg gagccagggg cgggccttgc gctttaggag ccccttcgcc tcgtgcttga    660

gttgaggcct ggcctgggcg ctggggccgc cgcgtgcgaa tctggtggca ccttcgcgcc    720

tgtctcgctg ctttcgataa gtctctagcc atttaaaatt tttgatgacg tgctgcgacg    780

ctttttttct ggcaagatag tcttgtaaat gcgggccagg atctgcacac tggtatttcg    840

gtttttgggc ccgcggccgg cgacggggcc cgtgcgtccc agcgcacatg ttcggcgagg    900

cggggcctgc gagcgcggcc accgagaatc ggacgggggt agtctcaagc tggccggcct    960

gctctggtgc ctggcctcgc gccgccgtgt atcgccccgc cctgggcggc aaggctggcc   1020

cggtcggcac cagttgcgtg agcggaaaga tggccgcttc ccggccctgc tccagggggc   1080

tcaaaatgga ggacgcggcg ctcgggagag cgggcgggtg agtcacccac acaaaggaaa   1140

agggcctttc cgtcctcagc cgtcgcttca tgtgactcca cggagtaccg ggcgccgtcc   1200
```

-continued

```
aggcacctcg attagttctg gagcttttgg agtacgtcgt ctttaggttg gggggagggg   1260
ttttatgcga tggagtttcc ccacactgag tgggtggaga ctgaagttag gccagcttgg   1320
cacttgatgt aattctcctt ggaatttggc ctttttgagt ttggatcttg gttcattctc   1380
aagcctcaga cagtggttca aagttttttt cttccatttc aggtgtcgtg aacacgtctc   1440
aggggaattc aaagcaagcc gccaccatga ttgtgtttgt ccggttcaac tcctcccatg   1500
gtttcccggt ggaagtggac tcagacacca gcatcttcca actgaaggaa gtggtggcca   1560
agcgtcaggg ggtcccggca gaccagttga gagtgatctt cgctggaaag gaactgagaa   1620
acgactggac tgtgcagaac tgtgacctgg accaacagtc cattgtgcac attgtccagc   1680
ggccttggcg gaaaggtcaa gagatgaacg ccactggtgg agatgacccc aggaatgcag   1740
ctgggggctg tgaacgggaa cctcagagcc tgaccagagt ggacctcagc tcctctgtcc   1800
tcccgggaga ctccgtggga ctggcagtca ttctgcacac tgacagccgc aaggattccc   1860
cccctgcggg ttcaccagct ggacggtcca tctacaactc cttctatgtg tactgcaagg   1920
gaccctgcca gagggtgcag ccgggaaagc tcagagtgca gtgcagcact tgcagacaag   1980
ccaccctgac cctgacccag ggcccatcct gctgggatga tgtcctgatc cccaaccgga   2040
tgtcagggga atgccaaagc cctcactgcc ctggaacctc ggccgagttc ttcttcaaat   2100
gtggagccca ccccacctcg gacaaggaaa cctcggtggc ccttcacctc attgccacca   2160
actcccgcaa catcacctgt atcacttgca ctgatgttcg ctctccggtg ctggtgttcc   2220
agtgcaactc ccgacacgtg atctgcctgg actgcttcca cctgtactgt gtgaccagac   2280
tgaatgacag gcagtttgtc cacgaccccc aactgggcta ctccttgcct tgtgtggctg   2340
gctgccccaa ctccctgatc aaggagttgc accacttccg gatcctggga gaggaacagt   2400
acaacagata ccagcagtac ggggcagagg aatgtgtcct ccaaatgggg ggagtgctgt   2460
gcccccggcc tggttgtgga gctggcctcc tgccggaacc tgaccagcgg aaggtcactt   2520
gcgagggtgg aaacggcctg ggctgtggct tcgccttctg tcgggagtgc aaggaggcct   2580
accacgaagg agaatgctcc gcggtgtttg aagcctcagg gaccaccaca caagcctaca   2640
gagtggatga gagggcagcg gagcaggccc gctgggaagc ggcctccaag gagactatca   2700
agaaaaccac caagccatgc cctaggtgcc atgtgcctgt ggaaaagaat ggaggctgca   2760
tgcacatgaa gtgcccccag ccacagtgcc gccttgaatg gtgctggaac tgtggctgcg   2820
agtggaacag agtgtgtatg gggaccact  ggtttgatgt gtgataatgg attcctgtta   2880
atcaacctct ggattacaaa atttgtgaaa gattgactgg tattcttaac tatgttgctc   2940
cttttacgct atgtggatac gctgctttaa tgcctttgta tcatgctatt gcttcccgta   3000
tggctttcat tttctcctcc ttgtataaat cctggttgct gtctctttat gaggagttgt   3060
ggcccgttgt caggcaacgt ggcgtggtgt gcactgtgtt tgctgacgca acccccactg   3120
gttggggcat tgccaccacc tgtcagctcc tttccgggac tttcgctttc cccctcccta   3180
ttgccacggc ggaactcatc gccgcctgcc ttgcccgctg ctggacaggg gctcggctgt   3240
tgggcactga caattccgtg gtgttgtcgg ggaagctgac gtcctttccg cggctgctcg   3300
cctgtgttgc cacctggatt ctgcgcggga cgtccttctg ctacgtccct tcggccctca   3360
atccagcgga ccttccttcc cgcggcctgc tgccggctct gcggcctctt ccgcctcttc   3420
gccttcgccc tcagacgagt cggatctccc tttgggccgc ctccccgccc atgtatcttt   3480
ttcacctgtg ccttgttttt gcctgtgttc cgcgtcctac ttttcaagcc tccaagctgt   3540
```

```
gccttgggcg gctttggggc atggacatag atccctataa agaatttggt tcatcttatc   3600
agttgttgaa ttttcttcct ttggacttgc cagccatctg ttgtttgccc ctcccccgtg   3660
ccttccttga ccctggaagg tgccactccc actgtccttt cctaataaaa tgaggaaatt   3720
gcatcgcatt gtctgagtag gtgtcattct attctggggg gtggggtggg gcaggacagc   3780
aagggggagg attgggaata caatagcagg catgctgggg atgcggtggg ctctatgggt   3840
acccaggtgc tgaagaattg acccggttcc tcctggggtt acccaggctg gagtgcagtg   3900
gcacatttct gctcactgca acctcctcct ccctgggttc aagcaattct cctgcctcag   3960
cctcccaagt agctgtgatt ataggtgcac accaccaagc ctggctaatt tttatatctt   4020
tagtagagac gggagtctca ccatgttggc caggctagtc tctggcaagc catggtaaaa   4080
tgtaactatt taaggctgct ttaaattaga ctaatagcag agtggtcaga ctatactgaa   4140
agcttggtga atcacaatta agtcag                                        4166
```

<210> SEQ ID NO 51
<211> LENGTH: 4187
<212> TYPE: DNA
<213> ORGANISM: Artificial Sequence
<220> FEATURE:
<223> OTHER INFORMATION: Made in Lab - AAV expression cassette construct

<400> SEQUENCE: 51

```
ctctggagac gcgttacata acttacggta aatggcccgc ctggctgacc gcccaacgac     60
ccccgcccat tgacgtcaat aatgacgtat gttcccatag taacgccaat agggactttc    120
cattgacgtc aatgggtgga gtatttacgg taaactgccc acttggcagt acatcaagtg    180
tatcatatgc caagtacgcc ccctattgac gtcaatgacg gtaaatggcc cgcctggcat    240
tatgcccagt acatgacctt atgggacttt cctacttggc agtacatcta cgtattagtc    300
atcgctatta ccactgcaga gggccctgcg tatgagtgca agtgggtttt aggaccagga    360
tgaggcgggg tgggggtgcc tacctgacga ccgaccccga cccactggac aagcacccaa    420
cccccattcc ccaaattgcg catcccctat cagagagggg gaggggaaac aggatgcggc    480
gaggcgcgtg cgcactgcca gcttcagcac cgcggacagt gccttcgccc ccgcctggcg    540
gcgcgcgcca ccgccgcctc agcactgaag gcgcgctgac gtcactcgcc ggtcccccgc    600
aaactcccct tcccggccac cttggtcgcg tccgcgccgc cgccggccca gccggaccgc    660
accacgcgag gcgcgagata gggggcacg ggcgcgacca tctgcgctgc ggcgccggcg    720
actcagcgct gcctcagtct gcggtgggca gcggaggagt cgtgtcgtgc ctgagagcgc    780
agctgtgctc ctgggcaccg cgcagtccgc ccccgcggct cctggccaga ccacccctag    840
gacccctgc cccaagtcgc aggggaattc aaagcaagcc gccaccatga ttgtgtttgt    900
ccggttcaac tcctcccatg gtttcccggt ggaagtggac tcagacacca gcatcttcca    960
actgaaggaa gtggtggcca agcgtcaggg ggtcccggca gaccagttga gagtgatctt   1020
cgctggaaag gaactgagaa acgactggac tgtgcagaac tgtgacctgg accaacagtc   1080
cattgtgcac attgtccagc ggccttggcg gaaaggtcaa gagatgaacg ccactggtgg   1140
agatgacccc aggaatgcag ctgggggctg tgaacgggaa cctcagagcc tgaccagagt   1200
ggacctcagc tcctctgtcc tcccgggaga ctccgtggga ctggcagtca ttctgcacac   1260
tgacagccgc aaggattccc cccctgcggg ttcaccagct ggacggtcca tctacaactc   1320
cttctatgtg tactgcaagg gaccctgcca gagggtgcag ccgggaaagc tcagagtgca   1380
gtgcagcact tgcagacaag ccaccctgac cctgacccag ggcccatcct gctgggatga   1440
```

-continued

```
tgtcctgatc cccaaccgga tgtcagggga atgccaaagc cctcactgcc ctggaacctc   1500
ggccgagttc ttcttcaaat gtggagccca ccccacctcg gacaaggaaa cctcggtggc   1560
ccttcacctc attgccacca actcccgcaa catcacctgt atcacttgca ctgatgttcg   1620
ctctccggtg ctggtgttcc agtgcaactc ccgacacgtg atctgcctgg actgcttcca   1680
cctgtactgt gtgaccagac tgaatgacag gcagtttgtc cacgaccccc aactgggcta   1740
ctccttgcct tgtgtggctg gctgccccaa ctccctgatc aaggagttgc accacttccg   1800
gatcctggga gaggaacagt acaacagata ccagcagtac ggggcagagg aatgtgtcct   1860
ccaaatgggg ggagtgctgt gcccccggcc tggttgtgga gctggcctcc tgccggaacc   1920
tgaccagcgg aaggtcactt gcgagggtgg aaacggcctg ggctgtggct tcgccttctg   1980
tcgggagtgc aaggaggcct accacgaagg agaatgctcc gcggtgtttg aagcctcagg   2040
gaccaccaca caagcctaca gagtggatga gagggcagcg gagcaggccc gctgggaagc   2100
ggcctccaag gagactatca agaaaaccac caagccatgc cctaggtgcc atgtgcctgt   2160
ggaaaagaat ggaggctgca tgcacatgaa gtgcccccag ccacagtgcc gccttgaatg   2220
gtgctggaac tgtggctgcg agtggaacag agtgtgtatg gggaccact ggtttgatgt    2280
gtgataatgg attcctgtaa acaggcctat tgattggaaa gtttgtcaac gaattgtggg   2340
tcttttgggg tttgctgccc cttttacgca atgtggatat cctgctttaa tgcctttata   2400
tgcatgtata caagcaaaac aggcttttac tttctcgcca acttacaagg cctttctcag   2460
taaacagtat atgacccttt accccgttgc tcggcaacgg cctggtctgt gccaagtgtt   2520
tgctgacgca acccccactg gttggggctt ggccataggc catcagcgca tgcgtggaac   2580
ctttgtgtct cctctgccga tccatactgc ggaactccta gccgcttgtt ttgctcgcag   2640
ctggactgga gcaaacctca tcgggaccga caattctgtc gtactctccc gcaagcactc   2700
accgtttccg cggctgctcg cctgtgttgc cacctggatt ctgcgcggga cgtccttctg   2760
ctacgtccct tcggccctca atccagcgga ccttccttcc cgcggcctgc tgccggctct   2820
gcggcctctt ccgcctcttc gccttcgccc tcagacgagt cggatctccc tttgggccgc   2880
ctccccgccc atgtatcttt ttcacctgtg ccttgttttt gcctgtgttc cgcgtcctac   2940
ttttcaagcc tccaagctgt gccttgggcg gctttggggc atggacatag atccctataa   3000
agaatttggt tcatcttatc agttgttgaa ttttcttcct ttggactggc taataaagga   3060
aatttatttt cattgcaata gtgtgttgga attttttgtg tctctcactc ggaagaacat   3120
atgggagggc aaatcattta aaacatcaga atgagtattt ggtttagagt ttggcaacat   3180
atgcccatat gctggctgcc atgaacaaag gttggctata aagaggtcat cagtatatga   3240
aacagccccc tgctgtccat tccttattcc atagaaaagc cttgacttga ggttagattt   3300
tttttatatt ttgttttgtg ttattttttt ctttaacatc cctaaaattt tccttacatg   3360
ttttactagc cagatttttc ctcctctcct gactactccc agtcatagct gtccctcttc   3420
tcttatggag atcgttaccc aggctggagt gcagtggcac atttctgctc actgcaacct   3480
cctcctccct gggttcaagc aattctcctg cctcagcctc ccaagtagct gtgattatag   3540
gtgcacacca ccaagcctgg ctaattttta tatctttagt agagacggga gtctcaccat   3600
gttggccagg ctagtctctg gcaagccatg gtaaaatgta actatttaag gctgctttaa   3660
attagactaa tagcagagtg gtcagactat actgaaagct tggtgaatca caattaagta   3720
cctcaaagaa ctattcttgt ttgccttatt cctatgtaaa taactgaaat ctttgttttt   3780
```

-continued

```
cttcctaaaa ggggtcatgt tgatttttac ttacaatgta ttttaagttt gtcactctaa   3840

atggttatga gcaagtttaa gaaaaatctt cagcaaatac taccttagat tatgacccca   3900

aaacacattt acttatgatt atgttgaaaa catagggtct ggggaaaaag ggatttaaaa   3960

taagaagaaa aagaagactt gggacttaaa aagtctttta gaggccagct caccaacatt   4020

cagaacaccc agtctgtgtt gcacaatatg ttacttaggt ataaatcaag gattcatgta   4080

attttgtcat tccttgcgtg atattttaaa aaacattctg tgtaaggtat ttataaagct   4140

ctcttctaaa aatacaaaaa tttgtggggc cttgtagtcc cagtcag                 4187
```

```
<210> SEQ ID NO 52
<211> LENGTH: 4187
<212> TYPE: DNA
<213> ORGANISM: Artificial Sequence
<220> FEATURE:
<223> OTHER INFORMATION: Made in Lab - AAV expression cassette construct

<400> SEQUENCE: 52

ctctggagac gcgttacata acttacggta aatggcccgc ctggctgacc gcccaacgac     60

ccccgcccat tgacgtcaat aatgacgtat gttcccatag taacgccaat agggactttc    120

cattgacgtc aatgggtgga gtatttacgg taaactgccc acttggcagt acatcaagtg    180

tatcatatgc caagtacgcc ccctattgac gtcaatgacg gtaaatggcc cgcctggcat    240

tatgcccagt acatgacctt atgggacttt cctacttggc agtacatcta cgtattagtc    300

atcgctatta ccaacttgtg gacaaagttt gctctattcc acctcctcca ggccctcctt    360

gggtccatca ccccaggggt gctgggtcca tcccaccccc aggcccacac aggcttgcag    420

tattgtgtgc ggtatggtca gggcgtccga gagcaggttt cgcagtggaa ggcaggcagg    480

tgttggggag gcagttaccg gggcaacggg aacagggcgt tttggaggtg gttgccatgg    540

ggacctggat gctgacgaag gctcgcgagg ctgtgagcag ccacagtgcc ctgctcagaa    600

gccccgggct cgtcagtcaa accggttctc tgtttgcact cggcagcacg ggcaggcaag    660

tggtccctag gttcggggaa ttcaaagcaa gccgccacca tgattgtgtt tgtccggttc    720

aactcctccc atggtttccc ggtggaagtg gactcagaca ccagcatctt ccaactgaag    780

gaagtggtgg ccaagcgtca gggggtcccg gcagaccagt tgagagtgat cttcgctgga    840

aaggaactga gaaacgactg gactgtgcag aactgtgacc tggaccaaca gtccattgtg    900

cacattgtcc agcggccttg gcggaaaggt caagagatga acgccactgg tggagatgac    960

cccaggaatg cagctggggg ctgtgaacgg gaacctcaga gcctgaccag agtggacctc   1020

agctcctctg tcctcccggg agactccgtg ggactggcag tcattctgca cactgacagc   1080

cgcaaggatt cccccccctgc gggttcacca gctggacggt ccatctacaa ctccttctat   1140

gtgtactgca agggaccctg ccagagggtg cagccgggaa agctcagagt gcagtgcagc   1200

acttgcagac aagccaccct gaccctgacc cagggcccat cctgctggga tgatgtcctg   1260

atccccaacc ggatgtcagg ggaatgccaa agccctcact gccctggaac ctcggccgag   1320

ttcttcttca aatgtggagc ccaccccacc tcggacaagg aaacctcggt ggcccttcac   1380

ctcattgcca ccaactcccg caacatcacc tgtatcactt gcactgatgt tcgctctccg   1440

gtgctggtgt tccagtgcaa ctcccgacac gtgatctgcc tggactgctt ccacctgtac   1500

tgtgtgacca gactgaatga caggcagttt gtccacgacc cccaactggg ctactccttg   1560

ccttgtgtgg ctggctgccc caactccctg atcaaggagt tgcaccactt ccggatcctg   1620

ggagaggaac agtacaacag ataccagcag tacggggcag aggaatgtgt cctccaaatg   1680
```

-continued

```
gggggagtgc tgtgcccccg gcctggttgt ggagctggcc tcctgccgga acctgaccag   1740
cggaaggtca cttgcgaggg tggaaacggc ctgggctgtg gcttcgcctt ctgtcgggag   1800
tgcaaggagg cctaccacga aggagaatgc tccgcggtgt ttgaagcctc agggaccacc   1860
acacaagcct acagagtgga tgagagggca gcggagcagg cccgctggga agcggcctcc   1920
aaggagacta tcaagaaaac caccaagcca tgccctaggt gccatgtgcc tgtggaaaag   1980
aatggaggct gcatgcacat gaagtgcccc cagccacagt gccgccttga atggtgctgg   2040
aactgtggct gcgagtggaa cagagtgtgt atgggggacc actggtttga tgtgtgataa   2100
tggattcctg taaacaggcc tattgattgg aaagtttgtc aacgaattgt gggtcttttg   2160
gggtttgctg cccctttac gcaatgtgga tatcctgctt taatgccttt atatgcatgt   2220
atacaagcaa aacaggcttt tactttctcg ccaacttaca aggcctttct cagtaaacag   2280
tatatgaccc tttaccccgt tgctcggcaa cggcctggtc tgtgccaagt gtttgctgac   2340
gcaaccccca ctggttgggg cttggccata ggccatcagc gcatgcgtgg aacctttgtg   2400
tctcctctgc cgatccatac tgcggaactc ctagccgctt gttttgctcg cagctggact   2460
ggagcaaacc tcatcgggac cgacaattct gtcgtactct cccgcaagca ctcaccgttt   2520
ccgcggctgc tcgcctgtgt tgccacctgg attctgcgcg ggacgtcctt ctgctacgtc   2580
ccttcggccc tcaatccagc ggaccttcct tcccgcggcc tgctgccggc tctgcggcct   2640
cttccgcctc ttcgccttcg ccctcagacg agtcggatct ccctttgggc cgcctccccg   2700
cccatgtatc tttttcacct gtgccttgtt tttgcctgtg ttccgcgtcc tacttttcaa   2760
gcctccaagc tgtgccttgg gcggctttgg ggcatggaca tagatcccta taaagaattt   2820
ggttcatctt atcagttgtt gaattttctt cctttggact ggctaataaa ggaaatttat   2880
tttcattgca atagtgtgtt ggaatttttt gtgtctctca ctcggaagaa catatgggag   2940
ggcaaatcat ttaaaacatc agaatgagta tttggtttag agtttggcaa catatgccca   3000
tatgctggct gccatgaaca aaggttggct ataaagaggt catcagtata tgaaacagcc   3060
ccctgctgtc cattccttat tccatagaaa agccttgact tgaggttaga tttttttat    3120
attttgtttt gtgttatttt tttctttaac atccctaaaa ttttccttac atgttttact   3180
agccagattt ttcctcctct cctgactact cccagtcata gctgtccctc ttctcttatg   3240
gagatcgtta cccaggctgg agtgcagtgg cacatttctg ctcactgcaa cctcctcctc   3300
cctgggttca agcaattctc ctgcctcagc ctcccaagta gctgtgatta taggtgcaca   3360
ccaccaagcc tggctaattt ttatatcttt agtagagacg ggagtctcac catgttggcc   3420
aggctagtct ctggcaagcc atggtaaaat gtaactattt aaggctgctt taaattagac   3480
taatagcaga gtggtcagac tatactgaaa gcttggtgaa tcacaattaa gtacctcaaa   3540
gaactattct tgtttgcctt attcctatgt aaataactga aatctttgtt tttcttccta   3600
aaaggggtca tgttgatttt tacttacaat gtattttaag tttgtcactc taaatggtta   3660
tgagcaagtt taagaaaaat cttcagcaaa tactacctta gattatgacc ccaaaacaca   3720
tttacttatg attatgttga aaacataggg tctggggaaa aagggattta aaataagaag   3780
aaaaagaaga cttgggactt aaaaagtctt ttagaggcca gctcaccaac attcagaaca   3840
cccagtctgt gttgcacaat atgttactta ggtataaatc aaggattcat gtaattttgt   3900
cattccttgc gtgatatttt aaaaaacatt ctgtgtaagg tatttataaa gctctcttct   3960
aaaaatacaa aaatttgtgg ggccttgtag tcccagctac ttgggaggct gaggcaggag   4020
```

gatttcttga actgggaggc agagcttgca gtgagcccac tgcactccag cctgggcaac 4080
agagtagaac tcctctcaaa aaaaaaaaaa aaaaagaaag aaagaaaaaa aagtggactg 4140
tgaaaactga aaggactaga aaaactacac tacaaagata cagtcag 4187

<210> SEQ ID NO 53
<211> LENGTH: 4177
<212> TYPE: DNA
<213> ORGANISM: Artificial Sequence
<220> FEATURE:
<223> OTHER INFORMATION: Made in Lab - AAV expression cassette construct

<400> SEQUENCE: 53
ctctggagac gcgttacata acttacggta aatggcccgc ctggctgacc gcccaacgac 60
ccccgcccat tgacgtcaat aatgacgtat gttcccatag taacgccaat agggactttc 120
cattgacgtc aatgggtgga gtatttacgg taaactgccc acttggcagt acatcaagtg 180
tatcatatgc caagtacgcc ccctattgac gtcaatgacg gtaaatggcc cgcctggcat 240
tatgcccagt acatgacctt atgggacttt cctacttggc agtacatcta cgtattagtc 300
atcgctatta ccatggtcga ggtgagcccc acgttctgct tcactctccc catctccccc 360
ccctccccac ccccaatttt gtatttattt atttttttaat tattttgtgc agcgatgggg 420
gcgggggggg ggggggcgcg cgccaggcgg ggcggggcgg ggcgaggggc ggggcggggc 480
gaggcggaga ggtgcggcgg cagccaatca gagcggcgcg ctccgaaagt ttccttttat 540
ggcgaggcgg cggcggcggc ggccctataa aaagcgaagc gcgcggcggg cgggagtcgc 600
tgcgcgctgc cttcgccccg tgccccgctc cgccgccgcc tcgcgccgcc cgccccggct 660
ctgactgacc gcgttactcc cacaggtgag cgggcgggac ggcccttctc ctccgggctg 720
taattagcgc ttggtttaat gacggcttgt ttcttttctg tggctgcgtg aaagccttga 780
ggggctccgg gagggccctt tgtgcggggg gagcggctcg gggggtgcgt gcgtgtgtgt 840
gtgcgtgggg agcgccgcgt gcggctccgc gctgcccggc ggctgtgagc gctgcgggcg 900
cggcgcgggg ctttgtgcgc tccgcagtgt gcgcgagggg agcgcggccg gggcggtgc 960 cccgcggtgc ggggggggct gcgaggggaa caaaggctgc gtgcggggtg tgtgcgtggg 1020
ggggtgagca gggggtgtgg gcgcgtcggt cgggctgcaa ccccccctgc acccccctcc 1080
ccgagttgct gagcacggcc cggcttcggg tgcggggctc cgtacggggc gtggcgcggg 1140
gctcgccgtg ccgggcgggg ggtggcggca ggtgggggtg ccgggcgggg cggggccgcc 1200
tcgggccggg gagggctcgg gggaggggcg cggcggcccc cggagcgccg gcggctgtcg 1260
aggcgcggcg agccgcagcc attgcctttt atggtaatcg tgcgagaggg cgcagggact 1320
tcctttgtcc caaatctgtg cggagccgaa atctgggagg cgccgccgca ccccctctag 1380
cgggcgcggg gcgaagcggt gcggcgccgg caggaaggaa atgggcgggg agggccttcg 1440
tgcgtcgccg cgccgccgtc cccttctccc tctccagcct cggggctgtc cgcgggggga 1500
cggctgcctt cggggggggac ggggcagggc ggggttcggc ttctggcgtg tgaccggcgg 1560
ctctagagcc tctgctaacc atgttcatgc cttcttcttt ttcctacagc tcctgggcaa 1620
cgtgctggtt attgtgctgt ctcatcattt tggcaaagaa ttcggcttga tcgaagccgt 1680
ctcaggggaa ttcaaagcaa gccgccacca tgattgtgtt tgtccggttc aactcctccc 1740
atggtttccc ggtggaagtg gactcagaca ccagcatctt ccaactgaag gaagtggtgg 1800
ccaagcgtca gggggtcccg gcagaccagt tgagagtgat cttcgctgga aaggaactga 1860
gaaacgactg gactgtgcag aactgtgacc tggaccaaca gtccattgtg cacattgtcc 1920

-continued

```
agcggccttg gcggaaaggt caagagatga acgccactgg tggagatgac cccaggaatg   1980
cagctggggg ctgtgaacgg gaacctcaga gcctgaccag agtggacctc agctcctctg   2040
tcctcccggg agactccgtg ggactggcag tcattctgca cactgacagc cgcaaggatt   2100
cccccccctgc gggttcacca gctggacggt ccatctacaa ctccttctat gtgtactgca   2160
agggaccctg ccagagggtg cagccgggaa agctcagagt gcagtgcagc acttgcagac   2220
aagccaccct gaccctgacc cagggcccat cctgctggga tgatgtcctg atccccaacc   2280
ggatgtcagg ggaatgccaa agccctcact gccctggaac ctcggccgag ttcttcttca   2340
aatgtggagc ccaccccacc tcggacaagg aaacctcggt ggcccttcac ctcattgcca   2400
ccaactcccg caacatcacc tgtatcactt gcactgatgt tcgctctccg gtgctggtgt   2460
tccagtgcaa ctcccgacac gtgatctgcc tggactgctt ccacctgtac tgtgtgacca   2520
gactgaatga caggcagttt gtccacgacc cccaactggg ctactccttg ccttgtgtgg   2580
ctggctgccc caactccctg atcaaggagt tgcaccactt ccggatcctg ggagaggaac   2640
agtacaacag ataccagcag tacggggcag aggaatgtgt cctccaaatg gggggagtgc   2700
tgtgcccccg gcctggttgt ggagctggcc tcctgccgga acctgaccag cggaaggtca   2760
cttgcgaggg tggaaacggc ctgggctgtg gcttcgcctt ctgtcgggag tgcaaggagg   2820
cctaccacga aggagaatgc tccgcggtgt ttgaagcctc agggaccacc acacaagcct   2880
acagagtgga tgagagggca gcggagcagg cccgctggga agcggcctcc aaggagacta   2940
tcaagaaaac caccaagcca tgccctaggt gccatgtgcc tgtggaaaag aatggaggct   3000
gcatgcacat gaagtgcccc cagccacagt gccgccttga atggtgctgg aactgtggct   3060
gcgagtggaa cagagtgtgt atgggggacc actggtttga tgtgtgataa tggattcctg   3120
ttaatcaacc tctggattac aaaatttgtg aaagattgac tggtattctt aactatgttg   3180
ctccttttac gctatgtgga tacgctgctt taatgccttt gtatcatgct attgcttccc   3240
gtatggcttt cattttctcc tccttgtata aatcctggtt gctgtctctt tatgaggagt   3300
tgtggcccgt tgtcaggcaa cgtggcgtgg tgtgcactgt gtttgctgac gcaaccccca   3360
ctggttgggg cattgccacc acctgtcagc tcctttccgg gactttcgct ttccccctcc   3420
ctattgccac ggcggaactc atcgccgcct gccttgcccg ctgctggaca ggggctcggc   3480
tgttgggcac tgacaattcc gtggtgttgt cggggaagct gacgtccttt ccgcggctgc   3540
tcgcctgtgt tgccacctgg attctgcgcg ggacgtcctt ctgctacgtc ccttcggccc   3600
tcaatccagc ggaccttcct tcccgcggcc tgctgccggc tctgcggcct cttccgcctc   3660
ttcgccttcg ccctcagacg agtcggatct ccctttgggc cgcctccccg cccatgtatc   3720
tttttcacct gtgccttgtt tttgcctgtg ttccgcgtcc tacttttcaa gcctccaagc   3780
tgtgccttgg gcggctttgg ggcatggaca tagatcccta taaagaattt ggttcatctt   3840
atcagttgtt gaattttctt cctttggacg ctggagcctc ggtagccgtt cctcctgccc   3900
gctgggcctc ccaacgggcc ctcctcccct ccttgcaccg gcccttcctg gtctttgaat   3960
aaattcattg cctgcccggg tggcatccct gtgacccctc cccagtgcct ctcctggccc   4020
tggaagttgc cactccagtg cccaccagcc ttgtcctaat aaaattaagt tgcatcattt   4080
tgtctgacta ggtgtccttc tataatatta tggggtggag gggggtggta tggagcaagg   4140
ggcccaagtt gggaagaaac ctgtagggcc tgctcag                              4177
```

<210> SEQ ID NO 54

<211> LENGTH: 4147
<212> TYPE: DNA
<213> ORGANISM: Artificial Sequence
<220> FEATURE:
<223> OTHER INFORMATION: Made in Lab - AAV expression cassette construct

<400> SEQUENCE: 54

```
ctctggagac gcgttacata acttacggta aatggcccgc ctggctgacc gcccaacgac     60
ccccgcccat tgacgtcaat aatgacgtat gttcccatag taacgccaat agggactttc    120
cattgacgtc aatgggtgga gtatttacgg taaactgccc acttggcagt acatcaagtg    180
tatcatatgc caagtacgcc ccctattgac gtcaatgacg gtaaatggcc cgcctggcat    240
tatgcccagt acatgacctt atgggacttt cctacttggc agtacatcta cgtattagtc    300
atcgctatta ccatggtcga ggtgagcccc acgttctgct tcactctccc catctccccc    360
ccctccccac ccccaatttt gtatttattt atttttaat tattttgtgc agcgatgggg    420
gcgggggggg ggggggcgcg cgccaggcgg ggcggggcgg ggcgaggggc ggggcggggc    480
gaggcggaga ggtgcggcgg cagccaatca gagcggcgcg ctccgaaagt ttccttttat    540
ggcgaggcgg cggcggcggc ggccctataa aaagcgaagc gcgcggcggg cgggagtcgc    600
tgcgcgctgc cttcgccccg tgccccgctc cgccgccgcc tcgcgccgcc cgccccggct    660
ctgactgacc gcgttactcc cacaggtgag cgggcgggac ggcccttctc ctccgggctg    720
taattagcgc ttggtttaat gacggcttgt ttcttttctg tggctgcgtg aaagccttga    780
ggggctccgg gagggccctt tgtgcggggg gagcggctcg gggggtgcgt gcgtgtgtgt    840
gtgcgtgggg agcgccgcgt gcggctccgc gctgcccggc ggctgtgagc gctgcgggcg    900
cggcgcgggg ctttgtgcgc tccgcagtgt gcgcgagggg agcgcggccg gggcggtgc     960
cccgcggtgc ggggggggct gcgaggggaa caaaggctgc gtgcggggtg tgtgcgtggg   1020
ggggtgagca gggggtgtgg gcgcgtcggt cgggctgcaa cccccccctgc accccccctcc   1080
ccgagttgct gagcacggcc cggcttcggg tgcggggctc cgtacggggc gtggcgcggg   1140
gctcgccgtg ccgggcgggg ggtggcggca ggtgggggtg ccgggcgggg cggggccgcc   1200
tcgggccggg gagggctcgg gggaggggcg cggcggcccc cggagcgccg gcggctgtcg   1260
aggcgcggcg agccgcagcc attgcctttt atggtaatcg tgcgagaggg cgcagggact   1320
tcctttgtcc caaatctgtg cggagccgaa atctgggagg cgccgccgca ccccctctag   1380
cgggcgcggg gcgaagcggt gcggcgccgg caggaaggaa atgggcgggg agggccttcg   1440
tgcgtcgccg cgccgccgtc cccttctccc tctccagcct cggggctgtc cgcgggggga   1500
cggctgcctt cggggggggac ggggcagggc ggggttcggc ttctggcgtg tgaccggcgg   1560
ctctagagcc tctgctaacc atgttcatgc cttcttcttt ttcctacagc tcctgggcaa   1620
cgtgctggtt attgtgctgt ctcatcattt tggcaaagaa ttcggcttga tcgaagccgt   1680
ctcaggggaa ttcaaagcaa gccgccacca tgattgtgtt tgtccggttc aactcctccc   1740
atggtttccc ggtggaagtg gactcagaca ccagcatctt ccaactgaag gaagtggtgg   1800
ccaagcgtca gggggtcccg gcagaccagt tgagagtgat cttcgctgga aaggaactga   1860
gaaacgactg gactgtgcag aactgtgacc tggaccaaca gtccattgtg cacattgtcc   1920
agcggccttg gcggaaaggt caagagatga acgccactgg tggagatgac cccaggaatg   1980
cagctggggg ctgtgaacgg gaacctcaga gcctgaccag agtggacctc agctcctctg   2040
tcctcccggg agactccgtg ggactggcag tcattctgca cactgacagc cgcaaggatt   2100
ccccccctgc gggttcacca gctggacggt ccatctacaa ctccttctat gtgtactgca   2160
```

```
agggaccctg ccagagggtg cagccgggaa agctcagagt gcagtgcagc acttgcagac   2220
aagccaccct gaccctgacc cagggcccat cctgctggga tgatgtcctg atccccaacc   2280
ggatgtcagg ggaatgccaa agccctcact gccctggaac ctcggccgag ttcttcttca   2340
aatgtggagc ccaccccacc tcggacaagg aaacctcggt ggcccttcac ctcattgcca   2400
ccaactcccg caacatcacc tgtatcactt gcactgatgt tcgctctccg gtgctggtgt   2460
tccagtgcaa ctcccgacac gtgatctgcc tggactgctt ccacctgtac tgtgtgacca   2520
gactgaatga caggcagttt gtccacgacc cccaactggg ctactccttg ccttgtgtgg   2580
ctggctgccc caactccctg atcaaggagt tgcaccactt ccggatcctg ggagaggaac   2640
agtacaacag ataccagcag tacggggcag aggaatgtgt cctccaaatg gggggagtgc   2700
tgtgcccccg gcctggttgt ggagctggcc tcctgccgga acctgaccag cggaaggtca   2760
cttgcgaggg tggaaacggc ctgggctgtg gcttcgcctt ctgtcgggag tgcaaggagg   2820
cctaccacga aggagaatgc tccgcggtgt ttgaagcctc agggaccacc acacaagcct   2880
acagagtgga tgagagggca gcggagcagg cccgctggga agcggcctcc aaggagacta   2940
tcaagaaaac caccaagcca tgccctaggt gccatgtgcc tgtggaaaag aatggaggct   3000
gcatgcacat gaagtgcccc cagccacagt gccgccttga atggtgctgg aactgtggct   3060
gcgagtggaa cagagtgtgt atgggggacc actggtttga tgtgtgataa tggagctgga   3120
gcctcggtag ccgttcctcc tgcccgctgg gcctcccaac gggccctcct cccctccttg   3180
caccggccct tcctggtctt tgaataaatt cattgctggc taataaagga aatttatttt   3240
cattgcaata gtgtgttgga atttttgtg tctctcactc ggaagaacat atgggagggc    3300
aaatcattta aaacatcaga atgagtattt ggtttagagt ttggcaacat atgcccatat   3360
gctggctgcc atgaacaaag gttggctata aagaggtcat cagtatatga aacagccccc   3420
tgctgtccat tccttattcc atagaaaagc cttgacttga ggttagattt tttttatatt   3480
ttgttttgtg ttattttttt ctttaacatc cctaaaattt tccttacatg ttttactagc   3540
cagatttttc ctcctctcct gactactccc agtcatagct gtccctcttc tcttatggag   3600
atcgttaccc aggctggagt gcagtggcac atttctgctc actgcaacct cctcctccct   3660
gggttcaagc aattctcctg cctcagcctc ccaagtagct gtgattatag gtgcacacca   3720
ccaagcctgg ctaattttta tatctttagt agagacggga gtctcaccat gttggccagg   3780
ctagtctctg gcaagccatg gtaaaatgta actatttaag gctgctttaa attagactaa   3840
tagcagagtg gtcagactat actgaaagct tggtgaatca caattaagta cctcaaagaa   3900
ctattcttgt ttgccttatt cctatgtaaa taactgaaat ctttgttttt cttcctaaaa   3960
ggggtcatgt tgatttttac ttacaatgta ttttaagttt gtcactctaa atggttatga   4020
gcaagtttaa gaaaaatctt cagcaaatac taccttagat tatgacccca aaacacattt   4080
acttatgatt atgttgaaaa catagggtct ggggaaaaag ggatttaaaa taagaagaaa   4140
aagtcag                                                             4147
```

<210> SEQ ID NO 55
<211> LENGTH: 4187
<212> TYPE: DNA
<213> ORGANISM: Artificial Sequence
<220> FEATURE:
<223> OTHER INFORMATION: Made in Lab - AAV expression cassette construct

<400> SEQUENCE: 55

-continued

```
ctctggagac gcgttacata acttacggta aatggcccgc ctggctgacc gcccaacgac     60
ccccgcccat tgacgtcaat aatgacgtat gttcccatag taacgccaat agggactttc    120
cattgacgtc aatgggtgga gtatttacgg taaactgccc acttggcagt acatcaagtg    180
tatcatatgc caagtacgcc ccctattgac gtcaatgacg gtaaatggcc cgcctggcat    240
tatgcccagt acatgacctt atgggacttt cctacttggc agtacatcta cgtattagtc    300
atcgctatta ccaacttgtg gacaaagttt gctctattcc acctcctcca ggccctcctt    360
gggtccatca ccccaggggt gctgggtcca tcccaccccc aggcccacac aggcttgcag    420
tattgtgtgc ggtatggtca gggcgtccga gagcaggttt cgcagtggaa ggcaggcagg    480
tgttggggag gcagttaccg gggcaacggg aacagggcgt tttggaggtg gttgccatgg    540
ggacctggat gctgacgaag gctcgcgagg ctgtgagcag ccacagtgcc ctgctcagaa    600
gccccgggct cgtcagtcaa accggttctc tgtttgcact cggcagcacg ggcaggcaag    660
tggtccctag gttcggggaa ttcaaagcaa gccgccacca tgattgtgtt tgtccggttc    720
aactcctccc atggtttccc ggtggaagtg gactcagaca ccagcatctt ccaactgaag    780
gaagtggtgg ccaagcgtca gggggtcccg gcagaccagt tgagagtgat cttcgctgga    840
aaggaactga gaaacgactg gactgtgcag aactgtgacc tggaccaaca gtccattgtg    900
cacattgtcc agcggccttg gcggaaaggt caagagatga acgccactgg tggagatgac    960
cccaggaatg cagctggggg ctgtgaacgg gaacctcaga gcctgaccag agtggacctc   1020
agctcctctg tcctcccggg agactccgtg ggactggcag tcattctgca cactgacagc   1080
cgcaaggatt cccccccctgc gggttcacca gctggacggt ccatctacaa ctccttctat   1140
gtgtactgca agggaccctg ccagagggtg cagccgggaa agctcagagt gcagtgcagc   1200
acttgcagac aagccaccct gaccctgacc cagggcccat cctgctggga tgatgtcctg   1260
atccccaacc ggatgtcagg ggaatgccaa agccctcact gccctggaac ctcggccgag   1320
ttcttcttca aatgtggagc ccaccccacc tcggacaagg aaacctcggt ggcccttcac   1380
ctcattgcca ccaactcccg caacatcacc tgtatcactt gcactgatgt tcgctctccg   1440
gtgctggtgt tccagtgcaa ctcccgacac gtgatctgcc tggactgctt ccacctgtac   1500
tgtgtgacca gactgaatga caggcagttt gtccacgacc cccaactggg ctactccttg   1560
ccttgtgtgg ctggctgccc caactccctg atcaaggagt tgcaccactt ccggatcctg   1620
ggagaggaac agtacaacag ataccagcag tacggggcag aggaatgtgt cctccaaatg   1680
gggggagtgc tgtgcccccg gcctggttgt ggagctggcc tcctgccgga acctgaccag   1740
cggaaggtca cttgcgaggg tggaaacggc ctgggctgtg gcttcgcctt ctgtcgggag   1800
tgcaaggagg cctaccacga aggagaatgc tccgcggtgt ttgaagcctc agggaccacc   1860
acacaagcct acagagtgga tgagagggca gcggagcagg cccgctggga agcggcctcc   1920
aaggagacta tcaagaaaac caccaagcca tgccctaggt gccatgtgcc tgtggaaaag   1980
aatggaggct gcatgcacat gaagtgcccc cagccacagt gccgccttga atggtgctgg   2040
aactgtggct gcgagtggaa cagagtgtgt atgggggacc actggtttga tgtgtgataa   2100
tggattcctg taaacaggcc tattgattgg aaagtttgtc aacgaattgt gggtcttttg   2160
gggtttgctg ccccttttac gcaatgtgga tatcctgctt taatgccttt atatgcatgt   2220
atacaagcaa aacaggcttt tactttctcg ccaacttaca aggcctttct cagtaaacag   2280
tatatgaccc tttaccccgt tgctcggcaa cggcctggtc tgtgccaagt gtttgctgac   2340
gcaaccccca ctggttgggg cttggccata ggccatcagc gcatgcgtgg aacctttgtg   2400
```

tctcctctgc cgatccatac tgcggaactc ctagccgctt gttttgctcg cagctggact 2460
ggagcaaacc tcatcgggac cgacaattct gtcgtactct cccgcaagca ctcaccgttt 2520
ccgcggctgc tcgcctgtgt tgccacctgg attctgcgcg ggacgtcctt ctgctacgtc 2580
ccttcggccc tcaatccagc ggaccttcct tcccgcggcc tgctgccggc tctgcggcct 2640
cttccgcctc ttcgccttcg ccctcagacg agtcggatct ccctttgggc cgcctccccg 2700
cccatgtatc tttttcacct gtgccttgtt tttgcctgtg ttccgcgtcc tacttttcaa 2760
gcctccaagc tgtgccttgg gcggctttgg ggcatggaca tagatcccta taaagaattt 2820
ggttcatctt atcagttgtt gaattttctt cctttggact tgccagccat ctgttgtttg 2880
cccctccccc gtgccttcct tgaccctgga aggtgccact cccactgtcc tttcctaata 2940
aaatgaggaa attgcatcgc attgtctgag taggtgtcat tctattctgg ggggtggggt 3000
ggggcaggac agcaaggggg aggattggga atacaatagc aggcatgctg gggatgcggt 3060
gggctctatg ggtacccagg tgctgaagaa ttgacccggt tcctcctggg gttacccagg 3120
ctggagtgca gtggcacatt tctgctcact gcaacctcct cctccctggg ttcaagcaat 3180
tctcctgcct cagcctccca agtagctgtg attataggtg cacaccacca agcctggcta 3240
atttttatat ctttagtaga gacgggagtc tcaccatgtt ggccaggcta gtctctggca 3300
agccatggta aaatgtaact atttaaggct gctttaaatt agactaatag cagagtggtc 3360
agactatact gaaagcttgg tgaatcacaa ttaagtacct caaagaacta ttcttgtttg 3420
ccttattcct atgtaaataa ctgaaatctt tgtttttctt cctaaaaggg gtcatgttga 3480
tttttactta caatgtattt taagtttgtc actctaaatg gttatgagca agtttaagaa 3540
aaatcttcag caaatactac cttagattat gaccccaaaa cacatttact tatgattatg 3600
ttgaaaacat agggtctggg gaaaaaggga tttaaaataa gaagaaaaag aagacttggg 3660
acttaaaaag tcttttagag gccagctcac caacattcag aacacccagt ctgtgttgca 3720
caatatgtta cttaggtata aatcaaggat tcatgtaatt ttgtcattcc ttgcgtgata 3780
ttttaaaaaa cattctgtgt aaggtattta taaagctctc ttctaaaaat acaaaaattt 3840
gtggggcctt gtagtcccag ctacttggga ggctgaggca ggaggatttc ttgaactggg 3900
aggcagagct tgcagtgagc ccactgcact ccagcctggg caacagagta gaactcctct 3960
caaaaaaaaa aaaaaaaaag aaagaaagaa aaaaaagtgg actgtgaaaa ctgaaaggac 4020
tagaaaaact acactacaaa gatacagaaa ccaagaaagc accaaaggtt tgccttcaac 4080
tgcttcccaa cttgttttcc tcttccaatt tgattgtggt ttcctctcca gaaggaactc 4140
cacagtactt agcgttggtc acatagtagg ttctcaaata ctttcag 4187

<210> SEQ ID NO 56
<211> LENGTH: 4143
<212> TYPE: DNA
<213> ORGANISM: Artificial Sequence
<220> FEATURE:
<223> OTHER INFORMATION: Made in Lab - AAV expression cassette construct

<400> SEQUENCE: 56
ctctggagac gcaacctttg gagctaagcc agcaatggta gagggaagat tctgcacgtc 60
ccttccaggc ggcctccccg tcaccacccc ccccaacccg ccccgaccgg agctgagagt 120
aattcataca aaaggactcg cccctgcctt ggggaatccc agggaccgtc gttaaactcc 180
cactaacgta gaacccagag atcgctgcgt tcccgccccc tcacccgccc gctctcgtca 240

-continued

```
tcactgaggt ggagaatagc atgcgtgagg ctccggtgcc cgtcagtggg cagagcgcac    300
atcgcccaca gtccccgaga agttgggggg aggggtcggc aattgaacgg gtgcctagag    360
aaggtggcgc ggggtaaact gggaaagtga tgtcgtgtac tggctccgcc tttttcccga    420
gggtggggga gaaccgtata taagtgcagt agtcgccgtg aacgttcttt ttcgcaacgg    480
gtttgccgcc agaacacagg taagtgccgt gtgtggttcc cgcgggcctg gcctctttac    540
gggttatggc ccttgcgtgc cttgaattac ttccacctgg ctccagtacg tgattcttga    600
tcccgagctg gagccagggg cgggccttgc gctttaggag ccccttcgcc tcgtgcttga    660
gttgaggcct ggcctgggcg ctggggccgc cgcgtgcgaa tctggtggca ccttcgcgcc    720
tgtctcgctg ctttcgataa gtctctagcc atttaaaatt tttgatgacg tgctgcgacg    780
ctttttttct ggcaagatag tcttgtaaat gcgggccagg atctgcacac tggtatttcg    840
gtttttgggc ccgcggccgg cgacggggcc cgtgcgtccc agcgcacatg ttcggcgagg    900
cggggcctgc gagcgcggcc accgagaatc ggacgggggt agtctcaagc tggccggcct    960
gctctggtgc ctggcctcgc gccgccgtgt atcgccccgc cctgggcggc aaggctggcc   1020
cggtcggcac cagttgcgtg agcggaaaga tggccgcttc ccggccctgc tccagggggc   1080
tcaaaatgga ggacgcggcg ctcgggagag cgggcgggtg agtcacccac acaaaggaaa   1140
agggcctttc cgtcctcagc cgtcgcttca tgtgactcca cggagtaccg ggcgccgtcc   1200
aggcacctcg attagttctg gagcttttgg agtacgtcgt ctttaggttg gggggagggg   1260
ttttatgcga tggagtttcc ccacactgag tgggtggaga ctgaagttag gccagcttgg   1320
cacttgatgt aattctcctt ggaatttggc ctttttgagt ttggatcttg gttcattctc   1380
aagcctcaga cagtggttca aagttttttt cttccatttc aggtgtcgtg aacacgtctc   1440
aggggaattc aaagcaagcc gccaccatga ttgtgtttgt ccggttcaac tcctcccatg   1500
gtttcccggt ggaagtggac tcagacacca gcatcttcca actgaaggaa gtggtggcca   1560
agcgtcaggg ggtcccggca gaccagttga gagtgatctt cgctggaaag gaactgagaa   1620
acgactggac tgtgcagaac tgtgacctgg accaacagtc cattgtgcac attgtccagc   1680
ggccttggcg gaaaggtcaa gagatgaacg ccactggtgg agatgacccc aggaatgcag   1740
ctgggggctg tgaacgggaa cctcagagcc tgaccagagt ggacctcagc tcctctgtcc   1800
tcccgggaga ctccgtggga ctggcagtca ttctgcacac tgacagccgc aaggattccc   1860
cccctgcggg ttcaccagct ggacggtcca tctacaactc cttctatgtg tactgcaagg   1920
gaccctgcca gagggtgcag ccgggaaagc tcagagtgca gtgcagcact tgcagacaag   1980
ccaccctgac cctgacccag ggcccatcct gctgggatga tgtcctgatc cccaaccgga   2040
tgtcagggga atgccaaagc cctcactgcc ctggaacctc ggccgagttc ttcttcaaat   2100
gtggagccca ccccacctcg gacaaggaaa cctcggtggc ccttcacctc attgccacca   2160
actcccgcaa catcacctgt atcacttgca ctgatgttcg ctctccggtg ctggtgttcc   2220
agtgcaactc ccgacacgtg atctgcctgg actgcttcca cctgtactgt gtgaccagac   2280
tgaatgacag gcagtttgtc cacgaccccc aactgggcta ctccttgcct tgtgtggctg   2340
gctgccccaa ctccctgatc aaggagttgc accacttccg gatcctggga gaggaacagt   2400
acaacagata ccagcagtac ggggcagagg aatgtgtcct ccaaatgggg ggagtgctgt   2460
gcccccggcc tggttgtgga gctggcctcc tgccggaacc tgaccagcgg aaggtcactt   2520
gcgagggtgg aaacggcctg ggctgtggct tcgccttctg tcgggagtgc aaggaggcct   2580
accacgaagg agaatgctcc gcggtgtttg aagcctcagg gaccaccaca caagcctaca   2640
```

```
gagtggatga gagggcagcg gagcaggccc gctgggaagc ggcctccaag gagactatca   2700
agaaaaccac caagccatgc cctaggtgcc atgtgcctgt ggaaaagaat ggaggctgca   2760
tgcacatgaa gtgcccccag ccacagtgcc gccttgaatg gtgctggaac tgtggctgcg   2820
agtggaacag agtgtgtatg gggaccact ggtttgatgt gtgataatgg attcctgtaa    2880
acaggcctat tgattggaaa gtttgtcaac gaattgtggg tcttttgggg tttgctgccc   2940
cttttacgca atgtggatat cctgctttaa tgcctttata tgcatgtata caagcaaaac   3000
aggcttttac tttctcgcca acttacaagg cctttctcag taaacagtat atgacccttt   3060
accccgttgc tcggcaacgg cctggtctgt gccaagtgtt tgctgacgca acccccactg   3120
gttggggctt ggccataggc catcagcgca tgcgtggaac ctttgtgtct cctctgccga   3180
tccatactgc ggaactccta gccgcttgtt ttgctcgcag ctggactgga gcaaacctca   3240
tcgggaccga caattctgtc gtactctccc gcaagcactc accgtttccg cggctgctcg   3300
cctgtgttgc cacctggatt ctgcgcggga cgtccttctg ctacgtccct tcggccctca   3360
atccagcgga ccttccttcc cgcggcctgc tgccggctct gcggcctctt ccgcctcttc   3420
gccttcgccc tcagacgagt cggatctccc tttgggccgc ctccccgccc atgtatcttt   3480
ttcacctgtg ccttgttttt gcctgtgttc cgcgtcctac ttttcaagcc tccaagctgt   3540
gccttgggcg gctttggggc atggacatag atccctataa agaatttggt tcatcttatc   3600
agttgttgaa ttttcttcct ttggacgctg gagcctcggt agccgttcct cctgcccgct   3660
gggcctccca acgggccctc ctcccctcct tgcaccggcc cttcctggtc tttgaataaa   3720
ttcattgcct gcccgggtgg catccctgtg acccctcccc agtgcctctc ctggccctgg   3780
aagttgccac tccagtgccc accagccttg tcctaataaa attaagttgc atcattttgt   3840
ctgactaggt gtccttctat aatattatgg ggtggagggg ggtggtatgg agcaaggggc   3900
ccaagttggg aagaaacctg tagggcctgc gttacccagg ctggagtgca gtggcacatt   3960
tctgctcact gcaacctcct cctccctggg ttcaagcaat tctcctgcct cagcctccca   4020
agtagctgtg attataggtg cacaccacca agcctggcta atttttatat ctttagtaga   4080
gacgggagtc tcaccatgtt ggccaggcta gtctctggca agccatggta aaatgtaact   4140
cag                                                                  4143
```

<210> SEQ ID NO 57
<211> LENGTH: 4140
<212> TYPE: DNA
<213> ORGANISM: Artificial Sequence
<220> FEATURE:
<223> OTHER INFORMATION: Made in Lab - AAV expression cassette construct

<400> SEQUENCE: 57

```
ctctccaaca ttaccgccat gttgacttca atgtctatat atggagatcc gcatattgac     60
gtcaatatcg gtaaatggcc cacttggctg accgccccac gaccccgcc cattgacgtc     120
aatggtggga ctttccattg acgtcaatgg gcggggaacg gatatgagcc atagaatgta    180
ctgccaagtg ggccatttac cgttcaccac gcccctattg acgtcaatga cggtaaatgg    240
cccgcctggc tgtacgccaa ttgcatcatc ctattgtttt tctatgggaa tttccctatt    300
ggcagtacat caacgtatta ctaatgggga tttccaatga ctaatacaac gggcagtacg    360
cccagtacgt atgactaatg ggactttcca taatcccgcc ccattgacgt caatgggcat    420
ccgttctggc accaaaatga atgggaattt ccaatatgag tcataaaccc cgccccattg    480
```

-continued

```
acgcacatta cacgtcaatg ggcggtaggc gtgccctatg ggcggtctat ataagcagag    540
cccgtttagt gaaccgtcac ttcgcttgga gccaccgtcc acgctgtttg gagctccata    600
gaaggaaccg ggacccagcc agcctccgta gccgggaacg gtgcattgga acgcggatac    660
agcgtgccaa tagtgacgta agtactgcct atagatatag gcgtggctat atactatcta    720
tagcatgcta tgcattatct tggctttgga ccagggcgct tccgcttact catactatag    780
ggtgatggta tagcttaaca tataggtgga gctattgatt gggactgccc cctattggtg    840
acggtgtttc ctatatctga tcaatactat ggccctctgc catgccgccc ctcttggcct    900
atagccaatc tatcggtgtc ggactctgct tagaccccct ttccaactcc cagagactga    960
cacgcggact ctgtttgttt ttaaggatgg ctcttttatt cttagacccc acaaacaccg   1020
tccggggcta acaggggatc tccacggcga tctcgggtac ccccggccac gggagtgtgg   1080
ttagtctgtc ctcctccggc tcctcgggcc aggtccccag cagctcttct tgttcttcat   1140
cgtcgctggg cacctctcgg ctgctaattg tcgaggccag actcaggcag atcacgatcc   1200
ccaccactat taccatgccg cccagggccg aggctgtggg gtatgcctct aacaacgagc   1260
ccggggaccc tacatgggtc cacggactct ctgctgtctg gagacttaag gccagggaag   1320
aagagacaga tgatgaagtc cctgacagct gagaagaaaa ggtaagggag ctcgttactc   1380
ccgtggtgtt gtgatagtta acagcggtgg agggcagtgt agtctgagca gtactcgttg   1440
ctgccgcgcg cgccaccaga cataatagct gacagactaa cagaagcctc tgctaaccat   1500
gttcatgcct tcttcttttt cctacagctc ctgggcaacg tgctggttat tgtgctgtct   1560
catcattttg gcaaagaatt gccaccatga ttgtgtttgt ccggttcaac tcctcccatg   1620
gtttcccggt ggaagtggac tcagacacca gcatcttcca actgaaggaa gtggtggcca   1680
agcgtcaggg ggtcccggca gaccagttga gagtgatctt cgctggaaag gaactgagaa   1740
acgactggac tgtgcagaac tgtgacctgg accaacagtc cattgtgcac attgtccagc   1800
ggccttggcg gaaaggtcaa gagatgaacg ccactggtgg agatgacccc aggaatgcag   1860
ctgggggctg tgaacgggaa cctcagagcc tgaccagagt ggacctcagc tcctctgtcc   1920
tcccgggaga ctccgtggga ctggcagtca ttctgcacac tgacagccgc aaggattccc   1980
cccctgcggg ttcaccagct ggacggtcca tctacaactc cttctatgtg tactgcaagg   2040
gaccctgcca gagggtgcag ccgggaaagc tcagagtgca gtgcagcact tgcagacaag   2100
ccaccctgac cctgacccag ggcccatcct gctgggatga tgtcctgatc cccaaccgga   2160
tgtcagggga atgccaaagc cctcactgcc ctggaacctc ggccgagttc ttcttcaaat   2220
gtggagccca ccccacctcg gacaaggaaa cctcggtggc ccttcacctc attgccacca   2280
actcccgcaa catcacctgt atcacttgca ctgatgttcg ctctccggtg ctggtgttcc   2340
agtgcaactc ccgacacgtg atctgcctgg actgcttcca cctgtactgt gtgaccagac   2400
tgaatgacag gcagtttgtc cacgaccccc aactgggcta ctccttgcct tgtgtggctg   2460
gctgccccaa ctccctgatc aaggagttgc accacttccg gatcctggga gaggaacagt   2520
acaacagata ccagcagtac ggggcagagg aatgtgtcct ccaaatgggg ggagtgctgt   2580
gcccccggcc tggttgtgga gctggcctcc tgccggaacc tgaccagcgg aaggtcactt   2640
gcgagggtgg aaacggcctg ggctgtggct tcgccttctg tcgggagtgc aaggaggcct   2700
accacgaagg agaatgctcc gcggtgtttg aagcctcagg gaccaccaca caagcctaca   2760
gagtggatga gagggcagcg gagcaggccc gctgggaagc ggcctccaag gagactatca   2820
agaaaaccac caagccatgc cctaggtgcc atgtgcctgt ggaaaagaat ggaggctgca   2880
```

tgcacatgaa gtgcccccag ccacagtgcc gccttgaatg gtgctggaac tgtggctgcg 2940
agtggaacag agtgtgtatg ggggaccact ggtttgatgt gtgataatgg attcctgtaa 3000
acaggcctat tgattggaaa gtttgtcaac gaattgtggg tcttttgggg tttgctgccc 3060
cttttacgca atgtggatat cctgctttaa tgcctttata tgcatgtata caagcaaaac 3120
aggcttttac tttctcgcca acttacaagg cctttctcag taaacagtat atgacccttt 3180
accccgttgc tcggcaacgg cctggtctgt gccaagtgtt tgctgacgca acccccactg 3240
gttggggctt ggccataggc catcagcgca tgcgtggaac ctttgtgtct cctctgccga 3300
tccatactgc ggaactccta gccgcttgtt ttgctcgcag ctggactgga gcaaacctca 3360
tcgggaccga caattctgtc gtactctccc gcaagcactc accgtttccg cggctgctcg 3420
cctgtgttgc cacctggatt ctgcgcggga cgtccttctg ctacgtccct tcggccctca 3480
atccagcgga ccttccttcc cgcggcctgc tgccggctct gcggcctctt ccgcctcttc 3540
gccttcgccc tcagacgagt cggatctccc tttgggccgc ctccccgccc atgtatcttt 3600
ttcacctgtg ccttgttttt gcctgtgttc cgcgtcctac ttttcaagcc tccaagctgt 3660
gccttgggcg gctttggggc atggacatag atccctataa agaatttggt tcatcttatc 3720
agttgttgaa ttttcttcct ttggacgctg gagcctcggt agccgttcct cctgcccgct 3780
gggcctccca acgggccctc ctcccctcct tgcaccggcc cttcctggtc tttgaataaa 3840
ttcattgcct gcccgggtgg catccctgtg acccctcccc agtgcctctc ctggccctgg 3900
aagttgccac tccagtgccc accagccttg tcctaataaa attaagttgc atcattttgt 3960
ctgactaggt gtccttctat aatattatgg ggtggagggg ggtggtatgg agcaaggggc 4020
ccaagttggg aagaaacctg tagggcctgc gttacccagg ctggagtgca gtggcacatt 4080
tctgctcact gcaacctcct cctccctggg ttcaagcaat tctcctgcct cagccttcag 4140

<210> SEQ ID NO 58
<211> LENGTH: 4148
<212> TYPE: DNA
<213> ORGANISM: Artificial Sequence
<220> FEATURE:
<223> OTHER INFORMATION: Made in Lab - AAV expression cassette construct

<400> SEQUENCE: 58
ctctccaaca ttaccgccat gttgacttca atgtctatat atggagatcc gcatattgac 60
gtcaatatcg gtaaatggcc cacttggctg accgccccac gacccccgcc cattgacgtc 120
aatggtggga ctttccattg acgtcaatgg gcggggaacg gatatgagcc atagaatgta 180
ctgccaagtg ggccatttac cgttcaccac gcccctattg acgtcaatga cggtaaatgg 240
cccgcctggc tgtacgccaa ttgcatcatc ctattgtttt tctatgggaa tttccctatt 300
ggcagtacat caacgtatta ctaatgggga tttccaatga ctaatacaac gggcagtacg 360
cccagtacgt atgactaatg ggactttcca taatcccgcc ccattgacgt caatgggcat 420
ccgttctggc accaaaatga atgggaattt ccaatatgag tcataaaccc cgccccattg 480
acgcacatta cacgtcaatg ggcggtaggc gtgccctatg ggcggtctat ataagcagag 540
cccgtttagt gaaccgtcac ttcgcttgga gccaccgtcc acgctgtttg gagctccata 600
gaaggaaccg ggacccagcc agcctccgta gccgggaacg gtgcattgga acgcggatac 660
agcgtgccaa tagtgacgta agtactgcct atagatatag gcgtggctat atactatcta 720
tagcatgcta tgcattatct tggctttgga ccagggcgct tccgcttact catactatag 780

-continued

```
ggtgatggta tagcttaaca tataggtgga gctattgatt gggactgccc cctattggtg    840
acggtgtttc ctatatctga tcaatactat ggccctctgc catgccgccc ctcttggcct    900
atagccaatc tatcggtgtc ggactctgct tagacccccct ttccaactcc cagagactga    960
cacgcggact ctgtttgttt ttaaggatgg ctcttttatt cttagacccc acaaacaccg   1020
tccggggcta acaggggatc tccacggcga tctcgggtac ccccggccac gggagtgtgg   1080
ttagtctgtc ctcctccggc tcctcgggcc aggtccccag cagctcttct tgttcttcat   1140
cgtcgctggg cacctctcgg ctgctaattg tcgaggccag actcaggcag atcacgatcc   1200
ccaccactat taccatgccg cccagggccg aggctgtggg gtatgcctct aacaacgagc   1260
ccggggaccc tacatgggtc cacggactct ctgctgtctg gagacttaag gccagggaag   1320
aagagacaga tgatgaagtc cctgacagct gagaagaaaa ggtaagggag ctcgttactc   1380
ccgtggtgtt gtgatagtta acagcggtgg agggcagtgt agtctgagca gtactcgttg   1440
ctgccgcgcg cgccaccaga cataatagct gacagactaa cagaagcctc tgctaaccat   1500
gttcatgcct tcttcttttt cctacagctc ctgggcaacg tgctggttat tgtgctgtct   1560
catcattttg gcaaagaatt gccaccatga ttgtgtttgt ccggttcaac tcctcccatg   1620
gtttcccggt ggaagtggac tcagacacca gcatcttcca actgaaggaa gtggtggcca   1680
agcgtcaggg ggtcccggca gaccagttga gagtgatctt cgctggaaag gaactgagaa   1740
acgactggac tgtgcagaac tgtgacctgg accaacagtc cattgtgcac attgtccagc   1800
ggccttggcg gaaaggtcaa gagatgaacg ccactggtgg agatgacccc aggaatgcag   1860
ctgggggctg tgaacgggaa cctcagagcc tgaccagagt ggacctcagc tcctctgtcc   1920
tcccgggaga ctccgtggga ctggcagtca ttctgcacac tgacagccgc aaggattccc   1980
cccctgcggg ttcaccagct ggacggtcca tctacaactc cttctatgtg tactgcaagg   2040
gaccctgcca gagggtgcag ccgggaaagc tcagagtgca gtgcagcact tgcagacaag   2100
ccaccctgac cctgacccag ggcccatcct gctgggatga tgtcctgatc cccaaccgga   2160
tgtcagggga atgccaaagc cctcactgcc ctggaacctc ggccgagttc ttcttcaaat   2220
gtggagccca ccccacctcg gacaaggaaa cctcggtggc ccttcacctc attgccacca   2280
actcccgcaa catcacctgt atcacttgca ctgatgttcg ctctccggtg ctggtgttcc   2340
agtgcaactc ccgacacgtg atctgcctgg actgcttcca cctgtactgt gtgaccagac   2400
tgaatgacag gcagtttgtc cacgaccccc aactgggcta ctccttgcct tgtgtggctg   2460
gctgccccaa ctccctgatc aaggagttgc accacttccg gatcctggga gaggaacagt   2520
acaacagata ccagcagtac ggggcagagg aatgtgtcct ccaaatgggg ggagtgctgt   2580
gcccccggcc tggttgtgga gctggcctcc tgccggaacc tgaccagcgg aaggtcactt   2640
gcgagggtgg aaacggcctg ggctgtggct tcgccttctg tcgggagtgc aaggaggcct   2700
accacgaagg agaatgctcc gcggtgtttg aagcctcagg gaccaccaca caagcctaca   2760
gagtggatga gagggcagcg gagcaggccc gctgggaagc ggcctccaag gagactatca   2820
agaaaaccac caagccatgc cctaggtgcc atgtgcctgt ggaaaagaat ggaggctgca   2880
tgcacatgaa gtgcccccag ccacagtgcc gccttgaatg gtgctggaac tgtggctgcg   2940
agtggaacag agtgtgtatg gggaccact ggtttgatgt gtgataatgg attaactgcc   3000
cgggtggcat ccctgtgacc cctccccagt gcctctcctg gccctggaag ttgccactcc   3060
agtgcccacc agccttgtcc taataaaatt aagttgcatc attttgtctg actaggtgtc   3120
cttctataat attatggggt ggaggggggt ggtatggagc aaggggccca agttgggaag   3180
```

```
aaacctgtag ggcctgcgtt acccaggctg gagtgcagtg gcacatttct gctcactgca   3240

acctcctcct ccctgggttc aagcaattct cctgcctcag cctcccaagt agctgtgatt   3300

ataggtgcac accaccaagc ctggctaatt tttatatctt tagtagagac gggagtctca   3360

ccatgttggc caggctagtc tctggcaagc catggtaaaa tgtaactatt taaggctgct   3420

ttaaattaga ctaatagcag agtggtcaga ctatactgaa agcttggtga atcacaatta   3480

agtacctcaa agaactattc ttgtttgcct tattcctatg taaataactg aaatctttgt   3540

ttttcttcct aaaaggggtc atgttgattt ttacttacaa tgtattttaa gtttgtcact   3600

ctaaatggtt atgagcaagt ttaagaaaaa tcttcagcaa atactacctt agattatgac   3660

cccaaaacac atttacttat gattatgttg aaaacatagg gtctggggaa aaagggattt   3720

aaaataagaa gaaaaagaag acttgggact taaaaagtct tttagaggcc agctcaccaa   3780

cattcagaac acccagtctg tgttgcacaa tatgttactt aggtataaat caaggattca   3840

tgtaattttg tcattccttg cgtgatattt taaaaaacat tctgtgtaag gtatttataa   3900

agctctcttc taaaaataca aaaatttgtg gggccttgta gtcccagcta cttgggaggc   3960

tgaggcagga ggatttcttg aactgggagg cagagcttgc agtgagccca ctgcactcca   4020

gcctgggcaa cagagtagaa ctcctctcaa aaaaaaaaaa aaaaaagaaa gaaagaaaaa   4080

aaagtggact gtgaaaactg aaaggactag aaaaactaca ctacaaagat acagaaacca   4140

agaatcag                                                            4148
```

```
<210> SEQ ID NO 59
<211> LENGTH: 253
<212> TYPE: DNA
<213> ORGANISM: Homo sapiens

<400> SEQUENCE: 59

gcccagcacc ccaaggcggc caacgccaaa actctccctc ctcctcttcc tcaatctcgc     60

tctcgctctt tttttttttc gcaaaaggag gggagagggg gtaaaaaaat gctgcactgt    120

gcggcgaagc cggtgagtga gcggcgcggg gccaatcagc gtgcgccgtt ccgaaagttg    180

ccttttatgg ctcgagcggc cgcggcggcg ccctataaaa cccagcggcg cgacgcgcca    240

ccaccgccga gtc                                                       253
```

```
<210> SEQ ID NO 60
<211> LENGTH: 281
<212> TYPE: DNA
<213> ORGANISM: Gallus gallus

<400> SEQUENCE: 60

ggtcgaggtg agccccacgt tctgcttcac tctccccatc tcccccccct ccccaccccc     60

aattttgtat ttatttattt tttaattatt ttgtgcagcg atgggggcgg gggggggggg    120

ggcgcgcgcc aggcggggcg gggcggggcg aggggcgggg cggggcgagg cggagaggtg    180

cggcggcagc caatcagagc ggcgcgctcc gaaagtttcc ttttatggcg aggcggcggc    240

ggcggcggcc ctataaaaag cgaagcgcgc ggcgggcggg a                        281
```

```
<210> SEQ ID NO 61
<211> LENGTH: 220
<212> TYPE: DNA
<213> ORGANISM: Human betaherpesvirus 5

<400> SEQUENCE: 61
```

-continued

```
tggtgatgcg gttttggcag tacaccaatg ggcgtggata gcggtttgac tcacggggat     60

ttccaagtct ccaccccatt gacgtcaatg ggagtttgtt ttggcaccaa aatcaacggg    120

actttccaaa atgtcgtaat aaccccgccc cgttgacgca aatgggcggt aggcgtgtac    180

ggtgggaggt ctatataagc agagctcgtt tagtgaaccg                          220


<210> SEQ ID NO 62
<211> LENGTH: 455
<212> TYPE: DNA
<213> ORGANISM: Homo sapiens

<400> SEQUENCE: 62

caacctttgg agctaagcca gcaatggtag agggaagatt ctgcacgtcc cttccaggcg     60

gcctccccgt caccaccccc cccaacccgc cccgaccgga gctgagagta attcatacaa    120

aaggactcgc ccctgccttg gggaatccca gggaccgtcg ttaaactccc actaacgtag    180

aacccagaga tcgctgcgtt cccgccccct cacccgcccg ctctcgtcat cactgaggtg    240

gagaatagca tgcgtgaggc tccggtgccc gtcagtgggc agagcgcaca tcgcccacag    300

tccccgagaa gttgggggga ggggtcggca attgaacggg tgcctagaga aggtggcgcg    360

gggtaaactg ggaaagtgat gtcgtgtact ggctccgcct ttttcccgag ggtgggggag    420

aaccgtatat aagtgcagta gtcgccgtga acgtt                               455


<210> SEQ ID NO 63
<211> LENGTH: 422
<212> TYPE: DNA
<213> ORGANISM: Homo sapiens

<400> SEQUENCE: 63

ctgcagaggg ccctgcgtat gagtgcaagt gggttttagg accaggatga ggcggggtgg     60

gggtgcctac ctgacgaccg accccgaccc actggacaag cacccaaccc ccattcccca    120

aattgcgcat cccctatcag agagggggag gggaaacagg atgcggcgag gcgcgtgcgc    180

actgccagct tcagcaccgc ggacagtgcc ttcgcccccg cctggcggcg cgcgccaccg    240

ccgcctcagc actgaaggcg cgctgacgtc actcgccggt cccccgcaaa ctccccttcc    300

cggccacctt ggtcgcgtcc gcgccgccgc cggcccagcc ggaccgcacc acgcgaggcg    360

cgagataggg gggcacgggc gcgaccatct gcgctgcggc gccggcgact cagcgctgcc    420

tc                                                                   422


<210> SEQ ID NO 64
<211> LENGTH: 281
<212> TYPE: DNA
<213> ORGANISM: Homo sapiens

<400> SEQUENCE: 64

acttgtggac aaagtttgct ctattccacc tcctccaggc cctccttggg tccatcaccc     60

caggggtgct gggtccatcc cacccccagg cccacacagg cttgcagtat tgtgtgcggt    120

atggtcaggg cgtccgagag caggtttcgc agtggaaggc aggcaggtgt tggggaggca    180

gttaccgggg caacgggaac agggcgtttt ggaggtggtt gccatgggga cctggatgct    240

gacgaaggct cgcgaggctg tgagcagcca cagtgccctg c                        281


<210> SEQ ID NO 65
<211> LENGTH: 953
<212> TYPE: DNA
<213> ORGANISM: Homo sapiens
```

<400> SEQUENCE: 65
cgcgtccgcc cgcgagcaca gagcctcgcc tttgccgatc cgccgcccgt ccacacccgc 60
cgccaggtaa gcccggccag ccgaccgggg catgcggccg cggcccttcg cccgtgcaga 120
gccgccgtct gggccgcagc ggggggcgca tggggcggaa ccggaccgcc gtgggggggcg 180 cgggagaagc ccctgggcct ccggagatgg gggacacccc acgccagttc gcaggcgcga 240
ggccgcgctc gggcgggcgc gctccggggg tgccgctctc ggggcggggg caaccggcgg 300
ggtctttgtc tgagccgggc tcttgccaat ggggatcgca cggtgggcgc ggcgtagccc 360
ccgtcaggcc cggtgggggc tggggcgcca tgcgcgtgcg cgctggtcct ttgggcgcta 420
actgcgtgcg cgctgggaat tggcgctaat tgcgcgtgcg cgctgggact caatggcgct 480
aatcgcgcgt gcgttctggg gcccgggcgc ttgcgccact tcctgcccga gccgctggcg 540
cccgagggtg tggccgctgc gtgcgcgcgc gcgacccggt cgctgtttga accgggcgga 600
ggcggggctg gcgcccggtt gggagggggt tggggcctgg cttcctgccg cgcgccgcgg 660
ggacgcctcc gaccagtgtt tgccttttat ggtaataacg cggccggccc ggcttccttt 720
gtccccaatc tgggcgcgcg ccggcgcccc ctggcggcct aaggactcgg cgcgccggaa 780
gtggccaggg cggcagcggc tgctcttggc ggccccgagg tgactatagc cttcttttgt 840
gtcttgatag ttcgccagcc tctgctaacc atgttcatgc cttcttcttt ttcctacagc 900
tcctgggcaa cgtgctggtt attgtgctgt ctcatcattt tggcaaagaa ttc 953

<210> SEQ ID NO 66
<211> LENGTH: 1068
<212> TYPE: DNA
<213> ORGANISM: Artificial Sequence
<220> FEATURE:
<223> OTHER INFORMATION: Made in Lab - Chicken beta-actin exon/intron + rabbit globin intron construct

<400> SEQUENCE: 66
gtcgctgcgc gctgccttcg ccccgtgccc cgctccgccg ccgcctcgcg ccgcccgccc 60
cggctctgac tgaccgcgtt actcccacag gtgagcgggc gggacggccc ttctcctccg 120
ggctgtaatt agcgcttggt ttaatgacgg cttgtttctt ttctgtggct gcgtgaaagc 180
cttgaggggc tccgggaggg ccctttgtgc ggggggagcg gctcgggggg tgcgtgcgtg 240
tgtgtgtgcg tggggagcgc cgcgtgcggc tccgcgctgc ccggcggctg tgagcgctgc 300
gggcgcggcg cggggctttg tgcgctccgc agtgtgcgcg aggggagcgc ggccgggggc 360
ggtgccccgc ggtgcggggg gggctgcgag gggaacaaag gctgcgtgcg gggtgtgtgc 420
gtgggggggt gagcaggggg tgtgggcgcg tcggtcgggc tgcaaccccc cctgcacccc 480
cctccccgag ttgctgagca cggcccggct tcgggtgcgg ggctccgtac ggggcgtggc 540
gcggggctcg ccgtgccggg cgggggggtgg cggcaggtgg gggtgccggg cggggcgggg 600
ccgcctcggg ccggggaggg ctcgggggag gggcgcggcg gcccccggag cgccggcggc 660
tgtcgaggcg cggcgagccg cagccattgc cttttatggt aatcgtgcga gagggcgcag 720
ggacttcctt tgtcccaaat ctgtgcggag ccgaaatctg ggaggcgccg ccgcaccccc 780
tctagcgggc gcggggcgaa gcggtgcggc gccggcagga aggaaatggg cggggagggc 840
cttcgtgcgt cgccgcgccg ccgtcccctt ctccctctcc agcctcgggg ctgtccgcgg 900
ggggacggct gccttcgggg gggacggggc agggcggggt tcggcttctg gcgtgtgacc 960
ggcggctcta gagcctctgc taaccatgtt catgccttct tctttttcct acagctcctg 1020
ggcaacgtgc tggttattgt gctgtctcat cattttggca aagaattc 1068

<210> SEQ ID NO 67
<211> LENGTH: 127
<212> TYPE: DNA
<213> ORGANISM: Homo sapiens

<400> SEQUENCE: 67
agtctgcggt gggcagcgga ggagtcgtgt cgtgcctgag agcgcagctg tgctcctggg 60
caccgcgcag tccgcccccg cggctcctgg ccagaccacc cctaggaccc cctgccccaa 120
gtcgcag 127

<210> SEQ ID NO 68
<211> LENGTH: 121
<212> TYPE: DNA
<213> ORGANISM: Human betaherpesvirus 5

<400> SEQUENCE: 68
tcagatcgcc tggagaggcc atccacgctg ttttgacctc catagtggac accgggaccg 60
atccagcctc cgcggccggg aacggtgcat tggaacgcgg attccccgtg ccaagagtga 120
c 121

<210> SEQ ID NO 69
<211> LENGTH: 512
<212> TYPE: DNA
<213> ORGANISM: Artificial Sequence
<220> FEATURE:
<223> OTHER INFORMATION: Synthetic construct

<400> SEQUENCE: 69
ctcactctct tccgcatcgc tgtctgcgag ggccagctgt tgggctcgcg gttgaggaca 60
aactcttcgc ggtctttcca gtactcttgg atcggaaacc cgtcggcctc cgaacggtac 120
tccgccaccg agggacctga gcgagtccgc atcgaccgga tcggaaaacc tctcgagaaa 180
ggcgtctaac cagtcacagt cgcaaggtag gctgagcacc gtggcgggcg gcagcgggtg 240
gcggtcgggg ttgtttctgg cggaggtgct gctgatgatg taattaaagt aggcggtctt 300
gagacggcgg atggtcgagg tgaggtgtgg caggcttgag atccagctgt tggggtgagt 360
actccctctc aaaagcgggc attacttctg cgctaagatt gtcagtttcc aaaaacgagg 420
aggatttgat attcacctgg cccgatctgg ccatacactt gagtgacaat gacatccact 480
ttgcctttct ctccacaggt gtccactccc ag 512

<210> SEQ ID NO 70
<211> LENGTH: 956
<212> TYPE: DNA
<213> ORGANISM: Homo sapiens

<400> SEQUENCE: 70
ctttttcgca acgggtttgc cgccagaaca caggtaagtg ccgtgtgtgg ttcccgcggg 60
cctggcctct ttacgggtta tggcccttgc gtgccttgaa ttacttccac ctggctccag 120
tacgtgattc ttgatcccga gctggagcca ggggcgggcc ttgcgcttta ggagcccctt 180
cgcctcgtgc ttgagttgag gcctggcctg ggcgctgggg ccgccgcgtg cgaatctggt 240
ggcaccttcg cgcctgtctc gctgctttcg ataagtctct agccatttaa aatttttgat 300
gacgtgctgc gacgcttttt ttctggcaag atagtcttgt aaatgcgggc caggatctgc 360

```
acactggtat ttcggttttt gggcccgcgg ccggcgacgg ggcccgtgcg tcccagcgca    420

catgttcggc gaggcggggc ctgcgagcgc ggccaccgag aatcggacgg gggtagtctc    480

aagctggccg gcctgctctg gtgcctggcc tcgcgccgcc gtgtatcgcc ccgccctggg    540

cggcaaggct ggcccggtcg gcaccagttg cgtgagcgga aagatggccg cttcccggcc    600

ctgctccagg gggctcaaaa tggaggacgc ggcgctcggg agagcgggcg ggtgagtcac    660

ccacacaaag gaaaagggcc tttccgtcct cagccgtcgc ttcatgtgac tccacggagt    720

accgggcgcc gtccaggcac ctcgattagt tctggagctt ttggagtacg tcgtctttag    780

gttgggggga ggggttttat gcgatggagt ttccccacac tgagtgggtg gagactgaag    840

ttaggccagc ttggcacttg atgtaattct ccttggaatt tggccttttt gagtttggat    900

cttggttcat tctcaagcct cagacagtgg ttcaaagttt ttttcttcca tttcag        956


<210> SEQ ID NO 71
<211> LENGTH: 83
<212> TYPE: DNA
<213> ORGANISM: Homo sapiens

<400> SEQUENCE: 71

tcagaagccc cgggctcgtc agtcaaaccg gttctctgtt tgcactcggc agcacgggca     60

ggcaagtggt ccctaggttc ggg                                             83


<210> SEQ ID NO 72
<211> LENGTH: 755
<212> TYPE: DNA
<213> ORGANISM: Artificial Sequence
<220> FEATURE:
<223> OTHER INFORMATION: Made in Lab - mutated woodchuck hepatitis
      regulatory element

<400> SEQUENCE: 72

ttcctgttaa tcaacctctg gattacaaaa tttgtgaaag attgactggt attcttaact     60

atgttgctcc ttttacgcta tgtggatacg ctgctttaat gcctttgtat catgctattg    120

cttcccgtat ggctttcatt ttctcctcct tgtataaatc ctggttgctg tctctttatg    180

aggagttgtg gcccgttgtc aggcaacgtg gcgtggtgtg cactgtgttt gctgacgcaa    240

cccccactgg ttggggcatt gccaccacct gtcagctcct ttccgggact ttcgctttcc    300

ccctccctat tgccacggcg gaactcatcg ccgcctgcct tgcccgctgc tggacagggg    360

ctcggctgtt gggcactgac aattccgtgg tgttgtcggg gaagctgacg tcctttccgc    420

ggctgctcgc ctgtgttgcc acctggattc tgcgcgggac gtccttctgc tacgtccctt    480

cggccctcaa tccagcggac cttccttccc gcggcctgct gccggctctg cggcctcttc    540

cgcctcttcg ccttcgccct cagacgagtc ggatctccct ttgggccgcc tccccgccca    600

tgtatctttt tcacctgtgc cttgtttttg cctgtgttcc gcgtcctact tttcaagcct    660

ccaagctgtg ccttgggcgg ctttggggca tggacataga tccctataaa gaatttggtt    720

catcttatca gttgttgaat ttcttccctt tggac                               755


<210> SEQ ID NO 73
<211> LENGTH: 755
<212> TYPE: DNA
<213> ORGANISM: Artificial Sequence
<220> FEATURE:
<223> OTHER INFORMATION: Made in Lab - HepB derived enhancer element

<400> SEQUENCE: 73
```

-continued

```
ttcctgtaaa caggcctatt gattggaaag tttgtcaacg aattgtgggt cttttggggt     60

ttgctgcccc ttttacgcaa tgtggatatc ctgctttaat gcctttatat gcatgtatac    120

aagcaaaaca ggcttttact ttctcgccaa cttacaaggc ctttctcagt aaacagtata    180

tgaccottta ccccgttgct cggcaacggc ctggtctgtg ccaagtgttt gctgacgcaa    240

cccccactgg ttggggcttg gccataggcc atcagcgcat gcgtggaacc tttgtgtctc    300

ctctgccgat ccatactgcg gaactcctag ccgcttgttt tgctcgcagc tggactggag    360

caaacctcat cgggaccgac aattctgtcg tactctcccg caagcactca ccgtttccgc    420

ggctgctcgc ctgtgttgcc acctggattc tgcgcgggac gtccttctgc tacgtccctt    480

cggccctcaa tccagcggac cttccttccc gcggcctgct gccggctctg cggcctcttc    540

cgcctcttcg ccttcgccct cagacgagtc ggatctccct ttgggccgcc tccccgccca    600

tgtatctttt tcacctgtgc cttgtttttg cctgtgttcc gcgtcctact tttcaagcct    660

ccaagctgtg ccttgggcgg ctttggggca tggacataga tccctataaa gaatttggtt    720

catcttatca gttgttgaat ttcttccttt tggac                               755
```

<210> SEQ ID NO 74
<211> LENGTH: 94
<212> TYPE: DNA
<213> ORGANISM: Homo sapiens

<400> SEQUENCE: 74

```
gctggagcct cggtagccgt tcctcctgcc cgctgggcct cccaacgggc cctcctcccc     60

tccttgcacc ggcccttcct ggtctttgaa taaa                                 94
```

<210> SEQ ID NO 75
<211> LENGTH: 596
<212> TYPE: DNA
<213> ORGANISM: Woodchuck hepatitis virus

<400> SEQUENCE: 75

```
attcgagcat cttaccgcca tttattccca tatttgttct gtttttcttg atttgggtat     60

acatttaaat gttaataaaa caaaatggtg gggcaatcat ttacattttt agggatatgt    120

aattactagt tcaggtgtat tgccacaaga caaacatgtt aagaaacttt cccgttattt    180

acgctctgtt cctgttaatc aacctctgga ttacaaaatt tgtgaaagat tgactgatat    240

tcttaactat gttgctcctt ttacgctgtg tggatatgct gctttaatgc ctctgtatca    300

tgctattgct tcccgtacgg ctttcgtttt ctcctccttg tataaatcct ggttgctgtc    360

tctttatgag gagttgtggc ccgttgtccg tcaacgtggc gtggtgtgct ctgtgtttgc    420

tgacgcaacc cccactggct ggggcattgc caccacctgt caactccttt ctgggacttt    480

cgctttcccc ctcccgatcg ccacggcaga actcatcgcc gcctgccttg cccgctgctg    540

gacaggggct aggttgctgg gcactgataa ttccgtggtg ttgtcgggga agggcc        596
```

<210> SEQ ID NO 76
<211> LENGTH: 387
<212> TYPE: DNA
<213> ORGANISM: Oryctolagus cuniculus

<400> SEQUENCE: 76

```
tggctaataa aggaaattta ttttcattgc aatagtgtgt tggaattttt tgtgtctctc     60

actcggaaga acatatggga gggcaaatca tttaaaacat cagaatgagt atttggttta    120

gagtttggca acatatgccc atatgctggc tgccatgaac aaaggttggc tataaagagg    180
```

```
tcatcagtat atgaaacagc cccctgctgt ccattcctta ttccatagaa aagccttgac    240

ttgaggttag attttttta tattttgttt tgtgttattt ttttctttaa catccctaaa    300

attttcctta catgttttac tagccagatt tttcctcctc tcctgactac tcccagtcat    360

agctgtccct cttctcttat ggagatc                                        387


<210> SEQ ID NO 77
<211> LENGTH: 251
<212> TYPE: DNA
<213> ORGANISM: Bos taurus

<400> SEQUENCE: 77

ttgccagcca tctgttgttt gcccctcccc cgtgccttcc ttgaccctgg aaggtgccac     60

tcccactgtc ctttcctaat aaaatgagga aattgcatcg cattgtctga gtaggtgtca    120

ttctattctg gggggtgggg tggggcagga cagcaagggg gaggattggg aatacaatag    180

caggcatgct ggggatgcgg tgggctctat gggtacccag gtgctgaaga attgacccgg    240

ttcctcctgg g                                                         251


<210> SEQ ID NO 78
<211> LENGTH: 202
<212> TYPE: DNA
<213> ORGANISM: Homo sapiens

<400> SEQUENCE: 78

ctgcccgggt ggcatccctg tgacccctcc ccagtgcctc tcctggccct ggaagttgcc     60

actccagtgc ccaccagcct tgtcctaata aaattaagtt gcatcatttt gtctgactag    120

gtgtccttct ataatattat ggggtggagg ggggtggtat ggagcaaggg gcccaagttg    180

ggaagaaacc tgtagggcct gc                                             202


<210> SEQ ID NO 79
<211> LENGTH: 304
<212> TYPE: DNA
<213> ORGANISM: Human betaherpesvirus 5

<400> SEQUENCE: 79

cgcgttacat aacttacggt aaatggcccg cctggctgac cgcccaacga cccccgccca     60

ttgacgtcaa taatgacgta tgttcccata gtaacgccaa tagggacttt ccattgacgt    120

caatgggtgg agtatttacg gtaaactgcc cacttggcag tacatcaagt gtatcatatg    180

ccaagtacgc cccctattga cgtcaatgac ggtaaatggc ccgcctggca ttatgcccag    240

tacatgacct tatgggactt tcctacttgg cagtacatct acgtattagt catcgctatt    300

acca                                                                 304


<210> SEQ ID NO 80
<211> LENGTH: 111
<212> TYPE: DNA
<213> ORGANISM: Artificial Sequence
<220> FEATURE:
<223> OTHER INFORMATION: Synthetic construct

<400> SEQUENCE: 80

gactataagg atgatgatga taagggagga ggaggatcgg ggggggagg atcgtaccca     60

tacgacgtgc cggactacgc cggtggcggc ggcagcggcg gcggcggatc g            111


<210> SEQ ID NO 81
```

-continued

```
<211> LENGTH: 37
<212> TYPE: PRT
<213> ORGANISM: Artificial Sequence
<220> FEATURE:
<223> OTHER INFORMATION: Synthetic construct

<400> SEQUENCE: 81

Asp Tyr Lys Asp Asp Asp Asp Lys Gly Gly Gly Gly Ser Gly Gly Gly
1               5                   10                  15

Gly Ser Tyr Pro Tyr Asp Val Pro Asp Tyr Ala Gly Gly Gly Gly Ser
            20                  25                  30

Gly Gly Gly Gly Ser
        35
```

GENE THERAPY FOR CNS DEGENERATION

CROSS-REFERENCE TO RELATED APPLICATIONS

This application is a National Stage application under 35 U.S.C. § 371 of International Application No. PCT/US2019/029744, filed Apr. 29, 2019, which claims benefit of priority to U.S. Provisional Patent Application No. 62/664,006, filed Apr. 27, 2018, the disclosure of which is incorporated herein by reference in its entirety for all purposes.

INCORPORATION OF SEQUENCE LISTING

The Sequence Listing associated with this application is provided in text format in lieu of a paper copy, and is hereby incorporated by reference into the specification. The name of the text file containing the Sequence Listing is ROPA_009_01WO_ST25.txt. The text file is 254 KB, was created on Apr. 29, 2019, and is being submitted electronically via EFS-Web.

FIELD OF THE DISCLOSURE

The present disclosure relates generally to gene therapy and/or gene editing for treatment of disorders associated with central nervous system degeneration, such as Parkinson's Disease. In particular, the disclosure provides compositions and methods for gene therapy or gene repair in neurons both ex vivo and in vivo.

BACKGROUND

Various genes have been implicated in disorders of central nervous system degeneration, such as Parkinson's Disease (PD). Those genes include PARK2, PINK1 (PARK6), DJ-1 (PARK7), LRRK2, α-synuclein, and DJ-1. Creed et al. (2018) *Mov Disord.* 33:717-729; Blesa et al. (2014) *Front. Neuroanat.* 8:1-12; Alcalay et al. (2010) *Arch Neurol.* 67:1116-1122). PARK2, also known as PRKN, has been implicated in a form of PD, autosomal recessive juvenile PD. Despite widespread attempts, there have been few reports of successful gene therapy for central nervous system degeneration.

There is a great need in the art for new compositions and methods of treating and preventing central nervous system degeneration.

SUMMARY OF THE DISCLOSURE

The present disclosure provides, in part, compositions and methods for treating, preventing, inhibiting, or delaying central nervous system degeneration. In particular, the inventors disclose various embodiments of, and methods related to, a recombinant gene therapy vector comprising a Parkinson protein 2, E3 ubiquitin protein ligase (PARK2) gene, a PTEN-induced putative kinase 1 (PINK1) gene, a protein deglycase DJ-1 (DJ-1) gene, a Leucine Rich Repeat Kinase 2 (LRRK2) gene, an alpha-synuclein (SCNA) gene, a Proto-oncogene c-Rel (c-Rel) gene, a Ubiquitin-like modifier-activating enzyme (ATG7) gene, Synaptic vesicular amine transporter (VMAT2) gene, or glucocerebrosidase (GBA) gene, or functional fragment or variant thereof.

The further inventors disclose various embodiments, and methods related to, of a gene editing system comprising a Cas protein, guide RNA, a repair template comprising a Parkinson protein 2, E3 ubiquitin protein ligase (PARK2) gene, a PTEN-induced putative kinase 1 (PINK1) gene, a protein deglycase DJ-1 (DJ-1) gene, a Leucine Rich Repeat Kinase 2 (LRRK2) gene, an alpha-synuclein (SCNA) gene, a Proto-oncogene c-Rel (c-Rel) gene, a Ubiquitin-like modifier-activating enzyme (ATG7) gene, Synaptic vesicular amine transporter (VMAT2) gene, or glucocerebrosidase (GBA) gene, or functional fragment or variant thereof.

In a first aspect, the disclosure provides a method of inhibiting degeneration or death of a dopaminergic neuron comprising a mutation in a gene associated with a Parkinson's Disease (PD). The mutated gene can be a Parkinson protein 2, E3 ubiquitin protein ligase (PARK2) gene, a PTEN-induced putative kinase 1 (PINK1) gene, a protein deglycase DJ-1 (DJ-1) gene, a Leucine Rich Repeat Kinase 2 (LRRK2) gene, alpha-synuclein (SCNA) gene, a Proto-oncogene c-Rel (c-Rel) gene, a Ubiquitin-like modifier-activating enzyme (ATG7) gene, Synaptic vesicular amine transporter (VMAT2) gene, or glucocerebrosidase (GBA) gene. In methods of this aspect, the method comprises contacting the neuron with a recombinant gene therapy vector comprising a polynucleotide encoding a wild-type protein expressed by a wild-type version of the mutated gene, or a functional variant or fragment thereof. Following contact with the recombinant gene therapy vector, the neuron expresses the wild-type protein, or functional variant or fragment thereof.

In some embodiments, the PARK2, PINK1, LRRK2, SCNA, c-Rel, ATG7, VMAT2, or GBA protein comprises the amino acid sequence set forth in SEQ ID NOs: 1-9, respectively. In some embodiments, the gene is the PARK2 gene, and the wild-type PARK2 protein comprises the amino acid sequence set forth in any of SEQ ID NOs: 10-17. In some embodiments, the polynucleotide comprises a sequence having at least 70%, 75%, 80%, 85%, 95%, or 99% identity to a PARK2, PINK1, LRRK2, SCNA, c-Rel, ATG7, VMAT2, or GBA polynucleotide sequence set forth in SEQ ID NOs: 18-26, respectively. In some embodiments, the gene is the PARK2 gene, and the polynucleotide comprises a sequence having at least 70%, 75%, 80%, 85%, 95%, or 99% identity to a PARK2 isoform polynucleotide sequence set forth in any of SEQ ID NOs: 27-34. In some embodiments, the polynucleotide is codon-optimized. In some embodiments, the polynucleotide comprises less than 40, less than 30, less than 20, or 10 or fewer CpG islands. In some embodiments, the polynucleotide comprises at least 1, at least 2, at least 3, at least 4, at least 5, at least 6, or at least 10 CpG islands. In some embodiments, it comprises between 5 and 20 CpG islands.

Various viral or non-viral vectors can be used. In some embodiments, the recombinant gene therapy vector is a recombinant adeno-associated virus (AAV). Any of the known serotypes can be used. In some embodiments, the AAV has serotype AAV1, AAV2, AAV5, AAV8, AAV9, AAVrh10, or AAVrh74. In some embodiments, the recombinant gene therapy vector comprises a self-complementary AAV. In some embodiments, the recombinant gene therapy vector comprises a single-stranded AAV. In some embodiments, the AAV is a wild-type AAV or a modified AAV. In some embodiments, the AAV comprises a capsid protein having at least 95% identity to a wild-type VP1, VP2, or VP3 capsid protein.

The recombinant gene therapy vector may include gene regulatory elements. In some embodiments, the recombinant gene therapy vector comprises a polynucleotide comprising, in the following 5' to 3' order, a eukaryotically active promoter sequence and the sequence encoding the wild-type protein, or functional fragment or variant thereof. The sequence encoding the wild-type protein, or functional fragment or variant thereof, is operably linked to the eukaryotically active promoter sequence.

Without being limited by examples of the disclosure, the recombinant gene therapy vector in some embodiments further comprises one or more of a neuron-specific promoter, optionally selected from the group consisting of hSYN1 (human synapsin), INA (alpha-internexin), NES (nestin), TH (tyrosine hydroxylase), FOXA2 (Forkhead box A2), CaMKII (calmodulin-dependent protein kinase II), and NSE (neuron-specific enolase) promoters; a ubiquitous promotor selected from the group consisting of CMV, CAG, UBC, PGK, EF1-alpha, GAPDH, SV40, HBV, and chicken beta-actin promoters; an enhancer; an intron; a poly-A signal; a WPRE (Woodchuck hepatitis virus posttranscriptional regulatory element); and a HPRE (Hepatitis posttranscriptional regulatory element). The WPRE may be a WPRE (r) or a WPRE(x).

In various embodiments of any of the vectors and methods disclosed herein, the vector comprises an expression cassette comprising in 5' to 3' order:

- HuBA promoter, the transgene, WPRE(x), and pAGlobin-Oc;
- CMV promoter, TPL-eMLP 5' enhancer, the transgene, WPRE(r), and pAGlobin-Oc;
- Syn promoter, the transgene, WPRE(r), 3'UTR(globin), and pAGH-Bt;
- CBA promoter, the transgene, and pAGH-Bt;
- EF1a promoter, the transgene, and pAGlobin-Oc;
- HuBA promoter, the transgene, R2V17, and pAGH-Bt;
- Syn promoter, the transgene, WPRE(x), 3'UTR(globin), and pAGH-Hs;
- CaMKIIa promoter, the transgene, WPRE(r), and pAGH-Hs;
- CMV and TPL promoter, the transgene, WPRE(r), and pAGH-Hs;
- HuBA promoter, the transgene, and pAGH-Hs;
- CMV and TPL promoter, eMPL, the transgene, R2V17, 3'UTR(globin), and pAGH-Bt;
- EF1α promoter, the transgene, WPRE(r), and pAGH-Bt;
- Syn promoter, the transgene, R2V17, and pAGlobin-Oc;
- CaMKIIa promoter, the transgene, R2V17, and pAGlobin-Oc;
- CBA promoter, the transgene, WPRE(x), 3'UTR(globin), and pAGH-Hs.
- CBA promoter, the transgene, 3'UTR(globin), and pAGlobin-Oc;
- CaMKIIa promoter, the transgene, R2V17, and pAGH-Bt;
- EF1a promoter, the transgene, R2V17, 3' aglobin, and pAGH-Hs.
- CMV promoter, the transgene, R2V17, 3'UTR(globin), and pAGH-Hs; or
- CMV promoter, the transgene, and pAGH-Hs, optionally wherein the transgene encodes PARK2.

The methods of the disclosure may have various effects. In some embodiments, the neuron expresses a reduced amount of alpha-synuclein and/or comprises a reduced amount of Lewy bodies following contact with the recombinant gene therapy vector. In some embodiments, the neuron expresses a reduced amount of monoamine oxidases following contact with the recombinant gene therapy vector. In some embodiments, the neuron produces and/or releases an increased amount of dopamine following contact with the recombinant gene therapy vector. In some embodiments, the neuron undergoes increased mitophagy following contact with the recombinant gene therapy vector.

In some embodiments, the neuron expresses a lower amount of monoamine oxidases as compared to an amount of monoamine oxidases expressed in a neuron not contacted with said recombinant gene therapy vector, optionally wherein said lower amount is at least 5%, at least 10%, at least 20%, at least 30%, at least 40%, at least 50%, at least 60%, at least 70%, or at least 80% lower than the amount expressed in the neuron not contacted with said recombinant gene therapy vector. In some embodiments, the neuron produces and/or releases an increased amount of dopamine as compared to an amount of dopamine produced and/or released by a neuron not contacted with said recombinant gene therapy vector, optionally wherein said increase amount is at least 5%, at least 10%, at least 20%, at least 30%, at least 40%, at least 50%, at least 60%, at least 70%, at least 80%, at least 90%, at least two-fold, at least three-fold, at least four-fold, at least five-fold, or at least 10-fold greater than the amount produced and/or released by the neuron not contacted with said recombinant gene therapy vector. In some embodiments, the neuron undergoes an increased amount of autophagy as compared to an amount of autophagy undergone by a neuron not contacted with said recombinant gene therapy vector, optionally wherein the increased amount is at least 5%, at least 10%, at least 20%, at least 30%, at least 40%, at least 50%, at least 60%, at least 70%, at least 80%, at least 90%, at least two-fold, at least three-fold, at least four-fold, at least five-fold, or at least 10-fold greater than the amount undergone by the neuron not contacted with said recombinant gene therapy vector.

The neuron used in the methods of the disclosure may have various characteristics. In some embodiments, the neuron is a primary tyrosine hydroxylase positive neuron. In some embodiments, the neuron was produced from an induced pluripotent stem cell prepared from cells obtained from a subject diagnosed with Parkinson's disease.

In another aspect, the disclosure provides a recombinant gene therapy vector comprising a polynucleotide encoding a wild-type Parkinson protein 2, E3 ubiquitin protein ligase (PARK2) gene, a PTEN-induced putative kinase 1 (PINK1) gene, a protein deglycase DJ-1 (DJ-1) gene, a Leucine Rich Repeat Kinase 2 (LRRK2) gene, an alpha-synuclein (SCNA) gene, a Proto-oncogene c-Rel (c-Rel) gene, a Ubiquitin-like modifier-activating enzyme (ATG7) gene, Synaptic vesicular amine transporter (VMAT2) gene, or glucocerebrosidase (GBA) gene, or a functional variant or fragment thereof; wherein the polynucleotide is operatively linked to a eukaryotically active promoter; and wherein a neuron transduced with said recombinant gene therapy vector expresses the wild-type protein, or functional variant or fragment thereof.

In some embodiments, the functional PARK2, PINK1, LRRK2, SCNA, c-Rel, ATG7, VMAT2, or GBA protein comprises the amino acid sequence set forth in SEQ ID NOs: 1-9, respectively. In some embodiments, the gene is the PARK2 gene, and the wild-type PARK2 protein comprises the amino acid sequence set forth in any of SEQ ID NOs: 10-17. In some embodiments, the polynucleotide comprises a sequence having at least 70%, 75%, 80%, 85%, 95%, or 99% identity to a PARK2, PINK1, LRRK2, SCNA, c-Rel, ATG7, VMAT2, or GBA polynucleotide sequence set forth in SEQ ID NOs: 18-26, respectively. In some embodiments, the gene is the PARK2 gene, and the polynucleotide comprises a sequence having at least 70%, 75%, 80%, 85%, 95%, or 99% identity to a PARK2 isoform polynucleotide sequence set forth in any of SEQ ID NOs: 27-34. In some embodiments, the vector comprises an expression cassette comprising in 5' to 3' order:

HuBA promoter, the transgene, WPRE(x), and pAGlobin-Oc;

CMV promoter, TPL-eMLP 5' enhancer, the transgene, WPRE(r), and pAGlobin-Oc;

Syn promoter, the transgene, WPRE(r), 3'UTR(globin), and pAGH-Bt;

CBA promoter, the transgene, and pAGH-Bt;

EF1a promoter, the transgene, and pAGlobin-Oc;

HuBA promoter, the transgene, R2V17, and pAGH-Bt;

Syn promoter, the transgene, WPRE(x), 3'UTR(globin), and pAGH-Hs;

CaMKIIa promoter, the transgene, WPRE(r), and pAGH-Hs;

CMV and TPL promoter, the transgene, WPRE(r), and pAGH-Hs;

HuBA promoter, the transgene, and pAGH-Hs;

CMV and TPL promoter, eMPL, the transgene, R2V17, 3'UTR(globin), and pAGH-Bt;

EF1a promoter, the transgene, WPRE(r), and pAGH-Bt;

Syn promoter, the transgene, R2V17, and pAGlobin-Oc;

CaMKIIa promoter, the transgene, R2V17, and pAGlobin-Oc;

CBA promoter, the transgene, WPRE(x), 3'UTR(globin), and pAGH-Hs.

CBA promoter, the transgene, 3'UTR(globin), and pAGlobin-Oc;

CaMKIIa promoter, the transgene, R2V17, and pAGH-Bt;

EF1a promoter, the transgene, R2V17, 3'UTR(globin), and pAGH-Hs.

CMV promoter, the transgene, R2V17, 3'UTR(globin), and pAGH-Hs; or

CMV promoter, the transgene, and pAGH-Hs, optionally wherein the transgene encodes PARK2.

In some embodiments, the polynucleotide is codon-optimized. In some embodiments, the polynucleotide comprises any of SEQ ID NOs: 35-38. In some embodiments, the recombinant gene therapy vector is a recombinant adeno-associated virus (rAAV). In some embodiments, the rAAV has serotype AAV1, AAV2, AAV5, AAV8, AAV9, AAVrh10, or AAVrh74. In some embodiments, the recombinant gene therapy vector comprises a self-complementary or a single-stranded AAV genome. In some embodiments, the AAV is a wild-type AAV or a modified AAV. In some embodiments, the AAV comprises a capsid protein having at least 95% identity to wild-type VP1, VP2, or VP3 capsid protein.

In another aspect, the disclosure provides a method of treating or inhibiting onset of a Parkinson's Disease (PD) in a subject suffering from or at risk of the PD, comprising administering a recombinant gene therapy vector comprising a polynucleotide encoding a wild-type a wild-type Parkinson protein 2, E3 ubiquitin protein ligase (PARK2) gene, a PTEN-induced putative kinase 1 (PINK1) gene, a protein deglycase DJ-1 (DJ-1) gene, a Leucine Rich Repeat Kinase 2 (LRRK2) gene, an alpha-synuclein (SCNA) gene, a Proto-oncogene c-Rel (c-Rel) gene, a Ubiquitin-like modifier-activating enzyme (ATG7) gene, Synaptic vesicular amine transporter (VMAT2) gene, or glucocerebrosidase (GBA) gene, or a functional variant or fragment thereof, to the subject; wherein administration of the recombinant gene therapy vector treats or inhibits onset of the Parkinson's Disease in the subject.

In some embodiments, the PD is an early-onset PD, optionally an early-onset autosomal recessive PD. In some embodiments, the subject comprises a mutation in a PARK2 gene, PINK1 gene, LRRK2 gene, SCNA gene, c-Rel gene, ATG7 gene, VMAT2, or GBA gene. In some embodiments, the PARK2, PINK1, LRRK2, SCNA, c-Rel, ATG7, VMAT2, or GBA protein comprises the amino acid sequence set forth in SEQ ID NOs: 1-9, respectively. In some embodiments, the gene is the PARK2 gene, and the wild-type PARK2 protein comprises the amino acid sequence set forth in any of SEQ ID NOs: 10-17. In some embodiments, the polynucleotide comprises a sequence having at least 70%, 75%, 80%, 85%, 95%, or 99% identity to a PARK2, PINK1, LRRK2, SCNA, c-Rel, ATG7, VMAT2, or GBA polynucleotide sequence set forth in SEQ ID NOs: 18-26, respectively. In some embodiments, the gene is the PARK2 gene, and the polynucleotide comprises a sequence having at least 70%, 75%, 80%, 85%, 95%, or 99% identity to a PARK2 isoform polynucleotide sequence set forth in any of SEQ ID NOs: 27-34. In some embodiments, the polynucleotide is codon-optimized. In some embodiments, the polynucleotide comprises a sequence having at least 70%, 75%, 80%, 85%, 95%, or 99% identity to a sequence set forth in any of SEQ ID NOs: 35-38.

In some embodiments, the recombinant gene therapy vector is a recombinant adeno-associated virus (AAV). In some embodiments, the AAV has serotype AAV1, AAV2, AAV5, AAV8, AAV9, AAVrh10, or AAVrh74. In some embodiments, the recombinant gene therapy vector comprises a self-complementary AAV genome. In some embodiments, the recombinant gene therapy vector comprises a single-stranded AAV. In some embodiments, the AAV is a wild-type AAV or a modified AAV. In some embodiments, the AAV comprises a capsid protein having at least 95% identity to wild-type VP1, VP2, or VP3 capsid protein.

In some embodiments, the recombinant gene therapy vector comprises a polynucleotide comprising in the following 5' to 3' order, a eukaryotically active promoter sequence; and the sequence encoding the wild-type protein, or functional fragment or variant thereof; wherein the sequence encoding the wild-type protein, or functional fragment or variant thereof, is operably linked to the eukaryotically active promoter sequence.

In some embodiments, the recombinant gene therapy vector further comprises one or more of a neuron-specific promoter, optionally selected from the group consisting of hSYN1 (human synapsin), INA (alpha-internexin), NES (nestin), TH (tyrosine hydroxylase), FOXA2 (Forkhead box A2), CaMKII (calmodulin-dependent protein kinase II), and NSE (neuron-specific enolase) promoters; a ubiquitous promotor selected from the group consisting of CMV, CAG, UBC, PGK, EF1-alpha, GAPDH, SV40, HBV, human beta-actin, and chicken beta-actin promoters; an enhancer; an intron; a poly-A signal; a WPRE(Woodchuck hepatitis virus posttranscriptional regulatory element); and a HPRE (Hepatitis posttranscriptional regulatory element).

The recombinant gene therapy vector or gene editing system can be administered in various ways. In some embodiments, the administering step comprises systemic, parenteral, intravenous, cerebral, cerebrospinal, intrathecal, intracisternal, intraputaminal, intrahippocampal, intra-striatal, or intra-cerebroventricular administration. In some embodiments, the administering step comprises intravenous, cerebral, cerebrospinal, intrathecal, intracisternal, intraputaminal, intrahippocampal, intra-striatal, or intra-cerebroventricular injection. In some embodiments, the administering step comprises intrathecal injection with Trendelenburg tilting. In some embodiments, the administering step comprises direct injection into the pars compacta of the substantia nigra of the brain. In some embodiments, the administering step comprises introducing the recombinant gene therapy vector into the subject's brain or cerebrospinal fluid (CSF).

In some embodiments, $1\times10^9$-$1\times10^{14}$ vector genomes per kilogram body mass of the subject (vg/kg) of the gene therapy vector are administered to the subject. In some embodiments, $1\times10^9$-$1\times10^{14}$ vector genomes per kilogram body mass of the subject (vg/kg) of the gene therapy vector are administered to the subject's brain. In some embodiments, $1\times10^9$-$1\times10^{14}$ vector genomes per kilogram body mass of the subject (vg/kg) of the gene therapy vector are administered to the subject's CSF. In some embodiments, $1\times10^7$-$1\times10^9$ vector genomes per kilogram body mass of the subject (vg/kg) of the gene therapy vector are administered to the subject.

The methods of the disclosure relate to both adult and juvenile forms of disease. In some embodiments, the subject is an adult. In some embodiments, the subject is a child.

The methods of the disclosure may have various effects on the subject. In some embodiments, the number of dopaminergic neurons in the subject after the administering step is greater than the number of dopaminergic neurons in the subject before the administering step. In some embodiments, the level of dopamine in the subject after the administering step is greater than the level of dopamine in the subject before the administering step. In some embodiments, the number of dopaminergic neurons in a subject treated by the method is increased compared to the number of dopaminergic neurons in a subject not so treated. In some embodiments, the level of dopamine of a subject treated by the method is increased compared to the level of dopamine in a subject not so treated. In some embodiments, the level of dopamine in the substantia nigra of a subject treated by method is increased compared to the level of dopamine in the substantia nigra of a subject not so treated. In some embodiments, the level of PRKN in the subject's CSF after the administering step is greater than the level of PRKN in the subject's CSF before the administering step. In some embodiments, the Unified Parkinson's Disease Rating Scale (UPDRS) score of the subject before the administering step is improved compared to the UPDRS score of the subject before the administering step. In some embodiments, the level of PRKN in the CSF of a subject treated by the method is increased compared to the level of PRKN in the CSF of a subject not so treated. In some embodiments, the level of PRKN in the subject's substantia nigra after the administering step is greater than the level of PRKN in the subject's substantia nigra before the administering step. In some embodiments, the UPDRS score of a subject treated by the method is improved compared to the UPDRS score of a subject not so treated. In some embodiments, the subject's neurons express a reduced amount of alpha-synuclein and/or comprises a reduced amount of Lewy bodies following contact with the recombinant gene therapy vector.

In another aspect, the disclosure provides a method of inhibiting degeneration or death of a dopaminergic neuron having a mutated Parkin (PRKN) gene, comprising contacting the neuron with a gene editing system comprising: Cas protein or a polynucleotide encoding a Cas protein; a guide-RNA (gRNA); and a repair template comprising a functional Parkinson protein 2, E3 ubiquitin protein ligase (PARK2) gene, a PTEN-induced putative kinase 1 (PINK1) gene, a protein deglycase DJ-1 (DJ-1) gene, a Leucine Rich Repeat Kinase 2 (LRRK2) gene, an alpha-synuclein (SCNA) gene, a Proto-oncogene c-Rel (c-Rel) gene, a Ubiquitin-like modifier-activating enzyme (ATG7) gene, Synaptic vesicular amine transporter (VMAT2) gene, or glucocerebrosidase (GBA) gene, or a functional variant or fragment thereof; wherein the gene editing system is capable of repairing an endogenous gene in the neuron or inserting a functional gene into the genome of the neuron.

In some embodiments, at least one component of the gene editing system is delivered by recombinant AAV. In some embodiments, the gene editing system is delivered by recombinant AAV.

In another aspect, the disclosure provides a gene editing system for a cell comprising: Cas protein or a polynucleotide encoding a Cas protein; a guide-RNA (gRNA); and a repair template comprising a functional Parkinson protein 2, E3 ubiquitin protein ligase (PARK2) gene, a PTEN-induced putative kinase 1 (PINK1) gene, a protein deglycase DJ-1 (DJ-1) gene, a Leucine Rich Repeat Kinase 2 (LRRK2) gene, an alpha-synuclein (SCNA) gene, a Proto-oncogene c-Rel (c-Rel) gene, a Ubiquitin-like modifier-activating enzyme (ATG7) gene, Synaptic vesicular amine transporter (VMAT2) gene, or glucocerebrosidase (GBA) gene, or a functional variant or fragment thereof; wherein the gene editing system is capable of repairing an endogenous gene in the cell or inserting a functional gene into the genome of the cell.

In some embodiments, at least one component of the gene editing system is delivered by recombinant AAV. In some embodiments, the gene editing system is delivered by recombinant AAV. In some embodiments, the cell is an ex vivo neuron. In some embodiments, the cell is a cell of a subject.

In another aspect, the disclosure provides recombinant gene therapy vector, comprising a transgene polynucleotide encoding E3 ubiquitin protein ligase (PARK2) gene, wherein the transgene polynucleotide is operably linked to a eukaryotically active promoter sequence.

In some embodiments, the transgene polynucleotide shares at least 95% identity to one of SEQ ID NOs: 35-38.

In some embodiments, the promoter sequence is selected from Table 5.

In some embodiments, the vector further comprises a CMV enhancer.

In some embodiments, the vector further comprises a 5' untranslated region (UTR) selected from Table 6.

In some embodiments, the vector further comprises a 3' untranslated region selected from Table 7.

In some embodiments, the vector further comprises a polyadenylation sequence (polyA) selected from Table 8.

In some embodiments, the polynucleotide is codon-optimized.

In some embodiments, the expression cassette shares at least 95% sequence identity to any one of SEQ ID NOs: 39-58.

In some embodiments, the vector is an adeno-associated virus (AAV) vector.

In some embodiments, the vector comprises two AAV inverted terminal repeats (ITRs) flanking the expression cassette.

In some embodiments, the AAV has serotype AAV1, AAV2, AAV5, AAV8, AAV9, AAVrh10, or AAVrh74.

In some embodiments, the recombinant gene therapy vector comprises a self-complementary AAV.

In some embodiments, the recombinant gene therapy vector comprises a single-stranded AAV.

In some embodiments, the AAV is a wild-type AAV or a modified AAV.

In some embodiments, the AAV comprises a capsid protein having at least 95% identity to wild-type VP1, VP2, or VP3 capsid protein.

In another aspect, the disclosure provides host cell comprising any of the foregoing recombinant gene therapy vectors.

In another aspect, the disclosure provides method of inhibiting degeneration or death of a dopaminergic neuron comprising a mutation in a gene associated with a Parkinson's Disease (PD), wherein the mutated gene is a Parkinson protein 2, E3 ubiquitin protein ligase (PARK2) gene, comprising contacting the neuron with the recombinant gene therapy vector of the disclosure, wherein following contact with the recombinant gene therapy vector, the neuron expresses the wild-type protein.

In some embodiments, the neuron expresses a reduced amount of alpha-synuclein and/or comprises a reduced amount of Lewy bodies following contact with the recombinant gene therapy vector.

In some embodiments, the neuron expresses a reduced amount of monoamine oxidases following contact with the recombinant gene therapy vector.

In some embodiments, the neuron produces and/or releases an increased amount of dopamine following contact with the recombinant gene therapy vector.

In some embodiments, the neuron undergoes increased mitophagy following contact with the recombinant gene therapy vector.

In some embodiments, the neuron expresses a lower amount of monoamine oxidases as compared to an amount of monoamine oxidases expressed in a neuron not contacted with said recombinant gene therapy vector, optionally wherein said lower amount is at least 5%, at least 10%, at least 20%, at least 30%, at least 40%, at least 50%, at least 60%, at least 70%, or at least 80% lower than the amount expressed in the neuron not contacted with said recombinant gene therapy vector.

In some embodiments, the neuron produces and/or releases an increased amount of dopamine as compared to an amount of dopamine produced and/or released by a neuron not contacted with said recombinant gene therapy vector, optionally wherein said increase amount is at least 5%, at least 10%, at least 20%, at least 30%, at least 40%, at least 50%, at least 60%, at least 70%, at least 80%, at least 90%, at least two-fold, at least three-fold, at least four-fold, at least five-fold, or at least 10-fold greater than the amount produced and/or released by the neuron not contacted with said recombinant gene therapy vector.

In some embodiments, the neuron undergoes an increased amount of autophagy as compared to an amount of autophagy undergone by a neuron not contacted with said recombinant gene therapy vector, optionally wherein the increased amount is at least 5%, at least 10%, at least 20%, at least 30%, at least 40%, at least 50%, at least 60%, at least 70%, at least 80%, at least 90%, at least two-fold, at least three-fold, at least four-fold, at least five-fold, or at least 10-fold greater than the amount undergone by the neuron not contacted with said recombinant gene therapy vector.

In some embodiments, the neuron is a primary tyrosine hydroxylase positive neuron.

In some embodiments, the neuron was produced from an induced pluripotent stem cell prepared from cells obtained from a subject diagnosed with Parkinson's disease.

In another aspect, the disclosure provides, a method of treating or inhibiting onset of a Parkinson's Disease (PD) in a subject suffering from or at risk of the PD, comprising administering a gene therapy vector of the disclosure, wherein administration of the recombinant gene therapy vector treats or inhibits onset of the Parkinson's Disease in the subject.

In some embodiments, the PD is an early-onset PD, optionally an early-onset autosomal recessive PD.

In some embodiments, the subject comprises a mutation in a PARK2 gene.

In some embodiments, the PARK2 comprises the amino acid sequence set forth in SEQ ID NO: 1.

In some embodiments, administering step comprises systemic, parenteral, intravenous, cerebral, cerebrospinal, intrathecal, intracisternal, intraputaminal, intrahippocampal, intra-striatal, or intra-cerebroventricular administration.

In some embodiments, the administering step comprises intravenous, cerebral, cerebrospinal, intrathecal, intracisternal, intraputaminal, intrahippocampal, intra-striatal, or intra-cerebroventricular injection.

In some embodiments, the administering step comprises intrathecal injection with Trendelenburg tilting.

In some embodiments, the administering step comprises direct injection into the pars compacta of the substantia nigra of the brain.

In some embodiments, the administering step comprises introducing the recombinant gene therapy vector into the subject's brain or cerebrospinal fluid (CSF).

In some embodiments, $1\times10^9$-$1\times10^{14}$ vector genomes per kilogram body mass of the subject (vg/kg) of the gene therapy vector are administered to the subject.

In some embodiments, $1\times10^9$-$1\times10^{14}$ vector genomes per kilogram body mass of the subject (vg/kg) of the gene therapy vector are administered to the subject's brain.

In some embodiments, $1\times10^9$-$1\times10^{14}$ vector genomes per kilogram body mass of the subject (vg/kg) of the gene therapy vector are administered to the subject's CSF.

In some embodiments, $1\times10^7$-$1\times10^9$ vector genomes per kilogram body mass of the subject (vg/kg) of the gene therapy vector are administered to the subject.

In some embodiments, $1\times10^7$-$1\times10^{11}$ total vector genomes are administered to the subject, e.g., via direct injection into the putamen or substantia nigra.

In some embodiments, the subject is an adult.

In some embodiments, the subject is a child.

In some embodiments, the number of dopaminergic neurons in the subject after the administering step is greater than the number of dopaminergic neurons in the subject before the administering step.

In some embodiments, the level of dopamine in the subject after the administering step is greater than the level of dopamine in the subject before the administering step.

In some embodiments, the number of dopaminergic neurons in a subject treated by the method is increased compared to the number of dopaminergic neurons in a subject not so treated.

In some embodiments, the level of dopamine of a subject treated by the method is increased compared to the level of dopamine in a subject not so treated.

In some embodiments, the level of dopamine in the substantia nigra of a subject treated by method is increased compared to the level of dopamine in the substantia nigra of a subject not so treated.

In some embodiments, the level of PRKN in the subject's CSF after the administering step is greater than the level of PRKN in the subject's CSF before the administering step.

In some embodiments, the Unified Parkinson's Disease Rating Scale (UPDRS) score of the subject before the administering step is improved compared to the UPDRS score of the subject before the administering step.

In some embodiments, the level of PRKN in the CSF of a subject treated by the method is increased compared to the level of PRKN in the CSF of a subject not so treated.

In some embodiments, the UPDRS score of a subject treated by the method is improved compared to the UPDRS score of a subject not so treated.

In some embodiments, the subject's neurons express a reduced amount of alpha-synuclein and/or comprises a reduced amount of Lewy bodies following contact with the recombinant gene therapy vector.

Other features and advantages of the invention will be apparent from and encompassed by the following detailed description and claims.

DETAILED DESCRIPTION

Figure 1:
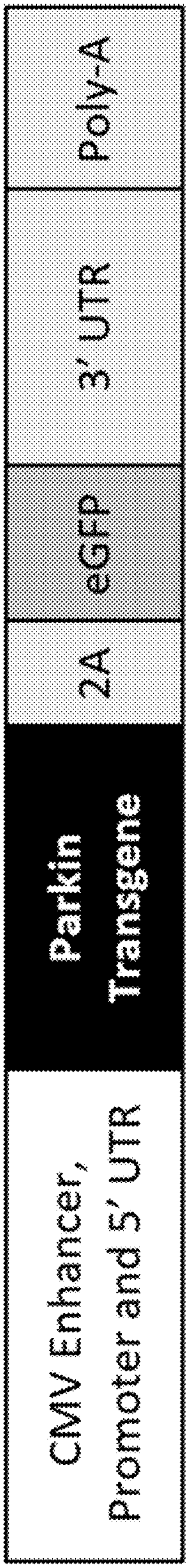
FIG. 1 shows an embodiment of the expression cassettes of the disclosure.

The present disclosure provides, in part, compositions and methods for treating, preventing, inhibiting, or delaying central nervous system degeneration, e.g., in the treatment of a Parkinson's Disease. In particular, the inventors disclose various embodiments of a recombinant gene therapy vector comprising a Parkinson protein 2, E3 ubiquitin protein ligase (PARK2) gene, a PTEN-induced putative kinase 1 (PINK1) gene, a protein deglycase DJ-1 (DJ-1) gene, a Leucine Rich Repeat Kinase 2 (LRRK2) gene, an alpha-synuclein (SCNA) gene, a Proto-oncogene c-Rel (c-Rel) gene, a Ubiquitin-like modifier-activating enzyme (ATG7) gene, a Synaptic vesicular amine transporter (VMAT2) gene, or a glucocerebrosidase (GBA) gene, or functional fragment or variant thereof. As used herein, the term "gene" or "transgene" are used interchangeably and refer to a polynucleotide sequence encoding a polypeptide or protein, such as any of the proteins disclosed in Table 1.

The disclosure further includes various embodiments of a gene editing system comprising a Cas protein, guide RNA, a repair template comprising a Parkinson protein 2, E3 ubiquitin protein ligase (PARK2) gene, a PTEN-induced putative kinase 1 (PINK1) gene, a protein deglycase DJ-1 (DJ-1) gene, a Leucine Rich Repeat Kinase 2 (LRRK2) gene, an alpha-synuclein (SCNA) gene, a Proto-oncogene c-Rel (c-Rel) gene, a Ubiquitin-like modifier-activating enzyme (ATG7) gene, a Synaptic vesicular amine transporter (VMAT2) gene, or a glucocerebrosidase (GBA) gene, or functional fragment or variant thereof.

The disclosure further includes methods of inhibiting degeneration or death of a dopaminergic neuron having a mutated PARK2 gene, and methods of treating or inhibiting onset or progression of Parkinson's Disease in a subject suffering from or at risk of Parkinson's disease. In particular embodiments, the Parkinson's disease is an early-onset or juvenile Parkinson's Disease. In certain embodiments, it is associated with or caused by an autosomal recessive mutation, e.g., in a subject's PARK2, PINK1, DJ-1, LRRK2, SCNA, c-Rel, ATG7, VMAT2, or GBA gene. In some embodiments, a viral vector, e.g., an adeno-associated virus (AAV), is used to deliver a recombinant gene therapy construct to the body or more particularly the brain of a subject. Also provided are recombinant gene therapy vectors or gene editing systems for PARK2, PINK1, DJ-1, LRRK2, SCNA, c-Rel, ATG7, VMAT2, or GBA. Table 1 provides protein sequences. Those genes are expressed as various isoforms. For example, and without limiting the disclosure to PARK2, the isoforms of PARK2 are provided in Table 2. Table 3 provides polynucleotide sequences. Table 4 provides polynucleotide sequences for the isoforms of PARK2. The disclosure provides compositions and methods comprising or encoding any of the isoforms as proteins or polynucleotides, including codon-optimized polynucleotides and spliced or un-spliced variants.

TABLE 1

<table>
<tr><th colspan="3">Non-Limiting Examples of Genes Associated with CNS Degradation</th></tr>
<tr><th>Gene (Synonym)</th><th>Protein Sequence</th><th>SEQ ID NO:</th></tr>
<tr><td>PARK2 (PRK2; PRKN; Parkin)</td><td>>sp|O60260|PRKN_HUMAN E3 ubiquitin-protein ligase parkin OS = Homo sapiens OX = 9606 GN = PRKN PE = 1 SV = 2<br>MIVFVRENSSHGFPVEVDSDTSIFQLKEVVAKRQGVPADQ<br>LRVIFAGKELRNDWTVQNCDLDQQSIVHIVQRPWRKGQEM<br>NATGGDDPRNAAGGCEREPQSLTRVDLSSSVLPGDSVGLA<br>VILHTDSRKDSPPAGSPAGRSIYNSFYVYCKGPCQRVQPG<br>KLRVQCSTCRQATLTLTQGPSCWDDVLIPNRMSGECQSPH<br>CPGTSAEFFFKCGAHPTSDKETSVALHLIATNSRNITCIT<br>CTDVRSPVLVFQCNSRHVICLDCFHLYCVTRLNDRQFVHD<br>PQLGYSLPCVAGCPNSLIKELHHFRILGEEQYNRYQQYGA<br>EECVLQMGGVLCPRPGCGAGLLPEPDQRKVTCEGGNGLGC<br>GFAFCRECKEAYHEGECSAVFEASGTTTQAYRVDERAAEQ<br>ARWEAASKETIKKTTKPCPRCHVPVEKNGGCMHMKCPQPQ<br>CRLEWCWNCGCEWNRVCMGDHWFDV</td><td>1</td></tr>
<tr><td>PARK6 (PRK6; PINK1)</td><td>>sp|Q9BXM7|PINK1_HUMAN Serine/threonine-protein kinase PINK1, mitochondrial OS = Homo sapiens OX = 9606 GN = PINK1 PE = 1 SV = 1<br>MAVRQALGRGLQLGRALLLRFTGKPGRAYGLGRPGPAAGC<br>VRGERPGWAAGPGAEPRRVGLGLPNRLRFFRQSVAGLAAR<br>LQRQFVVRAWGCAGPCGRAVFLAFGLGLGLIEEKQAESRR<br>AVSACQEIQAIFTQKSKPGPDPLDTRRLQGFRLEEYLIGQ<br>SIGKGCSAAVYEATMPTLPQNLEVTKSTGLLPGRGPGTSA<br>PGEGQERAPGAPAFPLAIKMMWNISAGSSSEAILNTMSQE<br>LVPASRVALAGEYGAVTYRKSKRGPKQLAPHPNIIRVLRA<br>FTSSVPLLPGALVDYPDVLPSRLHPEGLGHGRTLFLVMKN<br>YPCTLRQYLCVNTPSPRLAAMMLLQLLEGVDHLVQQGIAH<br>RDLKSDNILVELDPDGCPWLVIADFGCCLADESIGLQLPF<br>SSWYVDRGGNGCLMAPEVSTARPGPRAVIDYSKADAWAVG<br>AIAYEIFGLVNPFYGQGKAHLESRSYQEAQLPALPESVPP<br>DVRQLVRALLQREASKRPSARVAANVLHLSLWGEHILALK<br>NLKLDKMVGWLLQQSAATLLANRLTEKCCVETKMKMLFLA<br>NLECETLCQAALLLCSWRAAL</td><td>2</td></tr>
<tr><td>PARK7 (PRK7; DJ-1)</td><td>>sp |Q99497|PARK7_HUMAN Protein/nucleic acid deglycase DJ-1 OS = Homo sapiens OX = 9606 GN = PARK7 PE = 1 SV = 2<br>MASKRALVILAKGAEEMETVIPVDVMRRAGIKVTVAGLAG<br>KDPVQCSRDVVICPDASLEDAKKEGPYDVVVLPGGNLGAQ<br>NLSESAAVKEILKEQENRKGLIAAICAGPTALLAHEIGFG<br>SKVTTHPLAKDKMMNGGHYTYSENRVEKDGLILTSRGPGT<br>SFEFALAIVEALNGKEVAAQVKAPLVLKD</td><td>3</td></tr>
<tr><td>LRRK2 (PARK8; PRK8)</td><td>>sp|Q5S007|LRRK2 HUMAN Leucine-rich repeat serine/threonine-protein kinase 2 OS = Homo sapiens OX = 9606 GN = LRRK2 PE = 1 SV = 2<br>MASGSCQGCEEDEETLKKLIVRLNNVQEGKQIETLVQILE<br>DLLVFTYSERASKLFQGKNIHVPLLIVLDSYMRVASVQQV<br>GWSLLCKLIEVCPGTMQSLMGPQDVGNDWEVLGVHQLILK<br>MLTVHNASVNLSVIGLKTLDLLLTSGKITLLILDEESDIF<br>MLIFDAMHSFPANDEVQKLGCKALHVLFERVSEEQLTEFV<br>ENKDYMILLSALTNFKDEEEIVLHVLHCLHSLAIPCNNVE<br>VLMSGNVRCYNIVVEAMKAFPMSERIQEVSCCLLHRLTLG<br>NFFNILVLNEVHEFVVKAVQQYPENAALQISALSCLALLT<br>ETIFLNQDLEEKNENQENDDEGEEDKLFWLEACYKALTWH<br>RKNKHVQEAACWALNNLLMYQNSLHEKIGDEDGHFPAHRE<br>VMLSMLMHSSSKEVFQASANALSTLLEQNVNERKILLSKG<br>IHLNVLELMQKHIHSPEVAESGCKMLNHLFEGSNTSLDIM<br>AAVVPKILTVMKRHETSLPVQLEALRAILHFIVPGMPEES<br>REDTEFHHKLNMVKKQCFKNDIHKLVLAALNRFIGNPGIQ<br>KCGLKVISSIVHFPDALEMLSLEGAMDSVLHTLQMYPDDQ<br>EIQCLGLSLIGYLITKKNVFIGTGHLLAKILVSSLYRFKD<br>VAEIQTKGFQTILAILKLSASFSKLLVHHSEDLVIFHQMS<br>SNIMEQKDQQFLNLCCKCFAKVAMDDYLKNVMLERACDQN<br>NSIMVECLLLLGADANQAKEGSSLICQVCEKESSPKLVEL<br>LLNSGSREQDVRKALTISIGKGDSQIISLLLRRLALDVAN<br>NSICLGGFCIGKVEPSWLGPLFPDKTSNLRKQTNIASTLA<br>RMVIRYQMKSAVEEGTASGSDGNFSEDVLSKFDEWTFIPD<br>SSMDSVFAQSDDLDSEGSEGSFLVKKKSNSISVGEFYRDA<br>VLQRCSPNLQRHSNSLGPIFDHEDLLKRKRKILSSDDSLR</td><td>4</td></tr>
</table>

TABLE 1-continued

<table>
<tr><th colspan="3">Non-Limiting Examples of Genes Associated with CNS Degradation</th></tr>
<tr><th>Gene (Synonym)</th><th>Protein Sequence</th><th>SEQ ID NO:</th></tr>
<tr><td></td><td>SSKLQSHMRHSDSISSLASEREYITSLDLSANELRDIDAL<br>SQKCCISVHLEHLEKLELHQNALTSFPQQLCETLKSLTHL<br>DLHSNKFTSFPSYLLKMSCIANLDVSRNDIGPSVVLDPTV<br>KCPTLKQFNLSYNQLSFVPENLTDVVEKLEQLILEGNKIS<br>GICSPLRLKELKILNLSKNHISSLSENFLEACPKVESFSA<br>RMNFLAAMPFLPPSMTILKLSQNKFSCIPEAILNLPHLRS<br>LDMSSNDIQYLPGPAHWKSLNLRELLFSHNQISILDLSEK<br>AYLWSRVEKLHLSHNKLKEIPPEIGCLENLTSLDVSYNLE<br>LRSFPNEMGKLSKIWDLPLDELHLNFDFKHIGCKAKDIIR<br>FLQQRLKKAVPYNRMKLMIVGNTGSGKTTLLQQLMKTKKS<br>DLGMQSATVGIDVKDWPIQIRDKRKRDLVLNVWDFAGREE<br>FYSTHPHEMTQRALYLAVYDLSKGQAEVDAMKPWLFNIKA<br>RASSSPVILVGTHLDVSDEKQRKACMSKITKELLNKRGFP<br>AIRDYHFVNATEESDALAKLRKTIINESLNFKIRDQLVVG<br>QLIPDCYVELEKIILSERKNVPIEFPVIDRKRLLQLVREN<br>QLQLDENELPHAVHFLNESGVLLHFQDPALQLSDLYFVEP<br>KWLCKIMAQILTVKVEGCPKHPKGIISRRDVEKFLSKKRK<br>FPKNYMSQYFKLLEKFQIALPIGEEYLLVPSSLSDHRPVI<br>ELPHCENSEIIIRLYEMPYFPMGFWSRLINRLLEISPYML<br>SGRERALRPNRMYWRQGIYLNWSPEAYCLVGSEVLDNHPE<br>SFLKITVPSCRKGCILLGQVVDHIDSLMEEWFPGLLEIDI<br>CGEGETLLKKWALYSENDGEEHQKILLDDLMKKAEEGDLL<br>VNPDQPRLTIPISQIAPDLILADLPRNIMLNNDELEFEQA<br>PEFLLGDGSFGSVYRAAYEGEEVAVKIFNKHTSLRLLRQE<br>LVVLCHLHHPSLISLLAAGIRPRMLVMELASKGSLDRLLQ<br>QDKASLTRTLQHRIALHVADGLRYLHSAMIIYRDLKPHNV<br>LLFTLYPNAAIIAKIADYGIAQYCCRMGIKTSEGTPGFRA<br>PEVARGNVIYNQQADVYSFGLLLYDILTTGGRIVEGLKFP<br>NEFDELEIQGKLPDPVKEYGCAPWPMVEKLIKQCLKENPQ<br>ERPTSAQVEDILNSAELVCLTRRILLPKNVIVECMVATHH<br>NSRNASIWLGCGHTDRGQLSFLDLNTEGYTSEEVADSRIL<br>CLALVHLPVEKESWIVSGTQSGTLLVINTEDGKKRHTLEK<br>MTDSVTCLYCNSFSKQSKQKNFLLVGTADGKLAIFEDKTV<br>KLKGAAPLKILNIGNVSTPLMCLSESTNSTERNVMWGGCG<br>TKIFSFSNDFTIQKLIETRTSQLFSYAAFSDSNIITVVVD<br>TALYIAKQNSPVVEVWDKKTEKLCGLIDCVHFLREVMVKE<br>NKESKHKMSYSGRVKTLCLQKNTALWIGTGGGHILLLDLS<br>TRRLIRVIYNFCNSVRVMMTAQLGSLKNVMLVLGYNRKNT<br>EGTQKQKEIQSCLTVWDINLPHEVQNLEKHIEVRKELAEK<br>MRRTSVE</td><td></td></tr>
<tr><td>alpha-synuclein (PARK1; PRK1)</td><td>>sp|P37840|SYUA HUMAN Alpha-synuclein OS = Homo sapiens OX = 9606 GN = SNCA PE = 1 SV = 1<br>MDVFMKGLSKAKEGVVAAAEKTKQGVAEAAGKTKEGVLYV<br>GSKTKEGVVHGVATVAEKTKEQVTNVGGAVVTGVTAVAQK<br>TVEGAGSIAAATGFVKKDQLGKNEEGAPQEGILEDMPVDP<br>DNEAYEMPSEEGYQDYEPEA</td><td>5</td></tr>
<tr><td>c-Rel-NFKB</td><td>>sp|Q04864|REL HUMAN Proto-oncogene c-Rel OS = Homo sapiens OX = 9606 GN = REL PE = 1 SV = 1<br>MASGAYNPYIEIIEQPRQRGMRFRYKCEGRSAGSIPGEHS<br>TDNNRTYPSIQIMNYYGKGKVRITLVTKNDPYKPHPHDLV<br>GKDCRDGYYEAEFGQERRPLFFQNLGIRCVKKKEVKEAII<br>TRIKAGINPFNVPEKQLNDIEDCDLNVVRLCFQVELPDEH<br>GNLTTALPPVVSNPIYDNRAPNTAELRICRVNKNCGSVRG<br>GDEIFLLCDKVQKDDIEVRFVLNDWEAKGIFSQADVHRQV<br>AIVFKTPPYCKAITEPVTVKMQLRRPSDQEVSESMDFRYL<br>PDEKDTYGNKAKKQKTTLLFQKLCQDHVETGFRHVDQDGL<br>ELLTSGDPPTLASQSAGITVNFPERPRPGLLGSIGEGRYF<br>KKEPNLFSHDAVVREMPTGVSSQAESYYPSPGPISSGLSH<br>HASMAPLPSSSWSSVAHPTPRSGNINPLSSESTRTLPSNS<br>QGIPPFLRIPVGNDLNASNACIYNNADDIVGMEASSMPSA<br>DLYGISDPNMLSNCSVNMMTTSSDSMGETDNPRLLSMNLE<br>NPSCNSVLDPRDLRQLHQMSSSSMSAGANSNTTVFVSQSD<br>AFEGSDFSCADNSMINESGPSNSTNPNSHGFVQDSQYSGI<br>GSMQNEQLSDSFPYEFFQV</td><td>6</td></tr>
</table>

TABLE 1-continued

Non-Limiting Examples of Genes Associated with CNS Degradation

| Gene (Synonym) | Protein Sequence | SEQ ID NO: |
|---|---|---|
| ATG7 | >sp\|Q9D906\|ATG7 MOUSE Ubiquitin-like modifier-activating enzyme ATG7 OS = Mus musculus OX = 10090 GN = Atg7 PE = 1 SV=1 MGDPGLAKLQFAPFNSALDVGFWHELTQKKLNEYRLDEAPKDIKGYYYNGDSAGLPTRLTLEFSAFDMSASTPAHCCPAMGTLHNTNTLEAFKTADKKLLLEQSANEIWEAIKSGAALENPMLLNKFLLLTFADLKKYHFYYWFCCPALCLPESIPLIRGPVSLDQRLSPKQIQALEHAYDDLCRAEGVTALPYFLFKYDDDTVLVSLLKHYSDFFQGQRTKITVGVYDPCNLAQYPGWPLRNFLVLAAHRWSGSFQSVEVLCFRDRTMQGARDVTHSIIFEVKLPEMAFSPDCPKAVGWEKNQKGGMGPRMVNLSGCMDPKRLAESSVDLNLKLMCWRLVPTLDLDKVVSVKCLLLGAGTLGCNVARTLMGWGVRHVTFVDNAKISYSNPVRQPLYEFEDCLGGGKPKALAAAERLQKIFPGVNARGENMSIPMPGHPVNFSDVTMEQARRDVEQLEQLIDNHDVIFLLMDTRESRWLPTVIAASKRKLVINAALGFDTFVVMRHGLKKPKQQGAGDLCPSHLVAPADLGSSLFANIPGYKLGCYFCNDVVAPGDSTRDRTLDQQCTVSRPGLAVIAGALAVELMVSVLQHPEGGYAIASSSDDRMNEPPTSLGLVPHQIRGFLSREDNVLPVSLAFDKCTACSPKVLDQYEREGFTFLAKVENSSHSFLEDLTGLTLLHQETQAAEIWDMSDEETV | 7 |
| VMAT2 | >sp\|Q05940\|VMAT2 HUMAN Synaptic vesicular amine transporter OS = Homo sapiens OX = 9606 GN = SLC18A2 PE = 1 SV = 2 MALSELALVRWLQESRRSRKLILFIVFLALLLDNMLLTVVVPIIPSYLYSIKHEKNATEIQTARPVHTASISDSFQSIFSYYDNSTMVTGNATRDLTLHQTATQHMVTNASAVPSDCPSEDKDLLNENVQVGLLFASKATVQLITNPFIGLLINRIGYPIPIFAGFCIMFVSTIMFAFSSSYAFLLIARSLQGIGSSCSSVAGMGMLASVYTDDEERGNVMGIALGGLAMGVLVGPPFGSVLYEFVGKTAPFLVLAALVLLDGAIQLFVLQPSRVQPESQKGTPLTTLLKDPYILIAAGSICFANMGIAMLEPALPIWMMETMCSRKWQLGVAFLPASISYLIGTNIFGILAHKMGRWLCALLGMIIVGVSILCIPFAKNIYGLIAPNFGVGFAIGMVDSSMMPIMGYLVDLRHVSVYGSVYAIADVAFCMGYAIGPSAGGAIAKAIGFPWLMTIIGIIDILFAPLCFFLRSPPAKEEKMAILMDHNCPIKTKMYTQNNIQSYPIGEDEESESD | 8 |
| GBA | >sp\|P04062\|GLCM HUMAN Glucosylceramidase OS = Homo sapiens OX = 9606 GN = GBA PE = 1 SV = 3 MEFSSPSREECPKPLSRVSIMAGSLTGLLLLQAVSWASGARPCIPKSFGYSSVVCVCNATYCDSFDPPTFPALGTESRYESTRSGRRMELSMGPIQANHTGTGLLLTLQPEQKFQKVKGFGGAMTDAAALNILALSPPAQNLLLKSYFSEEGIGYNIIRVPMASCDESIRTYTYADTPDDFQLHNFSLPEEDTKLKIPLIHRALQLAQRPVSLLASPWTSPTWLKTNGAVNGKGSLKGQPGDIYHQTWARYFVKFLDAYAEHKLQFWAVTAENEPSAGLLSGYPFQCLGFTPEHQRDFIARDLGPTLANSTHHNVRLLMLDDQRLLLPHWAKVVLTDPEAAKYVHGIAVHWYLDFLAPAKATLGETHRLFPNTMLFASEACVGSKFWEQSVRLGSWDRGMQYSHSIITNLLYHVVGWTDWNLALNPEGGPNWVRNFVDSPIIVDITKDTFYKQPMFYHLGHFSKFIPEGSQRVGLVASQKNDLDAVALMHPDGSAVVVVLNRSSKDVPLTIKDPAVGFLETISPGYSIHTYLWRRQ | 9 |

TABLE 2

Isoforms of PARK2

| Gene (Isoform) | Protein Sequence | SEQ ID NO: |
|---|---|---|
| PARK2 (1) | >sp\|O60260\|PRKN_HUMAN E3 ubiquitin-protein ligase parkin OS = *Homo sapiens* OX = 9606 GN = PRKN PE = 1 SV = 2 MIVFVRFNSSHGFPVEVDSDTSIFQLKEVVAKRQGVPADQLRVIFAGKELRNDWTVQNCDLDQQSIVHIVQRPWRKGQEMNATGGDDPRNAAGGCEREPQSLTRVDLSSSVLPGDSVGLAVILHTDSRKDSPPAGSPAGRSIYNSFYVYCKGPCQRVQPGKLRVQCSTCRQATLTLTQGPSCWDDVLIPNRMSGECQSPHCPGTSAEFFFKCGAHPTSDKETSVALHLIATNSRNITCITCTDVRSPVLVFQCNSRHVICLDCFHLYCVTRLNDRQFVHDPQLGYSLPCVAGCPNSLIKELHHFRILGEEQYNRYQQYGAEECVLQMGGVLCPRPGCGAGLLPEPDQRKVTCEGGNGLGCGFAFCRECKEAYHEGECSAVFEASGTTTQAYRVDERAAEQARWEAASKETIKKTTKPCPRCHVPVEKNGGCMHMKCPQPQCRLEWCWNCGCEWNRVCMGDHWFDV | 10 |
| PARK2 (2) | >sp\|O60260-2\|PRKN_HUMAN Isoform 2 of E3 ubiquitin-protein ligase parkin OS = *Homo sapiens* OX = 9606 GN = PRKN MIVFVRFNSSHGFPVEVDSDTSIFQLKEVVAKRQGVPADQLRVIFAGKELRNDWTVQNCDLDQQSIVHIVQRPWRKGQEMNATGGDDPRNAAGGCEREPQSLTRVDLSSSVLPGDSVGLAVILHTDSRKDSPPAGSPAGRSIYNSFYVYCKGPCQRVQPGKLRVQCSTCRQATLTLTQEFFFKCGAHPTSDKETSVALHLIATNSRNITCITCTDVRSPVLVFQCNSRHVICLDCFHLYCVTRLNDRQFVHDPQLGYSLPCVAGCPNSLIKELHHFRILGEEQYNRYQQYGAEECVLQMGGVLCPRPGCGAGLLPEPDQRKVTCEGGNGLGCGFAFCRECKEAYHEGECSAVFEASGTTTQAYRVDERAAEQARWEAASKETIKKTTKPCPRCHVPVEKNGGCMHMKCPQPQCRLEWCWNCGCEWNRVCMGDHWFDV | 11 |

TABLE 2-continued

| Isoforms of PARK2 | | |
|---|---|---|
| Gene (Isoform) | Protein Sequence | SEQ ID NO: |
| PARK2 (3) | >sp\|O60260-3\|PRKN_HUMAN Isoform 3 of E3 ubiquitin-protein ligase parkin OS = *Homo sapiens* OX = 9606 GN = PRKN MNATGGDDPRNAAGGCEREPQSLTRVDLSSSVLPGDSVGLAVILHTDSRKDSPPAGSPAGRSIYNSFYVYCKGPCQRVQPGKLRVQCSTCRQATLTLTQGPSCWDDVLIPNRMSGECQSPHCPGTSAEFFFKCGAHPTSDKETSVALHLIATNSRNITCITCTDVRSPVLVFQCNSRHVICLDCFHLYCVTRLNDRQFVHDPQLGYSLPCVVCLLPGM | 12 |
| PARK2 (4) | >sp\|O60260-4\|PRKN_HUMAN Isoform 4 of E3 ubiquitin-protein ligase parkin OS = *Homo sapiens* OX = 9606 GN = PRKN MSGECQSPHCPGTSAEFFFKCGAHPTSDKETSVALHLIATNSRNITCITCTDVRSPVLVFQCNSRHVICLDCFHLYCVTRLNDRQFVHDPQLGYSLPCVAGCPNSLIKELHHFRILGEEQYNRYQQYGAEECVLQMGGVLCPRPGCGAGLLPEPDQRKVTCEGGNGLGCGFAFCRECKEAYHEGECSAVFEASGTTTQAYRVDERAAEQARWEAASKETIKKTTKPCPRCHVPVEKNGGCMHMKCPQPQCRLEWCWNCGCEWNRVCMGDHWFDV | 13 |
| PARK2 (5) | >sp\|O60260-5\|PRKN_HUMAN Isoform 5 of E3 ubiquitin-protein ligase parkin OS = *Homo sapiens* OX = 9606 GN = PRKN MIVFVRENSSHGFPVEVDSDTSIFQLKEVVAKRQGVPADQLRVIFAGKELRNDWTVQNCDLDQQSIVHIVQRPWRKGQEMNATGGDDPRNAAGGCEREPQSLTRVDLSSSVLPGDSVGLAVILHTDSRKDSPPAGSPAGRSIYNSFYVYCKGPCQRVQPGKLRVQCSTCRQATLTLTQGPSCWDDVLIPNRMSGECQSPHCPGTSAEFFFKCGAHPTSDKETSVALHLIATNSRNITCITCTDVRSPVLVFQCNSRHVICLDCFHLYCVTRLNDRQFVHDPQLGYSLPCVGTGDTVVLRGALGGFRRGVAGCPNSLIKELHHFRILGEEQYNRYQQYGAEECVLQMGGVLCPRPGCGAGLLPEPDQRKVTCEGGNGLGCGYGQRRTK | 14 |
| PARK2 (6) | >sp\|O60260-6\|PRKN_HUMAN Isoform 6 of E3 ubiquitin-protein ligase parkin OS = *Homo sapiens* OX = 9606 GN = PRKN MIVFVRENSSHGFPVEVDSDTSIFQLKEVVAKRQGVPADQLRVIFAGKELRNDWTVQEFFFKCGAHPTSDKETSVALHLIATNSRNITCITCTDVRSPVLVFQCNSRHVICLDCFHLYCVTRLNDRQFVHDPQLGYSLPCVAGCPNSLIKELHHFRILGEEQYNRYQQYGAEECVLQMGGVLCPRPGCGAGLLPEPDQRKVTCEGGNGLGCGFAFCRECKEAYHEGECSAVFEASGTTTQAYRVDERAAEQARWEAASKETIKKTTKPCPRCHVPVEKNGGCMHMKCPQPQCRLEWCWNCGCEWNRVCMGDHWFDV | 15 |
| PARK2 (7) | >sp\|O60260-7\|PRKN_HUMAN Isoform 7 of E3 ubiquitin-protein ligase parkin OS = *Homo sapiens* OX = 9606 GN = PRKN MIVFVRFNSSHGFPVEVDSDTSIFQLKEVVAKRQGVPADQLRVIFAGKELRNDWTVQNCDLDQQSIVHIVQRPWRKGQEMNATGGDDPRNAAGGCEREPQSLTRVDLSSSVLPGDSVGLAVILHTDSRKDSPPAGSPAGRSIYNSFYVYCKGPCQRVQPGKLRVQCSTCRQATLTLTQEFFFKCGAHPTSDKETSVALHLIATNSRNITCITCTDVRSPVLVFQCNSRHVICLDCFHLYCVTRLNDRQFVHDPQLGYSLPCVAGCPNSLIKELHHFRILGEEQFAFCRECKEAYHEGECSAVFEASGTTTQAYRVDERAAEQARWEAASKETIKKTTKPCPRCHVPVEKNGGCMHMKCPQPQCRLEWCWNCGCEWNRVCMGDHWFDV | 16 |
| PARK2 (8) | >sp\|O60260-8\|PRKN_HUMAN Isoform 8 of E3 ubiquitin-protein ligase parkin OS = *Homo sapiens* OX = 9606 GN = PRKN MIVFVRFNSSHGFPVEVDSDTSIFQLKEVVAKRQGVPADQLRVIFAGKELRNDWTVQNCDLDQQSIVHIVQRPWRKGQEMNATGGDDPRNAAGGCEREPQSLTRVDLSSSVLPGDSVGLAVILHTDSRKDSPPAGSPAGRSIYNSFYVYCKGPCQRVQPGKLRVQCSTCRQATLTLTQGPSCWDDVLIPNRMSGECQSPHCPGTSAEFFFKCGAHPTSDKETSVALHLIATNSRNITCITCTDVRSPVLVFQCNSRHVICLDCFHLYCVTRLNDRQFVHDPQLGYSLPCVAGCPNSLIKELHHFRILGEEQFAFCRECKE | 17 |

TABLE 2-continued

| Isoforms of PARK2 | | |
|---|---|---|
| Gene (Isoform) | Protein Sequence | SEQ ID NO: |
| | AYHEGECSAVFEASGTTTQAYRVDERAAEQARWEAASKET<br>IKKTTKPCPRCHVPVEKNGGCMHMKCPQPQCRLEWCWNCG<br>CEWNRVCMGDHWFDV | |

TABLE 3

| Polynucleotides of Non-Limiting Example Genes Associated with CNS Degradation | | |
|---|---|---|
| Gene (Synonym) | Nucleic Acid Sequence | SEQ ID NO: |
| PARK2 (PRK2; PRKN; Parkin) | >NM_004562.2: 135-1532 *Homo sapiens* parkin RBR E3 ubiquitin protein ligase (PRKN), transcript variant 1, mRNA<br>ATGATAGTGTTTGTCAGGTTCAACTCCAGCCATGGTTTCC<br>CAGTGGAGGTCGATTCTGACACCAGCATCTTCCAGCTCAA<br>GGAGGTGGTTGCTAAGCGACAGGGGGTTCCGGCTGACCAG<br>TTGCGTGTGATTTTCGCAGGGAAGGAGCTGAGGAATGACT<br>GGACTGTGCAGAATTGTGACCTGGATCAGCAGAGCATTGT<br>TCACATTGTGCAGAGACCGTGGAGAAAAGGTCAAGAAATG<br>AATGCAACTGGAGGCGACGACCCCAGAAACGCGGCGGGAG<br>GCTGTGAGCGGGAGCCCCAGAGCTTGACTCGGGTGGACCT<br>CAGCAGCTCAGTCCTCCCAGGAGACTCTGTGGGGCTGGCT<br>GTCATTCTGCACACTGACAGCAGGAAGGACTCACCACCAG<br>CTGGAAGTCCAGCAGGTAGATCAATCTACAACAGCTTTTA<br>TGTGTATTGCAAAGGCCCCTGTCAAAGAGTGCAGCCGGGA<br>AAACTCAGGGTACAGTGCAGCACCTGCAGGCAGGCAACGC<br>TCACCTTGACCCAGGGTCCATCTTGCTGGGATGATGTTTT<br>AATTCCAAACCGGATGAGTGGTGAATGCCAATCCCCACAC<br>TGCCCTGGGACTAGTGCAGAATTTTTCTTTAAATGTGGAG<br>CACACCCCACCTCTGACAAGGAAACATCAGTAGCTTTGCA<br>CCTGATCGCAACAAATAGTCGGAACATCACTTGCATTACG<br>TGCACAGACGTCAGGAGCCCCGTCCTGGTTTTCCAGTGCA<br>ACTCCCGCCACGTGATTTGCTTAGACTGTTTCCACTTATA<br>CTGTGTGACAAGACTCAATGATCGGCAGTTTGTTCACGAC<br>CCTCAACTTGGCTACTCCCTGCCTTGTGTGGCTGGCTGTC<br>CCAACTCCTTGATTAAAGAGCTCCATCACTTCAGGATTCT<br>GGGAGAAGAGCAGTACAACCGGTACCAGCAGTATGGTGCA<br>GAGGAGTGTGTCCTGCAGATGGGGGGCGTGTTATGCCCCC<br>GCCCTGGCTGTGGAGCGGGGCTGCTGCCGGAGCCTGACCA<br>GAGGAAAGTCACCTGCGAAGGGGGCAATGGCCTGGGCTGT<br>GGGTTTGCCTTCTGCCGGGAATGTAAAGAAGCGTACCATG<br>AAGGGGAGTGCAGTGCCGTATTTGAAGCCTCAGGAACAAC<br>TACTCAGGCCTACAGAGTCGATGAAAGAGCCGCCGAGCAG<br>GCTCGTTGGGAAGCAGCCTCCAAAGAAACCATCAAGAAAA<br>CCACCAAGCCCTGTCCCCGCTGCCATGTACCAGTGGAAAA<br>AAATGGAGGCTGCATGCACATGAAGTGTCCGCAGCCCCAG<br>TGCAGGCTCGAGTGGTGCTGGAACTGTGGCTGCGAGTGGA<br>ACCGCGTCTGCATGGGGGACCACTGGTTCGACGTGTAG | 18 |
| PARK6 (PRK6; PINK1) | >NM_032409.2: 95-1840 *Homo sapiens* PTEN induced putative kinase 1 (PINK1), mRNA<br>ATGGCGGTGCGACAGGCGCTGGGCCGCGGCCTGCAGCTGG<br>GTCGAGCGCTGCTGCTGCGCTTCACGGGCAAGCCCGGCCG<br>GGCCTACGGCTTGGGGCGGCCGGGCCCGGCGGCGGGCTGT<br>GTCCGCGGGGAGCGTCCAGGCTGGGCCGCAGGACCGGGCG<br>CGGAGCCTCGCAGGGTCGGGCTCGGGCTCCCTAACCGTCT<br>CCGCTTCTTCCGCCAGTCGGTGGCCGGGCTGGCGGCGCGG<br>TTGCAGCGGCAGTTCGTGGTGCGGGCCTGGGGCTGCGCGG<br>GCCCTTGCGGCCGGGCAGTCTTTCTGGCCTTCGGGCTAGG<br>GCTGGGCCTCATCGAGGAAAAACAGGCGGAGAGCCGGCGG<br>GCGGTCTCGGCCTGTCAGGAGATCCAGGCAATTTTTACCC<br>AGAAAAGCAAGCCGGGGCCTGACCCGTTGGACACGAGACG<br>CTTGCAGGGCTTTCGGCTGGAGGAGTATCTGATAGGGCAG<br>TCCATTGGTAAGGGCTGCAGTGCTGCTGTGTATGAAGCCA<br>CCATGCCTACATTGCCCCAGAACCTGGAGGTGACAAAGAG<br>CACCGGGTTGCTTCCAGGGAGAGGCCCAGGTACCAGTGCA<br>CCAGGAGAAGGGCAGGAGCGAGCTCCGGGGGCCCCTGCCT<br>TCCCCTTGGCCATCAAGATGATGTGGAACATCTCGGCAGG<br>TTCCTCCAGCGAAGCCATCTTGAACACAATGAGCCAGGAG<br>CTGGTCCCAGCGAGCCGAGTGGCCTTGGCTGGGGAGTATG | 19 |

TABLE 3-continued

| Polynucleotides of Non-Limiting Example Genes Associated with CNS Degradation | | |
|---|---|---|
| Gene (Synonym) | Nucleic Acid Sequence | SEQ ID NO: |
| | GAGCAGTCACTTACAGAAAATCCAAGAGAGGTCCCAAGCA ACTAGCCCCTCACCCCAACATCATCCGGGTTCTCCGCGCC TTCACCTCTTCCGTGCCGCTGCTGCCAGGGGCCCTGGTCG ACTACCCTGATGTGCTGCCCTCACGCCTCCACCCTGAAGG CCTGGGCCATGGCCGGACGCTGTTCCTCGTTATGAAGAAC TATCCCTGTACCCTGCGCCAGTACCTTTGTGTGAACACAC CCAGCCCCCGCCTCGCCGCCATGATGCTGCTGCAGCTGCT GGAAGGCGTGGACCATCTGGTTCAACAGGGCATCGCGCAC AGAGACCTGAAATCCGACAACATCCTTGTGGAGCTGGACC CAGACGGCTGCCCCTGGCTGGTGATCGCAGATTTTGGCTG CTGCCTGGCTGATGAGAGCATCGGCCTGCAGTTGCCCTTC AGCAGCTGGTACGTGGATCGGGGCGGAAACGGCTGTCTGA TGGCCCCAGAGGTGTCCACGGCCCGTCCTGGCCCCAGGGC AGTGATTGACTACAGCAAGGCTGATGCCTGGGCAGTGGGA GCCATCGCCTATGAAATCTTCGGGCTTGTCAATCCCTTCT ACGGCCAGGGCAAGGCCCACCTTGAAAGCCGCAGCTACCA AGAGGCTCAGCTACCTGCACTGCCCGAGTCAGTGCCTCCA GACGTGAGACAGTTGGTGAGGGCACTGCTCCAGCGAGAGG CCAGCAAGAGACCATCTGCCCGAGTAGCCGCAAATGTGCT TCATCTAAGCCTCTGGGGTGAACATATTCTAGCCCTGAAG AATCTGAAGTTAGACAAGATGGTTGGCTGGCTCCTCCAAC AATCGGCCGCCACTTTGTTGGCCAACAGGCTCACAGAGAA GTGTTGTGTGGAAACAAAAATGAAGATGCTCTTTCTGGCT AACCTGGAGTGTGAAACGCTCTGCCAGGCAGCCCTCCTCC TCTGCTCATGGAGGGCAGCCCTGTGA | |
| PARK7 (PRK7; DJ-1) | >NM_007262.4: 164-733 *Homo sapiens* Parkinsonism associated deglycase (PARK7), transcript variant 1, mRNA ATGGCTTCCAAAAGAGCTCTGGTCATCCTGGCTAAAGGAG CAGAGGAAATGGAGACGGTCATCCCTGTAGATGTCATGAG GCGAGCTGGGATTAAGGTCACCGTTGCAGGCCTGGCTGGA AAAGACCCAGTACAGTGTAGCCGTGATGTGGTCATTTGTC CTGATGCCAGCCTTGAAGATGCAAAAAAAGAGGGACCATA TGATGTGGTGGTTCTACCAGGAGGTAATCTGGGCGCACAG AATTTATCTGAGTCTGCTGCTGTGAAGGAGATACTGAAGG AGCAGGAAAACCGGAAGGGCCTGATAGCCGCCATCTGTGC AGGTCCTACTGCTCTGTTGGCTCATGAAATAGGTTTTGGA AGTAAAGTTACAACACACCCTCTTGCTAAAGACAAAATGA TGAATGGAGGTCATTACACCTACTCTGAGAATCGTGTGGA AAAAGACGGCCTGATTCTTACAAGCCGGGGGCCTGGGACC AGCTTCGAGTTTGCGCTTGCAATTGTTGAAGCCCTGAATG GCAAGGAGGTGGCGGCTCAAGTGAAGGCTCCACTTGTTCT TAAAGACTAG | 20 |
| LRRK2 (PARK8; PRK8) | >NM 198578.3: 122-7705 Homo sapiens leucine rich repeat kinase 2 (LRRK2), mRNA ATGGCTAGTGGCAGCTGTCAGGGGTGCGAAGAGGACGAGG AAACTCTGAAGAAGTTGATAGTCAGGCTGAACAATGTCCA GGAAGGAAAACAGATAGAAACGCTGGTCCAAATCCTGGAG GATCTGCTGGTGTTCACGTACTCCGAGCACGCCTCCAAGT TATTTCAAGGCAAAAATATCCATGTGCCTCTGTTGATCGT CTTGGACTCCTATATGAGAGTCGCGAGTGTGCAGCAGGTG GGTTGGTCACTTCTGTGCAAATTAATAGAAGTCTGTCCAG GTACAATGCAAAGCTTAATGGGACCCCAGGATGTTGGAAA TGATTGGGAAGTCCTTGGTGTTCACCAATTGATTCTTAAA ATGCTAACAGTTCATAATGCCAGTGTAAACTTGTCAGTGA TTGGACTGAAGACCTTAGATCTCCTCCTAACTTCAGGTAA AATCACCTTGCTGATATTGGATGAAGAAAGTGATATTTTC ATGTTAATTTTTGATGCCATGCACTCATTTCCAGCCAATG ATGAAGTCCAGAAACTTGGATGCAAAGCTTTACATGTGCT GTTTGAGAGAGTCTCAGAGGAGCAACTGACTGAATTTGTT GAGAACAAAGATTATATGATATTGTTAAGTGCGTTAACAA ATTTTAAAGATGAAGAGGAAATTGTGCTTCATGTGCTGCA TTGTTTACATTCCCTAGCGATTCCTTGCAATAATGTGGAA GTCCTCATGAGTGGCAATGTCAGGTGTTATAATATTGTGG TGGAAGCTATGAAAGCATTCCCTATGAGTGAAAGAATTCA AGAAGTGAGTTGCTGTTTGCTCCATAGGCTTACATTAGGT AATTTTTTCAATATCCTGGTATTAAACGAAGTCCATGAGT TTGTGGTGAAAGCTGTGCAGCAGTACCCAGAGAATGCAGC ATTGCAGATCTCAGCGCTCAGCTGTTTGGCCCTCCTCACT GAGACTATTTTCTTAAATCAAGATTTAGAGGAAAAGAATG AGAATCAAGAGAATGATGATGAGGGGGAAGAAGATAAATT | 21 |

TABLE 3-continued

Polynucleotides of Non-Limiting Example Genes Associated with CNS Degradation

| Gene (Synonym) | Nucleic Acid Sequence | SEQ ID NO: |
|---|---|---|
| | GTTTTGGCTGGAAGCCTGTTACAAAGCATTAACGTGGCAT<br>AGAAAGAACAAGCACGTGCAGGAGGCCGCATGCTGGGCAC<br>TAAATAATCTCCTTATGTACCAAAACAGTTTACATGAGAA<br>GATTGGAGATGAAGATGGCCATTTCCCAGCTCATAGGGAA<br>GTGATGCTCTCCATGCTGATGCATTCTTCATCAAAGGAAG<br>TTTTCCAGGCATCTGCGAATGCATTGTCAACTCTCTTAGA<br>ACAAAATGTTAATTTCAGAAAAATACTGTTATCAAAAGGA<br>ATACACCTGAATGTTTTGGAGTTAATGCAGAAGCATATAC<br>ATTCTCCTGAAGTGGCTGAAAGTGGCTGTAAAATGCTAAA<br>TCATCTTTTTGAAGGAAGCAACACTTCCCTGGATATAATG<br>GCAGCAGTGGTCCCCAAAATACTAACAGTTATGAAACGTC<br>ATGAGACATCATTACCAGTGCAGCTGGAGGCGCTTCGAGC<br>TATTTTACATTTTATAGTGCCTGGCATGCCAGAAGAATCC<br>AGGGAGGATACAGAATTTCATCATAAGCTAAATATGGTTA<br>AAAAACAGTGTTTCAAGAATGATATTCACAAACTGGTCCT<br>AGCAGCTTTGAACAGGTTCATTGGAAATCCTGGGATTCAG<br>AAATGTGGATTAAAAGTAATTTCTTCTATTGTACATTTTC<br>CTGATGCATTAGAGATGTTATCCCTGGAAGGTGCTATGGA<br>TTCAGTGCTTCACACACTGCAGATGTATCCAGATGACCAA<br>GAAATTCAGTGTCTGGGTTTAAGTCTTATAGGATACTTGA<br>TTACAAAGAAGAATGTGTTCATAGGAACTGGACATCTGCT<br>GGCAAAAATTCTGGTTTCCAGCTTATACCGATTTAAGGAT<br>GTTGCTGAAATACAGACTAAAGGATTTCAGACAATCTTAG<br>CAATCCTCAAATTGTCAGCATCTTTTTCTAAGCTGCTGGT<br>GCATCATTCATTTGACTTAGTAATATTCCATCAAATGTCT<br>TCCAATATCATGGAACAAAAGGATCAACAGTTTCTAAACC<br>TCTGTTGCAAGTGTTTTGCAAAAGTAGCTATGGATGATTA<br>CTTAAAAAATGTGATGCTAGAGAGAGCGTGTGATCAGAAT<br>AACAGCATCATGGTTGAATGCTTGCTTCTATTGGGAGCAG<br>ATGCCAATCAAGCAAAGGAGGGATCTTCTTTAATTTGTCA<br>GGTATGTGAGAAAGAGAGCAGTCCCAAATTGGTGGAACTC<br>TTACTGAATAGTGGATCTCGTGAACAAGATGTACGAAAAG<br>CGTTGACGATAAGCATTGGGAAAGGTGACAGCCAGATCAT<br>CAGCTTGCTCTTAAGGAGGCTGGCCCTGGATGTGGCCAAC<br>AATAGCATTTGCCTTGGAGGATTTTGTATAGGAAAAGTTG<br>AACCTTCTTGGCTTGGTCCTTTATTTCCAGATAAGACTTC<br>TAATTTAAGGAAACAAACAAATATAGCATCTACACTAGCA<br>AGAATGGTGATCAGATATCAGATGAAAAGTGCTGTGGAAG<br>AAGGAACAGCCTCAGGCAGCGATGGAAATTTTTCTGAAGA<br>TGTGCTGTCTAAATTTGATGAATGGACCTTTATTCCTGAC<br>TCTTCTATGGACAGTGTGTTTGCTCAAAGTGATGACCTGG<br>ATAGTGAAGGAAGTGAAGGCTCATTTCTTGTGAAAAAGAA<br>ATCTAATTCAATTAGTGTAGGAGAATTTTACCGAGATGCC<br>GTATTACAGCGTTGCTCACCAAATTTGCAAAGACATTCCA<br>ATTCCTTGGGGCCCATTTTTGATCATGAAGATTTACTGAA<br>GCGAAAAAGAAAAATATTATCTTCAGATGATTCACTCAGG<br>TCATCAAAACTTCAATCCCATATGAGGCATTCAGACAGCA<br>TTTCTTCTCTGGCTTCTGAGAGAGAATATATTACATCACT<br>AGACCTTTCAGCAAATGAACTAAGAGATATTGATGCCCTA<br>AGCCAGAAATGCTGTATAAGTGTTCATTTGGAGCATCTTG<br>AAAAGCTGGAGCTTCACCAGAATGCACTCACGAGCTTTCC<br>ACAACAGCTATGTGAAACTCTGAAGAGTTTGACACATTTG<br>GACTTGCACAGTAATAAATTTACATCATTTCCTTCTTATT<br>TGTTGAAAATGAGTTGTATTGCTAATCTTGATGTCTCTCG<br>AAATGACATTGGACCCTCAGTGGTTTTAGATCCTACAGTG<br>AAATGTCCAACTCTGAAACAGTTTAACCTGTCATATAACC<br>AGCTGTCTTTTGTACCTGAGAACCTCACTGATGTGGTAGA<br>GAAACTGGAGCAGCTCATTTTAGAAGGAAATAAAATATCA<br>GGGATATGCTCCCCCTTGAGACTGAAGGAACTGAAGATTT<br>TAAACCTTAGTAAGAACCACATTTCATCCCTATCAGAGAA<br>CTTTCTTGAGGCTTGTCCTAAAGTGGAGAGTTTCAGTGCC<br>AGAATGAATTTTCTTGCTGCTATGCCTTTCTTGCCTCCTT<br>CTATGACAATCCTAAAATTATCTCAGAACAAATTTTCCTG<br>TATTCCAGAAGCAATTTTAAATCTTCCACACTTGCGGTCT<br>TTAGATATGAGCAGCAATGATATTCAGTACCTACCAGGTC<br>CCGCACACTGGAAATCTTTGAACTTAAGGGAACTCTTATT<br>TAGCCATAATCAGATCAGCATCTTGGACTTGAGTGAAAAA<br>GCATATTTATGGTCTAGAGTAGAGAAACTGCATCTTTCTC<br>ACAATAAACTGAAAGAGATTCCTCCTGAGATTGGCTGTCT<br>TGAAAATCTGACATCTCTGGATGTCAGTTACAACTTGGAA<br>CTAAGATCCTTTCCCAATGAAATGGGGAAATTAAGCAAAA<br>TATGGGATCTTCCTTTGGATGAACTGCATCTTAACTTTGA<br>TTTTAAACATATAGGATGTAAAGCCAAAGACATCATAAGG<br>TTTCTTCAACAGCGATTAAAAAAGGCTGTGCCTTATAACC | |

TABLE 3-continued

Polynucleotides of Non-Limiting Example Genes Associated with CNS Degradation

| Gene (Synonym) | Nucleic Acid Sequence | SEQ ID NO: |
|---|---|---|
| | GAATGAAACTTATGATTGTGGGAAATACTGGGAGTGGTAA | |
| | AACCACCTTATTGCAGCAATTAATGAAAACCAAGAAATCA | |
| | GATCTTGGAATGCAAAGTGCCACAGTTGGCATAGATGTGA | |
| | AAGACTGGCCTATCCAAATAAGAGACAAAAGAAAGAGAGA | |
| | TCTCGTCCTAAATGTGTGGGATTTTGCAGGTCGTGAGGAA | |
| | TTCTATAGTACTCATCCCCATTTTATGACGCAGCGAGCAT | |
| | TGTACCTTGCTGTCTATGACCTCAGCAAGGGACAGGCTGA | |
| | AGTTGATGCCATGAAGCCTTGGCTCTTCAATATAAAGGCT | |
| | CGCGCTTCTTCTTCCCCTGTGATTCTCGTTGGCACACATT | |
| | TGGATGTTTCTGATGAGAAGCAACGCAAAGCCTGCATGAG | |
| | TAAAATCACCAAGGAACTCCTGAATAAGCGAGGGTTCCCT | |
| | GCCATACGAGATTACCACTTTGTGAATGCCACCGAGGAAT | |
| | CTGATGCTTTGGCAAAACTTCGGAAAACCATCATAAACGA | |
| | GAGCCTTAATTTCAAGATCCGAGATCAGCTTGTTGTTGGA | |
| | CAGCTGATTCCAGACTGCTATGTAGAACTTGAAAAAATCA | |
| | TTTTATCGGAGCGTAAAAATGTGCCAATTGAATTTCCCGT | |
| | AATTGACCGGAAACGATTATTACAACTAGTGAGAGAAAAT | |
| | CAGCTGCAGTTAGATGAAAATGAGCTTCCTCACGCAGTTC | |
| | ACTTTCTAAATGAATCAGGAGTCCTTCTTCATTTTCAAGA | |
| | CCCAGCACTGCAGTTAAGTGACTTGTACTTTGTGGAACCC | |
| | AAGTGGCTTTGTAAAATCATGGCACAGATTTTGACAGTGA | |
| | AAGTGGAAGGTTGTCCAAAACACCCTAAGGGCATTATTTC | |
| | GCGTAGAGATGTGGAAAAATTTCTTTCAAAAAAAAGGAAA | |
| | TTTCCAAAGAACTACATGTCACAGTATTTTAAGCTCCTAG | |
| | AAAAATTCCAGATTGCTTTGCCAATAGGAGAAGAATATTT | |
| | GCTGGTTCCAAGCAGTTTGTCTGACCACAGGCCTGTGATA | |
| | GAGCTTCCCCATTGTGAGAACTCTGAAATTATCATCCGAC | |
| | TATATGAAATGCCTTATTTTCCAATGGGATTTTGGTCAAG | |
| | ATTAATCAATCGATTACTTGAGATTTCACCTTACATGCTT | |
| | TCAGGGAGAGAACGAGCACTTCGCCCAAACAGAATGTATT | |
| | GGCGACAAGGCATTTACTTAAATTGGTCTCCTGAAGCTTA | |
| | TTGTCTGGTAGGATCTGAAGTCTTAGACAATCATCCAGAG | |
| | AGTTTCTTAAAAATTACAGTTCCTTCTTGTAGAAAAGGCT | |
| | GTATTCTTTTGGGCCAAGTTGTGGACCACATTGATTCTCT | |
| | CATGGAAGAATGGTTTCCTGGGTTGCTGGAGATTGATATT | |
| | TGTGGTGAAGGAGAAACTCTGTTGAAGAAATGGGCATTAT | |
| | ATAGTTTTAATGATGGTGAAGAACATCAAAAAATCTTACT | |
| | TGATGACTTGATGAAGAAAGCAGAGGAAGGAGATCTCTTA | |
| | GTAAATCCAGATCAACCAAGGCTCACCATTCCAATATCTC | |
| | AGATTGCCCCTGACTTGATTTTGGCTGACCTGCCTAGAAA | |
| | TATTATGTTGAATAATGATGAGTTGGAATTTGAACAAGCT | |
| | CCAGAGTTTCTCCTAGGTGATGGCAGTTTTGGATCAGTTT | |
| | ACCGAGCAGCCTATGAAGGAGAAGAAGTGGCTGTGAAGAT | |
| | TTTTAATAAACATACATCACTCAGGCTGTTAAGACAAGAG | |
| | CTTGTGGTGCTTTGCCACCTCCACCACCCCAGTTTGATAT | |
| | CTTTGCTGGCAGCTGGGATTCGTCCCCGGATGTTGGTGAT | |
| | GGAGTTAGCCTCCAAGGGTTCCTTGGATCGCCTGCTTCAG | |
| | CAGGACAAAGCCAGCCTCACTAGAACCCTACAGCACAGGA | |
| | TTGCACTCCACGTAGCTGATGGTTTGAGATACCTCCACTC | |
| | AGCCATGATTATATACCGAGACCTGAAACCCCACAATGTG | |
| | CTGCTTTTCACACTGTATCCCAATGCTGCCATCATTGCAA | |
| | AGATTGCTGACTACGGCATTGCTCAGTACTGCTGTAGAAT | |
| | GGGGATAAAAACATCAGAGGGCACACCAGGGTTTCGTGCA | |
| | CCTGAAGTTGCCAGAGGAAATGTCATTTATAACCAACAGG | |
| | CTGATGTTTATTCATTTGGTTTACTACTCTATGACATTTT | |
| | GACAACTGGAGGTAGAATAGTAGAGGGTTTGAAGTTTCCA | |
| | AATGAGTTTGATGAATTAGAAATACAAGGAAAATTACCTG | |
| | ATCCAGTTAAAGAATATGGTTGTGCCCCATGGCCTATGGT | |
| | TGAGAAATTAATTAAACAGTGTTTGAAAGAAAATCCTCAA | |
| | GAAAGGCCTACTTCTGCCCAGGTCTTTGACATTTTGAATT | |
| | CAGCTGAATTAGTCTGTCTGACGAGACGCATTTTATTACC | |
| | TAAAAACGTAATTGTTGAATGCATGGTTGCTACACATCAC | |
| | AACAGCAGGAATGCAAGCATTTGGCTGGGCTGTGGGCACA | |
| | CCGACAGAGGACAGCTCTCATTTCTTGACTTAAATACTGA | |
| | AGGATACACTTCTGAGGAAGTTGCTGATAGTAGAATATTG | |
| | TGCTTAGCCTTGGTGCATCTTCCTGTTGAAAAGGAAAGCT | |
| | GGATTGTGTCTGGGACACAGTCTGGTACTCTCCTGGTCAT | |
| | CAATACCGAAGATGGGAAAAAGAGACATACCCTAGAAAAG | |
| | ATGACTGATTCTGTCACTTGTTTGTATTGCAATTCCTTTT | |
| | CCAAGCAAAGCAAACAAAAAAATTTTCTTTTGGTTGGAAC | |
| | CGCTGATGGCAAGTTAGCAATTTTTGAAGATAAGACTGTT | |
| | AAGCTTAAAGGAGCTGCTCCTTTGAAGATACTAAATATAG | |
| | GAAATGTCAGTACTCCATTGATGTGTTTGAGTGAATCCAC | |
| | AAATTCAACGGAAAGAAATGTAATGTGGGGAGGATGTGGC | |

TABLE 3-continued

Polynucleotides of Non-Limiting Example Genes Associated with CNS Degradation

| Gene (Synonym) | Nucleic Acid Sequence | SEQ ID NO: |
|---|---|---|
| | ACAAAGATTTTCTCCTTTTCTAATGATTTCACCATTCAGA<br>AACTCATTGAGACAAGAACAAGCCAACTGTTTTCTTATGC<br>AGCTTTCAGTGATTCCAACATCATAACAGTGGTGGTAGAC<br>ACTGCTCTCTATATTGCTAAGCAAAATAGCCCTGTTGTGG<br>AAGTGTGGGATAAGAAAACTGAAAAACTCTGTGGACTAAT<br>AGACTGCGTGCACTTTTTAAGGGAGGTAATGGTAAAAGAA<br>AACAAGGAATCAAAACACAAAATGTCTTATTCTGGGAGAG<br>TGAAAACCCTCTGCCTTCAGAAGAACACTGCTCTTTGGAT<br>AGGAACTGGAGGAGGCCATATTTTACTCCTGGATCTTTCA<br>ACTCGTCGACTTATACGTGTAATTTACAACTTTTGTAATT<br>CGGTCAGAGTCATGATGACAGCACAGCTAGGAAGCCTTAA<br>AAATGTCATGCTGGTATTGGGCTACAACCGGAAAAATACT<br>GAAGGTACACAAAAGCAGAAAGAGATACAATCTTGCTTGA<br>CCGTTTGGGACATCAATCTTCCACATGAAGTGCAAAATTT<br>AGAAAAACACATTGAAGTGAGAAAAGAATTAGCTGAAAAA<br>ATGAGACGAACATCTGTTGAGTAA | |
| alpha-synuclein (PARK1; PRK1) | >NM_000345.3: 264-686 *Homo sapiens* synuclein alpha (SNCA), transcript variant 1, mRNA<br>ATGGATGTATTCATGAAAGGACTTTCAAAGGCCAAGGAGG<br>GAGTTGTGGCTGCTGCTGAGAAAACCAAACAGGGTGTGGC<br>AGAAGCAGCAGGAAAGACAAAAGAGGGTGTTCTCTATGTA<br>GGCTCCAAAACCAAGGAGGGAGTGGTGCATGGTGTGGCAA<br>CAGTGGCTGAGAAGACCAAAGAGCAAGTGACAAATGTTGG<br>AGGAGCAGTGGTGACGGGTGTGACAGCAGTAGCCCAGAAG<br>ACAGTGGAGGGAGCAGGGAGCATTGCAGCAGCCACTGGCT<br>TTGTCAAAAAGGACCAGTTGGGCAAGAATGAAGAAGGAGC<br>CCCACAGGAAGGAATTCTGGAAGATATGCCTGTGGATCCT<br>GACAATGAGGCTTATGAAATGCCTTCTGAGGAAGGGTATC<br>AAGACTACGAACCTGAAGCCTAA | 22 |
| c-Rel-NFKB | >NM_002908.3: 347-2206 *Homo sapiens* REL proto-oncogene, NF-KB subunit (REL), transcript variant 1, mRNA<br>ATGGCCTCCGGTGCGTATAACCCGTATATAGAGATAATTG<br>AACAACCCAGGCAGAGGGGAATGCGTTTTAGATACAAATG<br>TGAAGGGCGATCAGCAGGCAGCATTCCAGGGGAGCACAGC<br>ACAGACAACAACCGAACATACCCTTCTATCCAGATTATGA<br>ACTATTATGGAAAAGGAAAAGTGAGAATTACATTAGTAAC<br>AAAGAATGACCCATATAAACCTCATCCTCATGATTTAGTT<br>GGAAAAGACTGCAGAGACGGCTACTATGAAGCAGAATTTG<br>GACAAGAACGCAGACCTTTGTTTTTCCAAAATTTGGGTAT<br>TCGATGTGTGAAGAAAAAAGAAGTAAAAGAAGCTATTATT<br>ACAAGAATAAAGGCAGGAATCAATCCATTCAATGTCCCTG<br>AAAAACAGCTGAATGATATTGAAGATTGTGACCTCAATGT<br>GGTGAGACTGTGTTTTCAAGTTTTTCTCCCTGATGAACAT<br>GGTAATTTGACGACTGCTCTTCCTCCTGTTGTCTCGAACC<br>CAATTTATGACAACCGTGCTCCAAATACTGCAGAATTAAG<br>GATTTGTCGTGTAAACAAGAATTGTGGAAGTGTCAGAGGA<br>GGAGATGAAATATTTCTACTTTGTGACAAAGTTCAGAAAG<br>ATGACATAGAAGTTCGTTTTGTGTTGAACGATTGGGAAGC<br>AAAAGGCATCTTTTCACAAGCTGATGTACACCGTCAAGTA<br>GCCATTGTTTTCAAAACTCCACCATATTGCAAAGCTATCA<br>CAGAACCCGTAACAGTAAAAATGCAGTTGCGGAGACCTTC<br>TGACCAGGAAGTTAGTGAATCTATGGATTTTAGATATCTG<br>CCAGATGAAAAAGATACTTACGGCAATAAAGCAAAGAAAC<br>AAAAGACAACTCTGCTTTTCCAGAAACTGTGCCAGGATCA<br>CGTAGAAACAGGGTTTCGCCATGTTGACCAGGATGGTCTT<br>GAACTCCTGACATCAGGTGATCCACCCACCTTGGCCTCCC<br>AAAGTGCTGGGATTACAGTTAATTTTCCTGAGAGACCAAG<br>ACCTGGTCTCCTCGGTTCAATTGGAGAAGGAAGATACTTC<br>AAAAAAGAACCAAACTTGTTTTCTCATGATGCAGTTGTGA<br>GAGAAATGCCTACAGGGGTTTCAAGTCAAGCAGAATCCTA<br>CTATCCCTCACCTGGGCCCATCTCAAGTGGATTGTCACAT<br>CATGCCTCAATGGCACCTCTGCCTTCTTCAAGCTGGTCAT<br>CAGTGGCCCACCCCACCCCACGCTCAGGCAATACAAACCC<br>ACTGAGTAGTTTTTCAACAAGGACACTTCCTTCTAATTCG<br>CAAGGTATCCCACCATTCCTGAGAATACCTGTTGGGAATG<br>ATTTAAATGCTTCTAATGCTTGCATTTACAACAATGCCGA<br>TGACATAGTCGGAATGGAAGCGTCATCCATGCCATCAGCA<br>GATTTATATGGTATTTCTGATCCCAACATGCTGTCTAATT<br>GTTCTGTGAATATGATGACAACCAGCAGTGACAGCATGGG<br>AGAGACTGATAATCCAAGACTTCTGAGCATGAATCTTGAA | 23 |

TABLE 3-continued

Polynucleotides of Non-Limiting Example Genes Associated with CNS Degradation

| Gene (Synonym) | Nucleic Acid Sequence | SEQ ID NO: |
|---|---|---|
| | AACCCCTCATGTAATTCAGTGTTAGACCCAAGAGACTTGA GACAGCTCCATCAGATGTCCTCTTCCAGTATGTCAGCAGG CGCCAATTCCAATACTACTGTTTTTGTTTCACAATCAGAT GCATTTGAGGGATCTGACTTCAGTTGTGCAGATAACAGCA TGATAAATGAGTCGGGACCATCAAACAGTACTAATCCAAA CAGTCATGGTTTTGTTCAAGATAGTCAGTATTCAGGTATT GGCAGTATGCAAAATGAGCAATTGAGTGACTCCTTTCCAT ATGAATTTTTTCAAGTATAA | |
| ATG7 | >NM_028835.4: 74-2170 *Mus musculus* autophagy related 7 (Atg7), transcript variant 3, mRNA ATGGGGGACCCTGGACTGGCCAAGTTGCAGTTCGCCCCCT TTAATAGTGCCCTGGACGTTGGCTTCTGGCACGAACTGAC CCAGAAGAAGTTGAACGAGTACCGCCTGGACGAGGCACCC AAAGACATCAAGGGCTATTACTACAATGGTGACTCTGCTG GTCTGCCCACCCGCTTGACGTTGGAGTTCAGTGCTTTTGA CATGAGTGCCTCCACGCCTGCCCACTGCTGCCCGGCCATG GGAACCCTGCACAACACCAACACACTTGAGGCTTTTAAGA CAGCAGACAAGAAGCTCCTTCTGGAGCAGTCAGCAAATGA GATCTGGGAAGCCATAAAGTCAGGTGCTGCTCTCGAAAAC CCCATGCTCCTCAACAAGTTTCTGCTCCTGACCTTCGCGG ACCTAAAGAAGTACCACTTCTACTACTGGTTTTGCTGCCC CGCCCTCTGTCTTCCTGAGAGCATCCCTCTAATCCGGGGA CCTGTGAGCTTGGATCAAAGGCTTTCACCAAAACAGATCC AGGCCCTGGAGCATGCCTATGATGATCTGTGTCGAGCCGA AGGCGTCACGGCCCTGCCCTACTTCTTATTCAAGTACGAT GACGACACTGTTCTGGTCTCCTTGCTCAAACACTACAGTG ATTTCTTCCAAGGTCAAAGGACAAAGATAACAGTTGGTGT GTACGATCCCTGTAACCTAGCCCAGTACCCTGGATGGCCT TTGAGGAATTTTTTGGTCCTGGCAGCCCACAGATGGAGCG GCAGTTTCCAGTCCGTTGAAGTCCTCTGCTTTCGGGACCG CACCATGCAGGGAGCTAGAGACGTGACACATAGCATCATC TTTGAAGTGAAACTTCCAGAAATGGCATTTAGCCCAGATT GTCCTAAAGCTGTTGGCTGGGAGAAGAACCAGAAAGGAGG CATGGGTCCGAGGATGGTGAACCTCAGTGGATGTATGGAC CCCAAAAGGCTGGCTGAGTCATCTGTGGATCTGAATCTCA AGCTGATGTGCTGGCGATTGGTCCCCACCTTGGACTTGGA CAAGGTCGTGTCTGTCAAGTGCCTGCTGCTGGGAGCTGGT ACCTTGGGGTGTAATGTGGCTAGGACACTGATGGGCTGGG GCGTCAGACATGTCACCTTTGTGGATAACGCCAAGATCTC CTACTCCAATCCCGTGAGGCAGCCTCTGTATGAATTTGAA GATTGTCTAGGGGGTGGCAAGCCCAAGGCCCTGGCTGCAG CAGAGCGGCTACAGAAAATATTTCCCGGAGTGAATGCCAG AGGGTTCAACATGAGCATCCCCATGCCAGGACACCCTGTG AACTTCTCTGACGTCACGATGGAGCAGGCCCGCAGAGATG TGGAGCAGCTGGAGCAGCTCATTGATAACCATGATGTCAT CTTCCTGCTAATGGACACCAGGGAGAGCCGGTGGCTTCCT ACTGTTATTGCAGCCAGCAAGCGAAAGCTGGTCATCAACG CTGCCTTGGGGTTTGATACCTTTGTTGTCATGAGACATGG CCTGAAGAAACCCAAGCAGCAGGGAGCCGGAGACCTCTGC CCAAGCCATCTTGTAGCACCTGCTGACCTGGGCTCCTCAC TTTTTGCCAACATCCCTGGATACAAGCTTGGCTGCTACTT CTGCAATGATGTGGTGGCTCCAGGAGATTCAACCAGAGAC CGGACTCTGGACCAGCAGTGCACAGTGAGCCGCCCAGGCC TGGCCGTGATTGCAGGTGCCCTGGCTGTGGAGCTGATGGT CTCTGTCCTGCAGCATCCTGAGGGGGGCTACGCCATCGCC AGCAGCAGTGATGACCGCATGAATGAGCCTCCCACCTCGC TGGGACTTGTGCCTCACCAGATCCGGGGTTTTCTGTCACG GTTCGATAATGTTCTTCCTGTCAGCCTGGCATTTGATAAA TGTACAGCCTGTTCACCCAAAGTTCTTGATCAGTACGAGC GAGAAGGATTCACCTTCCTAGCGAAGGTTTTTAACTCCTC ACATTCCTTCTTAGAAGACTTGACCGGTCTTACCCTGCTC CATCAAGAGACCCAAGCTGCTGAGATCTGGGACATGAGTG ACGAGGAGACTGTCTGA | 24 |
| VMAT2 | >NM_003054.4: 164-1708 *Homo sapiens* solute carrier family 18 member A2 (SLC18A2), mRNA ATGGCCCTGAGCGAGCTGGCGCTGGTCCGCTGGCTGCAGG AGAGCCGCCGCTCGCGGAAGCTCATCCTGTTCATCGTGTT CCTGGCGCTGCTGCTGGACAACATGCTGCTCACTGTCGTG GTCCCCATCATCCCAAGTTATCTGTACAGCATTAAGCATG AGAAGAATGCTACAGAAATCCAGACGGCCAGGCCAGTGCA | 25 |

TABLE 3-continued

Polynucleotides of Non-Limiting Example Genes Associated with CNS Degradation

| Gene (Synonym) | Nucleic Acid Sequence | SEQ ID NO: |
|---|---|---|
| | CACTGCCTCCATCTCAGACAGCTTCCAGAGCATCTTCTCC<br>TATTATGATAACTCGACTATGGTCACCGGGAATGCTACCA<br>GAGACCTGACACTTCATCAGACCGCCACACAGCACATGGT<br>GACCAACGCGTCCGCTGTTCCTTCCGACTGTCCCAGTGAA<br>GACAAAGACCTCCTGAATGAAAACGTGCAAGTTGGTCTGT<br>TGTTTGCCTCGAAAGCCACCGTCCAGCTCATCACCAACCC<br>TTTCATAGGACTACTGACCAACAGAATTGGCTATCCAATT<br>CCCATATTTGCGGGATTCTGCATCATGTTTGTCTCAACAA<br>TTATGTTTGCCTTCTCCAGCAGCTATGCCTTCCTGCTGAT<br>TGCCAGGTCGCTGCAGGGCATCGGCTCGTCCTGCTCCTCT<br>GTGGCTGGGATGGGCATGCTTGCCAGTGTCTACACAGATG<br>ATGAAGAGAGAGGCAACGTCATGGGAATCGCCTTGGGAGG<br>CCTGGCCATGGGGGTCTTAGTGGGCCCCCCCTTCGGGAGT<br>GTGCTCTATGAGTTTGTGGGGAAGACGGCTCCGTTCCTGG<br>TGCTGGCCGCCCTGGTACTCTTGGATGGAGCTATTCAGCT<br>CTTTGTGCTCCAGCCGTCCCGGGTGCAGCCAGAGAGTCAG<br>AAGGGGACACCCCTAACCACGCTGCTGAAGGACCCGTACA<br>TCCTCATTGCTGCAGGCTCCATCTGCTTTGCAAACATGGG<br>CATCGCCATGCTGGAGCCAGCCCTGCCCATCTGGATGATG<br>GAGACCATGTGTTCCCGAAAGTGGCAGCTGGGCGTTGCCT<br>TCTTGCCAGCTAGTATCTCTTATCTCATTGGAACCAATAT<br>TTTTGGGATACTTGCACACAAAATGGGGAGGTGGCTTTGT<br>GCTCTTCTGGGAATGATAATTGTTGGAGTCAGCATTTTAT<br>GTATTCCATTTGCAAAAAACATTTATGGACTCATAGCTCC<br>GAACTTTGGAGTTGGTTTTGCAATTGGAATGGTGGATTCG<br>TCAATGATGCCTATCATGGGCTACCTCGTAGACCTGCGGC<br>ACGTGTCCGTCTATGGGAGTGTGTACGCCATTGCGGATGT<br>GGCATTTTGTATGGGGTATGCTATAGGTCCTTCTGCTGGT<br>GGTGCTATTGCAAAGGCAATTGGATTTCCATGGCTCATGA<br>CAATTATTGGGATAATTGATATTCTTTTTGCCCCTCTCTG<br>CTTTTTTCTTCGAAGTCCACCTGCCAAAGAAGAAAAAATG<br>GCTATTCTCATGGATCACAACTGCCCTATTAAAACAAAAA<br>TGTACACTCAGAATAATATCCAGTCATATCCGATAGGTGA<br>AGATGAAGAATCTGAAAGTGACTGA | |
| GBA | >NM_000157.3 *Homo sapiens*<br>glucosylceramidase beta (GBA),<br>transcript variant 1, mRNA<br>ATCACATGACCCATCCACATCGGGAAGCCGGAATTACTTG<br>CAGGGCTAACCTAGTGCCTATAGCTAAGGCAGGTACCTGC<br>ATCCTTGTTTTTGTTTAGTGGATCCTCTATCCTTCAGAGA<br>CTCTGGAACCCCTGTGGTCTTCTCTTCATCTAATGACCCT<br>GAGGGGATGGAGTTTTCAAGTCCTTCCAGAGAGGAATGTC<br>CCAAGCCTTTGAGTAGGGTAAGCATCATGGCTGGCAGCCT<br>CACAGGATTGCTTCTACTTCAGGCAGTGTCGTGGGCATCA<br>GGTGCCCGCCCCTGCATCCCTAAAAGCTTCGGCTACAGCT<br>CGGTGGTGTGTGTCTGCAATGCCACATACTGTGACTCCTT<br>TGACCCCCCGACCTTTCCTGCCCTTGGTACCTTCAGCCGC<br>TATGAGAGTACACGCAGTGGGCGACGGATGGAGCTGAGTA<br>TGGGGCCCATCCAGGCTAATCACACGGGCACAGGCCTGCT<br>ACTGACCCTGCAGCCAGAACAGAAGTTCCAGAAAGTGAAG<br>GGATTTGGAGGGGCCATGACAGATGCTGCTGCTCTCAACA<br>TCCTTGCCCTGTCACCCCCTGCCCAAAATTTGCTACTTAA<br>ATCGTACTTCTCTGAAGAAGGAATCGGATATAACATCATC<br>CGGGTACCCATGGCCAGCTGTGACTTCTCCATCCGCACCT<br>ACACCTATGCAGACACCCCTGATGATTTCCAGTTGCACAA<br>CTTCAGCCTCCCAGAGGAAGATACCAAGCTCAAGATACCC<br>CTGATTCACCGAGCCCTGCAGTTGGCCCAGCGTCCCGTTT<br>CACTCCTTGCCAGCCCCTGGACATCACCCACTTGGCTCAA<br>GACCAATGGAGCGGTGAATGGGAAGGGGTCACTCAAGGGA<br>CAGCCCGGAGACATCTACCACCAGACCTGGGCCAGATACT<br>TTGTGAAGTTCCTGGATGCCTATGCTGAGCACAAGTTACA<br>GTTCTGGGCAGTGACAGCTGAAAATGAGCCTTCTGCTGGG<br>CTGTTGAGTGGATACCCCTTCCAGTGCCTGGGCTTCACCC<br>CTGAACATCAGCGAGACTTCATTGCCCGTGACCTAGGTCC<br>TACCCTCGCCAACAGTACTCACCACAATGTCCGCCTACTC<br>ATGCTGGATGACCAACGCTTGCTGCTGCCCCACTGGGCAA<br>AGGTGGTACTGACAGACCCAGAAGCAGCTAAATATGTTCA<br>TGGCATTGCTGTACATTGGTACCTGGACTTTCTGGCTCCA<br>GCCAAAGCCACCCTAGGGGAGACACACCGCCTGTTCCCCA<br>ACACCATGCTCTTTGCCTCAGAGGCCTGTGTGGGCTCCAA<br>GTTCTGGGAGCAGAGTGTGCGGCTAGGCTCCTGGGATCGA<br>GGGATGCAGTACAGCCACAGCATCATCACGAACCTCCTGT<br>ACCATGTGGTCGGCTGGACCGACTGGAACCTTGCCCTGAA | 26 |

TABLE 3-continued

| Polynucleotides of Non-Limiting Example Genes Associated with CNS Degradation | | |
|---|---|---|
| Gene (Synonym) | Nucleic Acid Sequence | SEQ ID NO: |
| | CCCCGAAGGAGGACCCAATTGGGTGCGTAACTTTGTCGAC<br>AGTCCCATCATTGTAGACATCACCAAGGACACGTTTTACA<br>AACAGCCCATGTTCTACCACCTTGGCCACTTCAGCAAGTT<br>CATTCCTGAGGGCTCCCAGAGAGTGGGGCTGGTTGCCAGT<br>CAGAAGAACGACCTGGACGCAGTGGCACTGATGCATCCCG<br>ATGGCTCTGCTGTTGTGGTCGTGCTAAACCGCTCCTCTAA<br>GGATGTGCCTCTTACCATCAAGGATCCTGCTGTGGGCTTC<br>CTGGAGACAATCTCACCTGGCTACTCCATTCACACCTACC<br>TGTGGCGTCGCCAGTGATGGAGCAGATACTCAAGGAGGCA<br>CTGGGCTCAGCCTGGGCATTAAAGGGACAGAGTCAGCTCA<br>CACGCTGTCTGTGACTAAAGAGGGCACAGCAGGGCCAGTG<br>TGAGCTTACAGCGACGTAAGCCCAGGGGCAATGGTTTGGG<br>TGACTCACTTTCCCCTCTAGGTGGTGCCAGGGGCTGGAGG<br>CCCCTAGAAAAAGATCAGTAAGCCCCAGTGTCCCCCCAGC<br>CCCCATGCTTATGTGAACATGCGCTGTGTGCTGCTTGCTT<br>TGGAAACTGGGCCTGGGTCCAGGCCTAGGGTGAGCTCACT<br>GTCCGTACAAACACAAGATCAGGGCTGAGGGTAAGGAAAA<br>GAAGAGACTAGGAAAGCTGGGCCCAAAACTGGAGACTGTT<br>TGTCTTTCCTGGAGATGCAGAACTGGGCCCGTGGAGCAGC<br>AGTGTCAGCATCAGGGCGGAAGCCTTAAAGCAGCAGCGGG<br>TGTGCCCAGGCACCCAGATGATTCCTATGGCACCAGCCAG<br>GAAAAATGGCAGCTCTTAAAGGAGAAAATGTTTGAGCCCA<br>GTCA | |

TABLE 4

| Polynucleotides for Isoforms of PARK2 | | |
|---|---|---|
| Gene (Iso-form) | Protein Sequence | SEQ ID NO: |
| PARK2 (1) | >NM_004562.2:135-1532 *Homo sapiens* parkin RBR E3 ubiquitin protein ligase (PRKN), transcript variant 1, mRNA<br>ATGATAGTGTTTGTCAGGTTCAACTCCAGCCATGGTTTCC<br>CAGTGGAGGTCGATTCTGACACCAGCATCTTCCAGCTCAA<br>GGAGGTGGTTGCTAAGCGACAGGGGGTTCCGGCTGACCAG<br>TTGCGTGTGATTTTCGCAGGGAAGGAGCTGAGGAATGACT<br>GGACTGTGCAGAATTGTGACCTGGATCAGCAGAGCATTGT<br>TCACATTGTGCAGAGACCGTGGAGAAAAGGTCAAGAAATG<br>AATGCAACTGGAGGCGACGACCCCAGAAACGCGGCGGGAG<br>GCTGTGAGCGGGAGCCCCAGAGCTTGACTCGGGTGGACCT<br>CAGCAGCTCAGTCCTCCCAGGAGACTCTGTGGGGCTGGCT<br>GTCATTCTGCACACTGACAGCAGGAAGGACTCACCACCAG<br>CTGGAAGTCCAGCAGGTAGATCAATCTACAACAGCTTTTA<br>TGTGTATTGCAAAGGCCCCTGTCAAAGAGTGCAGCCGGGA<br>AAACTCAGGGTACAGTGCAGCACCTGCAGGCAGGCAACGC<br>TCACCTTGACCCAGGGTCCATCTTGCTGGGATGATGTTTT<br>AATTCCAAACCGGATGAGTGGTGAATGCCAATCCCCACAC<br>TGCCCTGGGACTAGTGCAGAATTTTTCTTTAAATGTGGAG<br>CACACCCCACCTCTGACAAGGAAACATCAGTAGCTTTGCA<br>CCTGATCGCAACAAATAGTCGGAACATCACTTGCATTACG<br>TGCACAGACGTCAGGAGCCCCGTCCTGGTTTTCCAGTGCA<br>ACTCCCGCCACGTGATTTGCTTAGACTGTTTCCACTTATA<br>CTGTGTGACAAGACTCAATGATCGGCAGTTTGTTCACGAC<br>CCTCAACTTGGCTACTCCCTGCCTTGTGTGGCTGGCTGTC<br>CCAACTCCTTGATTAAAGAGCTCCATCACTTCAGGATTCT<br>GGGAGAAGAGCAGTACAACCGGTACCAGCAGTATGGTGCA<br>GAGGAGTGTGTCCTGCAGATGGGGGGCGTGTTATGCCCCC<br>GCCCTGGCTGTGGAGCGGGGCTGCTGCCGGAGCCTGACCA<br>GAGGAAAGTCACCTGCGAAGGGGGCAATGGCCTGGGCTGT<br>GGGTTTGCCTTCTGCCGGGAATGTAAAGAAGCGTACCATG<br>AAGGGGAGTGCAGTGCCGTATTTGAAGCCTCAGGAACAAC<br>TACTCAGGCCTACAGAGTCGATGAAAGAGCCGCCGAGCAG<br>GCTCGTTGGGAAGCAGCCTCCAAAGAAACCATCAAGAAAA<br>CCACCAAGCCCTGTCCCCGCTGCCATGTACCAGTGGAAAA<br>AAATGGAGGCTGCATGCACATGAAGTGTCCGCAGCCCCAG<br>TGCAGGCTCGAGTGGTGCTGGAACTGTGGCTGCGAGTGGA<br>ACCGCGTCTGCATGGGGGACCACTGGTTCGACGTGTAG | 27 |

TABLE 4-continued

| Polynucleotides for Isoforms of PARK2 | | |
|---|---|---|
| Gene (Iso-form) | Protein Sequence | SEQ ID NO: |
| PARK2 (2) | >NM_013987.2:135-1448 *Homo sapiens* parkin RBR E3 ubiquitin protein ligase (PRKN), transcript variant 2, mRNA<br>ATGATAGTGTTTGTCAGGTTCAACTCCAGCCATGGTTTCC<br>CAGTGGAGGTCGATTCTGACACCAGCATCTTCCAGCTCAA<br>GGAGGTGGTTGCTAAGCGACAGGGGGTTCCGGCTGACCAG<br>TTGCGTGTGATTTTCGCAGGGAAGGAGCTGAGGAATGACT<br>GGACTGTGCAGAATTGTGACCTGGATCAGCAGAGCATTGT<br>TCACATTGTGCAGAGACCGTGGAGAAAAGGTCAAGAAATG<br>AATGCAACTGGAGGCGACGACCCCAGAAACGCGGCGGGAG<br>GCTGTGAGCGGGAGCCCCAGAGCTTGACTCGGGTGGACCT<br>CAGCAGCTCAGTCCTCCCAGGAGACTCTGTGGGGCTGGCT<br>GTCATTCTGCACACTGACAGCAGGAAGGACTCACCACCAG<br>CTGGAAGTCCAGCAGGTAGATCAATCTACAACAGCTTTTA<br>TGTGTATTGCAAAGGCCCCTGTCAAAGAGTGCAGCCGGGA<br>AAACTCAGGGTACAGTGCAGCACCTGCAGGCAGGCAACGC<br>TCACCTTGACCCAGGAATTTTTCTTTAAATGTGGAGCACA<br>CCCCACCTCTGACAAGGAAACATCAGTAGCTTTGCACCTG<br>ATCGCAACAAATAGTCGGAACATCACTTGCATTACGTGCA<br>CAGACGTCAGGAGCCCCGTCCTGGTTTTCCAGTGCAACTC<br>CCGCCACGTGATTTGCTTAGACTGTTTCCACTTATACTGT<br>GTGACAAGACTCAATGATCGGCAGTTTGTTCACGACCCTC<br>AACTTGGCTACTCCCTGCCTTGTGTGGCTGGCTGTCCCAA<br>CTCCTTGATTAAAGAGCTCCATCACTTCAGGATTCTGGGA<br>GAAGAGCAGTACAACCGGTACCAGCAGTATGGTGCAGAGG<br>AGTGTGTCCTGCAGATGGGGGGCGTGTTATGCCCCCGCCC<br>TGGCTGTGGAGCGGGGCTGCTGCCGGAGCCTGACCAGAGG<br>AAAGTCACCTGCGAAGGGGGCAATGGCCTGGGCTGTGGGT<br>TTGCCTTCTGCCGGGAATGTAAAGAAGCGTACCATGAAGG<br>GGAGTGCAGTGCCGTATTTGAAGCCTCAGGAACAACTACT<br>CAGGCCTACAGAGTCGATGAAAGAGCCGCCGAGCAGGCTC<br>GTTGGGAAGCAGCCTCCAAAGAAACCATCAAGAAAACCAC<br>CAAGCCCTGTCCCCGCTGCCATGTACCAGTGGAAAAAAAT<br>GGAGGCTGCATGCACATGAAGTGTCCGCAGCCCCAGTGCA<br>GGCTCGAGTGGTGCTGGAACTGTGGCTGCGAGTGGAACCG<br>CGTCTGCATGGGGGACCACTGGTTCGACGTGTAG | 28 |

TABLE 4-continued

Polynucleotides for Isoforms of PARK2

| Gene (Isoform) | Protein Sequence | SEQ ID NO: |
|---|---|---|
| PARK2 (3) | >Ensembl ENST00000479615.5<br>ATGAATGCAACTGGAGGCGACGACCCCAGAAACGCGGCGG<br>GAGGCTGTGAGCGGGAGCCCCAGAGCTTGACTCGGGTGGA<br>CCTCAGCAGCTCAGTCCTCCCAGGAGACTCTGTGGGGCTG<br>GCTGTCATTCTGCACACTGACAGCAGGAAGGACTCACCAC<br>CAGCTGGAAGTCCAGCAGGTAGATCAATCTACAACAGCTT<br>TTATGTGTATTGCAAAGGCCCCTGTCAAAGAGTGCAGCCG<br>GGAAAACTCAGGGTACAGTGCAGCACCTGCAGGCAGGCAA<br>CGCTCACCITGACCCAGGGTCCATCTTGCTGGGATGATGT<br>TTTAATTCCAAACCGGATGAGTGGTGAATGCCAATCCCCA<br>CACTGCCCTGGGACTAGTGCAGAATTTTTCTTTAAATGTG<br>GAGCACACCCCACCTCTGACAAGGAAACATCAGTAGCITT<br>GCACCTGATCGCAACAAATAGTCGGAACATCACTTGCATT<br>ACGTGCACAGACGTCAGGAGCCCCGTCCTGGTTTTCCAGT<br>GCAACTCCCGCCACGTGATTTGCTTAGACTGTTTCCACTT<br>ATACTGTGTGACAAGACTCAATGATCGGCAGTTTGTTCAC<br>GACCCICAACTTGGCTACTCCCTGCCTTGIGTGGTTTGCC<br>TTCTGCCGGGAATGTAA | 29 |
| PARK2 (4) | >Ensembl ENST00000338468.7<br>ATGAGTGGTGAATGCCAATCCCCACACTGCCCTGGGACTA<br>GIGCAGAATTTTTCTTTAAATGTGGAGCACACCCCACCTC<br>TGACAAGGAAACATCAGTAGCTTTGCACCTGATCGCAACA<br>AATAGTCGGAACATCACTTGCATTACGTGCACAGACGTCA<br>GGAGCCCCGTCCTGGTTTTCCAGTGCAACTCCCGCCACGT<br>GATITGCTTAGACTGTTTCCACTTATACTGTGTGACAAGA<br>CTCAATGATCGGCAGTTTGTTCACGACCCTCAACTTGGCT<br>ACTCCCTGCCTTGTGTGGCTGGCTGTCCCAACTCCTTGAT<br>TAAAGAGCTCCATCACTTCAGGATTCIGGGAGAAGAGCAG<br>TACAACCGGIACCAGCAGTATGGTGCAGAGGAGTGTGICC<br>TGCAGATGGGGGGCGTGTTATGCCCCCGCCCTGGCTGTGG<br>AGCGGGGCTGCTGCCGGAGCCTGACCAGAGGAAAGTCACC<br>TGCGAAGGGGGCAATGGCCTGGGCTGTGGGTTTGCCTTCT<br>GCCGGGAATGTAAAGAAGCGTACCATGAAGGGGAGIGCAG<br>TGCCGTATTTGAAGCCTCAGGAACAACTACTCAGGCCTAC<br>AGAGTCGATGAAAGAGCCGCCGAGCAGGCTCGTTGGGAAG<br>CAGCCTCCAAAGAAACCATCAAGAAAACCACCAAGCCCTG<br>TCCCCGCTGCCATGTACCAGTGGAAAAAAATGGAGGCIGC<br>ATGCACATGAAGTGTCCGCAGCCCCAGTGCAGGCTCGAGT<br>GGTGCTGGAACTGTGGCTGCGAGTGGAACCGCGTCTGCAT<br>GGGGGACCACTGGTTCGACGTGTAG | 30 |
| PARK2 (5) | >ENA\|ALQ33698\|ALQ33698.1 *Homo sapiens* (human) partial parkinson protein 2 E3 ubiquitin protein ligase isoform 1<br>ATGATAGTGTTTGTCAGGTTCAACTCCAGCCATGGTTTCC<br>CAGTGGAGGTCGATTCTGACACCAGCATCTTCCAGCTCAA<br>GGAGGTGGTTGCTAAGCGACAGGGGGTTCCGGCTGACCAG<br>TTGCGTGTGATTTTCGCAGGGAAGGAGCTGAGGAATGACT<br>GGACTGTGCAGAATTGTGACCTGGATCAGCAGAGCATTGT<br>TCACATTGTGCAGAGACCGTGGAGAAAAGGTCAAGAAATG<br>AATGCAACTGGAGGCGACGACCCCAGAAACGCGGCGGGAG<br>GCTGTGAGCGGGAGCCCCAGAGCTTGACTCGGGTGGACCT<br>CAGCAGCTCAGTCCTCCCAGGAGACTCTGTGGGGCTGGCT<br>GTCATTCTGCACACTGACAGCAGGAAGGACTCACCACCAG<br>CTGGAAGTCCAGCAGGTAGATCAATCTACAACAGCTTTTA<br>TGTGTATTGCAAAGGCCCCTGTCAAAGAGTGCAGCCGGGA<br>AAACTCAGGGTACAGTGCAGCACCTGCAGGCAGGCAACGC<br>TCACCTTGACCCAGGGTCCATCTTGCTGGGATGATGTTTT<br>AATTCCAAACCGGATGAGTGGTGAATGCCAATCCCCACAC<br>TGCCCTGGGACTAGTGCAGAATTTTTCTTTAAATGTGGAG<br>CACACCCCACCTCTGACAAGGAAACATCAGTAGCTTTGCA<br>CCTGATCGCAACAAATAGTCGGAACATCACTTGCATTACG<br>TGCACAGACGTCAGGAGCCCCGTCCTGGTTTTCCAGTGCA<br>ACTCCCGCCACGTGATTTGCTTAGACTGTTTCCACTTATA<br>CTGTGTGACAAGACTCAATGATCGGCAGTTTGTTCACGAC<br>CCTCAACTTGGCTACTCCCTGCCTTGTGTGGGAACTGGAG<br>ACACAGTGGTGCTTAGAGGAGCTCTGGGGGGATTCAGGAG<br>AGGAGTCGCTGGCTGTCCCAACTCCTTGATTAAAGAGCTC<br>CATCACTTCAGGATTCTGGGAGAAGAGCAGTACAACCGGT<br>ACCAGCAGTATGGTGCAGAGGAGTGTGTCCTGCAGATGGG<br>GGGCGTGTTATGCCCCCGCCCTGGCTGTGGAGCGGGGCTG<br>CTGCCGGAGCCTGACCAGAGGAAAGTCACCTGCGAAGGGG<br>GCAATGGCCTGGGCTGTGGGTATGGACAACGAAGAACAAA | 31 |
| PARK2 (6) | >NM_013988.2:135-1085 *Homo sapiens* parkin RBR E3 ubiquitin protein ligase (PRKN), transcript variant 3, mRNA<br>ATGATAGTGTTTGTCAGGTTCAACTCCAGCCATGGTTTCC<br>CAGTGGAGGTCGATTCTGACACCAGCATCTTCCAGCTCAA<br>GGAGGTGGTTGCTAAGCGACAGGGGGTTCCGGCTGACCAG<br>TTGCGTGTGATTTTCGCAGGGAAGGAGCTGAGGAATGACT<br>GGACTGTGCAGGAATTTTTCTTTAAATGTGGAGCACACCC<br>CACCTCTGACAAGGAAACATCAGTAGCTTTGCACCTGATC<br>GCAACAAATAGTCGGAACATCACTTGCATTACGTGCACAG<br>ACGTCAGGAGCCCCGTCCTGGTTTTCCAGTGCAACTCCCG<br>CCACGTGATTTGCTTAGACTGTTTCCACTTATACTGTGTG<br>ACAAGACTCAATGATCGGCAGTTTGTTCACGACCCTCAAC<br>TTGGCTACTCCCTGCCTTGTGTGGCTGGCTGTCCCAACTC<br>CTTGATTAAAGAGCTCCATCACTTCAGGATTCTGGGAGAA<br>GAGCAGTACAACCGGTACCAGCAGTATGGTGCAGAGGAGT<br>GTGTCCTGCAGATGGGGGGCGTGTTATGCCCCCGCCCTGG<br>CTGTGGAGCGGGGCTGCTGCCGGAGCCTGACCAGAGGAAA<br>GTCACCTGCGAAGGGGGCAATGGCCTGGGCTGTGGGTTTG<br>CCTTCTGCCGGGAATGTAAAGAAGCGTACCATGAAGGGGA<br>GTGCAGTGCCGTATTTGAAGCCTCAGGAACAACTACTCAG<br>GCCTACAGAGTCGATGAAAGAGCCGCCGAGCAGGCTCGTT<br>GGGAAGCAGCCTCCAAAGAAACCATCAAGAAAACCACCAA<br>GCCCTGTCCCCGCTGCCATGTACCAGTGGAAAAAAATGGA<br>GGCTGCATGCACATGAAGTGTCCGCAGCCCCAGTGCAGGC<br>TCGAGTGGTGCTGGAACTGTGGCTGCGAGTGGAACCGCGT<br>CTGCATGGGGGACCACTGGTTCGACGTGTAG | 32 |
| PARK2 (7) | >ENA\|ADB91979\|ADB91979.1 *Homo sapiens* (human) parkin variant SV5, 9DEL<br>ATGATAGTGTTTGTCAGGTTCAACTCCAGCCATGGTTTCC<br>CAGTGGAGGTCGATTCTGACACCAGCATCTTCCAGCTCAA<br>GGAGGTGGTTGCTAAGCGACAGGGGGTTCCGGCTGACCAG<br>TTGCGTGTGATTTTCGCAGGGAAGGAGCTGAGGAATGACT<br>GGACTGTGCAGAATTGTGACCTGGATCAGCAGAGCATTGT<br>TCACATTGTGCAGAGACCGTGGAGAAAAGGTCAAGAAATG<br>AATGCAACTGGAGGCGACGACCCCAGAAACGCGGCGGGAG<br>GCTGTGAGCGGGAGCCCCAGAGCTTGACTCGGGTGGACCT<br>CAGCAGCTCAGTCCTCCCAGGAGACTCTGTGGGGCTGGCT<br>GTCATTCTGCACACTGACAGCAGGAAGGACTCACCACCAG<br>CTGGAAGTCCAGCAGGTAGATCAATCTACAACAGCTTTTA<br>TGTGTATTGCAAAGGCCCCTGTCAAAGAGTGCAGCCGGGA<br>AAACTCAGGGTACAGTGCAGCACCTGCAGGCAGGCAACGC<br>TCACCTTGACCCAGGAATTTTTCTTTAAATGTGGAGCACA<br>CCCCACCTCTGACAAGGAAACATCAGTAGCTTTGCACCTG<br>ATCGCAACAAATAGTCGGAACATCACTTGCATTACGTGCA<br>CAGACGTCAGGAGCCCCGTCCTGGTTTTCCAGTGCAACTC<br>CCGCCACGTGATTTGCTTAGACTGTTTCCACTTATACTGT<br>GTGACAAGACTCAATGATCGGCAGTTTGTTCACGACCCTC<br>AACTTGGCTACTCCCTGCCTTGTGTGGCTGGCTGTCCCAA<br>CTCCTTGATTAAAGAGCTCCATCACTTCAGGATTCTGGGA<br>GAAGAGCAGTTTGCCTTCTGCCGGGAATGTAAAGAAGCGT<br>ACCATGAAGGGGAGTGCAGTGCCGTATTTGAAGCCTCAGG<br>AACAACTACTCAGGCCTACAGAGTCGATGAAAGAGCCGCC<br>GAGCAGGCTCGTTGGGAAGCAGCCTCCAAAGAAACCATCA<br>AGAAAACCACCAAGCCCTGTCCCCGCTGCCATGTACCAGT<br>GGAAAAAAATGGAGGCTGCATGCACATGAAGTGTCCGCAG<br>CCCCAGTGCAGGCTCGAGTGGTGCTGGAACTGTGGCTGCG<br>AGTGGAACCGCGTCTGCATGGGGGACCACTGGTTCGACGT<br>GTAG | 33 |
| PARK2 (8) | >ENA\|ADB90271\|ADB90271.1 *Homo sapiens* (human) parkin variant SV9DEL<br>ATGATAGTGTTTGTCAGGTTCAACTCCAGCCATGGTTTCC<br>CAGTGGAGGTCGATTCTGACACCAGCATCTTCCAGCTCAA<br>GGAGGTGGTTGCTAAGCGACAGGGGGTTCCGGCTGACCAG<br>TTGCGTGTGATTTTCGCAGGGAAGGAGCTGAGGAATGACT<br>GGACTGTGCAGAATTGTGACCTGGATCAGCAGAGCATTGT<br>TCACATTGTGCAGAGACCGTGGAGAAAAGGTCAAGAAATG<br>AATGCAACTGGAGGCGACGACCCCAGAAACGCGGCGGGAG | 34 |

TABLE 4-continued

| Polynucleotides for Isoforms of PARK2 | | |
|---|---|---|
| Gene (Iso-form) | Protein Sequence | SEQ ID NO: |
| | GCTGTGAGCGGGAGCCCCAGAGCTTGACTCGGGTGGACCT CAGCAGCTCAGTCCTCCCAGGAGACTCTGTGGGGCTGGCT GTCATTCTGCACACTGACAGCAGGAAGGACTCACCACCAG CTGGAAGTCCAGCAGGTAGATCAATCTACAACAGCTTTTA TGTGTATTGCAAAGGCCCCTGTCAAAGAGTGCAGCCGGGA AAACTCAGGGTACAGTGCAGCACCTGCAGGCAGGCAACGC TCACCTTGACCCAGGGTCCATCTTGCTGGGATGATGTTTT AATTCCAAACCGGATGAGTGGTGAATGCCAATCCCCACAC TGCCCTGGGACTAGTGCAGAATTTTTCTTTAAATGTGGAG CACACCCCACCTCTGACAAGGAAACATCAGTAGCTTTGCA CCTGATCGCAACAAATAGTCGGAACATCACTTGCATTACG TGCACAGACGTCAGGAGCCCCGTCCTGGTTTTCCAGTGCA ACTCCCGCCACGTGATTTGCTTAGACTGTTTCCACTTATA CTGTGTGACAAGACTCAATGATCGGCAGTTTGTTCACGAC CCTCAACTTGGCTACTCCCTGCCTTGTGTGGCTGGCTGTC CCAACTCCTTGATTAAAGAGCTCCATCACTTCAGGATTCT GGGAGAAGAGCAGTTTGCCTTCTGCCGGGAATGTAAAGAA GCGTACCATGAAGGGGAGTGCAGTGCCGTATTTGAAGCCT CAGGAACAACTACTCAGGCCTACAGAGTCGATGAAAGAGC CGCCGAGCAGGCTCGTTGGGAAGCAGCCTCCAAAGAAACC ATCAAGAAAACCACCAAGCCCTGTCCCCGCTGCCATGTAC CAGTGGAAAAAAATGGAGGCTGCATGCACATGAAGTGTCC GCAGCCCCAGTGCAGGCTCGAGTGGTGCTGGAACTGTGGC TGCGAGTGGAACCGCGTCTGCATGGGGGACCACTGGTTCG ACGTGTAG | |

In particular embodiments, the compositions and methods disclosed herein contemplate the use of functional variants and functional fragments of any of these protein or polynucleotide sequences. Functional fragments and variants retain the biological properties or activities of the corresponding wild-type protein, although the properties or activities may in certain instances be reduced, e.g., to about 50%, about 60%, about 70%, or about 80% as compared to the wild-type protein, or increased, e.g., 1.1-fold, 1.2-fold, 1.3-fold, 1.4-fold, 1.5-fold, 2-fold, 3-fold, 4-fold, or 5-fold as compared to the wild-type protein. In certain embodiments, a functional fragment or variant of a protein has at least 70%, at least 80%, at least 90%, at least 95%, at least 98%, or at least 99% sequence identity to the corresponding wild-type protein. In certain embodiments, a functional fragment of a protein comprises at least 20%, at least 30%, at least 40%, at least 50%, at least 60%, at least 70%, at least 80%, at least 90%, at least 95%, at least 98%, or at least 99% of the corresponding wild-type protein.

In another aspect, the disclosure provides recombinant gene therapy vector, comprising a transgene polynucleotide encoding E3 ubiquitin protein ligase (PARK2), wherein the transgene polynucleotide is operably linked to a eukaryotically active promoter sequence. In some embodiments, the transgene polynucleotide shares at least 95% identity to one of SEQ ID NOs: 35-38.

In some embodiments, the disclosure provides a codon-optimized polynucleotide encoding PARK2. In some cases, the entire transgene sequence is codon optimized for expression in a mammalian cell. Codon optimization refers to the discovery that the frequency of occurrence of synonymous codons (i.e., codons that code for the same amino acid) in coding DNA is biased in different species. Such codon degeneracy allows an identical polypeptide to be encoded by a variety of nucleotide sequences. A variety of codon optimization methods is known in the art, and include, e.g., methods disclosed in at least U.S. Pat. Nos. 5,786,464 and 6,114,148.

In some embodiments, the codon-optimized polynucleotide encoding PARK2 comprises fewer CpG islands than the native human polynucleotide sequence encoding human PARK2. For example, in some embodiments, the native human sequence comprises 95 CpG islands, whereas the codon-optimized polynucleotides comprise less than 95, less than 90, less than 85, less than 80, less than 75, less than 70, less than 65, less than 60, less than 55, less than 50, less than 45, less than 40, less than 35, less than 30, less than 25, less than 20, less than 15, less than 10, less than 5, or no CpG islands. In some embodiments, the codon-optimized polynucleotide sequence comprises 2-20, 5-20, about 5, or about 10 CpG islands. In some embodiments, the codon-optimized polynucleotide sequence comprises one or more CpG island. In some embodiments, the expression cassette shares at least 80%, at least 85%, at least 90%, at least 91%, at least 92%, at least 93%, at least 94%, at least 95%, at least 96%, at least 97%, at least 98%, at least 99%, or 100% sequence identity to any one of SEQ ID NOs: 39-58. In some embodiments, the expression cassette comprises, consists essentially of, or consists of a sequence having at least 80%, at least 85%, at least 90%, at least 91%, at least 92%, at least 93%, at least 94%, at least 95%, at least 96%, at least 97%, at least 98%, at least 99%, or 100% sequence identity to any one of SEQ ID NOs: 39-58.

In some embodiments, the vector is an adeno-associated virus (AAV) vector. In some embodiments, the vector comprises two AAV inverted terminal repeats (ITRs) flanking the expression cassette. In some embodiments, the AAV has serotype AAV1, AAV2, AAV5, AAV8, AAV9, AAVrh10, or AAVrh74. In some embodiments, the recombinant gene therapy vector comprises a self-complementary AAV. In some embodiments, the recombinant gene therapy vector comprises a single-stranded AAV. In some embodiments, the AAV is a wild-type AAV or a modified AAV. In some embodiments, the AAV comprises a capsid protein having at least 80%, 85%, 90%, 91%, 92%, 93%, 94%, 95%, 96%, 97%, 98%, 99%, or 100% sequence identity to wild-type VP1, VP2, or VP3 capsid protein.

In another aspect, the disclosure provides host cell comprising any of the foregoing recombinant gene therapy vectors. Exemplary host cells include HEK293, 293T, HeLa, Vero, and Sf9 cells.

In another aspect, the disclosure provides a method of inhibiting, reducing, or delaying degeneration or death of a dopaminergic neuron comprising a mutation in a gene associated with a Parkinson's Disease (PD), wherein the mutated gene is a Parkinson protein 2, E3 ubiquitin protein ligase (PARK2) gene, comprising contacting the neuron with the recombinant gene therapy vector of the disclosure, wherein following contact with the recombinant gene therapy vector, the neuron expresses the wild-type protein. The method may be practiced in vitro, or in vivo, e.g., in a subject in need thereof.

In some embodiments, the neuron expresses a reduced amount of alpha-synuclein and/or comprises a reduced amount of Lewy bodies following contact with the recombinant gene therapy vector. In some embodiments, alpha-synuclein and/or comprises a reduced amount of Lewy bodies are reduced by at least 5%, at least 10%, at least 15%, at least 20%, at least 25%, at least 30%, at least 35%, at least 40% or more.

In some embodiments, the neuron expresses a reduced amount of monoamine oxidases following contact with the recombinant gene therapy vector. In some embodiments, the amount of monoamine oxidases is reduced by at least 5%, at least 10%, at least 15%, at least 20%, at least 25%, at least 30%, at least 35%, at least 40% or more.

In some embodiments, the neuron produces and/or releases an increased amount of dopamine following contact with the recombinant gene therapy vector. In some embodiments, the amount of dopamine produced and/or released is increased at least 5%, at least 10%, at least 15%, at least 20%, at least 25%, at least 30%, at least 35%, at least 40% or more.

In some embodiments, the neuron undergoes increased mitophagy following contact with the recombinant gene therapy vector. In some embodiments, mitophagy is increased at least 5%, at least 10%, at least 15%, at least 20%, at least 25%, at least 30%, at least 35%, at least 40% or more.

In some embodiments, the neuron expresses a lower amount of monoamine oxidases as compared to an amount of monoamine oxidases expressed in a neuron not contacted with said recombinant gene therapy vector, optionally wherein said lower amount is at least 5%, at least 10%, at least 20%, at least 30%, at least 40%, at least 50%, at least 60%, at least 70%, or at least 80% lower than the amount expressed in the neuron not contacted with said recombinant gene therapy vector.

In some embodiments, the neuron produces and/or releases an increased amount of dopamine as compared to an amount of dopamine produced and/or released by a neuron not contacted with said recombinant gene therapy vector, optionally wherein said increase amount is at least 5%, at least 10%, at least 20%, at least 30%, at least 40%, at least 50%, at least 60%, at least 70%, at least 80%, at least 90%, at least two-fold, at least three-fold, at least four-fold, at least five-fold, or at least 10-fold greater than the amount produced and/or released by the neuron not contacted with said recombinant gene therapy vector.

In some embodiments, the neuron undergoes an increased amount of autophagy as compared to an amount of autophagy undergone by a neuron not contacted with said recombinant gene therapy vector, optionally wherein the increased amount is at least 5%, at least 10%, at least 20%, at least 30%, at least 40%, at least 50%, at least 60%, at least 70%, at least 80%, at least 90%, at least two-fold, at least three-fold, at least four-fold, at least five-fold, or at least 10-fold greater than the amount undergone by the neuron not contacted with said recombinant gene therapy vector.

In some embodiments, the neuron is a primary tyrosine hydroxylase positive neuron. In some embodiments, the neuron was produced from an induced pluripotent stem cell prepared from cells obtained from a subject diagnosed with Parkinson's disease.

In another aspect, the disclosure provides a method of treating or inhibiting or delaying onset or progression of a Parkinson's Disease (PD) in a subject suffering from or at risk of the PD, comprising administering a gene therapy vector of the disclosure to the subject, wherein administration of the recombinant gene therapy vector treats or inhibits or delays onset or progression of the Parkinson's Disease in the subject.

In some embodiments, the PD is an early-onset PD. In some embodiments, the PD is an early-onset autosomal recessive PD. In some embodiments, the subject comprises a mutation in a PARK2 gene.

In some embodiments, the gene therapy vector comprises an expression cassette comprising a transgene that encodes for PARK2 or a functional fragment or variant thereof. In some embodiments, the PARK2 comprises the amino acid sequence set forth in SEQ ID NO: 1 or an amino acid sequence at least about 90%, 91%, 92%, 93%, 94%, 95%, 96%, 97%, 98%, 99%, 100% identical thereto. In some embodiments, the transgene polynucleotide shares at least 95% identity to one of SEQ ID NOs: 35-38.

In some embodiments, administering step comprises systemic, parenteral, intravenous, cerebral, cerebrospinal, intrathecal, intracisternal, intraputaminal, intrahippocampal, intra-striatal, or intra-cerebroventricular administration.

In some embodiments, the administering step comprises intravenous, cerebral, cerebrospinal, intrathecal, intracisternal, intraputaminal, intrahippocampal, intra-striatal, or intra-cerebroventricular injection.

In some embodiments, the administering step comprises intrathecal injection with Trendelenburg tilting.

In some embodiments, the administering step comprises direct injection into the pars compacta of the substantia nigra of the brain.

In some embodiments, the administering step comprises introducing the recombinant gene therapy vector into the subject's brain or cerebrospinal fluid (CSF).

In some embodiments, $1\times10^9$-$1\times10^{14}$ vector genomes per kilogram body mass of the subject (vg/kg) of the gene therapy vector are administered to the subject.

In some embodiments, $1\times10^9$-$1\times10^{14}$ vector genomes per kilogram body mass of the subject (vg/kg) of the gene therapy vector are administered to the subject's brain.

In some embodiments, $1\times10^9$-$1\times10^{14}$ vector genomes per kilogram body mass of the subject (vg/kg) of the gene therapy vector are administered to the subject's CSF.

In some embodiments, $1\times10^7$-$1\times10^9$ vector genomes per kilogram body mass of the subject (vg/kg) of the gene therapy vector are administered to the subject.

In some embodiments, the subject is an adult or a child.

In some embodiments, the number of dopaminergic neurons in the subject after the administering step is greater than the number of dopaminergic neurons in the subject before the administering step.

In some embodiments, the level of dopamine in the subject after the administering step is greater than the level of dopamine in the subject before the administering step.

In some embodiments, the number of dopaminergic neurons in a subject treated by the method is increased compared to the number of dopaminergic neurons in a subject not so treated.

In some embodiments, the level of dopamine of a subject treated by the method is increased compared to the level of dopamine in a subject not so treated.

In some embodiments, the level of dopamine in the substantia nigra of a subject treated by method is increased compared to the level of dopamine in the substantia nigra of a subject not so treated.

In some embodiments, the level of PRKN in the subject's CSF after the administering step is greater than the level of PRKN in the subject's CSF before the administering step.

In some embodiments, the Unified Parkinson's Disease Rating Scale (UPDRS) score of the subject before the administering step is improved compared to the UPDRS score of the subject before the administering step.

In some embodiments, the level of PRKN in the CSF of a subject treated by the method is increased compared to the level of PRKN in the CSF of a subject not so treated.

In some embodiments, the UPDRS score of a subject treated by the method is improved compared to the UPDRS score of a subject not so treated.

In some embodiments, the subject's neurons express a reduced amount of alpha-synuclein and/or comprises a reduced amount of Lewy bodies following contact with the recombinant gene therapy vector.

Definitions

Unless otherwise defined, all technical and scientific terms used herein have the same meaning as commonly understood by one of ordinary skill in the art to which this invention pertains. Although methods and materials similar or equivalent to those described herein can be used in the practice of the present invention, suitable methods and materials are described below. All publications, patent applications, patents, and other references mentioned herein are expressly incorporated by reference in their entirety. In cases of conflict, the present specification, including definitions, will control. In addition, the materials, methods, and examples described herein are illustrative only and are not intended to be limiting.

All publications and patents mentioned herein are hereby incorporated by reference in their entirety as if each individual publication or patent was specifically and individually indicated to be incorporated by reference. In case of conflict, the present application, including any definitions herein, will control. However, mention of any reference, article, publication, patent, patent publication, and patent application cited herein is not, and should not be taken as an acknowledgment, or any form of suggestion, that they constitute valid prior art or form part of the common general knowledge in any country in the world.

In the present description, any concentration range, percentage range, ratio range, or integer range is to be understood to include the value of any integer within the recited range and, when appropriate, fractions thereof (such as one tenth and one hundredth of an integer), unless otherwise indicated. The term "about", when immediately preceding a number or numeral, means that the number or numeral ranges plus or minus 10%. It should be understood that the terms "a" and "an" as used herein refer to "one or more" of the enumerated components unless otherwise indicated. The use of the alternative (e.g., "or") should be understood to mean either one, both, or any combination thereof of the alternatives. The term "and/or" should be understood to mean either one, or both of the alternatives. As used herein, the terms "include" and "comprise" are used synonymously.

The abbreviations PRKN and PARK2 are used interchangeably herein.

The section headings used herein are for organizational purposes only and are not to be construed as limiting the subject matter described.

Adeno-Associated Virus (AAV)

As used herein, the term "AAV" is a standard abbreviation for adeno-associated virus or a recombinant vector thereof. Adeno-associated virus is a single-stranded DNA parvovirus that grows only in cells in which certain functions are provided by a co-infecting helper virus. General information and reviews of AAV can be found in, for example, Carter, 1989, Handbook of Parvoviruses, Vol. 1, pp. 169-228, and Berns, 1990, Virology, pp. 1743-1764, Raven Press, (New York). It is fully expected that the same principles described in these reviews will be applicable to additional AAV serotypes characterized after the publication dates of the reviews because it is well known that the various serotypes are quite closely related, both structurally and functionally, even at the genetic level. (See, for example, Blacklowe, 1988, pp. 165-174 of Parvoviruses and Human Disease, J. R. Pattison, ed.; and Rose, Comprehensive Virology 3:1-61 (1974)). For example, all AAV serotypes apparently exhibit very similar replication properties mediated by homologous rep genes; and all bear three related capsid proteins such as those expressed in AAV2. The degree of relatedness is further suggested by heteroduplex analysis which reveals extensive cross-hybridization between serotypes along the length of the genome; and the presence of analogous self-annealing segments at the termini that correspond to "inverted terminal repeat sequences" (ITRs). The similar infectivity patterns also suggest that the replication functions in each serotype are under similar regulatory control.

As used herein, an "AAV vector" or "rAAV vector" refers to a recombinant vector comprising one or more polynucleotides of interest (or transgenes) that are flanked by AAV terminal repeat sequences (ITRs). Such AAV vectors can be replicated and packaged into infectious viral particles when present in a host cell that has been transfected with a plasmid encoding and expressing rep and cap gene products. Alternatively, AAV vectors can be packaged into infectious particles using a host cell that has been stably engineered to express rep and cap genes.

As used herein, an "AAV virion" or "AAV viral particle" or "AAV vector particle" refers to a viral particle composed of at least one AAV capsid protein and an encapsidated polynucleotide AAV vector. As used herein, if the particle comprises a heterologous polynucleotide (i.e. a polynucleotide other than a wild-type AAV genome such as a transgene to be delivered to a mammalian cell), it is typically referred to as an "AAV vector particle" or simply an "AAV vector." Thus, production of AAV vector particle necessarily includes production of AAV vector, as such a vector is contained within an AAV vector particle.

Adeno-associated virus (AAV) is a replication-deficient parvovirus, the single-stranded DNA genome of which is about 4.7 kb in length including two 145-nucleotide inverted terminal repeat (ITRs). There are multiple known variants of AAV, also sometimes called serotypes when classified by antigenic epitopes. The nucleotide sequences of the genomes of the AAV serotypes are known. For example, the complete genome of AAV-1 is provided in GenBank Accession No. NC_002077; the complete genome of AAV-2 is provided in GenBank Accession No. NC_001401 and Srivastava et al., J. Virol., 45:555-564 {1983); the complete genome of AAV-3 is provided in GenBank Accession No. NC_1829; the complete genome of AAV-4 is provided in GenBank Accession No. NC_001829; the AAV-5 genome is provided in GenBank Accession No. AF085716; the complete genome of AAV-6 is provided in GenBank Accession No. NC_00 1862; at least portions of AAV-7 and AAV-8 genomes are provided in GenBank Accession Nos. AX753246 and AX753249, respectively; the AAV-9 genome is provided in Gao et al., J. Virol., 78:6381-6388 (2004); the AAV-10 genome is provided in Mol. Ther., 13 (1): 67-76 (2006); and the AAV-11 genome is provided in Virology, 330 (2): 375-383 (2004). The sequence of the AAVrh.74 genome is provided in U.S. Pat. No. 9,434,928, incorporated herein by reference. Cis-acting sequences directing viral DNA replication (rep), encapsidation/packaging and host cell chromosome integration are contained within the AAV ITRs. Three AAV promoters (named p5, p19, and p40 for their relative map locations) drive the expression of the two AAV internal open reading frames encoding rep and cap genes. The two rep promoters (p5 and p19), coupled with the differential splicing of the single AAV intron (at nucleotides 2107 and 2227), result in the production of four rep proteins (rep78, rep68, rep52, and rep40) from the rep gene. Rep proteins possess multiple enzymatic properties that are ultimately responsible for replicating the viral genome. The cap gene is expressed from the p40 promoter and it encodes the three capsid proteins VP1, VP2, and VP3. Alternative splicing and non-consensus translational start sites are responsible for the production of the three related capsid proteins. A single consensus polyadenylation site is located at map position 95 of the AAV genome. The life cycle and genetics of AAV are reviewed in Muzyczka, Current Topics in Microbiology and Immunology, 158:97-129 (1992).

AAV possesses unique features that make it attractive as a vector for delivering foreign DNA to cells, for example, in gene therapy. AAV infection of cells in culture is noncytopathic, and natural infection of humans and other animals is silent and asymptomatic. Moreover, AAV infects many mammalian cells allowing the possibility of targeting many different tissues in vivo. Moreover, AAV transduces slowly dividing and non-dividing cells, and can persist essentially for the lifetime of those cells as a transcriptionally active nuclear episome (extrachromosomal element). The AAV proviral genome is inserted as cloned DNA in plasmids, which makes construction of recombinant genomes feasible. Furthermore, because the signals directing AAV replication and genome encapsidation are contained within the ITRs of the AAV genome, some or all of the internal approximately 4.3 kb of the genome (encoding replication and structural capsid proteins, rep-cap) may be replaced with foreign DNA. To generate AAV vectors, the rep and cap proteins may be provided in trans. Another significant feature of AAV is that it is an extremely stable and hearty virus. It easily withstands the conditions used to inactivate adenovirus (56° to 65° C. for several hours), making cold preservation of AAV less critical. AAV may even be lyophilized. Finally, AAV-infected cells are not resistant to superinfection.

AAV DNA in the rAAV genomes may be from any AAV variant or serotype for which a recombinant virus can be derived including, but not limited to, AAV variants or serotypes AAV-1, AAV-2, AAV-3, AAV-4, AAV-5, AAV-6, AAV-7, AAV-8, AAV-9, AAV-10, AAV-11, AAV-12, AAV-13 and AAVrh10. Production of pseudotyped rAAV is disclosed in, for example, WO 01/83692. Other types of rAAV variants, for example rAAV with capsid mutations, are also contemplated. See, for example, Marsic et al., Molecular Therapy, 22 (11): 1900-1909 (2014). The nucleotide sequences of the genomes of various AAV serotypes are known in the art. To promote eye-specific expression, AAV6, AAV8 or AAV9 may be used.

In some cases, the rAAV comprises a self-complementary genome. As defined herein, an rAAV comprising a "self-complementary" or "double stranded" genome refers to an rAAV which has been engineered such that the coding region of the rAAV is configured to form an intra-molecular double-stranded DNA template, as described in McCarty et al. Self-complementary recombinant adeno-associated virus (scAAV) vectors promote efficient transduction independently of DNA synthesis. Gene Therapy. 8 (16): 1248-54 (2001). The present disclosure contemplates the use, in some cases, of an rAAV comprising a self-complementary genome because upon infection (such transduction), rather than waiting for cell mediated synthesis of the second strand of the rAAV genome, the two complementary halves of scAAV will associate to form one double stranded DNA (dsDNA) unit that is ready for immediate replication and transcription. It will be understood that instead of the full coding capacity found in rAAV (4.7-6 kb), rAAV comprising a self-complementary genome can only hold about half of that amount (~2.4 kb).

In other cases, the rAAV vector comprises a single stranded genome. As defined herein, a "single standard" genome refers to a genome that is not self-complementary. In most cases, non-recombinant AAVs are have singled stranded DNA genomes. There have been some indications that rAAVs should be scAAVs to achieve efficient transduction of cells, such as ocular cells. The present disclosure contemplates, however, rAAV vectors that maybe have singled stranded genomes, rather than self-complementary genomes, with the understanding that other genetic modifications of the rAAV vector may be beneficial to obtain optimal gene transcription in target cells. In some cases, the present disclosure relates to single-stranded rAAV vectors capable of achieving efficient gene transfer to anterior segment in the mouse eye. See Wang et al. Single stranded adeno-associated virus achieves efficient gene transfer to anterior segment in the mouse eye. PLoS ONE 12(8): e0182473 (2017).

In some cases, the rAAV vector is of the serotype AAV1, AAV2, AAV4, AAV5, AAV6, AAV7, AAV8, AAV9, AAV10, AAV11, AAV12, AAV13, or AAVrh10. Production of pseudotyped rAAV is disclosed in, for example, WO 01/83692. Other types of rAAV variants, for example rAAV with capsid mutations, are also contemplated. See, for example, Marsic et al., Molecular Therapy, 22 (11): 1900-1909 (2014). In some cases, the rAAV vector is of the serotype AAV9. In some embodiments, said rAAV vector is of serotype AAV9 and comprises a single stranded genome. In some embodiments, said rAAV vector is of serotype AAV9 and comprises a self-complementary genome. In some embodiments, a rAAV vector comprises the inverted terminal repeat (ITR) sequences of AAV2. In some embodiments, the rAAV vector comprises an AAV2 genome, such that the rAAV vector is an AAV-2/9 vector, an AAV-2/6 vector, or an AAV-2/8 vector.

Full-length sequences and sequences for capsid genes for most known AAVs are provided in U.S. Pat. No. 8,524,446, which is incorporated herein in its entirety.

AAV vectors may comprise wild-type AAV sequence or they may comprise one or more modifications to a wild-type AAV sequence. In certain embodiments, an AAV vector comprises one or more amino acid modifications, e.g., substitutions, deletions, or insertions, within a capsid protein, e.g., VP1, VP2 and/or VP3. In particular embodiments, the modification provides for reduced immunogenicity when the AAV vector is provided to a subject.

Promoters

In some embodiments, the polynucleotide sequence encoding wild-type PARK2, PINK1, LRRK2, SCNA, c-Rel, ATG7, VMAT2, or GBA protein, or functional variant or fragment thereof is operably linked to a CMV promoter. The present disclosure further contemplates the use of other promoter sequences. Promoters useful in embodiments of the present disclosure include, without limitation, a cytomegalovirus (CMV) promoterphosphoglycerate kinase (PGK) promoter, or a promoter sequence comprised of the CMV enhancer and portions of the chicken beta-actin promoter and the rabbit beta-globin gene (CAG). In some cases, the promoter may be a synthetic promoter. Exemplary synthetic promoters are provided by Schlabach et al. Synthetic design of strong promoters. Proc Natl Acad Sci USA. 2010 Feb. 9; 107(6): 2538-2543.

In some cases, a polynucleotide sequence encoding a therapeutic protein or a wild-type PARK2, PINK1, LRRK2, SCNA, c-Rel, ATG7, VMAT2, or GBA protein, or functional variant or fragment thereof, is operatively linked to an inducible promoter. A polynucleotide sequence operatively linked to an inducible promoter may be configured to cause the polynucleotide sequence to be transcriptionally expressed or not transcriptionally expressed in response to addition or accumulation of an agent or in response to removal, degradation, or dilution of an agent. The agent may be a drug. The agent may be tetracycline or one of its derivatives, including, without limitation, doxycycline. In some cases, the inducible promoter is a tet-on promoter, a tet-off promoter, a chemically-regulated promoter, a physically-regulated promoter (i.e. a promoter that responds to presence or absence of light or to low or high temperature). This list of inducible promoters is non-limiting.

As used herein, "eukaryotically active promoter" or "promoter" are used interchangeably and refer to promoter capable of promoting initiation of RNA transcription from a polynucleotide in a eukaryotic cell. In some cases, the promoter is a tissue-specific promoter, such as a promoter capable of driving expression in a neuron to a greater extent than in a non-neuronal cell. In some embodiments, tissue-specific promoter is a selected from a list of neuron-specific promoters consisting of: hSYN1 (human synapsin), INA (alpha-internexin), NES (nestin), TH (tyrosine hydroxylase), FOXA2 (Forkhead box A2), CaMKII (calmodulin-dependent protein kinase II), and NSE (neuron-specific enolase). In some cases, the promoter is a ubiquitous promoter. A "ubiquitous promoter" refers to a promoter that is not tissue-specific under experimental or clinical conditions. In some cases, the ubiquitous promoter is selected from the group consisting of: CMV, CAG, UBC, PGK, EF1-alpha, GAPDH, SV40, HBV, chicken beta-actin, and human beta-actin.

In some embodiments, the promoter sequence is selected from Table 5, and sequences having at least 95%, at least 98%, or least 99% identity thereto.

TABLE 5

| PROMOTER | SEQUENCE | SEQ ID NO: |
|---|---|---|
| Human beta-actin (HuBa) | GCCCAGCACCCCAAGGCGGCCAACGCCAAAACT<br>CTCCCTCCTCCTCTTCCTCAATCTCGCTCTCGC<br>TCTTTTTTTTTTTCGCAAAAGGAGGGGAGAGGG<br>GGTAAAAAAATGCTGCACTGTGCGGCGAAGCCG<br>GTGAGTGAGCGGCGCGGGGCCAATCAGCGTGCG<br>CCGTTCCGAAAGTTGCCTTTTATGGCTCGAGCG<br>GCCGCGGCGGCGCCCTATAAAACCCAGCGGCGC<br>GACGCGCCACCACCGCCGAGTC | 59 |
| Chicken beta-actin (CBA) | GGTCGAGGTGAGCCCCACGTTCTGCTTCACTCT<br>CCCCATCTCCCCCCCCTCCCCACCCCCAATTTT<br>GTATTTATTTATTTTTTAATTATTTTGTGCAGC<br>GATGGGGGCGGGGGGGGGGGGGGCGCGCGCCAG<br>GCGGGGCGGGGCGGGGCGAGGGGCGGGGCGGGG<br>CGAGGCGGAGAGGTGCGGCGGCAGCCAATCAGA<br>GCGGCGCGCTCCGAAAGTTTCCTTTTATGGCGA<br>GGCGGCGGCGGCGGCGGCCCTATAAAAAGCGAA<br>GCGCGCGGCGGGCGGGA | 60 |
| Cytomegalo-virus (CMV) | TGGTGATGCGGTTTTGGCAGTACACCAATGGGC<br>GTGGATAGCGGTTTGACTCACGGGGATTTCCAA<br>GTCTCCACCCCATTGACGTCAATGGGAGTTTGT<br>TTTGGCACCAAAATCAACGGGACTTTCCAAAAT<br>GTCGTAATAACCCCGCCCCGTTGACGCAAATGG<br>GCGGTAGGCGTGTACGGTGGGAGGTCTATATAA<br>GCAGAGCTCGTTTAGTGAACCG | 61 |
| Human EF1-alpha (EF1-α) | CAACCTTTGGAGCTAAGCCAGCAATGGTAGAGG<br>GAAGATTCTGCACGTCCCTTCCAGGCGGCCTCC<br>CCGTCACCACCCCCCCCAACCCGCCCCGACCGG<br>AGCTGAGAGTAATTCATACAAAAGGACTCGCCC<br>CTGCCTTGGGGAATCCCAGGGACCGTCGTTAAA<br>CTCCCACTAACGTAGAACCCAGAGATCGCTGCG<br>TTCCCGCCCCCTCACCCGCCCGCTCTCGTCATC<br>ACTGAGGTGGAGAATAGCATGCGTGAGGCTCCG | 62 |

TABLE 5-continued

| PROMOTER | SEQUENCE | SEQ ID NO: |
|---|---|---|
| | GTGCCCGTCAGTGGGCAGAGCGCACATCGCCCA<br>CAGTCCCCGAGAAGTTGGGGGGAGGGGTCGGCA<br>ATTGAACGGGTGCCTAGAGAAGGTGGCGCGGGG<br>TAAACTGGGAAAGTGATGTCGTGTACTGGCTCC<br>GCCTTTTTCCCGAGGGTGGGGGAGAACCGTATA<br>TAAGTGCAGTAGTCGCCGTGAACGTT | |
| Human Synapsin1 (Syn) | CTGCAGAGGGCCCTGCGTATGAGTGCAAGTGGG<br>TTTTAGGACCAGGATGAGGCGGGGTGGGGGTGC<br>CTACCTGACGACCGACCCCGACCCACTGGACAA<br>GCACCCAACCCCCATTCCCCAAATTGCGCATCC<br>CCTATCAGAGAGGGGGAGGGGAAACAGGATGCG<br>GCGAGGCGCGTGCGCACTGCCAGCTTCAGCACC<br>GCGGACAGTGCCTTCGCCCCCGCCTGGCGGCGC<br>GCGCCACCGCCGCCTCAGCACTGAAGGCGCGCT<br>GACGTCACTCGCCGGTCCCCCGCAAACTCCCCT<br>TCCCGGCCACCTTGGTCGCGTCCGCGCCGCCGC<br>CGGCCCAGCCGGACCGCACCACGCGAGGCGCGA<br>GATAGGGGGGCACGGGCGCGACCATCTGCGCTG<br>CGGCGCCGGCGACTCAGCGCTGCCTC | 63 |
| Human CamKIIa (CaMKIIa) | ACTTGTGGACAAAGTTTGCTCTATTCCACCTCC<br>TCCAGGCCCTCCTTGGGTCCATCACCCCAGGGG<br>TGCTGGGTCCATCCCACCCCCAGGCCCACACAG<br>GCTTGCAGTATTGTGTGCGGTATGGTCAGGGCG<br>TCCGAGAGCAGGTTTCGCAGTGGAAGGCAGGCA<br>GGTGTTGGGGAGGCAGTTACCGGGGCAACGGGA<br>ACAGGGCGTTTTGGAGGTGGTTGCCATGGGAC<br>CTGGATGCTGACGAAGGCTCGCGAGGCTGTGAG<br>CAGCCACAGTGCCCTGC | 64 |

Further illustrative examples of promoters are the SV40 late promoter from simian virus 40, the Baculovirus polyhedron enhancer/promoter element, Herpes Simplex Virus thymidine kinase (HSV tk), the immediate early promoter from cytomegalovirus (CMV) and various retroviral promoters including LTR elements. Inducible promoters include heavy metal ion inducible promoters (such as the mouse mammary tumor virus (mMTV) promoter or various growth hormone promoters), and the promoters from T7 phage which are active in the presence of T7 RNA polymerase. By way of illustration, examples of tissue-specific promoters include various surfactin promoters (for expression in the lung), myosin promoters (for expression in muscle), and albumin promoters (for expression in the liver). A large variety of other promoters are known and generally available in the art, and the sequences of many such promoters are available in sequence databases such as the GenBank database.

In some embodiments, the vector further comprises a CMV enhancer.

Other Regulatory Elements

In some cases, vectors of the present disclosure further comprise one or more regulatory elements selected from the group consisting of an enhancer, an intron, a poly-A signal, a 2A peptide encoding sequence, a WPRE (Woodchuck hepatitis virus posttranscriptional regulatory element), and a HPRE (Hepatitis B posttranscriptional regulatory element).

In certain embodiments, the vectors comprise one or more enhancers. In particular embodiments, the enhancer is a CMV enhancer sequence, a GAPDH enhancer sequence, a β-actin enhancer sequence, or an EF1-α enhancer sequence. Sequences of the foregoing are known in the art. For example, the sequence of the CMV immediate early (IE) enhancer is:

(SEQ ID NO: 79)

CGCGTTACATAACTTACGGTAAATGGCCCGCCTGGCTGACCGCCCAACG

ACCCCCGCCCATTGACGTCAATAATGACGTATGTTCCCATAGTAACGCC

AATAGGGACTTTCCATTGACGTCAATGGGTGGAGTATTTACGGTAAACT

GCCCACTTGGCAGTACATCAAGTGTATCATATGCCAAGTACGCCCCCTA

TTGACGTCAATGACGGTAAATGGCCCGCCTGGCATTATGCCCAGTACAT

GACCTTATGGGACTTTCCTACTTGGCAGTACATCTACGTATTAGTCATC

GCTATTACCA

In certain embodiments, the vectors comprise one or more introns. In particular embodiments, the intron is a rabbit globin intron sequence, a chicken β-actin intron sequence, a synthetic intron sequence, or an EF1-α intron sequence.

In certain embodiments, the vectors comprise a polyA sequence. In particular embodiments, the polyA sequence is a rabbit globin polyA sequence, a human growth hormone polyA sequence, a bovine growth hormone polyA sequence, a PGK polyA sequence, an SV40 polyA sequence, or a TK polyA sequence. In some embodiments, the poly-A signal may be a bovine growth hormone polyadenylation signal (bGHpA).

In certain embodiments, the vectors comprise one or more transcript stabilizing element. In particular embodiments, the transcript stabilizing element is a WPRE sequence, a HPRE sequence, a scaffold-attachment region, a 3' UTR, or a 5' UTR. In particular embodiments, the vectors comprise both a 5' UTR and a 3' UTR.

In some embodiments, the vector comprises a 5' untranslated region (UTR) selected from Table 6.

TABLE 6

| 5' UN-TRANSLATED REGION | SEQUENCE | SEQ ID NO: |
|---|---|---|
| Human beta-actin exon/intron | CGCGTCCGCCCGCGAGCACAGAGCCTCGCCTTTGC<br>CGATCCGCCGCCCGTCCACACCCGCCGCCAGGTAA<br>GCCCGGCCAGCCGACCGGGGCATGCGGCCGCGGCC<br>CTTCGCCCGTGCAGAGCCGCCGTCTGGGCCGCAGC<br>GGGGGGCGCATGGGGCGGAACCGGACCGCCGTGGG<br>GGGCGCGGGAGAAGCCCCTGGGCCTCCGGAGATGG<br>GGGACACCCCACGCCAGTTCGCAGGCGCGAGGCCG<br>CGCTCGGGCGGGCGCGCTCCGGGGGTGCCGCTCTC<br>GGGGCGGGGGCAACCGGCGGGGTCTTTGTCTGAGC<br>CGGGCTCTTGCCAATGGGGATCGCACGGTGGGCGC<br>GGCGTAGCCCCCGTCAGGCCCGGTGGGGGCTGGGG<br>CGCCATGCGCGTGCGCGCTGGTCCTTTGGGCGCTA<br>ACTGCGTGCGCGCTGGGAATTGGCGCTAATTGCGC<br>GTGCGCGCTGGGACTCAATGGCGCTAATCGCGCGT<br>GCGTTCTGGGGCCCGGGCGCTTGCGCCACTTCCTG<br>CCCGAGCCGCTGGCGCCCGAGGGTGTGGCCGCTGC<br>GTGCGCGCGCGCGACCCGGTCGCTGTTTGAACCGG<br>GCGGAGGCGGGGCTGGCGCCCGGTTGGGAGGGGGT<br>TGGGGCCTGGCTTCCTGCCGCGCGCCGCGGGGACG<br>CCTCCGACCAGTGTTTGCCTTTTATGGTAATAACG<br>CGGCCGGCCCGGCTTCCTTTGTCCCCAATCTGGGC<br>GCGCGCCGGCGCCCCCTGGCGGCCTAAGGACTCGG<br>CGCGCCGGAAGTGGCCAGGGCGGCAGCGGCTGCTC<br>TTGGCGGCCCCGAGGTGACTATAGCCTTCTTTTGT<br>GTCTTGATAGTTCGCCAGCCTCTGCTAACCATGTT<br>CATGCCTTCTTCTTTTTCCTACAGCTCCTGGGCAA<br>CGTGCTGGTTATTGTGCTGTCTCATCATTTTGGCA<br>AAGAATTC | 65 |

TABLE 6-continued

| 5' UN-TRANSLATED REGION | SEQUENCE | SEQ ID NO: |
|---|---|---|
| Chicken beta-actin exon/ intron + rabbit globin intron | GTCGCTGCGCGCTGCCTTCGCCCCGTGCCCCGCTC<br>CGCCGCCGCCTCGCGCCGCCCGCCCCGGCTCTGAC<br>TGACCGCGTTACTCCCACAGGTGAGCGGGCGGGAC<br>GGCCCTTCTCCTCCGGGCTGTAATTAGCGCTTGGT<br>TTAATGACGGCTTGTTTCTTTTCTGTGGCTGCGTG<br>AAAGCCTTGAGGGGCTCCGGGAGGGCCCTTTGTGC<br>GGGGGGAGCGGCTCGGGGGGTGCGTGCGTGTGTGT<br>GTGCGTGGGGAGCGCCGCGTGCGGCTCCGCGCTGC<br>CCGGCGGCTGTGAGCGCTGCGGGCGCGGCGCGGGG<br>CTTTGTGCGCTCCGCAGTGTGCGCGAGGGGAGCGC<br>GGCCGGGGGCGGTGCCCCGCGGTGCGGGGGGGGCT<br>GCGAGGGGAACAAAGGCTGCGTGCGGGGTGTGTGC<br>GTGGGGGGGTGAGCAGGGGGTGTGGGCGCGTCGGT<br>CGGGCTGCAACCCCCCCTGCACCCCCCTCCCCGAG<br>TTGCTGAGCACGGCCCGGCTTCGGGTGCGGGGCTC<br>CGTACGGGGCGTGGCGCGGGGCTCGCCGTGCCGGG<br>CGGGGGGTGGCGGCAGGTGGGGGTGCCGGGCGGGG<br>CGGGGCCGCCTCGGGCCGGGGAGGGCTCGGGGGAG<br>GGGCGCGGCGGCCCCCGGAGCGCCGGCGGCTGTCG<br>AGGCGCGGCGAGCCGCAGCCATTGCCTTTTATGGT<br>AATCGTGCGAGAGGGCGCAGGGACTTCCTTTGTCC<br>CAAATCTGTGCGGAGCCGAAATCTGGGAGGCGCCG<br>CCGCACCCCCTCTAGCGGGCGCGGGGCGAAGCGGT<br>GCGGCGCCGGCAGGAAGGAAATGGGCGGGGAGGGC<br>CTTCGTGCGTCGCCGCGCCGCCGTCCCCTTCTCCC<br>TCTCCAGCCTCGGGGCTGTCCGCGGGGGGACGGCT<br>GCCTTCGGGGGGGACGGGGCAGGGCGGGGTTCGGC<br>TTCTGGCGTGTGACCGGCGGCTCTAGAGCCTCTGC<br>TAACCATGTTCATGCCTTCTTCTTTTTCCTACAGC<br>TCCTGGGCAACGTGCTGGTTATTGTGCTGTCTCAT<br>CATTTTGGCAAAGAATTC | 66 |
| Synapsin1 exon | AGTCTGCGGTGGGCAGCGGAGGAGTCGTGTCGTGC<br>CTGAGAGCGCAGCTGTGCTCCTGGGCACCGCGCAG<br>TCCGCCCCCGCGGCTCCTGGCCAGACCACCCCTAG<br>GACCCCCTGCCCCAAGTCGCAG | 67 |
| CMV IE exon | TCAGATCGCCTGGAGAGGCCATCCACGCTGTTTTG<br>ACCTCCATAGTGGACACCGGGACCGATCCAGCCTC<br>CGCGGCCGGGAACGGTGCATTGGAACGCGGATTCC<br>CCGTGCCAAGAGTGAC | 68 |
| TPL-eMLP (adenovirus derived enhancer element) | CTCACTCTCTTCCGCATCGCTGTCTGCGAGGGCCA<br>GCTGTTGGGCTCGCGGTTGAGGACAAACTCTTCGC<br>GGTCTTTCCAGTACTCTTGGATCGGAAACCCGTCG<br>GCCTCCGAACGGTACTCCGCCACCGAGGGACCTGA<br>GCGAGTCCGCATCGACCGGATCGGAAAACCTCTCG<br>AGAAAGGCGTCTAACCAGTCACAGTCGCAAGGTAG<br>GCTGAGCACCGTGGCGGGCGGCAGCGGGTGGCGGT<br>CGGGGTTGTTTCTGGCGGAGGTGCTGCTGATGATG<br>TAATTAAAGTAGGCGGTCTTGAGACGGCGGATGGT<br>CGAGGTGAGGTGTGGCAGGCTTGAGATCCAGCTGT<br>TGGGGTGAGTACTCCCTCTCAAAAGCGGGCATTAC<br>TTCTGCGCTAAGATTGTCAGTTTCCAAAAACGAGG<br>AGGATTTGATATTCACCTGGCCCGATCTGGCCATA<br>CACTTGAGTGACAATGACATCCACTTTGCCTTTCT<br>CTCCACAGGTGTCCACTCCCAG | 69 |
| Human EF1a intron/exon | CTTTTTCGCAACGGGTTTGCCGCCAGAACACAGGT<br>AAGTGCCGTGTGTGGTTCCCGCGGGCCTGGCCTCT<br>TTACGGGTTATGGCCCTTGCGTGCCTTGAATTACT<br>TCCACCTGGCTCCAGTACGTGATTCTTGATCCCGA<br>GCTGGAGCCAGGGGGGGGCCTTGCGCTTTAGGAGC<br>CCCTTCGCCTCGTGCTTGAGTTGAGGCCTGGCCTG<br>GGCGCTGGGGCCGCCGCGTGCGAATCTGGTGGCAC<br>CTTCGCGCCTGTCTCGCTGCTTTCGATAAGTCTCT<br>AGCCATTTAAAATTTTTGATGACGTGCTGCGACGC<br>TTTTTTTCTGGCAAGATAGTCTTGTAAATGCGGGC<br>CAGGATCTGCACACTGGTATTTCGGTTTTTGGGCC<br>CGCGGCCGGCGACGGGGCCCGTGCGTCCCAGCGCA<br>CATGTTCGGCGAGGCGGGGCCTGCGAGCGCGGCCA<br>CCGAGAATCGGACGGGGGTAGTCTCAAGCTGGCCG<br>GCCTGCTCTGGTGCCTGGCCTCGCGCCGCCGTGTA<br>TCGCCCCGCCCTGGGCGGCAAGGCTGGCCCGGTCG | 70 |

TABLE 6-continued

| 5' UN-TRANSLATED REGION | SEQUENCE | SEQ ID NO: |
|---|---|---|
| | GCACCAGTTGCGTGAGCGGAAAGATGGCCGCTTCCCGGCCCTGCTCCAGGGGGCTCAAAATGGAGGACGCGGCGCTCGGGAGAGCGGGCGGGTGAGTCACCCACACAAAGGAAAAGGGCCTTTCCGTCCTCAGCCGTCGCTTCATGTGACTCCACGGAGTACCGGGCGCCGTCCAGGCACCTCGATTAGTTCTGGAGCTTTTGGAGTACGTCGTCTTTAGGTTGGGGGGAGGGGTTTTATGCGATGGAGTTTCCCCACACTGAGTGGGTGGAGACTGAAGTTAGGCCAGCTTGGCACTTGATGTAATTCTCCTTGGAATTTGGCCTTTTTGAGTTTGGATCTTGGTTCATTCTCAAGCCTCAGACAGTGGTTCAAAGTTTTTTTCTTCCATTTCAG | |
| 5' UTR human CamKIIa | TCAGAAGCCCCGGGCTCGTCAGTCAAACCGGTTCTCTGTTTGCACTCGGCAGCACGGGCAGGCAAGTGGTCCCTAGGTTCGGG | 71 |

In some embodiments, the vector comprises a 3' untranslated region selected from Table 7.

TABLE 7

| 3' UN-TRANSLATED REGION | SEQUENCE | SEQ ID NO: |
|---|---|---|
| WPRE(x) (mutated woodchuck hepatitis regulatory element) | TTCCTGTTAATCAACCTCTGGATTACAAAATTTGTGAAAGATTGACTGGTATTCTTAACTATGTTGCTCCTTTTACGCTATGTGGATACGCTGCTTTAATGCCTTTGTATCATGCTATTGCTTCCCGTATGGCTTTCATTTTCTCCTCCTTGTATAAATCCTGGTTGCTGTCTCTTTATGAGGAGTTGTGGCCCGTTGTCAGGCAACGTGGCGTGGTGTGCACTGTGTTTGCTGACGCAACCCCCACTGGTTGGGGCATTGCCACCACCTGTCAGCTCCTTTCCGGGACTTTCGCTTTCCCCCTCCCTATTGCCACGGCGGAACTCATCGCCGCCTGCCTTGCCCGCTGCTGGACAGGGGCTCGGCTGTTGGGCACTGACAATTCCGTGGTGTTGTCGGGGAAGCTGACGTCCTTTCCGCGGCTGCTCGCCTGTGTTGCCACCTGGATTCTGCGCGGGACGTCCTTCTGCTACGTCCCTTCGGCCCTCAATCCAGCGGACCTTCCTTCCCGCGGCCTGCTGCCGGCTCTGCGGCCTCTTCCGCCTCTTCGCCTTCGCCCTCAGACGAGTCGGATCTCCCTTTGGGCCGCCTCCCCGCCCATGTATCTTTTTCACCTGTGCCTTGTTTTTGCCTGTGTTCCGCGTCCTACTTTTCAAGCCTCCAAGCTGTGCCTTGGGCGGCTTTGGGGCATGGACATAGATCCCTATAAAGAATTTGGTTCATCTTATCAGTTGTTGAATTTTCTTCCTTTGGAC | 72 |
| R2V17 (HepB derived enhancer element) | TTCCTGTAAACAGGCCTATTGATTGGAAAGTTTGTCAACGAATTGTGGGTCTTTTGGGGTTTGCTGCCCCTTTTACGCAATGTGGATATCCTGCTTTAATGCCTTTATATGCATGTATACAAGCAAAACAGGCTTTTACTTTCTCGCCAACTTACAAGGCCTTTCTCAGTAAACAGTATATGACCCTTTACCCCGTTGCTCGGCAACGGCCTGGTCTGTGCCAAGTGTTTGCTGACGCAACCCCCACTGGTTGGGGCTTGGCCATAGGCCATCAGCGCATGCGTGGAACCTTTGTGTCTCCTCTGCCGATCCATACTGCGGAACTCCTAGCCGCTTGTTTTGCTCGCAGCTGGACTGGAGCAAACCTCATCGGGACCGACAATTCTGTCGTACTCTCCCGCAAGCACTCACCGTTTCCGCGGCTGCTCGCCTGTGTTGCCACCTGGATTCTGCGCGGGACGTCCTTCTGCTACGTCCCTTCGGCCCTCAATCCAGCGGACCTTCCTTCCCGCGGCCTGCTGCCGGCTCTGCGGCCTCTTCCGCCTCTTCGCCTTCGCCCTCAGACGAGTCGGATCTCCCTTTGGGCCGCCTCCCCGCCCATGTATCTTTTTCACCTGTGCCTTGTTTTTGCCTGTGTTCCGCGTCCTACTTTTCAAGCCTCCAAGCTGTGCCTTGGGCGGCTTTGGGGCATGGACATAGATCCCTATAAAGAATTTGGTTCATCTTATCAGTTGTTGAATTTTCTTCCTTTGGAC | 73 |

TABLE 7-continued

| 3' UN-TRANSLATED REGION | SEQUENCE | SEQ ID NO: |
|---|---|---|
| 3'UTR (globin) | GCTGGAGCCTCGGTAGCCGTTCCTCCTGCCCGCTGGGCCTCCCAACGGGCCCTCCTCCCCTCCTTGCACCGGCCCTTCCTGGTCTTTGAATAAA | 74 |
| WPRE(r) | ATTCGAGCATCTTACCGCCATTTATTCCCATATTTGTTCTGTTTTTCTTGATTTGGGTATACATTTAAATGTTAATAAAACAAAATGGTGGGGCAATCATTTACATTTTTAGGGATATGTAATTACTAGTTCAGGTGTATTGCCACAAGACAAACATGTTAAGAAACTTTCCCGTTATTTACGCTCTGTTCCTGTTAATCAACCTCTGGATTACAAAATTTGTGAAAGATTGACTGATATTCTTAACTATGTTGCTCCTTTTACGCTGTGTGGATATGCTGCTTTAATGCCTCTGTATCATGCTATTGCTTCCCGTACGGCTTTCGTTTTCTCCTCCTTGTATAAATCCTGGTTGCTGTCTCTTTATGAGGAGTTGTGGCCCGTTGTCCGTCAACGTGGCGTGGTGTGCTCTGTGTTTGCTGACGCAACCCCCACTGGCTGGGGCATTGCCACCACCTGTCAACTCCTTTCTGGGACTTTCGCTTTCCCCCTCCCGATCGCCACGGCAGAACTCATCGCCGCCTGCCTTGCCCGCTGCTGGACAGGGGCTAGGTTGCTGGGCACTGATAATTCCGTGGTGTTGTCGGGGAAGGGCC | 75 |

In some embodiments, the vector comprises a polyadenylation sequence (polyA) selected from Table 8.

TABLE 8

| POLY-ADENYLATION | SEQUENCE | SEQ ID NO: |
|---|---|---|
| Rabbit globin (pAGlobin-Oc) | TGGCTAATAAAGGAAATTTATTTTCATTGCAATAGTGTGTTGGAATTTTTTGTGTCTCTCACTCGGAAGAACATATGGGAGGGCAAATCATTTAAAACATCAGAATGAGTATTTGGTTTAGAGTTTGGCAACATATGCCCATATGCTGGCTGCCATGAACAAAGGTTGGCTATAAAGAGGTCATCAGTATATGAAACAGCCCCCTGCTGTCCATTCCTTATTCCATAGAAAAGCCTTGACTTGAGGTTAGATTTTTTTTATATTTTGTTTTGTGTTATTTTTTTCTTTAACATCCCTAAAATTTTCCTTACATGTTTTACTAGCCAGATTTTTCCTCCTCTCCTGACTACTCCCAGTCATAGCTGTCCCTCTTCTCTTATGGAGATC | 76 |
| Bovine growth hormone (pAGH-Bt) | TTGCCAGCCATCTGTTGTTTGCCCCTCCCCCGTGCCTTCCTTGACCCTGGAAGGTGCCACTCCCACTGTCCTTTCCTAATAAAATGAGGAAATTGCATCGCATTGTCTGAGTAGGTGTCATTCTATTCTGGGGGGTGGGGTGGGGCAGGACAGCAAGGGGGAGGATTGGGAATACAATAGCAGGCATGCTGGGGATGCGGTGGGCTCTATGGGTACCCAGGTGCTGAAGAATTGACCCGGTTCCTCCTGGG | 77 |
| Human growth hormone (pAGH-Hs) | CTGCCCGGGTGGCATCCCTGTGACCCCTCCCCAGTGCCTCTCCTGGCCCTGGAAGTTGCCACTCCAGTGCCCACCAGCCTTGTCCTAATAAAATTAAGTTGCATCATTTTGTCTGACTAGGTGTCCTTCTATAATATTATGGGGTGGAGGGGGGTGGTATGGAGCAAGGGGCCCAAGTTGGGAAGAAACCTGTAGGGCCTGC | 78 |

Figure 13:
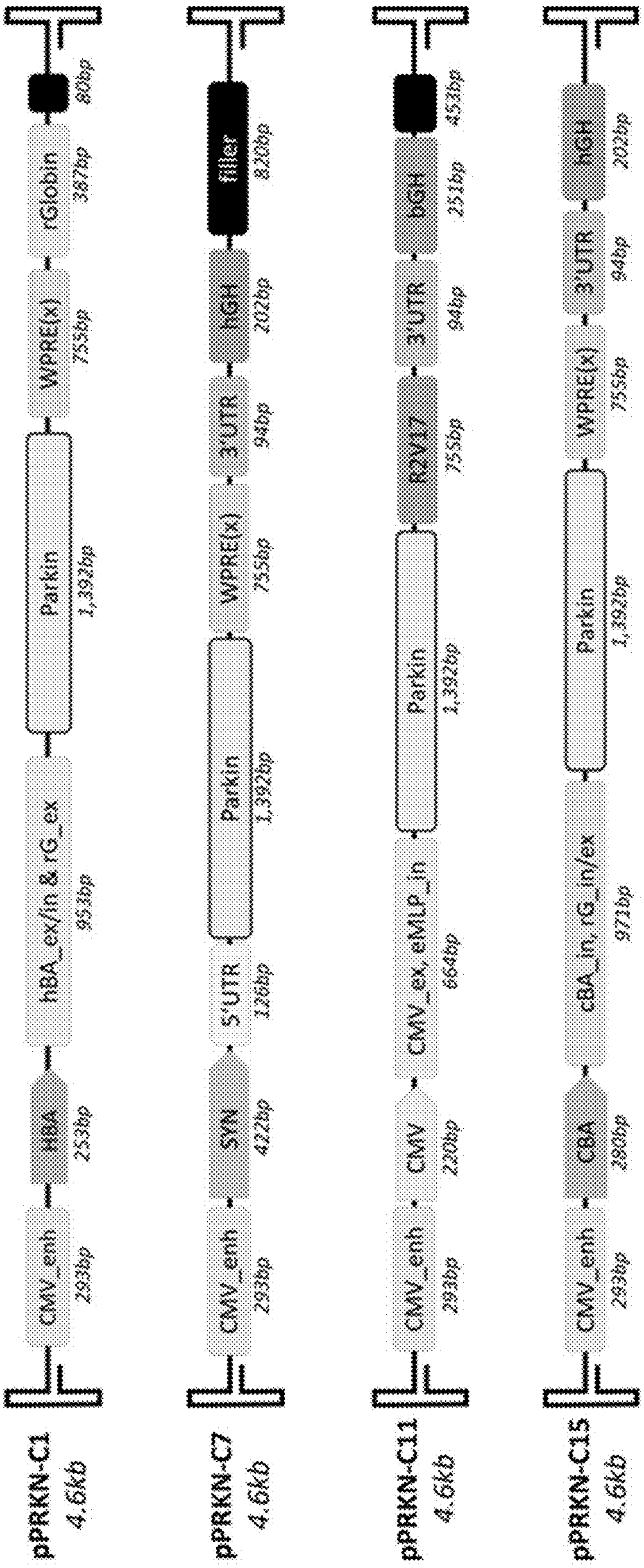
FIG. 13 provides diagrams of illustrative construct designs.

Illustrative expression cassettes are depicted in FIG. 13 and provided as SEQ ID NOs: 39-58, listed in Table 10. In some embodiments, the expression cassette comprises, consists essentially of, or consists of a polynucleotide sequence that shares at least 90%, 91%, 92%, 93%, 94%, 95%, 96%, 97%, 98%, 99%, or 100% identity with any one of SEQ ID NOs: 39-58. In some embodiments, the expression cassette comprises, consists essentially of, or consists of a polynucleotide sequence that shares at least 90%, 91%, 92%, 93%, 94%, 95%, 96%, 97%, 98%, 99%, or 100% identity with any one of SEQ ID NOs: 39-58 excluding the sequence encoding the therapeutic gene product. In some embodiments, the sequence encoding the therapeutic gene product si replaced by a sequence encoding a different therapeutic gene product.

In an embodiment, the expression cassette comprises, in 5' to 3' order, HuBA promoter, the transgene, WPRE(x), and pAGlobin-Oc. In certain embodiments, the transgene encodes PARK2, PINK1 (PARK6), DJ-1 (PARK7), LRRK2, α-synuclein, and DJ-1. In particular embodiments, it encodes PARK2, and in certain embodiments, in comprises a sequence set forth in any of SEQ ID NOs: 27 or 35-38.

In an embodiment, the expression cassette comprises, in 5' to 3' order, CMV promoter, TPL-eMLP enhancer, the transgene, WPRE(r), and pAGlobin-Oc. In certain embodiments, the transgene encodes PARK2, PINK1 (PARK6), DJ-1 (PARK7), LRRK2, α-synuclein, and DJ-1. In particular embodiments, it encodes PARK2, and in certain embodiments, in comprises a sequence set forth in any of SEQ ID NOs: 27 or 35-38.

In an embodiment, the expression cassette comprises, in 5' to 3' order, Syn promoter, the transgene, WPRE(r), 3'UTR (globin), and pAGH-Bt. In certain embodiments, the transgene encodes PARK2, PINK1 (PARK6), DJ-1 (PARK7), LRRK2, α-synuclein, and DJ-1. In particular embodiments, it encodes PARK2, and in certain embodiments, in comprises a sequence set forth in any of SEQ ID NOs: 27 or 35-38.

In an embodiment, the expression cassette comprises, in 5' to 3' order, CBA promoter, the transgene, and pAGH-Bt. In certain embodiments, the transgene encodes PARK2, PINK1 (PARK6), DJ-1 (PARK7), LRRK2, α-synuclein, and DJ-1. In particular embodiments, it encodes PARK2, and in certain embodiments, in comprises a sequence set forth in any of SEQ ID NOs: 27 or 35-38.

In an embodiment, the expression cassette comprises, in 5' to 3' order, EF1α promoter, the transgene, and pAGlobin-Oc. In certain embodiments, the transgene encodes PARK2, PINK1 (PARK6), DJ-1 (PARK7), LRRK2, α-synuclein, and DJ-1. In particular embodiments, it encodes PARK2, and in certain embodiments, in comprises a sequence set forth in any of SEQ ID NOs: 27 or 35-38.

In an embodiment, the expression cassette comprises, in 5' to 3' order, HuBA promoter, the transgene, R2V17, and pAGH-Bt. In certain embodiments, the transgene encodes PARK2, PINK1 (PARK6), DJ-1 (PARK7), LRRK2, α-synuclein, and DJ-1. In particular embodiments, it encodes PARK2, and in certain embodiments, in comprises a sequence set forth in any of SEQ ID NOs: 27 or 35-38.

In an embodiment, the expression cassette comprises, in 5' to 3' order, Syn promoter, the transgene, WPRE(x), 3'UTR(globin), and pAGH-Hs. In certain embodiments, the transgene encodes PARK2, PINK1 (PARK6), DJ-1 (PARK7), LRRK2, α-synuclein, and DJ-1. In particular embodiments, it encodes PARK2, and in certain embodiments, in comprises a sequence set forth in any of SEQ ID NOs: 27 or 35-38.

In an embodiment, the expression cassette comprises, in 5' to 3' order, CaMKIIa promoter, the transgene, WPRE(r), and pAGH-Hs. In certain embodiments, the transgene encodes PARK2, PINK1 (PARK6), DJ-1 (PARK7), LRRK2, α-synuclein, and DJ-1. In particular embodiments, it encodes PARK2, and in certain embodiments, in comprises a sequence set forth in any of SEQ ID NOs: 27 or 35-38.

In an embodiment, the expression cassette comprises, in 5' to 3' order, CMV promoter, TPL-eMLP enhancer, the transgene, WPRE(r), and pAGH-Hs. In certain embodiments, the transgene encodes PARK2, PINK1 (PARK6), DJ-1 (PARK7), LRRK2, α-synuclein, and DJ-1. In particular embodiments, it encodes PARK2, and in certain embodiments, in comprises a sequence set forth in any of SEQ ID NOs: 27 or 35-38.

In an embodiment, the expression cassette comprises, in 5' to 3' order, HuBA promoter, the transgene, and pAGH-Hs. In certain embodiments, the transgene encodes PARK2, PINK1 (PARK6), DJ-1 (PARK7), LRRK2, α-synuclein, and DJ-1. In particular embodiments, it encodes PARK2, and in certain embodiments, in comprises a sequence set forth in any of SEQ ID NOs: 27 or 35-38.

In an embodiment, the expression cassette comprises, in 5' to 3' order, CMV promoter, TPL/eMLP enhancer, the transgene, R2V17, 3'UTR(globin), and pAGH-Bt. In certain embodiments, the transgene encodes PARK2, PINK1 (PARK6), DJ-1 (PARK7), LRRK2, α-synuclein, and DJ-1. In particular embodiments, it encodes PARK2, and in certain embodiments, in comprises a sequence set forth in any of SEQ ID NOs: 27 or 35-38.

In an embodiment, the expression cassette comprises, in 5' to 3' order, EF1α promoter, the transgene, WPRE(r), and pAGH-Bt. In certain embodiments, the transgene encodes PARK2, PINK1 (PARK6), DJ-1 (PARK7), LRRK2, α-synuclein, and DJ-1. In particular embodiments, it encodes PARK2, and in certain embodiments, in comprises a sequence set forth in any of SEQ ID NOs: 27 or 35-38.

In an embodiment, the expression cassette comprises, in 5' to 3' order, Syn promoter, the transgene, R2V17, and pAGlobin-Oc. In certain embodiments, the transgene encodes PARK2, PINK1 (PARK6), DJ-1 (PARK7), LRRK2, α-synuclein, and DJ-1. In particular embodiments, it encodes PARK2, and in certain embodiments, in comprises a sequence set forth in any of SEQ ID NOs: 27 or 35-38.

In an embodiment, the expression cassette comprises, in 5' to 3' order, CaMKIIa promoter, the transgene, R2V17, and pAGlobin-Oc. In certain embodiments, the transgene encodes PARK2, PINK1 (PARK6), DJ-1 (PARK7), LRRK2, α-synuclein, and DJ-1. In particular embodiments, it encodes PARK2, and in certain embodiments, in comprises a sequence set forth in any of SEQ ID NOs: 27 or 35-38.

In an embodiment, the expression cassette comprises, in 5' to 3' order, CBA promoter, the transgene, WPRE(x), 3'UTR(globin), and pAGH-Hs. In certain embodiments, the transgene encodes PARK2, PINK1 (PARK6), DJ-1 (PARK7), LRRK2, α-synuclein, and DJ-1. In particular embodiments, it encodes PARK2, and in certain embodiments, in comprises a sequence set forth in any of SEQ ID NOs: 27 or 35-38.

In an embodiment, the expression cassette comprises, in 5' to 3' order, CBA promoter, the transgene, 3'UTR(globin), and pAGlobin-Oc. In certain embodiments, the transgene encodes PARK2, PINK1 (PARK6), DJ-1 (PARK7), LRRK2, α-synuclein, and DJ-1. In particular embodiments, it encodes PARK2, and in certain embodiments, in comprises a sequence set forth in any of SEQ ID NOs: 27 or 35-38.

In an embodiment, the expression cassette comprises, in 5' to 3' order, CaMKIIa promoter, the transgene, R2V17, and pAGH-Bt. In certain embodiments, the transgene encodes PARK2, PINK1 (PARK6), DJ-1 (PARK7), LRRK2, α-synuclein, and DJ-1. In particular embodiments, it encodes PARK2, and in certain embodiments, in comprises a sequence set forth in any of SEQ ID NOs: 27 or 35-38.

In an embodiment, the expression cassette comprises, in 5' to 3' order, EF1α promoter, the transgene, R2V17, 3'UTR (globin), and pAGH-Hs. In certain embodiments, the transgene encodes PARK2, PINK1 (PARK6), DJ-1 (PARK7), LRRK2, α-synuclein, and DJ-1. In particular embodiments, it encodes PARK2, and in certain embodiments, in comprises a sequence set forth in any of SEQ ID NOs: 27 or 35-38.

In an embodiment, the expression cassette comprises, in 5' to 3' order, CMV promoter, the transgene, R2V17, 3'UTR (globin), and pAGH-Hs. In certain embodiments, the transgene encodes PARK2, PINK1 (PARK6), DJ-1 (PARK7), LRRK2, α-synuclein, and DJ-1. In particular embodiments, it encodes PARK2, and in certain embodiments, in comprises a sequence set forth in any of SEQ ID NOs: 27 or 35-38.

In an embodiment, the expression cassette comprises, in 5' to 3' order, CMV promoter, the transgene, and pAGH-Hs. In certain embodiments, the transgene encodes PARK2, PINK1 (PARK6), DJ-1 (PARK7), LRRK2, α-synuclein, and DJ-1. In particular embodiments, it encodes PARK2, and in certain embodiments, in comprises a sequence set forth in any of SEQ ID NOs: 27 or 35-38.

In embodiments of the foregoing, the order of the elements 5' to the transgene are reversed so that the promoter precedes the enhancer elements or the enhancer element precedes the promoter element.

Therapeutic Compositions and Methods

As used herein, the term "patient in need" or "subject in need" refers to a patient or subject at risk of, or suffering from, a disease, disorder or condition that is amenable to treatment or amelioration with a recombinant gene therapy vector or gene editing system disclosed herein. A patient or subject in need may, for instance, be a patient or subject diagnosed with a disorder associated with central nervous system degradation. A subject may have a mutation or a malfunction in a PARK2, PARK6, PARK7, LRRK2, or α-synuclein, gene or protein. "Subject" and "patient" are used interchangeably herein. The subject treated by the methods described herein may be an adult or a child. Subjects may range in age. The subject may be a person identified as at risk for a Parkinson's Disease, e.g., an early-onset Parkinson's Disease.

Combination therapies are also contemplated by the invention. Combination as used herein includes simultaneous treatment or sequential treatment. Combinations of methods of the invention with standard medical treatments (e.g., corticosteroids or topical pressure reducing medications) are specifically contemplated, as are combinations with novel therapies. In some cases, a subject may be treated with a steroid to prevent or to reduce an immune response to administration of a rAAV described herein. In certain cases, a subject may receive topical pressure reducing medications before, during, or after administrating of a rAAV described herein.

A therapeutically effective amount of the rAAV vector is a dose of rAAV ranging from about 1e7 vg/kg to about 5e15 vg/kg, or about 1e7 vg/kg to about 1e14 vg/kg, or about 1e8 vg/kg to about 1e14 vg/kg, or about 1e9 vg/kg to about 1e13 vg/kg, or about 1e9 vg/kg to about 1e12 vg/kg, or about 1e7 vg/kg to about 5e7 vg/kg, or about 1e8 vg/kg to about 5e8 vg/kg, or about 1e9 vg/kg to about 5e9 vg/kg, or about 1e10 vg/kg to about 5e10 vg/kg, or about 1e11 vg/kg to about 5e11 vg/kg, or about 1e12 vg/kg to about 5e12 vg/kg, or about 1e13 vg/kg to about 5e13 vg/kg, or about 1e14 vg/kg to about 5e14 vg/kg, or about 1e15 vg/kg to about 5e15 vg/kg. The invention also comprises compositions comprising these ranges of rAAV vector.

For example, in particular embodiments, a therapeutically effective amount of rAAV vector is a dose of about 1e10 vg/kg, about 2e10 vg/kg, about 3e10 vg/kg, about 4e10 vg/kg, about 5e10 vg/kg, about 6e10 vg/kg, about 7e10 vg/kg, about 8e10 vg/kg, about 9e10 vg/kg, about 1e12 vg/kg, about 2e12 vg/kg, about 3e12 vg/kg, about 4e12 vg/kg and 5e12 vg/kg. The invention also comprises compositions comprising these doses of rAAV vector.

In some embodiments, for example where direct injection into substantia nigra is performed, a therapeutically effective amount of rAAV vector is a dose in the range of 1e7 vg to 1e11 vg, or about 1e7 vg, about 1e8 vg, about 1e9 vg, about 1e10 vg, or about 1e11 vg.

In some embodiments, for example where direct injection into intraputaminal is performed, a therapeutically effective amount of rAAV vector is a dose in the range of 1e7 vg to 1e11 vg, or about 1e7 vg, about 1e8 vg, about 1e9 vg, about 1e10 vg, or about 1e11 vg.

In some cases, the therapeutic composition comprises more than about 1e9, 1e10, or 1e11 genomes of the rAAV vector per volume of therapeutic composition injected. In some cases, the therapeutic composition comprises more than about 1e9, 1e10, or 1e11 genomes of the rAAV vector per volume of therapeutic composition injected. In some cases, the therapeutic composition comprises more than approximately 1e10, 1e11, 1e12, or 1e13 genomes of the rAAV vector per mL. In certain embodiments, the therapeutic composition comprises less than about 1e14, 1e13 or Ie1e12 genomes of the rAAV vector per mL.

Administration of Compositions

Administration of an effective dose of the compositions may be by routes standard in the art including, but not limited to, systemic, local, direct injection, parenteral, intravenous, cerebral, cerebrospinal, intrathecal, intracisternal, intraputaminal, intrahippocampal, intra-striatal, or intra-cerebroventricular administration. In some cases, administration comprises intravenous, cerebral, cerebrospinal, intrathecal, intracisternal, intraputaminal, intrahippocampal, intra-striatal, or intra-cerebroventricular injection. Administration may be performed by intrathecal injection with Trendelenburg tilting. Route(s) of administration and serotype(s) of AAV components of the rAAV (in particular, the AAV ITRs and capsid protein) of the invention may be chosen and/or matched by those skilled in the art taking into account the disorder being treated and the target cells/tissue (s) that are to express the repaired and/or exogenously provided gene.

In certain embodiment, the disclosure provides for local administration and systemic administration of an effective dose of rAAV and compositions of the invention. For example, systemic administration may be administration into the circulatory system so that the entire body is affected. Systemic administration includes enteral administration such as absorption through the gastrointestinal tract and parental administration through injection, infusion or implantation.

In particular, actual administration of rAAV of the present invention may be accomplished by using any physical method that will transport the rAAV recombinant vector into the target tissue of an animal. Administration according to the invention includes, but is not limited to, injection into the central nervous system (CNS) or cerebrospinal fluid (CSF) and/or directly into the brain.

Capsid proteins of a rAAV may be modified so that the rAAV is targeted to a particular target tissue of interest such as neurons or more particularly a dopaminergic neuron. See, for example, Albert et al. AAV Vector-Mediated Gene Delivery to Substantia Nigra Dopamine Neurons: Implications for Gene Therapy and Disease Models. Genes. 2017 Feb. 8; see also U.S. Pat. No. 6,180,613 and U.S. Patent Pub. No. US20120082650A1, the disclosures of both of which are incorporated by reference herein. In some embodiments, the rAAV is directly injected into the substantia nigra of the subject.

For purposes of administration, e.g., by injection, various solutions can be employed, such as sterile aqueous solutions. Such aqueous solutions can be buffered, if desired, and the liquid diluent first rendered isotonic with saline or glucose. Solutions of rAAV as a free acid (DNA contains acidic phosphate groups) or a pharmacologically acceptable salt can be prepared in water suitably mixed with a surfactant such as hydroxypropylcellulose. A dispersion of rAAV can also be prepared in glycerol, liquid polyethylene glycols and mixtures thereof and in oils. Under ordinary conditions of storage and use, these preparations contain a preservative to prevent the growth of microorganisms. In this connection, the sterile aqueous media employed are all readily obtainable by standard techniques well-known to those skilled in the art.

The pharmaceutical forms suitable for injectable use include but are not limited to sterile aqueous solutions or dispersions and sterile powders for the extemporaneous preparation of sterile injectable solutions or dispersions. In all cases the form is sterile and must be fluid to the extent that easy syringability exists. It must be stable under the conditions of manufacture and storage and must be preserved against the contaminating actions of microorganisms such as bacteria and fungi. The carrier can be a solvent or dispersion medium containing, for example, water, ethanol, polyol (for example, glycerol, propylene glycol, liquid polyethylene glycol and the like), suitable mixtures thereof, and vegetable oils. The proper fluidity can be maintained, for example, by the use of a coating such as lecithin, by the maintenance of the required particle size in the case of a dispersion and by the use of surfactants. The prevention of the action of microorganisms can be brought about by various antibacterial and antifungal agents, for example, parabens, chlorobutanol, phenol, sorbic acid, thimerosal and the like. In many cases it will be preferable to include isotonic agents, for example, sugars or sodium chloride. Prolonged absorption of the injectable compositions can be brought about by use of agents delaying absorption, for example, aluminum monostearate and gelatin.

Sterile injectable solutions may be prepared by incorporating rAAV in the required amount in the appropriate solvent with various other ingredients enumerated above, as required, followed by filter sterilization. Generally, dispersions are prepared by incorporating the sterilized active ingredient into a sterile vehicle which contains the basic dispersion medium and the required other ingredients from those enumerated above. In the case of sterile powders for the preparation of sterile injectable solutions, the preferred methods of preparation are vacuum drying and the freeze-drying technique that yield a powder of the active ingredient plus any additional desired ingredient from the previously sterile-filtered solution thereof.

Transduction with rAAV may also be carried out in vitro. In one embodiment, desired target cells are removed from the subject, transduced with rAAV and reintroduced into the subject.

Suitable methods for the transduction and reintroduction of transduced cells into a subject are known in the art. In one embodiment, cells can be transduced in vitro by combining rAAV with cells, e.g., in appropriate media, and screening for those cells harboring the DNA of interest using conventional techniques such as Southern blots and/or PCR, or by using selectable markers. Transduced cells can then be formulated into pharmaceutical compositions, and the composition introduced into the subject by various techniques, such as by systemic, local, direct injection, parenteral, intravenous, cerebral, cerebrospinal, intrathecal, intracisternal, intraputaminal, intrahippocampal, intra-striatal, or intra-cerebroventricular administration. In some cases, administration comprises intravenous, cerebral, cerebrospinal, intrathecal, intracisternal, intraputaminal, intrahippocampal, intra-striatal, or intra-cerebroventricular injection. Administration may be performed by intrathecal injection with Trendelenburg tilting.

Transduction of cells with rAAV of the invention results in sustained expression of a gene of interest, such as PARK2, PARK6, PARK7, LRRK2, or α-synuclein. The present invention thus provides methods of administering or delivering recombinant gene therapy vectors (e.g. rAAV vectors) which express a gene related to a CNS degeneration to a mammalian subject, preferably a human being. These methods include transducing tissues (including, but not limited to, the tissues of the brain) with one or more rAAV of the present invention. Transduction may be carried out with gene cassettes comprising tissue specific control elements. For example, one embodiment of the invention provides methods of transducing neuronal cells and brain tissues directed by neuron-specific control elements, including, but not limited to, those derived from neuron-enriched promoters, and other control elements.

Gene-Editing System

As used herein, a gene-editing system is a system comprising one or more proteins or polynucleotides capable of editing an endogenous target gene or locus in a sequence specific manner. In some embodiments, the gene-editing system is a protein-based gene regulating system comprising a protein comprising one or more zinc-finger binding domains and an enzymatic domain. In some embodiments, the protein-based gene regulating system comprises a protein comprising a Transcription activator-like effector nuclease (TALEN) domain and an enzymatic domain. Such embodiments are referred to herein as "TALENs".

1. Zinc Finger-Based Systems

Zinc finger-based systems comprise a fusion protein comprising two protein domains: a zinc finger DNA binding domain and an enzymatic domain. A "zinc finger DNA binding domain", "zinc finger protein", or "ZFP" is a protein, or a domain within a larger protein, that binds DNA in a sequence-specific manner through one or more zinc fingers, which are regions of amino acid sequence within the binding domain whose structure is stabilized through coordination of a zinc ion. The zinc finger domain, by binding to a target DNA sequence, directs the activity of the enzymatic domain to the vicinity of the sequence and, hence, induces modification of the endogenous target gene in the vicinity of the target sequence. A zinc finger domain can be engineered to bind to virtually any desired sequence. Accordingly, after identifying a target genetic locus containing a target DNA sequence at which cleavage or recombination is desired (e.g., a target locus in a target gene referenced in Table 1), one or more zinc finger binding domains can be engineered to bind to one or more target DNA sequences in the target genetic locus. Expression of a fusion protein comprising a zinc finger binding domain and an enzymatic domain in a cell, effects modification in the target genetic locus.

In some embodiments, a zinc finger binding domain comprises one or more zinc fingers. Miller et al. (1985) EMBO J. 4:16010-1714; Rhodes (1993) Scientific American February: 56-65; U.S. Pat. No. 6,453,242. Typically, a single zinc finger domain is about 30 amino acids in length. An individual zinc finger binds to a three-nucleotide (i.e., triplet) sequence (or a four-nucleotide sequence which can overlap, by one nucleotide, with the four-nucleotide binding site of an adjacent zinc finger). Therefore, the length of a sequence to which a zinc finger binding domain is engineered to bind (e.g., a target sequence) will determine the number of zinc fingers in an engineered zinc finger binding domain. For example, for ZFPs in which the finger motifs do not bind to overlapping subsites, a six-nucleotide target sequence is bound by a two-finger binding domain; a nine-nucleotide target sequence is bound by a three-finger binding domain, etc. Binding sites for individual zinc fingers (i.e., subsites) in a target site need not be contiguous, but can be separated by one or several nucleotides, depending on the length and nature of the amino acid sequences between the zinc fingers (i.e., the inter-finger linkers) in a multi-finger binding domain. In some embodiments, the DNA-binding domains of individual ZFNs comprise between three and six individual zinc finger repeats and can each recognize between 9 and 18 basepairs.

Zinc finger binding domains can be engineered to bind to a sequence of choice. See, for example, Beerli et al. (2002) Nature Biotechnol. 20:135-141; Pabo et al. (2001) Ann. Rev. Biochem. 70:313-340; Isalan et al. (2001) Nature Biotechnol. 19:656-660; Segal et al. (2001) Curr. Opin. Biotechnol. 12:632-637; Choo et al. (2000) Curr. Opin. Struct. Biol. 10:411-416. An engineered zinc finger binding domain can have a novel binding specificity, compared to a naturally-occurring zinc finger protein. Engineering methods include, but are not limited to, rational design and various types of selection.

Selection of a target DNA sequence for binding by a zinc finger domain can be accomplished, for example, according to the methods disclosed in U.S. Pat. No. 6,453,242. It will be clear to those skilled in the art that simple visual inspection of a nucleotide sequence can also be used for selection of a target DNA sequence. Accordingly, any means for target DNA sequence selection can be used in the methods described herein. A target site generally has a length of at least 9 nucleotides and, accordingly, is bound by a zinc finger binding domain comprising at least three zinc fingers. However binding of, for example, a 4-finger binding domain to a 12-nucleotide target site, a 5-finger binding domain to a 15-nucleotide target site or a 6-finger binding domain to an 18-nucleotide target site, is also possible. As will be apparent, binding of larger binding domains (e.g., 7-, 8-, 9-finger and more) to longer target sites is also possible.

In some embodiments, the zinc finger binding domains bind to a target DNA sequence that is at least 90% identical to a target DNA sequence within a target locus of a target gene selected those listed in Table 1. In some embodiments, the zinc finger binding domains bind to a target DNA sequence that is at least 95%, 96%, 97%, 98%, or 99% identical to a target DNA sequence within a target locus of a target gene selected those listed in Table 1. In some embodiments, the zinc finger binding domains bind to a target DNA sequence that is 100% identical to a target DNA sequence within a target locus of a target gene selected those listed in Table 1.

The enzymatic domain portion of the zinc finger fusion proteins can be obtained from any endo- or exonuclease. Exemplary endonucleases from which an enzymatic domain can be derived include, but are not limited to, restriction endonucleases and homing endonucleases. See, for example, 2002-2003 Catalogue, New England Biolabs, Beverly, Mass.; and Belfort et al. (1997) Nucleic Acids Res. 25:3379-3388. Additional enzymes which cleave DNA are known (e.g., 51 Nuclease; mung bean nuclease; pancreatic DNase I; micrococcal nuclease; yeast HO endonuclease; see also Linn et al. (eds.) Nucleases, Cold Spring Harbor Laboratory Press, 1993). One or more of these enzymes (or functional fragments thereof) can be used as a source of cleavage domains.

Exemplary restriction endonucleases (restriction enzymes) suitable for use as an enzymatic domain of the ZFPs described herein are present in many species and are capable of sequence-specific binding to DNA (at a recognition site), and cleaving DNA at or near the site of binding. Certain restriction enzymes (e.g., Type IIS) cleave DNA at sites removed from the recognition site and have separable binding and cleavage domains. For example, the Type IIS enzyme Fok I catalyzes double-stranded cleavage of DNA, at 9 nucleotides from its recognition site on one strand and 13 nucleotides from its recognition site on the other. See, for example, U.S. Pat. Nos. 5,356,802; 5,436,150 and 5,487,994; as well as Li et al. (1992) Proc. Natl. Acad. Sci. USA 89:4275-4279; Li et al. (1993) Proc. Natl. Acad. Sci. USA 90:2764-2768; Kim et al. (1994a) Proc. Natl. Acad. Sci. USA 91:883-887; Kim et al. (1994b) J. Biol. Chem. 269:31,978-31,982. Thus, in one embodiment, fusion proteins comprise the enzymatic domain from at least one Type IIS restriction enzyme and one or more zinc finger binding domains.

An exemplary Type IIS restriction enzyme, whose cleavage domain is separable from the binding domain, is Fok I. This particular enzyme is active as a dimer. Bitinaite et al. (1998) Proc. Natl. Acad. Sci. USA 95:10,570-10,575. Thus, for targeted double-stranded DNA cleavage using zinc finger-Fok I fusions, two fusion proteins, each comprising a FokI enzymatic domain, can be used to reconstitute a catalytically active cleavage domain. Alternatively, a single polypeptide molecule containing a zinc finger binding domain and two FokI enzymatic domains can also be used. Exemplary ZFPs comprising FokI enzymatic domains are described in U.S. Pat. No. 9,782,437.

2. TALEN-Based Systems

TALEN-based systems comprise a protein comprising a TAL effector DNA binding domain and an enzymatic domain. They are made by fusing a TAL effector DNA-binding domain to a DNA cleavage domain (a nuclease which cuts DNA strands). The FokI restriction enzyme described above is an exemplary enzymatic domain suitable for use in TALEN-based gene regulating systems.

TAL effectors are proteins that are secreted by *Xanthomonas* bacteria via their type III secretion system when they infect plants. The DNA binding domain contains a repeated, highly conserved, 33-34 amino acid sequence with divergent 12th and 13th amino acids. These two positions, referred to as the Repeat Variable Diresidue (RVD), are highly variable and strongly correlated with specific nucleotide recognition. Therefore, the TAL effector domains can be engineered to bind specific target DNA sequences by selecting a combination of repeat segments containing the appropriate RVDs. The nucleic acid specificity for RVD combinations is as follows: HD targets cytosine, NI targets adenine, NG targets thymine, and NN targets guanine (though, in some embodiments, NN can also bind adenine with lower specificity).

In some embodiments, the TAL effector domains bind to a target DNA sequence that is at least 90% identical to a target DNA sequence within a target locus of a target gene selected those listed in Table 1. In some embodiments, the TAL effector domains bind to a target DNA sequence that is at least 95%, 96%, 97%, 98%, or 99% identical to a target DNA sequence within a target locus of a target gene selected those listed in Table 1. In some embodiments, the TAL effector domains bind to a target DNA sequence that is 100% identical to a target DNA sequence within a target locus of a target gene selected those listed in Table 1.

Methods and compositions for assembling the TAL-effector repeats are known in the art. See e.g., Cermak et al, Nucleic Acids Research, 39:12, 2011, e82. Plasmids for constructions of the TAL-effector repeats are commercially available from Addgene.

In some embodiments, the gene-editing system is a combination gene-regulating system comprising a site-directed modifying polypeptide and a nucleic acid guide molecule. Herein, a "site-directed modifying polypeptide" refers to a polypeptide that binds to a nucleic acid guide molecule, is targeted to a target nucleic acid sequence, such as, for example, a DNA sequence, by the nucleic acid guide molecule to which it is bound, and modifies the target DNA sequence (e.g., cleavage, mutation, or methylation of target DNA). A site-directed modifying polypeptide comprises two portions, a portion that binds the nucleic acid guide and an activity portion. In some embodiments, a site-directed modifying polypeptide comprises an activity portion that exhibits site-directed enzymatic activity (e.g., DNA methylation, DNA cleavage, histone acetylation, histone methylation, etc.), wherein the site of enzymatic activity is determined by the guide nucleic acid.

The nucleic acid guide comprises two portions: a first portion that is complementary to, and capable of binding with, an endogenous target DNA sequence (referred to herein as a "DNA-binding segment"), and a second portion that is capable of interacting with the site-directed modifying polypeptide (referred to herein as a "protein-binding segment"). In some embodiments, the DNA-binding segment and protein-binding segment of a nucleic acid guide are comprised within a single polynucleotide molecule. In some embodiments, the DNA-binding segment and protein-binding segment of a nucleic acid guide are each comprised within separate polynucleotide molecules, such that the nucleic acid guide comprises two polynucleotide molecules that associate with each other to form the functional guide.

The nucleic acid guide mediates the target specificity of the combined protein/nucleic gene regulating systems by specifically hybridizing with a target DNA sequence comprised within the DNA sequence of a target gene. Reference herein to a target gene encompasses the full-length DNA sequence for that particular gene and a full-length DNA sequence for a particular target gene will comprise a plurality of target genetic loci, which refer to portions of a particular target gene sequence (e.g., an exon or an intron). Within each target genetic loci are shorter stretches of DNA sequences referred to herein as "target DNA sequences" or "target sequences" that can be modified by the gene-regulating systems described herein. Further, each target genetic loci comprises a "target modification site," which refers to the precise location of the modification induced by the gene-regulating system (e.g., the location of an insertion, a deletion, or mutation, the location of a DNA break, or the location of an epigenetic modification). The gene-regulating systems described herein may comprise a single nucleic acid guide, or may comprise a plurality of nucleic acid guides (e.g., 2, 3, 4, 5, 6, 7, 8, 9, 10, or more nucleic acid guides).

The CRISPR/Cas systems described below are exemplary embodiments of a combination protein/nucleic acid system.

3. CRISPR/Cas Gene Regulating Systems

In some embodiments, the gene editing systems described herein are CRISPR (Clustered Regularly Interspaced Short Palindromic Repeats)/Cas (CRISPR Associated) nuclease systems. In such embodiments, the site-directed modifying polypeptide is a CRISPR-associated endonuclease (a "Cas "endonuclease) and the nucleic acid guide molecule is a guide RNA (gRNA).

A Cas polypeptide refers to a polypeptide that can interact with a gRNA molecule and, in concert with the gRNA molecule, homes or localizes to a target DNA sequence and includes naturally occurring Cas proteins and engineered, altered, or otherwise modified Cas proteins that differ by one or more amino acid residues from a naturally-occurring Cas sequence.

In some embodiments, the Cas protein is a Cas9 protein. Cas9 is a multi-domain enzyme that uses an HNH nuclease domain to cleave the target strand of DNA and a RuvC-like domain to cleave the non-target strand. In some embodiments, mutants of Cas9 can be generated by selective domain inactivation enabling the conversion of WT Cas9 into an enzymatically inactive mutant (e.g., dCas9), which is unable to cleave DNA, or a nickase mutant, which is able to produce single-stranded DNA breaks by cleaving one or the other of the target or non-target strand.

A guide RNA (gRNA) comprises two segments, a DNA-binding segment and a protein-binding segment. In some embodiments, the protein-binding segment of a gRNA is comprised in one RNA molecule and the DNA-binding segment is comprised in another separate RNA molecule. Such embodiments are referred to herein as "double-molecule gRNAs" or "two-molecule gRNA" or "dual gRNAs." In some embodiments, the gRNA is a single RNA molecule and is referred to herein as a "single-guide RNA" or an "sgRNA." The term "guide RNA" or "gRNA" is inclusive, referring both to two-molecule guide RNAs and sgRNAs.

The protein-binding segment of a gRNA comprises, in part, two complementary stretches of nucleotides that hybridize to one another to form a double stranded RNA duplex (dsRNA duplex), which facilitates binding to the Cas protein.

The DNA-binding segment (or "DNA-binding sequence") of a gRNA comprises a nucleotide sequence that is complementary to and capable of binding to a specific sequence target DNA sequence. The protein-binding segment of the gRNA interacts with a Cas polypeptide and the interaction of the gRNA molecule and site-directed modifying polypeptide results in Cas binding to the endogenous DNA and produces one or more modifications within or around the target DNA sequence. The precise location of the target modification site is determined by both (i) base-pairing complementarity between the gRNA and the target DNA sequence; and (ii) the location of a short motif, referred to as the protospacer adjacent motif (PAM), in the target DNA sequence. The PAM sequence is required for Cas binding to the target DNA sequence. A variety of PAM sequences are known in the art and are suitable for use with a particular Cas endonuclease (e.g., a Cas9 endonuclease) are known in the art (See e.g., Nat Methods. 2013 November; 10(11): 1116-1121 and Sci Rep. 2014; 4:5405). In some embodiments, the PAM sequence is located within 50 base pairs of the target modification site. In some embodiments, the PAM sequence is located within 10 base pairs of the target modification site. The DNA sequences that can be targeted by this method are limited only by the relative distance of the PAM sequence to the target modification site and the presence of a unique 20 base pair sequence to mediate sequence-specific, gRNA-mediated Cas binding. In some embodiments, the target modification site is located at the 5' terminus of the target locus. In some embodiments, the target modification site is located at the 3' end of the target locus. In some embodiments, the target modification site is located within an intron or an exon of the target locus.

In some embodiments, the present disclosure provides a polynucleotide encoding a gRNA. In some embodiments, a gRNA-encoding nucleic acid is comprised in an expression vector, e.g., a recombinant expression vector. In some embodiments, the present disclosure provides a polynucleotide encoding a site-directed modifying polypeptide. In some embodiments, the polynucleotide encoding a site-directed modifying polypeptide is comprised in an expression vector, e.g., a recombinant expression vector.

a. Cas Proteins

In some embodiments, the site-directed modifying polypeptide is a Cas protein. Cas molecules of a variety of species can be used in the methods and compositions described herein, including Cas molecules derived from *S. pyogenes, S. aureus, N. meningitidis*, S. thermophiles, *Acidovorax avenae, Actinobacillus pleuropneumoniae, Actinobacillus succinogenes, Actinobacillus suis, Actinomyces* sp., Cycliphilusdenitrificans, *Aminomonas paucivorans, Bacillus cereus, Bacillus smithii, Bacillus thuringiensis, Bacteroides* sp., *Blastopirellula marina, Bradyrhizobium* sp., *Brevibacillus laterospoxus, Campylobacter coli, Campylobacter jejuni, Campylobacter lari, Candidatus puniceispirillum, Clostridium cellulolyticum, Clostridium perfringens, Corynebacterium accolens, Corynebacterium diphtheria, Corynebacterium matruchotii, Dinoroseobacter shibae, Eubacterium dolichum*, Gammaproteobacterium, *Gluconacetobacter diazotrophicus, Haemophilus parainfluenzae, Haemophilus sputomm, Helicobacter canadensis, Helicobacter cinaedi, Helicobacter mustelae, Ilyobacter polytropus, Kingella kingae, Lactobacillus crispatus, Listeria ivanovii, Listeria monocytogenes, Listeriaceae bacterium, Methylocystis* sp., *Methylosinus trichosporium, Mobiluncus mulieris, Neisseria bacilliformis, Neisseria cinerea, Neisseria flavescens, Neisseria lactamica, Neisseria meningitidis, Neisseria* sp., *Neisseria wadsworthii, Nitrosomonas* sp., *Parvibaculum lavamentivorans, Pasteurella multocida, Phascolarctobacterium succinatutens, Ralstonia syzygii, Rhodopseudomonas palustris, Rhodovulum* sp., *Simonsiella muelleri, Sphingomonas* sp., *Sporolactobacillus vineae, Staphylococcus aureus, Staphylococcus lugdunensis, Streptococcus* sp., *Subdoligranulum* sp., *Tistrella mobilis, Treponema* sp., or *Verminephrobacter eiseniae*.

In some embodiments, the Cas protein is a Cas9 protein or a Cas9 ortholog and is selected from the group consisting of SpCas9, SpCas9-HF1, SpCas9-HF2, SpCas9-HF3, SpCas9-HF4, SaCas9, FnCpf, FnCas9, eSpCas9, and NmeCas9. In some embodiments, the endonuclease is selected from the group consisting of C2C1, C2C3, Cpf1 (also referred to as Cas12a), CasI, CasIB, Cas2, Cas3, Cas4, Cas5, Cas6, Cas7, Cas8, Cas9 (also known as Csn1 and Csx12), Cas10, Csy1, Csy2, Csy3, Cse1, Cse2, CscI, Csc2, Csa5, Csn2, Csm2, Csm3, Csm4, Csm5, Csm6, CmrI, Cmr3, Cmr4, Cmr5, Cmr6, CsbI, Csb2, Csb3, Csx17, Csx14, Csx10, Csx16, CsaX, Csx3, Csx1, Csx15, Csf1, Csf2, Csf3, and Csf4. Additional Cas9 orthologs are described in International PCT Publication No. WO 2015/071474.

In some embodiments, the Cas9 protein is a naturally-occurring Cas9 protein. Exemplary naturally occurring Cas9 molecules are described in Chylinski et al., RNA Biology 2013 10:5, 727-737. Such Cas9 molecules include Cas9 molecules of a cluster 1 bacterial family, cluster 2 bacterial family, cluster 3 bacterial family, cluster 4 bacterial family, cluster 5 bacterial family, cluster 6 bacterial family, a cluster 7 bacterial family, a cluster 8 bacterial family, a cluster 9 bacterial family, a cluster 10 bacterial family, a cluster 11 bacterial family, a cluster 12 bacterial family, a cluster 13 bacterial family, a cluster 14 bacterial family, a cluster 15 bacterial family, a cluster 16 bacterial family, a cluster 17 bacterial family, a cluster 18 bacterial family, a cluster 19 bacterial family, a cluster 20 bacterial family, a cluster 21 bacterial family, a cluster 22 bacterial family, a cluster 23 bacterial family, a cluster 24 bacterial family, a cluster 25 bacterial family, a cluster 26 bacterial family, a cluster 27 bacterial family, a cluster 28 bacterial family, a cluster 29 bacterial family, a cluster 30 bacterial family, a cluster 31 bacterial family, a cluster 32 bacterial family, a cluster 33 bacterial family, a cluster 34 bacterial family, a cluster 35 bacterial family, a cluster 36 bacterial family, a cluster 37 bacterial family, a cluster 38 bacterial family, a cluster 39 bacterial family, a cluster 40 bacterial family, a cluster 41 bacterial family, a cluster 42 bacterial family, a cluster 43 bacterial family, a cluster 44 bacterial family, a cluster 45 bacterial family, a cluster 46 bacterial family, a cluster 47 bacterial family, a cluster 48 bacterial family, a cluster 49 bacterial family, a cluster 50 bacterial family, a cluster 51 bacterial family, a cluster 52 bacterial family, a cluster 53 bacterial family, a cluster 54 bacterial family, a cluster 55 bacterial family, a cluster 56 bacterial family, a cluster 57 bacterial family, a cluster 58 bacterial family, a cluster 59 bacterial family, a cluster 60 bacterial family, a cluster 61 bacterial family, a cluster 62 bacterial family, a cluster 63 bacterial family, a cluster 64 bacterial family, a cluster 65 bacterial family, a cluster 66 bacterial family, a cluster 67 bacterial family, a cluster 68 bacterial family, a cluster 69 bacterial family, a cluster 70 bacterial family, a cluster 71 bacterial family, a cluster 72 bacterial family, a cluster 73 bacterial family, a cluster 74 bacterial family, a cluster 75 bacterial family, a cluster 76 bacterial family, a cluster 77 bacterial family, or a cluster 78 bacterial family.

In some embodiments, a Cas9 protein comprises an amino acid sequence having at least 60%, 65%, 70%, 75%, 80%, 85%, 90%, 95%, 96%, 97%, 98%, 99%, or 100% sequence identity to a Cas9 amino acid sequence described in Chylinski et al., RNA Biology 2013 10:5, 727-737; Hou et al., PNAS Early Edition 2013, 1-6).

In some embodiments, a Cas polypeptide comprises one or more of the following activities:

a) a nickase activity, i.e., the ability to cleave a single strand, e.g., the non-complementary strand or the complementary strand, of a nucleic acid molecule;
b) a double stranded nuclease activity, i.e., the ability to cleave both strands of a double stranded nucleic acid and create a double stranded break, which in an embodiment is the presence of two nickase activities;
c) an endonuclease activity;
d) an exonuclease activity; and/or
e) a helicase activity, i.e., the ability to unwind the helical structure of a double stranded nucleic acid.

In some embodiments, the Cas9 is a wildtype (WT) Cas9 protein or ortholog. WT Cas9 comprises two catalytically active domains (HNH and RuvC). Binding of WT Cas9 to DNA based on gRNA specificity results in double-stranded DNA breaks that can be repaired by non-homologous end joining (NHEJ) or homology-directed repair (HDR). In some embodiments, Cas9 is fused to heterologous proteins that recruit DNA-damage signaling proteins, exonucleases, or phosphatases to further increase the likelihood or the rate of repair of the target sequence by one repair mechanism or another. In some embodiments, a WT Cas9 is co-expressed with a nucleic acid repair template to facilitate the incorporation of an exogenous nucleic acid sequence by homology-directed repair.

In some embodiments, different Cas9 proteins (i.e., Cas9 proteins from various species) may be advantageous to use in the various provided methods in order to capitalize on various enzymatic characteristics of the different Cas9 proteins (e.g., for different PAM sequence preferences; for increased or decreased enzymatic activity; for an increased or decreased level of cellular toxicity; to change the balance between NHEJ, homology-directed repair, single strand breaks, double strand breaks, etc.).

In some embodiments, the Cas protein is a Cas9 protein derived from *S. pyogenes* and recognizes the PAM sequence motif NGG, NAG, NGA (Mali et al, Science 2013; 339 (6121): 823-826). In some embodiments, the Cas protein is a Cas9 protein derived from S. thermophiles and recognizes the PAM sequence motif NGGNG and/or NNAGAAW (W=A or T) (See, e.g., Horvath et al, Science, 2010; 327 (5962): 167-170, and Deveau et al, J BACTERIOL 2008; 190 (4): 1390-1400). In some embodiments, the Cas protein is a Cas9 protein derived from *S. mutans* and recognizes the PAM sequence motif NGG and/or NAAR (R=A or G) (See, e.g., Deveau et al, J BACTERIOL 2008; 190 (4): 1390-1400). In some embodiments, the Cas protein is a Cas9 protein derived from *S. aureus* and recognizes the PAM sequence motif NNGRR (R=A or G). In some embodiments, the Cas protein is a Cas9 protein derived from *S. aureus* and recognizes the PAM sequence motif N GRRT (R=A or G). In some embodiments, the Cas protein is a Cas9 protein derived from *S. aureus* and recognizes the PAM sequence motif N GRRV (R=A or G). In some embodiments, the Cas protein is a Cas9 protein derived from *N. meningitidis* and recognizes the PAM sequence motif N GATT or N GCTT (R=A or G, V=A, G or C) (See, e.g., Hou et ah, PNAS 2013, 1-6). In the aforementioned embodiments, N can be any nucleotide residue, e.g., any of A, G, C or T.

In some embodiments, a polynucleotide encoding a Cas protein is provided. In some embodiments, the polynucleotide encodes a Cas protein that is at least 90% identical to a Cas protein described in International PCT Publication No. WO 2015/071474 or Chylinski et al., RNA Biology 2013 10:5, 727-737. In some embodiments, the polynucleotide encodes a Cas protein that is at least 95%, 96%, 97%, 98%, or 99% identical to a Cas protein described in International PCT Publication No. WO 2015/071474 or Chylinski et al., RNA Biology 2013 10:5, 727-737. In some embodiments, the polynucleotide encodes a Cas protein that is 100% identical to a Cas protein described in International PCT Publication No. WO 2015/071474 or Chylinski et al., RNA Biology 2013 10:5, 727-737.

i. Cas Mutants

In some embodiments, the Cas polypeptides are engineered to alter one or more properties of the Cas polypeptide. For example, in some embodiments, the Cas polypeptide comprises altered enzymatic properties, e.g., altered nuclease activity, (as compared with a naturally occurring or other reference Cas molecule) or altered helicase activity. In some embodiments, an engineered Cas polypeptide can have an alteration that alters its size, e.g., a deletion of amino acid sequence that reduces its size without significant effect on another property of the Cas polypeptide. In some embodiments, an engineered Cas polypeptide comprises an alteration that affects PAM recognition. For example, an engineered Cas polypeptide can be altered to recognize a PAM sequence other than the PAM sequence recognized by the corresponding wild-type Cas protein.

Cas polypeptides with desired properties can be made in a number of ways, including alteration of a naturally occurring Cas polypeptide or parental Cas polypeptide, to provide a mutant or altered Cas polypeptide having a desired property. For example, one or more mutations can be introduced into the sequence of a parental Cas polypeptide (e.g., a naturally occurring or engineered Cas polypeptide). Such mutations and differences may comprise substitutions (e.g., conservative substitutions or substitutions of non-essential amino acids); insertions; or deletions. In some embodiments, a mutant Cas polypeptide comprises one or more mutations (e.g., at least 1, 2, 3, 4, 5, 10, 15, 20, 30, 40 or 50 mutations) relative to a parental Cas polypeptide.

In an embodiment, a mutant Cas polypeptide comprises a cleavage property that differs from a naturally occurring Cas polypeptide. In some embodiments, the Cas is a Cas nickase mutant. Cas nickase mutants comprise only one catalytically active domain (either the HNH domain or the RuvC domain). The Cas nickase mutants retain DNA binding based on gRNA specificity, but are capable of cutting only one strand of DNA resulting in a single-strand break (e.g. a "nick"). In some embodiments, two complementary Cas nickase mutants (e.g., one Cas nickase mutant with an inactivated RuvC domain, and one Cas nickase mutant with an inactivated HNH domain) are expressed in the same cell with two gRNAs corresponding to two respective target sequences; one target sequence on the sense DNA strand, and one on the antisense DNA strand. This dual-nickase system results in staggered double stranded breaks and can increase target specificity, as it is unlikely that two off-target nicks will be generated close enough to generate a double stranded break. In some embodiments, a Cas nickase mutant is co-expressed with a nucleic acid repair template to facilitate the incorporation of an exogenous nucleic acid sequence by homology-directed repair.

In some embodiments, the Cas polypeptides described herein can be engineered to alter the PAM specificity of the Cas polypeptide. In some embodiments, a mutant Cas polypeptide has a PAM specificity that is different from the PAM specificity of the parental Cas polypeptide. For example, a naturally occurring Cas protein can be modified to alter the PAM sequence that the mutant Cas polypeptide recognizes to decrease off target sites, improve specificity, or eliminate a PAM recognition requirement. In some embodiments, a Cas protein can be modified to increase the length of the PAM recognition sequence. In some embodiments, the length of the PAM recognition sequence is at least 4, 5, 6, 7, 8, 9, 10 or 15 amino acids in length. Cas polypeptides that recognize different PAM sequences and/or have reduced off-target activity can be generated using directed evolution. Exemplary methods and systems that can be used for directed evolution of Cas polypeptides are described, e.g., in Esvelt et al. Nature 2011, 472 (7344): 499-503.

Exemplary Cas mutants are described in International PCT Publication No. WO 2015/161276, which is incorporated herein by reference in its entirety.

2. gRNAs

The present disclosure provides guide RNAs (gRNAs) that direct a site-directed modifying polypeptide to a specific target DNA sequence. A gRNA comprises a DNA-targeting segment and protein-binding segment. The DNA-targeting segment of a gRNA comprises a nucleotide sequence that is complementary to a sequence in the target DNA sequence. As such, the DNA-targeting segment of a gRNA interacts with a target DNA in a sequence-specific manner via hybridization (i.e., base pairing), and the nucleotide sequence of the DNA-targeting segment determines the location within the target DNA that the gRNA will bind. The DNA-targeting segment of a gRNA can be modified (e.g., by genetic engineering) to hybridize to any desired sequence within a target DNA sequence.

The protein-binding segment of a guide RNA interacts with a site-directed modifying polypeptide (e.g. a Cas9 protein) to form a complex. The guide RNA guides the bound polypeptide to a specific nucleotide sequence within target DNA via the above-described DNA-targeting segment. The protein-binding segment of a guide RNA comprises two stretches of nucleotides that are complementary to one another and which form a double stranded RNA duplex.

In some embodiments, a gRNA comprises two separate RNA molecules. In such embodiments, each of the two RNA molecules comprises a stretch of nucleotides that are complementary to one another such that the complementary nucleotides of the two RNA molecules hybridize to form the double-stranded RNA duplex of the protein-binding segment. In some embodiments, a gRNA comprises a single RNA molecule (sgRNA).

The specificity of a gRNA for a target loci is mediated by the sequence of the DNA-binding segment, which comprises about 20 nucleotides that are complementary to a target DNA sequence within the target locus. In some embodiments, the corresponding target DNA sequence is approximately 20 nucleotides in length. In some embodiments, the DNA-binding segments of the gRNA sequences of the present invention are at least 90% complementary to a target DNA sequence within a target locus. In some embodiments, the DNA-binding segments of the gRNA sequences of the present invention are at least 95%, 96%, 97%, 98%, or 99% complementary to a target DNA sequence within a target locus. In some embodiments, the DNA-binding segments of the gRNA sequences of the present invention are 100% complementary to a target DNA sequence within a target locus.

In some embodiments, the DNA-binding segments of the gRNA sequences bind to a target DNA sequence that is at least 90% identical to a target DNA sequence within a target locus of a target gene selected those listed in Table 1. In some embodiments, the DNA-binding segments of the gRNA sequences bind to a target DNA sequence that is at least 95%, 96%, 97%, 98%, or 99% identical to a target DNA sequence within a target locus of a target gene selected those listed in Table 1. In some embodiments, the DNA-binding segments of the gRNA sequences bind to a target DNA sequence that is 100% identical to a target DNA sequence within a target locus of a target gene selected those listed in Table 1.

In some embodiments, the DNA-binding segments of the gRNA sequences described herein are designed to minimize off-target binding using algorithms known in the art (e.g., Cas-OFF finder) to identify target sequences that are unique to a particular target locus or target gene.

In some embodiments, the gRNAs described herein can comprise one or more modified nucleosides or nucleotides which introduce stability toward nucleases. In such embodiments, these modified gRNAs may elicit a reduced innate immune as compared to a non-modified gRNA. The term "innate immune response" includes a cellular response to exogenous nucleic acids, including single stranded nucleic acids, generally of viral or bacterial origin, which involves the induction of cytokine expression and release, particularly the interferons, and cell death.

In some embodiments, the gRNAs described herein are modified at or near the 5' end (e.g., within 1-10, 1-5, or 1-2 nucleotides of their 5' end). In some embodiments, the 5' end of a gRNA is modified by the inclusion of a eukaryotic mRNA cap structure or cap analog (e.g., a G(5')ppp(5')G cap analog, a m7G(5')ppp(5')G cap analog, or a 3'-O-Me-m7G (5')ppp(5')G anti reverse cap analog (ARCA)). In some embodiments, an in vitro transcribed gRNA is modified by treatment with a phosphatase (e.g., calf intestinal alkaline phosphatase) to remove the 5' triphosphate group. In some embodiments, a gRNA comprises a modification at or near its 3' end (e.g., within 1-10, 1-5, or 1-2 nucleotides of its 3' end). For example, in some embodiments, the 3' end of a gRNA is modified by the addition of one or more (e.g., 25-200) adenine (A) residues.

In some embodiments, modified nucleosides and modified nucleotides can be present in a gRNA, but also may be present in other gene-regulating systems, e.g., mRNA, RNAi, or siRNA-based systems. In some embodiments, modified nucleosides and nucleotides can include one or more of:

a) alteration, e.g., replacement, of one or both of the non-linking phosphate oxygens and/or of one or more of the linking phosphate oxygens in the phosphodiester backbone linkage;
b) alteration, e.g., replacement, of a constituent of the ribose sugar, e.g., of the 2' hydroxyl on the ribose sugar;
c) wholesale replacement of the phosphate moiety with "dephospho" linkers;
d) modification or replacement of a naturally occurring nucleobase;
e) replacement or modification of the ribose-phosphate backbone;
f) modification of the 3' end or 5' end of the oligonucleotide, e.g., removal, modification or replacement of a terminal phosphate group or conjugation of a moiety; and
g) modification of the sugar.

In some embodiments, the modifications listed above can be combined to provide modified nucleosides and nucleotides that can have two, three, four, or more modifications. For example, in some embodiments, a modified nucleoside or nucleotide can have a modified sugar and a modified nucleobase. In some embodiments, every base of a gRNA is modified. In some embodiments, each of the phosphate groups of a gRNA molecule are replaced with phosphorothioate groups.

In some embodiments, a software tool can be used to optimize the choice of gRNA within a user's target sequence, e.g., to minimize total off-target activity across the genome. Off target activity may be other than cleavage. For example, for each possible gRNA choice using *S. pyogenes* Cas9, software tools can identify all potential off-target sequences (preceding either NAG or NGG PAMs) across the genome that contain up to a certain number (e.g., 1, 2, 3, 4, 5, 6, 7, 8, 9, or 10) of mismatched base-pairs. The cleavage efficiency at each off-target sequence can be predicted, e.g., using an experimentally-derived weighting scheme. Each possible gRNA can then be ranked according to its total predicted off-target cleavage; the top-ranked gRNAs represent those that are likely to have the greatest on-target and the least off-target cleavage. Other functions, e.g., automated reagent design for gRNA vector construction, primer design for the on-target Surveyor assay, and primer design for high-throughput detection and quantification of off-target cleavage via next-generation sequencing, can also be included in the tool.

The invention is further described in the following Examples, which do not limit the scope of the invention described in the claims.

EXAMPLES

Example 1

Evaluation of Parkin Transgene Variants

A series of plasmid vectors were generated to evaluate expression of Parkin transgene variants. The expression cassette (FIG. 1) contained, in 5' to 3' order, a CMV immediate early (IE) enhancer/promoter and 5' UTR, a Parkin transgene 2A-linked to enhanced green fluorescence protein (eGFP), a 3' UTR, and rabbit globin polyadenylation sequence (polyA). For the Parkin transgene, either the wild-type sequence of human PRKN (WT) or one of four codon optimized variants (CO1 to CO4) was tested. The sequences of the wild-type and codon-optimized Parkin transgenes are provided in SEQ ID NOs: 27, 35, 36, 37 and 38.

One consideration in design of codon-optimized CO1 to CO4 was the number of CpG sites. CpG islands are regions of DNA where a cytosine nucleotide is followed by a guanine nucleotide in the linear sequence of bases along its 5'→3' direction. CpG islands (which are typically defined as a polynucleotide sequence of at least 200 bp, a GC percentage greater than 50%, and an observed-to-expected CpG ratio greater than 60%) are known to be associated with vector immunogenicity. Therefore, it was expected that decreasing the number of CpG sites would improve vector performance by decreasing immunogenicity. The number of CpG sites (5'-C-G-3') in each Parkin codon variant is given in Table 9.

TABLE 9

CpG Sites in Exemplary Parkin Codon Variants

| Construct | Number of CpG Islands | SEQ ID NO: |
|---|---|---|
| Wild type (WT) | 95 | 27 |
| Construct 1 (CO1) | 0 | 35 |
| Construct 2 (CO2) | 0 | 36 |
| Construct 3 (CO3) | 0 | 37 |
| Construct 4 (CO4) | 10 | 38 |

SH-SY5Y cells. A human neuroblastoma cell line, SH-SY5Y, was used to evaluate gene expression in neuronal lineage cells. SH-SY5Y cells were cultured on 96-well plates at a seeding density of 10,000 cells per well. After 24 hours, the cells were transfected with 0.10 μg of WT, CO1, CO2, or CO3 plasmid complexed with 4 μL Fugene HD per μg plasmid. Cells were cultured for an additional 48 hours and then assayed for eGFP expression by fluorescence microscopy.

Figures 2A, 2B, 2C, 2D, 2E, 2F, 2G, 2H, 2I, 2J:
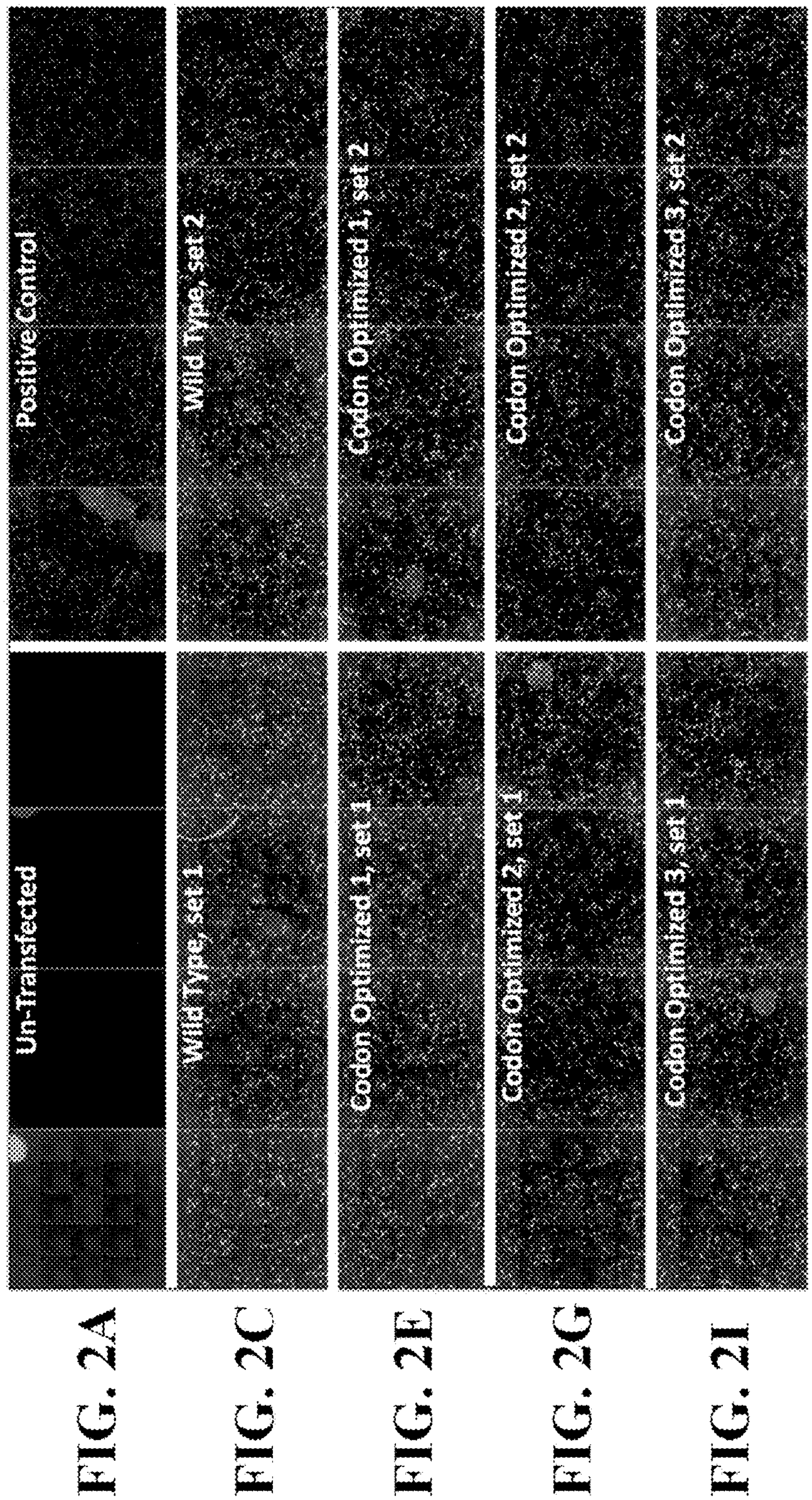
FIGS. 2A-2J show representative micrographs of gene expression in SH-SY5Y cells for untransfected negative control (FIG. 2A) and a positive control (FIG. 2B). Expression cassettes were tested in duplicate: WT (FIG. 2C and FIG. 2D), CO1 (FIG. 2E and FIG. 2F), CO2 (FIG. 2G and FIG. 2H), and CO3 (FIG. 2I and FIG. 2J).
Figure 2K:
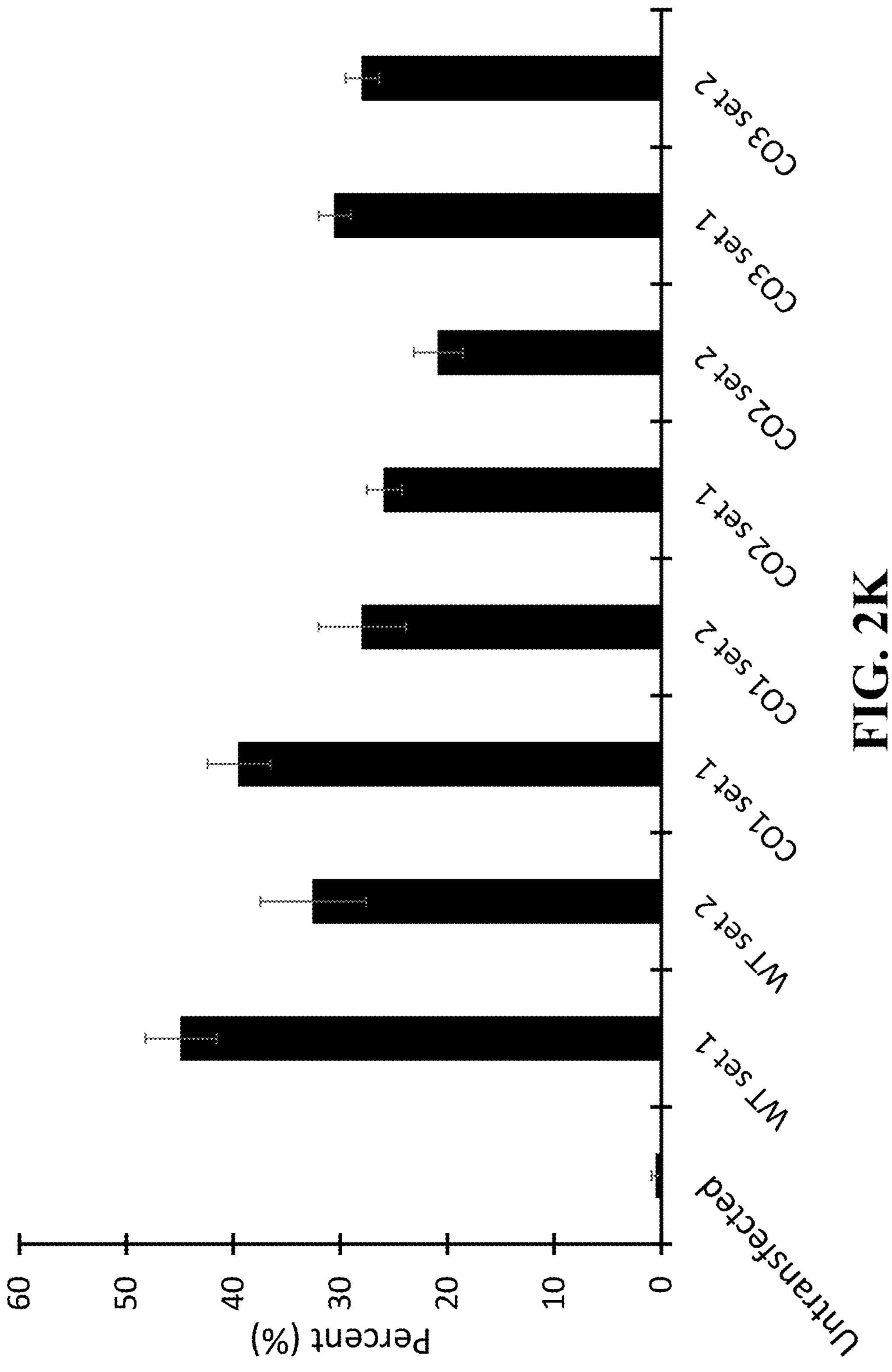
FIG. 2K shows the percentage of GFP+ cells.
Figure 2L:
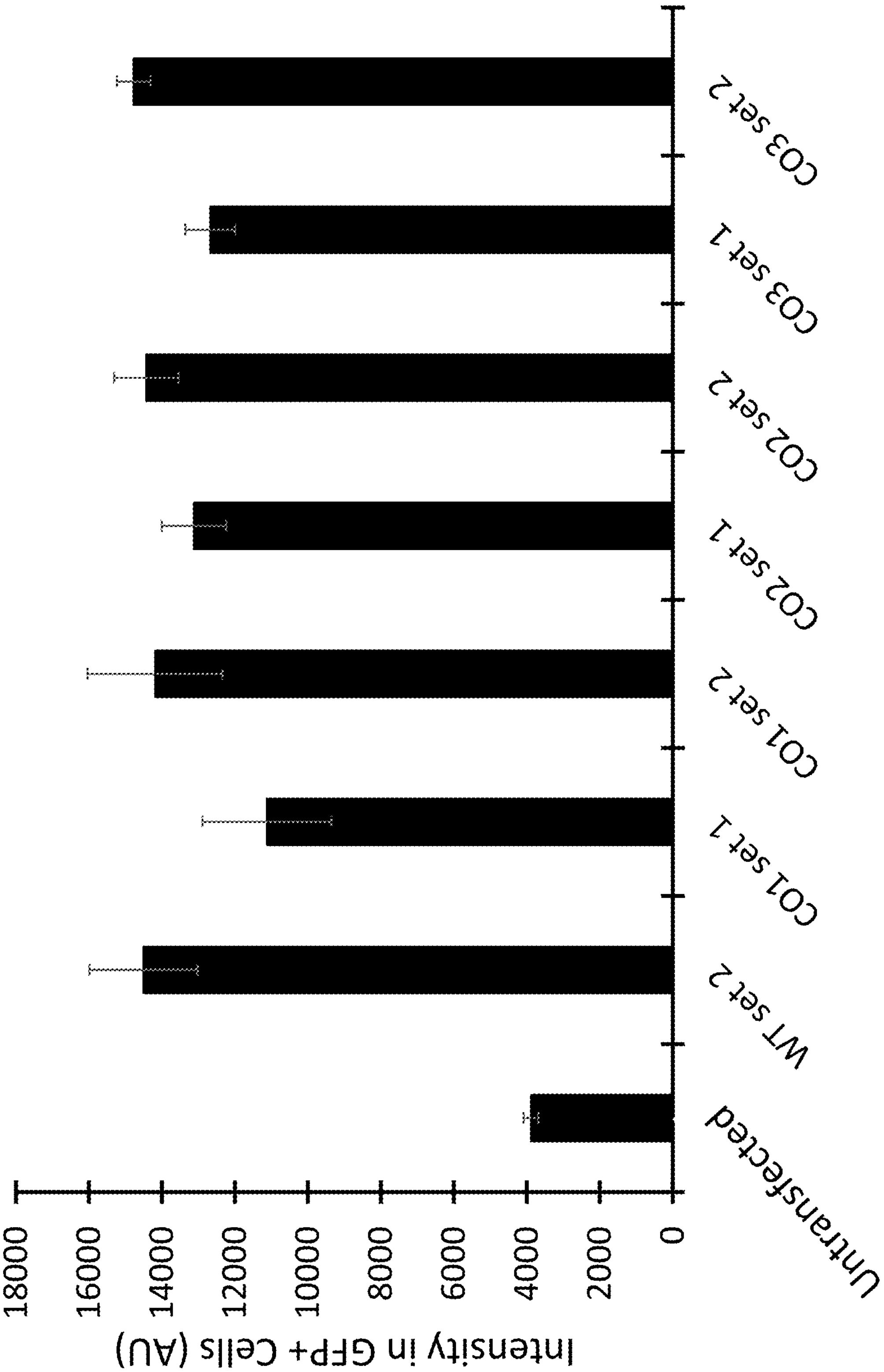
FIG. 2L shows the fluorescence intensity of GFP+ cells.
Figure 3:
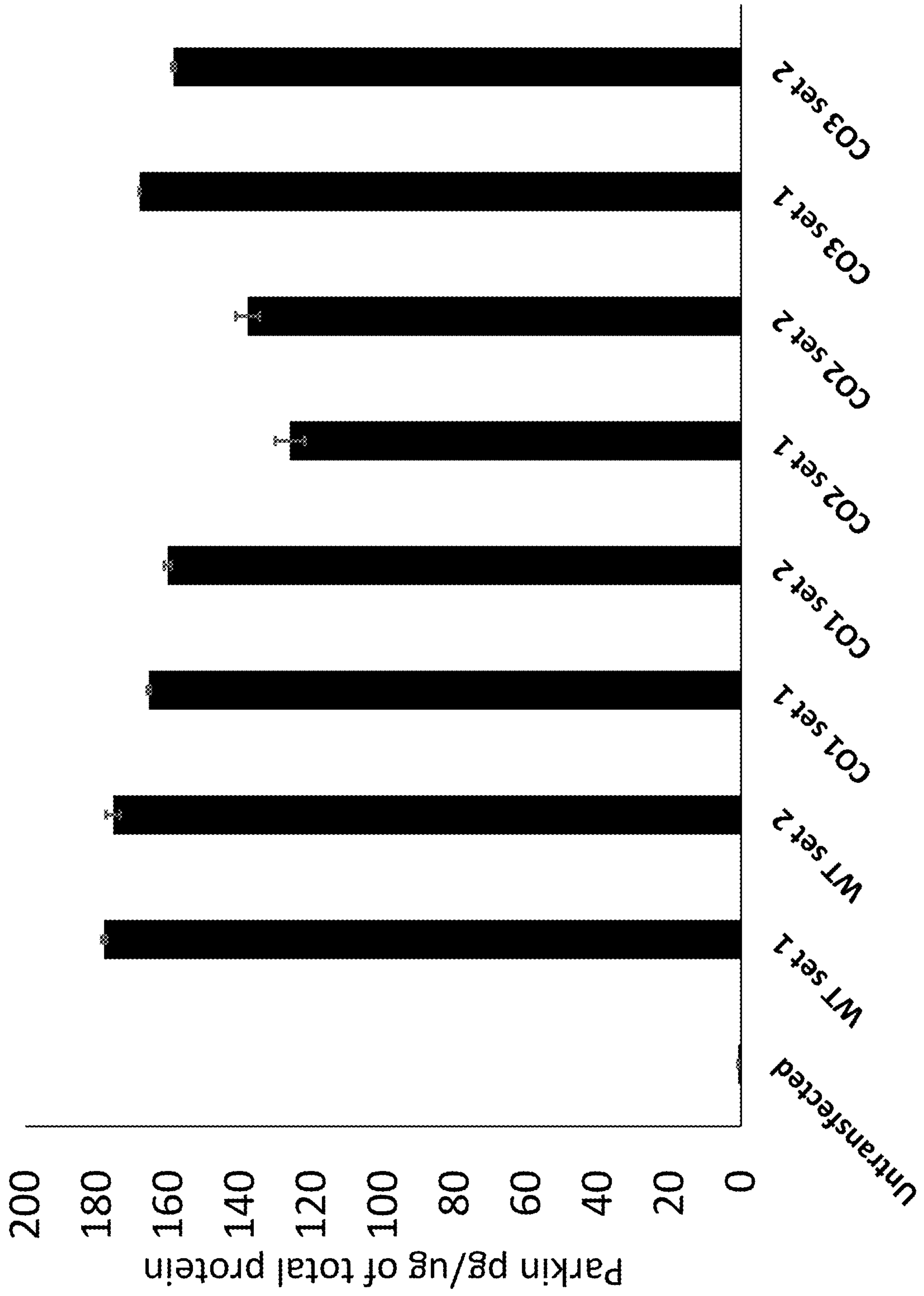
FIG. 3 shows an enzyme-linked immunosorbent assay (ELISA) for Parkin performed on cell lysates from transfected cells.

Representative micrographs are shown in FIGS. 2A-2J. Controls were untransfected cells as negative control (FIG. 2A) and a known plasmid as a positive control (FIG. 2B). Expression cassettes were tested in duplicate: WT (FIGS. 2C-2D), CO1 (FIGS. 2E-2F), CO2 (FIGS. 2G-2H), and CO3 (FIGS. 2I-2J). The percentage of GFP+ cell and the fluorescence intensity of GFP+ cells are plotted in FIG. 2H and FIG. 2K, respectively. Cell lysate was collected seven days after transfection and assayed by enzyme-linked immunosorbent assay (ELISA) for Parkin, as shown in FIG. 3. These experiments demonstrated that CO1 to CO3 did not increase Parkin expression and indeed decreased the percentage of cells that expressed Parkin and the overall level of Parkin expression.

Figures 4A, 4B, 4C, 4D:
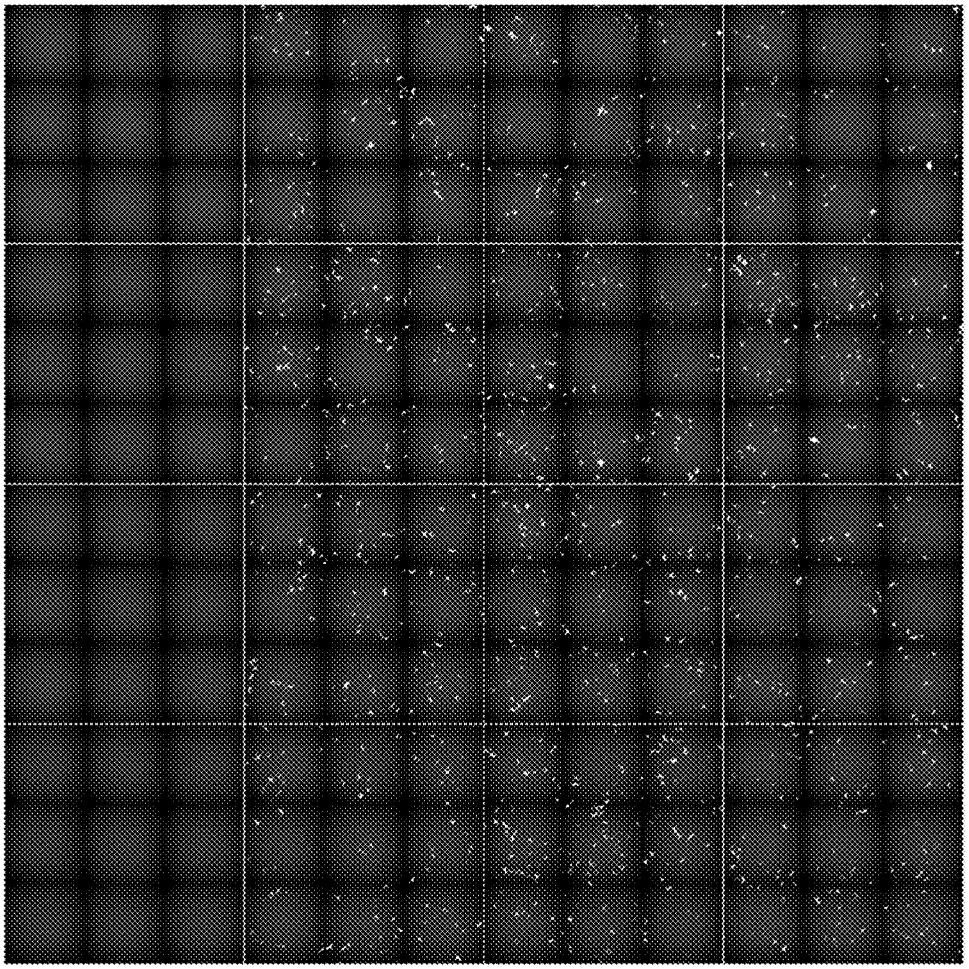
FIGS. 4A-4D show representative micrographs of gene expression in SH-SY5Y cells for untransfected negative control (FIG. 4A), WT (FIG. 4B), CO1 (FIG. 4C), or CO4 (FIG. 4D).
Figure 4E:
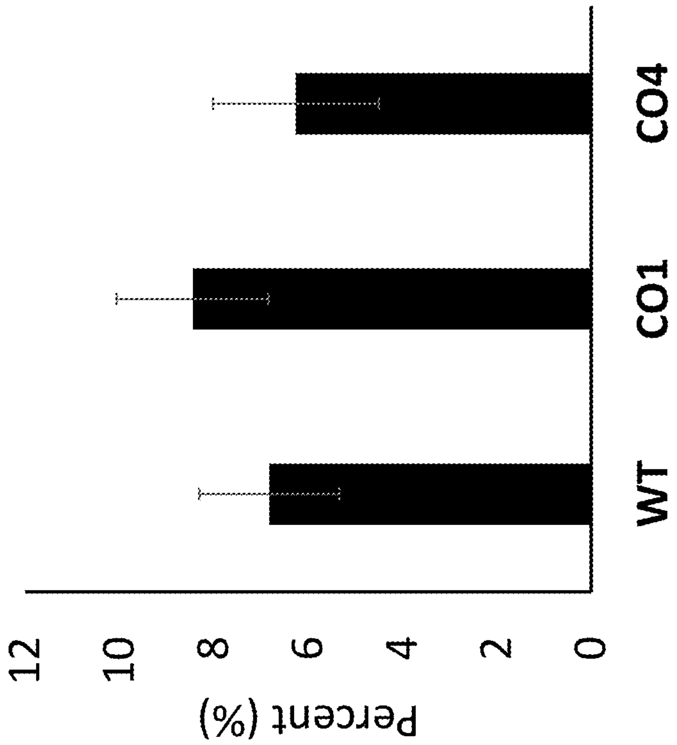
FIG. 4E shows the percentage of GFP+ cells.
Figure 4F:
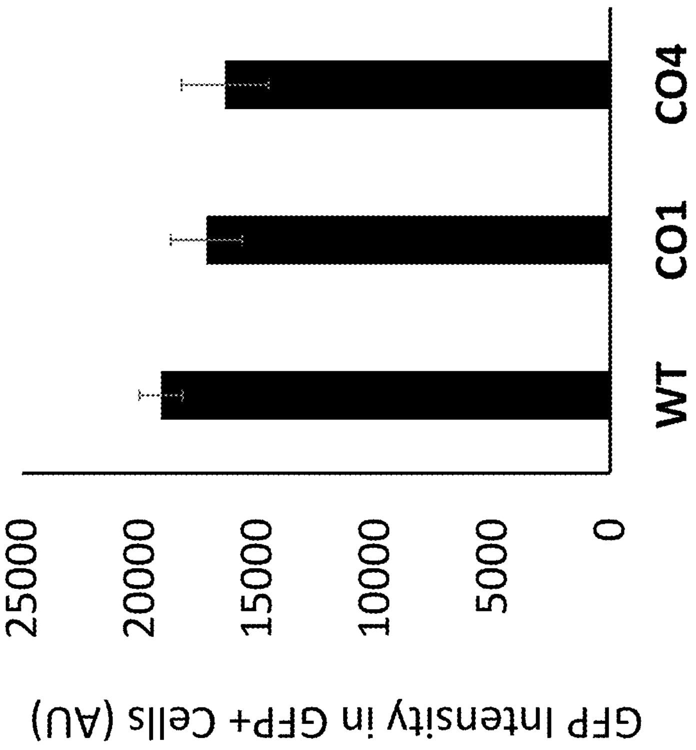
FIG. 4F shows and the fluorescence intensity of GFP+ cells.
Figure 5:
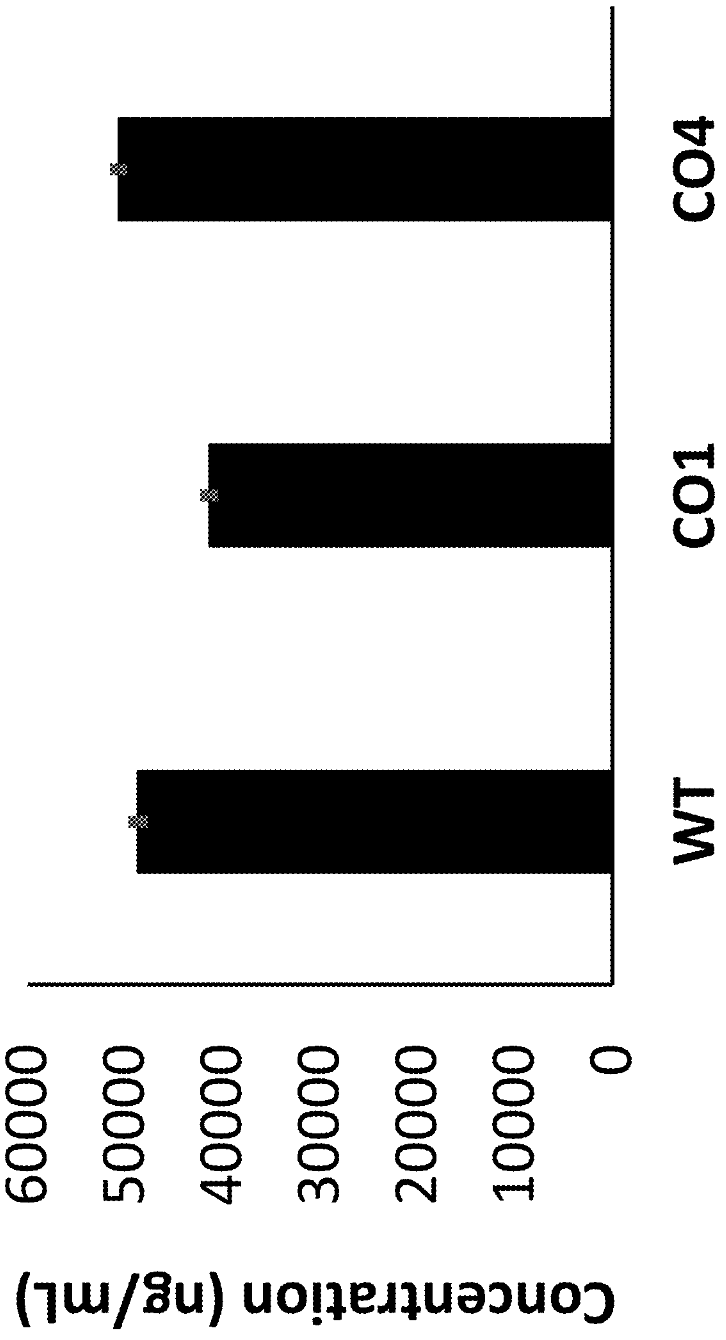
FIG. 5 shows an enzyme-linked immunosorbent assay (ELISA) for Parkin performed on cell lysates from transfected cells.
Figure 6A:
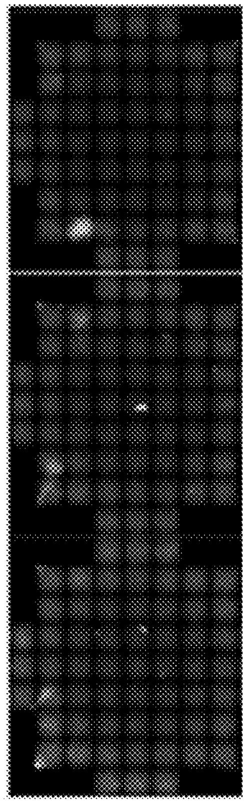
FIGS. 6A-6D show representative micrographs of gene expression in induced pluripotent stem cell (iPSC)-derived, Parkin knockout dopaminergic precursors cells for untransfected negative control (FIG. 6A), WT (FIG. 6B), CO1 (FIG. 6C), or CO4 (FIG. 6D).
Figure 6B:
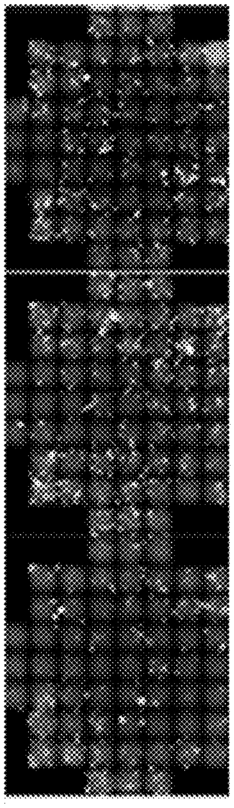
Figure 6C:
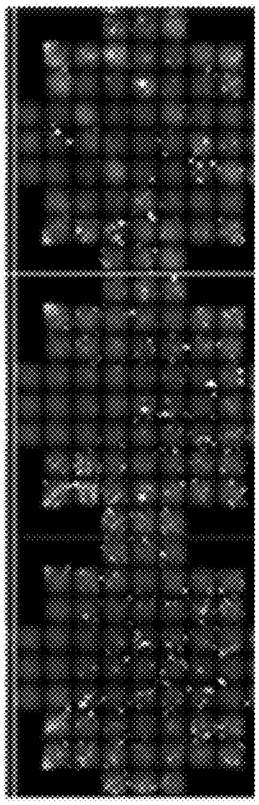
Figure 6D:
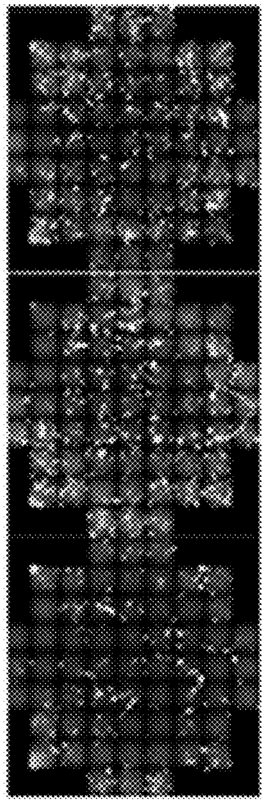
Figure 6E:
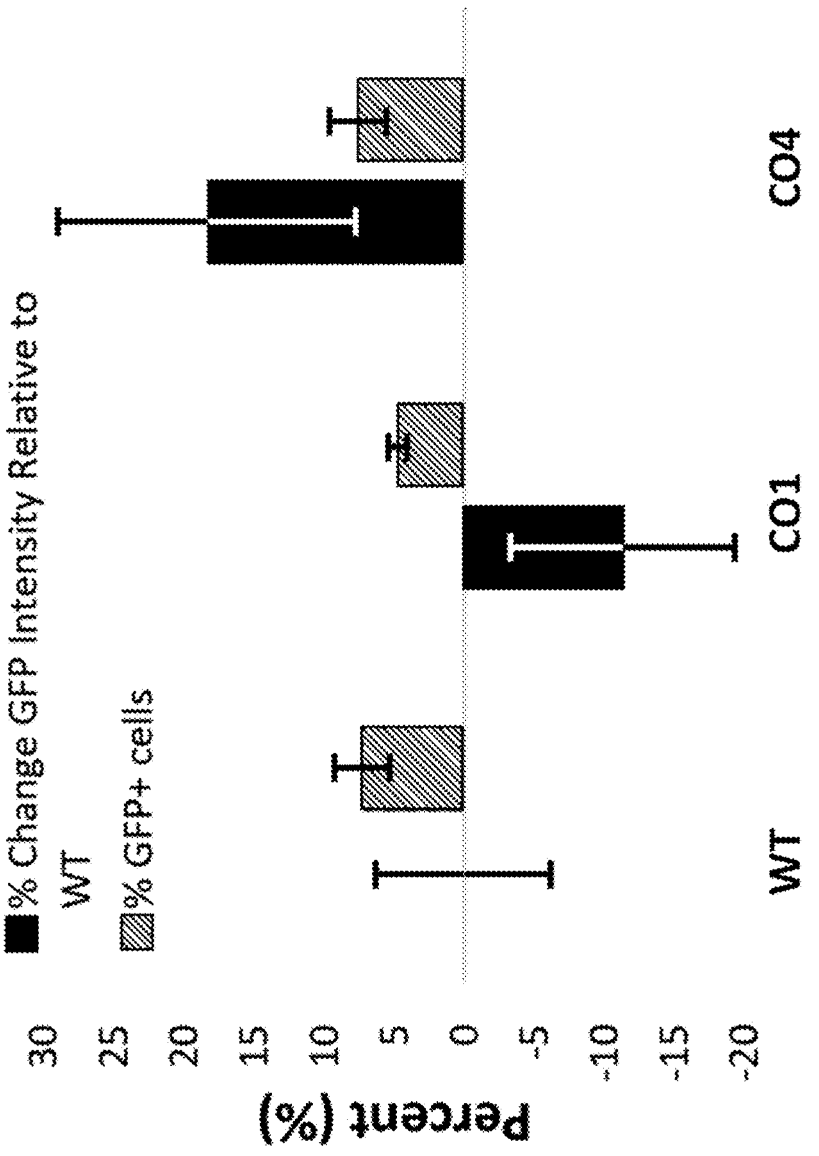
FIG. 6E shows the percentage of GFP+ cells and the fluorescence intensity of GFP+ cells. For each of WT, CO1, and CO$, the left bar indicates % change GFP intensity relative to WT, and the right bar indicates % GFP+ cells.

Codon variant CO4 was then tested against WT and CO1. Fluorescence micrographs of SH-SY5Y cells for untransfected negative control (FIG. 4A), WT (FIG. 4B), CO1 (FIG. 4C), or CO4 (FIG. 4D) are shown, and the results were quantitated for percent GFP+ (FIG. 4E) and intensity (FIG. 4F). Cell lysates were assayed for Parkin expression by ELISA (FIG. 5). In SH-SY5Y cells, CO4 expression was similar to WT and CO1.

iPSC-derived, Parkin knockout dopaminergic precursor cells. Human induced pluripotent stem cell (iPSC)-derived, Parkin knockout dopaminergic precursor cells were cultured in 96-well plates at a seeding density of 10,000 cells per well. After 7 days, the cells were transfected with 0.15 μg WT, CO1, and CO4 plasmid complexed with 4 μL ViaFect per μg plasmid). Transgene expression was evaluated 7 days after transfection in untransfected wells (FIG. 6A), WT (FIG. 6B), CO1 (FIG. 6C), or CO4 (FIG. 6D) wells. As shown in FIG. 6E, the three transgenes (WT, CO1, and CO4) resulted in similar percentages of GFP+ cells, but, surprisingly, CO4 caused a 20% increase in GFP intensity compared to WT.

Example 2

Selection of Cassette for Expression of CO4 Parkin Transgene

Figure 7:
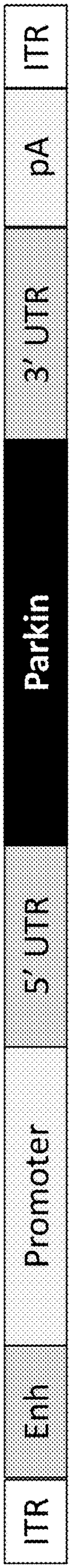
FIG. 7 shows an embodiment of the AAV vector expression cassettes of the disclosure.
Figure 8:
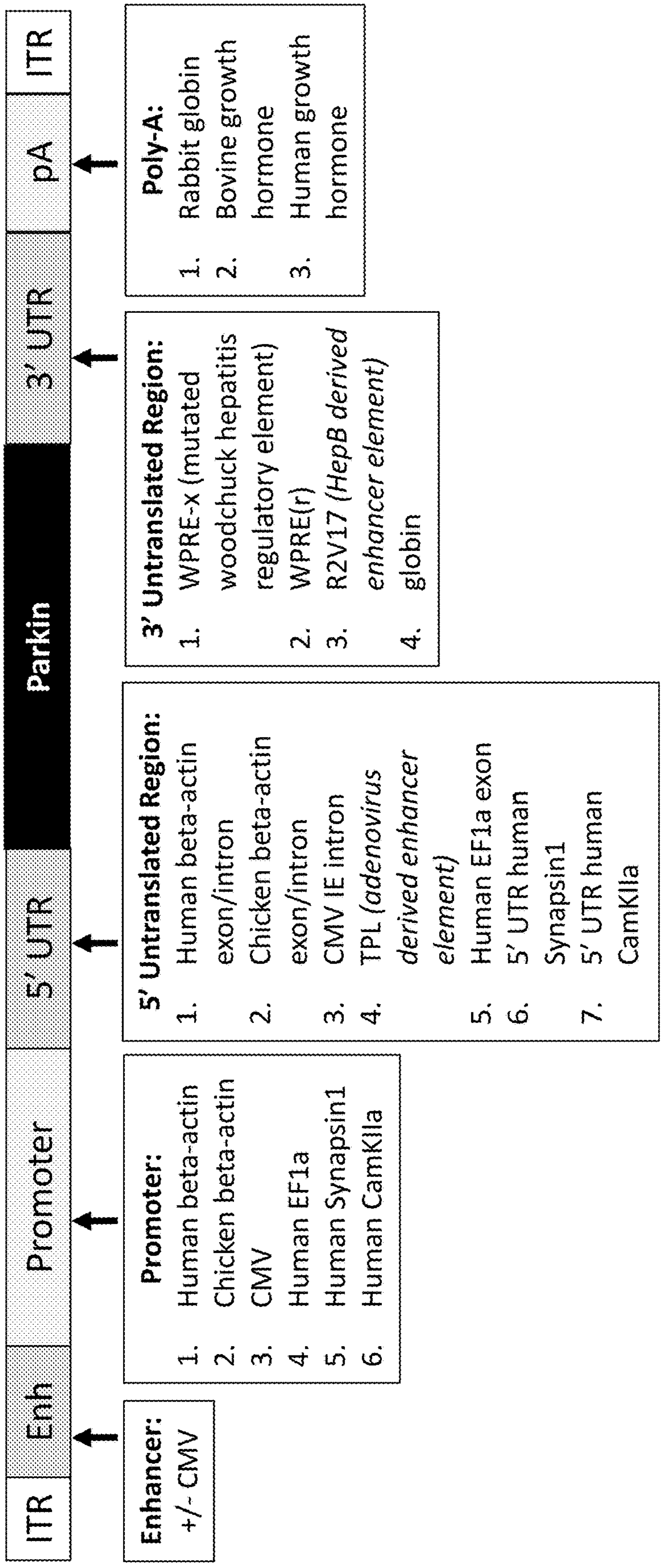
FIG. 8 shows a diagram of transgene cassettes and various elements thereof.

To evaluate other regulatory elements, a variety of AAV expression cassettes were constructed in the form of transfer plasmids for use in a helper-free AAV packaging system. The AAV expression cassettes (FIG. 7) contained, in 5' to 3' order, the 5' ITR of AAV2, the CMV enhancer (Enh) or no enhancer, a promoter selected from Table 5, a 5' untranslated region (UTR) selected from Table 6, the Parkin transgene variant CO4 (SEQ ID NO: 38), a 3' untranslated region selected from Table 7, a polyadenylation sequence (polyA) selected from Table 8, and the 3' ITR of AAV2. A diagram of the cassette and various elements is provided in FIG. 8. For detection of transgene expression in in vitro testing, a polynucleotide sequence (SEQ ID NO: 80) encoding an N-terminal FLAG/HA-tag (SEQ ID NO: 81) was inserted after the start codon on the Parkin transgene in each of the sequences listed in Table 10.

Figure 9:
FIG. 9 shows Parkin transgene expression in SH-SY5Y cells for each of the constructs listed in Table 10.

SH-SY5Y cells. SH-SY5Y cells were cultured on 24-well plates at a seeding density of 50,000 cells per well. After 24 hours, the cells were transfected with 0.75 μg of plasmid complexed with 4 μL Fugene6 per μg plasmid. Cells were cultured for an additional 48 hours, and Parkin expression was assayed by performing an ELISA on cell lysates with an anti-Parkin primary antibody. Results for each construct are shown in Table 10 and graphed in FIG. 9. Notably, protein expression was lower with the neuro-specific promoters (Syn and CaMKIIa).

TABLE 10

Figure 10:
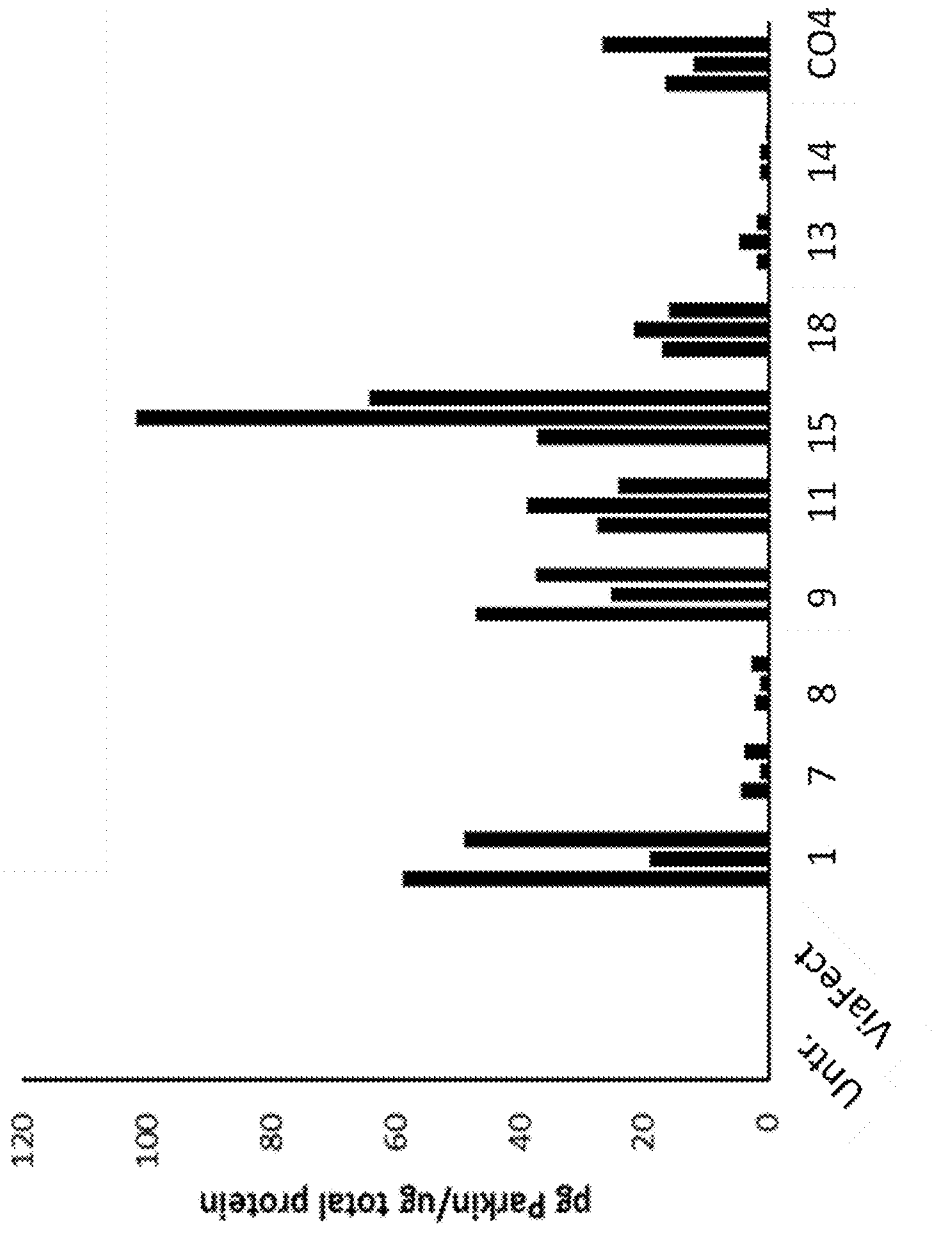
FIG. 10 shows Parkin transgene expression in iPSC-derived, Parkin knockout dopaminergic precursor cells for each of the constructs listed in Table 11.

| Expression of Parkin in SH-SY5Y Cells (Average of Replicates) | | | |
|---|---|---|---|
| No. | Promoter/5'UTR/3'UTR/polyA | Expression cassette SEQ ID NO: | pg Parkin per ug total protein |
| 1 | HuBA/WPRE(x)/pAGlobin-Oc | 39 | 931 |
| 2 | CMV/TPL-eMLP/WPRE(r)/pAGlobin-Oc | 40 | 207 |
| 3 | Syn/WPRE(r)/3'UTR(globin)/pAGH-Bt | 41 | 74 |
| 4 | CBA/pAGH-Bt | 42 | 200 |
| 5 | EF1α/pAGlobin-Oc | 43 | 221 |
| 6 | HuBA/R2V17/pAGH-Bt | 44 | 234 |
| 7 | Syn/WPRE(x)/3'UTR(globin)/pAGH-Hs | 45 | 58 |
| 8 | CaMKIIa/WPRE(r)/pAGH-Hs | 46 | 68 |
| 9 | CMV/TPL-eMLP/WPRE(r)/pAGH-Hs | 47 | 290 |
| 10 | HuBA/pAGH-Hs | 48 | 336 |
| 11 | CMV/TPL-eMPL/R2V17/3'UTR(globin)/pAGH-Bt | 49 | 365 |
| 12 | EF1α/WPRE(r)/pAGH-Bt | 50 | 251 |
| 13 | Syn/R2V17/pAGlobin-Oc | 51 | 40 |
| 14 | CaMKIIa/R2V17/pAGlobin-Oc | 52 | 38 |
| 15 | CBA/WPRE(x)/3'UTR(globin)/pAGH-Hs | 53 | 722 |
| 16 | CBA/3'UTR(globin)/pAGlobin-Oc | 54 | 533 |
| 17 | CaMKIIa/R2V17/pAGH-Bt | 55 | 46 |
| 18 | EF1a/R2V17/3'UTR(globin)/pAGH-Hs | 56 | 667 |
| 19 | CMV/R2V17/3'UTR(globin)/pAGH-Hs | 57 | 228 |
| 20 | CMV/pAGH-Hs | 58 | 191 |

iPSC-derived, Parkin knockout dopaminergic precursor cells. iPSC-derived, Parkin knockout dopaminergic precursors cells were cultured in 96-well plates at a seeding density of 10,000 cells per well. After 15 days, the cells were transfected with 0.15 μg plasmid complexed with 4 μL ViaFect per μg plasmid). Parkin expression was assayed 2 days after by performing an ELISA on cell lysates with an anti-Parkin primary antibody. Results for each construct are shown in Table 11 and graphed in FIG. 10 (three replicates shown for each construct).

TABLE 11

| Expression of Parkin in iPSC-derived Cells (Average of Replicates) | | | |
|---|---|---|---|
| No. | Promoter/5'UTR/3'UTR/polyA | Expression cassette SEQ ID NO: | Average pg Parkin per total ug protein |
| 1 | HuBA/WPRE(x)/pAGlobin-Oc | 39 | 58 |
| 7 | Syn/WPRE(x)/3'UTR(globin)/pAGH-Hs | 45 | 3.2 |
| 8 | CaMKIIa/WPRE(x)/pAGH-Hs | 46 | 2.1 |
| 9 | CMV/TPL-eMLP/WPRE(r)/pAGH-Hs | 47 | 34.7 |
| 11 | CMV/TPL-eMLP/R2V17/3'UTR(globin)/pAGH-Bt | 49 | 35.5 |
| 13 | Syn/R2V17/pAGlobin-Oc | 51 | 2.9 |
| 14 | CaMKIIa/R2V17/pAGlobin-Oc | 52 | 1.1 |
| 15 | CBA/WPRE(x)-3'UTR(globin)/pAGH-Hs | 53 | 70.9 |
| 18 | EF1α/R2V17/3'UTR(globin)/pAGH-Hs | 56 | 24.6 |

Figure 11A:
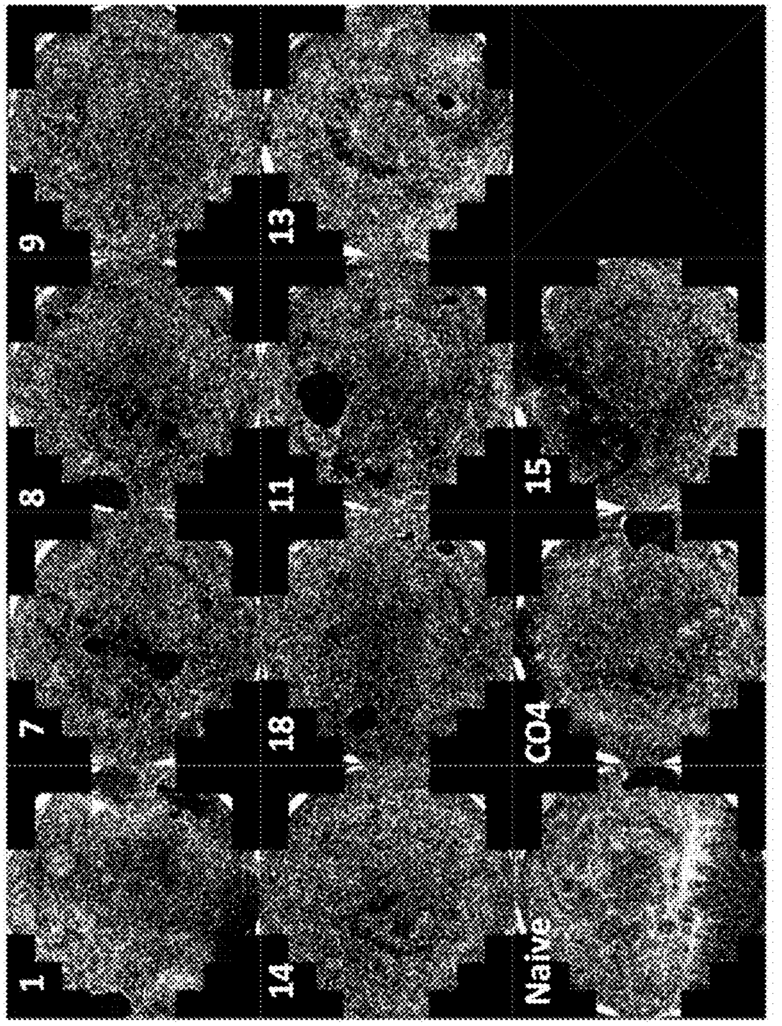
FIGS. 11A-11D show representative fluorescent micrographs for iPSC-derived, Parkin knockout dopaminergic precursor cells transfected with each of the constructs in Table 11 imaged in brightfield (FIG. 11A), or by immunofluorescence for Parkin (FIG. 11B), neuronal marker NeuN (FIG. 11C), or astrocyte marker GFAP (FIG. 11D)
Figure 11B:
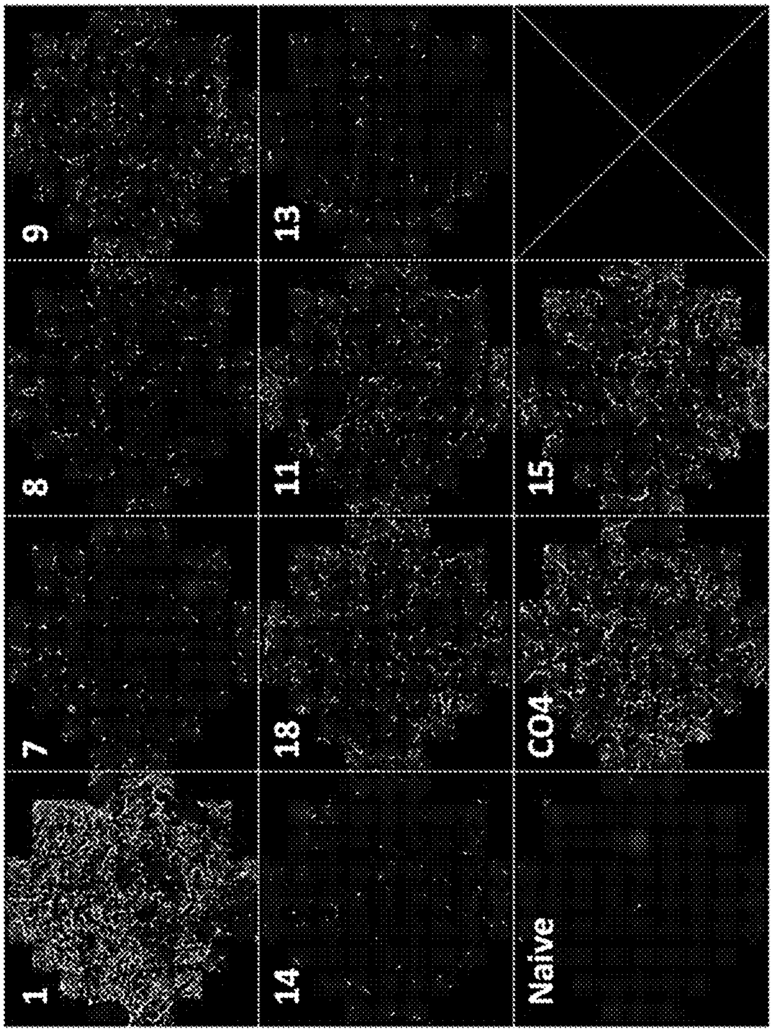
Figure 11C:
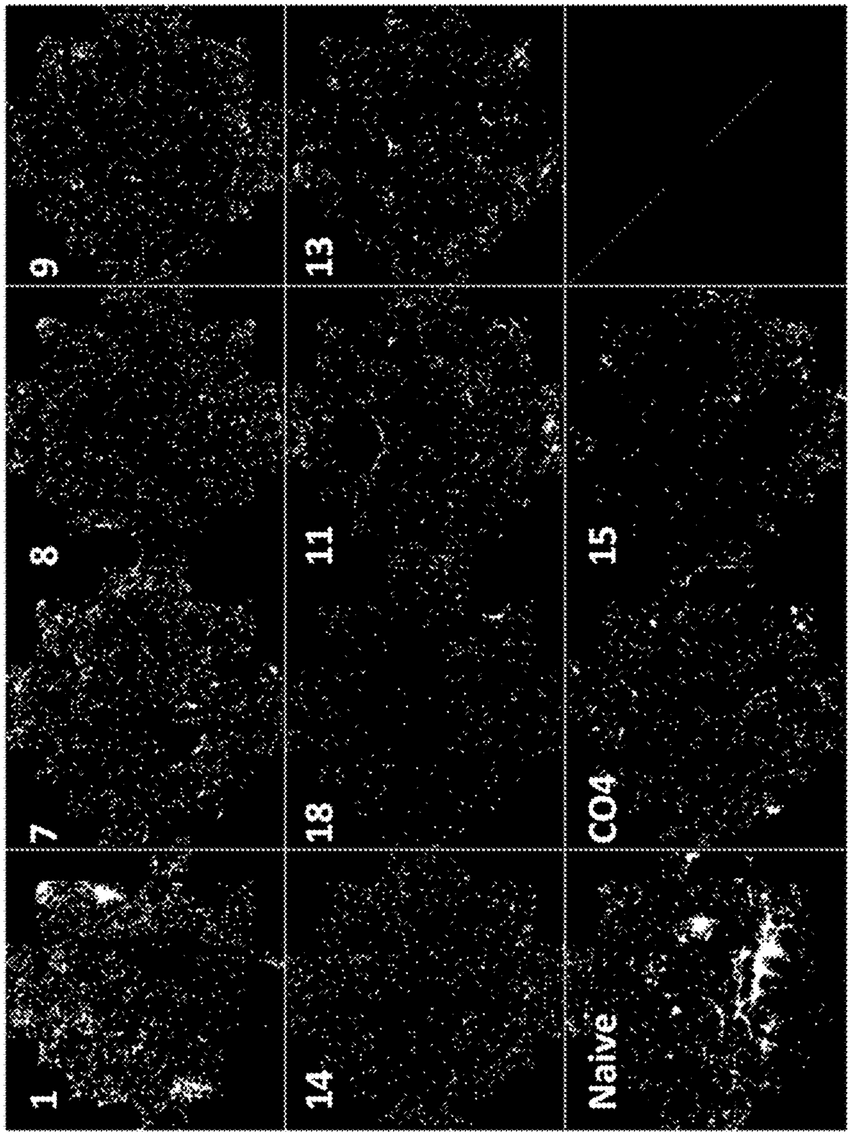
Figure 11D:
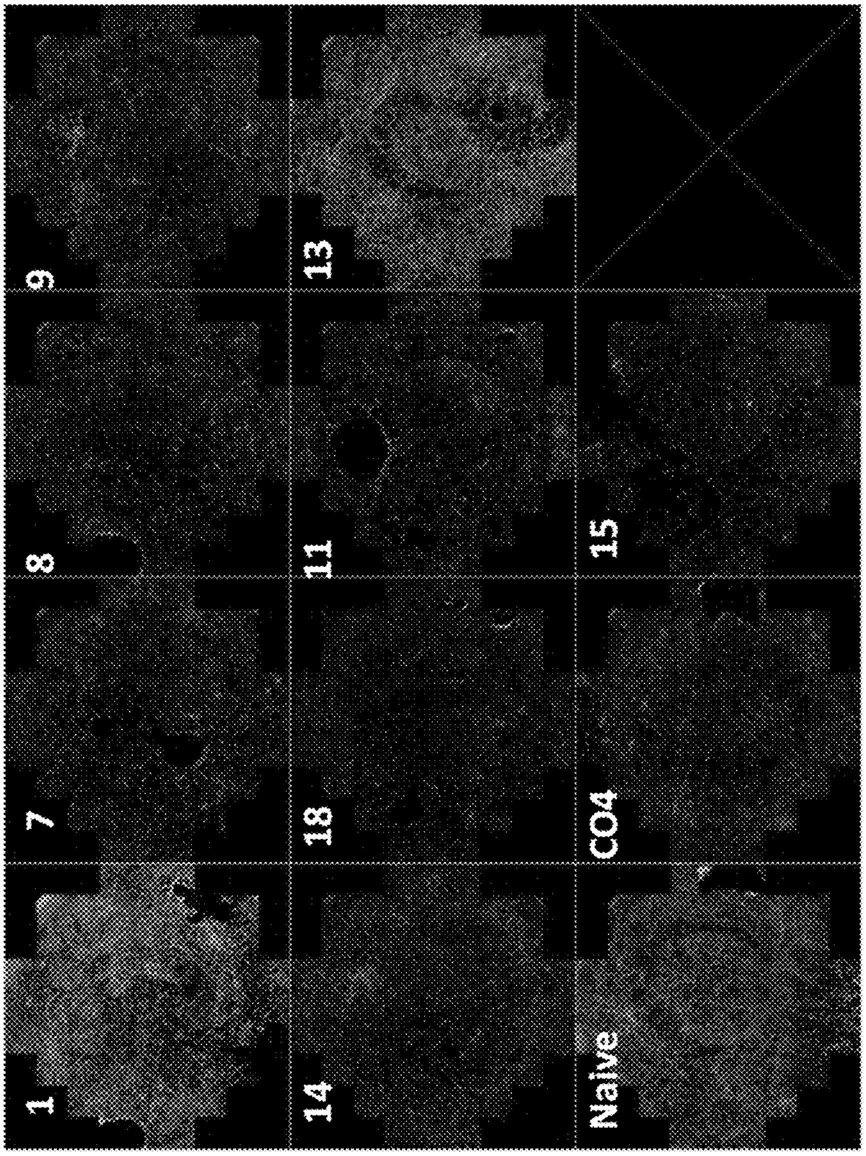
Figure 12A:
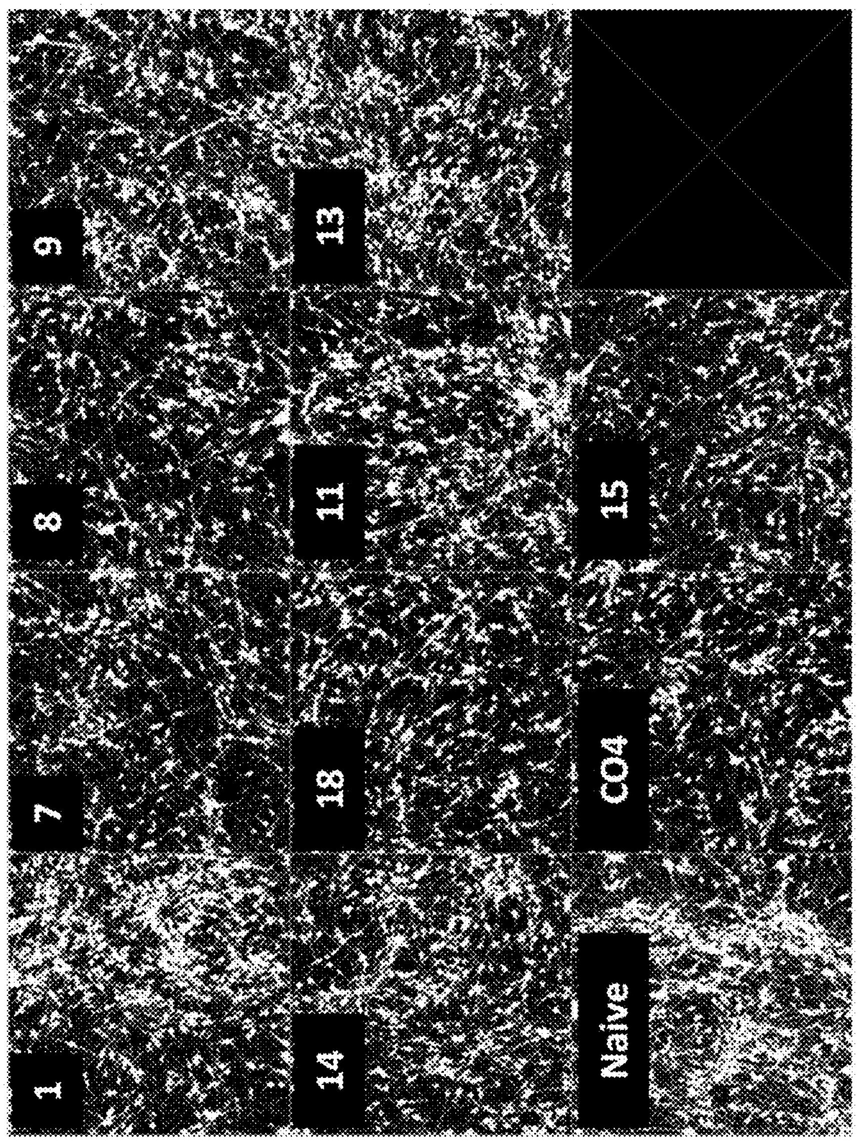
FIG. 12A shows an enlarged image of FIG. 11A.
Figure 12B:
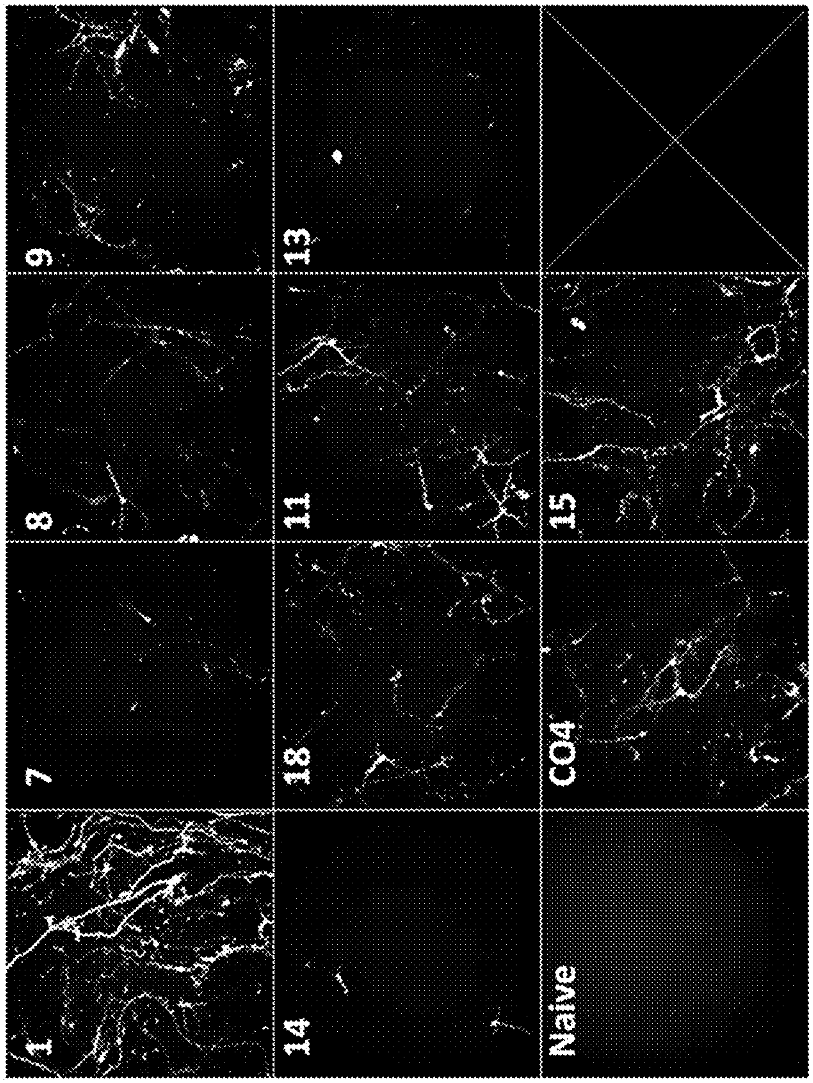
FIG. 12B shows an enlarged image of FIG. 11B.
Figure 12C:
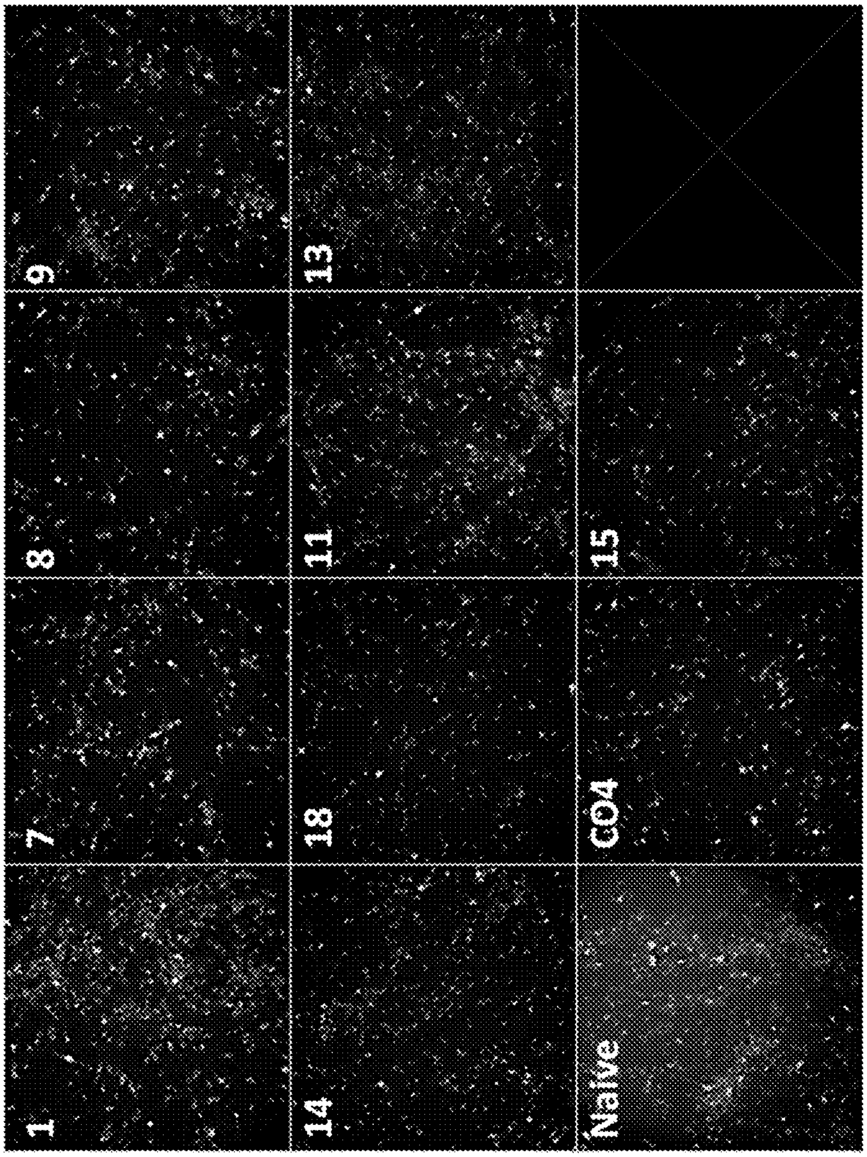
FIG. 12C shows an enlarged image of FIG. 11C.
Figure 12D:
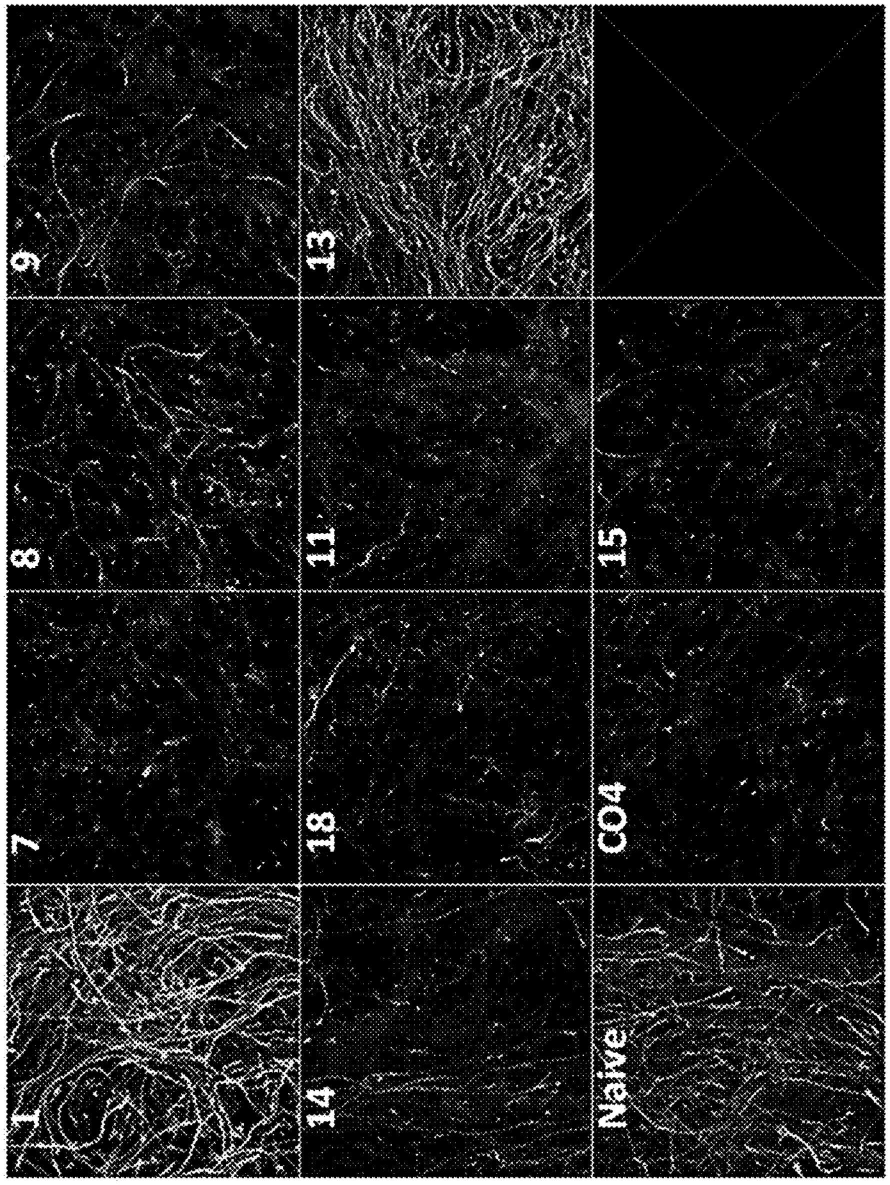
FIG. 12D shows an enlarged image of FIG. 11D.

For fluorescence microscopy, transfected cells were fixed 8 days after transfection, stained, and imaged in brightfield (FIG. 11A and FIG. 12A), or by immunofluorescence for Parkin (FIG. 11B and FIG. 12B), neuronal marker NeuN (FIG. 11C and FIG. 12C), or astrocyte marker GFAP (FIG. 11D and FIG. 12D). FIGS. 12A-12D show enlarged images of FIGS. 11A-11D.

Example 3

In Vivo and Clinical Testing of Parkin AAV Gene Therapy

AAV vectors are generated by packaging of AAV vector genomes from constructs 1 to 20 in Example 2, in particular constructs 1, 7, 11, and 15 from Table 11. Testing is performed in rats and one or more constructs are selected for testing in non-human primates (NHPs). Dose finding studies are performed and a starting dose for clinical trials is determined by measurement of protein expression and toxicity observed.

Clinical trials are performed in subjects identified has having recessive mutations in the PRKN gene (also known as PRK2). Protein expression and observed toxicity is used to determine an optimal dose. Efficacy is evaluated using improvement on the Unified Parkinson's Disease Rating Scale (UPDRS).

Example 4

In Vitro Testing

Recombinant cassettes are tested in a human neuroblastoma cell line (SH-SY5Y). (See Jiang et al. Extracellular dopamine induces the oxidative toxicity of SH-SY5Y cells. Synapse. 2008 November; 62 (11): 797-803. doi: 10.1002/syn.20554.) The genes of interest tested are a Parkinson protein 2, E3 ubiquitin protein ligase (PARK2) gene, a PTEN-induced putative kinase 1 (PINK1) gene, a protein deglycase DJ-1 (DJ-1) gene, a Leucine Rich Repeat Kinase 2 (LRRK2) gene, an alpha-synuclein (SCNA) gene, a Proto-oncogene c-Rel (c-Rel) gene, a Ubiquitin-like modifier-activating enzyme (ATG7) gene, Synaptic vesicular amine transporter (VMAT2) gene, or glucocerebrosidase (GBA) gene.

Each cell line is treated with a recombinant gene therapy vector for each gene of interest. Expression of the gene of interest is increased. Function of the gene of interest is improved. In some cases, improved mitophagy, reduced cellular toxicity, and/or reduced oxidative stress is observed.

Example 5

In Vivo Testing

A rodent or non-human primate having a combination of one or more known mutations in a gene of interest is treated with a recombinant gene therapy vector for that gene of interest. The genes of interest tested are a Parkinson protein 2, E3 ubiquitin protein ligase (PARK2) gene, a PTEN-induced putative kinase 1 (PINK1) gene, a protein deglycase DJ-1 (DJ-1) gene, a Leucine Rich Repeat Kinase 2 (LRRK2) gene, an alpha-synuclein (SCNA) gene, a Proto-oncogene c-Rel (c-Rel) gene, an Ubiquitin-like modifier-activating enzyme (ATG7) gene, Synaptic vesicular amine transporter (VMAT2) gene, or glucocerebrosidase (GBA) gene The test subject has one or more of the following features: Loss of dopamine (DA), ≥20% nigral cell loss, dyskinesia, Lewy bodies, indications of mitochondrial dysfunction, ROS, inflammation, other locomotor behavioral deficits, and neurodegenerative symptoms.

Animals in which the methods of the present disclosure are tested include non-diseased and diseased animals and mutation-carrier and non-carrier animals. Animal models and illustrative motor behavior readouts in which the methods of the present disclosure are tested are provided in Table 12.

TABLE 12

| | Animal model | Motor behavior |
|---|---|---|
| Toxin-based | MPTP Mice | Reduced locomotion, bradykinesia |
| | MPTP Monkeys | Reduced locomotion, altered behavior, tremor and rigidity |
| | 6-OHDA rat | Reduced locomotion, altered behavior |
| | Rotenone | Reduced locomotion |
| | Paraquat/maneb | Reduced locomotion |
| | MET/MDMA | Reduced locomotion |
| Genetic mutations | α-Synuclein | Altered behavior, reduced or increased motor activity |
| | LRKK2 | Mild behavioral alteration |
| | PINK1 | No obvious alterations or reduced locomotion |
| | PARKIN | No obvious alterations or reduced locomotion |
| | PRKN Exon3 mutated mice | No obvious alterations or reduced locomotion |
| | PRKN knockout rats | No obvious alterations or reduced locomotion |
| | DJ-1 | Decreased locomotor activity |
| | ATP13A2 | Late onset sensorimotor deficits |
| Others | SHH | Reduced locomotion |
| | Nurr1 | Reduced locomotion |
| | Engrailed 1 | Reduced locomotion |
| | Pitx3 | Reduced locomotion |
| | C-Rel-NFKB | Gait, bradykinesia, rigidity |
| | MitoPark | Reduced locomotion, tremor, and rigidity |
| | Atg7 | Late onset locomotor deficits |
| | VMAT2 | Reduced locomotion and altered behavior |

The test subject exhibits improvement in any of the motor behavior readouts or one or more of the following features: Gain of DA in the striatum, nigral cell gain, reduced Lewy bodies, improved behavioral or other locomotor deficits, improved mitochondrial function, reduced inflammatory markers, improved life span.

Example 6

Clinical Testing

The diagnosis of parkin type of early-onset Parkinson disease is considered primarily in individuals with early-onset parkinsonism (age <40 years), particularly if autosomal recessive inheritance is suspected. PRKN (formerly termed PARK2), the gene encoding the protein parkin, is the primary gene in which pathogenic variants are known to cause parkin type of early-onset Parkinson disease. The diagnosis of parkin type of early-onset Parkinson disease can only be confirmed when pathogenic variants are identified on both alleles of PRKN (i.e., the individual is homozygous for the same pathogenic allele or compound heterozygous for two different pathogenic alleles). The variant detection frequency varies by family history and age of onset.

Other mutants related to Parkinson's Disease are provided in Table 13.

TABLE 13

| Gene | Human Mutations | Mode of inheritance | Rat model mutations |
|---|---|---|---|
| α-Synuclein (PRK 1) | A53T, A53E, A30P, H50Q, E46K, G51D | Dominant | Human E46K expressed via BAC transgenic |
| LRRK2 (PRK8) | N1437H, R1441C/G/H, Y1699C, G2019S, I2020T | Dominant | Human G2019S expressed via BAC transgenic; human R1441C expressed via BAC transgenic |
| Parkin (PRK2) | Deletions, Insertions, frameshifts, missense and nonsense mutations in every exon; deletions and duplications of 1 or more exons are most common mutations | Recessive | 5-bp deletion in exon 4 |
| PINK1 (PRK6) | Missense and nonsense mutations Q21X, G440E, Q456X, Q1290fxX157, W437X, A271D, G309D, exon deletions or duplications | Recessive | 26-bp deletion in exon 4 |
| DJ-1 (PRK7) | L166P, D149A, R98Q, exon deletions or splice-site alterations | Recessive | 9-bp deletion and 1-bp insertion in exon 5 |

Human subjects having one or more mutations associated with Parkinson's Disease are treated with recombinant gene therapy vectors encoding wild-type or functional variants of the mutated gene. The subjects exhibit improvement in any of the motor behavior readouts listed in Table 12, or any of the following features: increased dopamine in the brain, especially the substantia nigra, increased numbers of dopaminergic neurons, increased expression of genes of interesting, including PRKN, or improvement on the Unified Parkinson's Disease Rating Scale (UPDRS).

All of the above U.S. patents, U.S. patent application publications, U.S. patent applications, foreign patents, foreign patent applications and non-patent publications referred to in this specification and/or listed in the Application Data Sheet, are incorporated herein by reference, in their entirety.

The present invention may be embodied in other specific forms without departing from its structures, methods, or other essential characteristics as broadly described herein and claimed hereinafter. The described embodiments are to be considered in all respects only as illustrative, and not restrictive. The scope of the invention is, therefore, indicated by the appended claims, rather than by the foregoing description. All changes that come within the meaning and range of equivalency of the claims are to be embraced within their scope.

The invention claimed is:

1. A recombinant gene therapy vector comprising an expression cassette comprising a transgene polynucleotide sequence encoding an E3 ubiquitin protein ligase (PARK2), wherein the transgene polynucleotide is operably linked to a eukaryotically active promoter sequence, wherein the transgene polynucleotide sequence shares at least 95% identity to any one of the sequences set forth in SEQ ID NOs: 35-38.

2. The vector of claim 1, wherein the promoter sequence is selected from any one of the sequences set forth in SEQ ID NOs: 59-64.

3. The vector of claim 1, wherein the expression cassette further comprises a CMV enhancer.

4. The vector of claim 3, wherein the expression cassette further comprises a 5' untranslated region (UTR) selected from any one of the sequences set forth in SEQ ID NOs: 65-71.

5. The vector of claim 4, wherein the expression cassette further comprises a 3' untranslated region selected from any one of the sequences set forth in SEQ ID NOs: 72-75.

6. The vector of claim 5, wherein the expression cassette further comprises a polyadenylation sequence (polyA) selected from any one of the sequences set forth in SEQ ID NOs: 76-78.

7. The vector of claim 6, wherein the transgene is codon-optimized.

8. The vector of claim 6, wherein the expression cassette shares at least 95% sequence identity to any one of the sequences set forth in SEQ ID NOs: 39-58.

9. The vector of claim 1, wherein the expression cassette comprises in 5' to 3' order:

HuBA promoter, the transgene, WPRE(x), and pAGlobin-Oc;

CMV promoter, TPL-eMLP enhancer, the transgene, WPRE(r), and pAGlobin-Oc;

Syn promoter, the transgene, WPRE(r), 3'UTR(globin), and pAGH-Bt;

CBA promoter, the transgene, and pAGH-Bt;

EF1α promoter, the transgene, and pAGlobin-Oc;

HuBA promoter, the transgene, R2V17, and pAGH-Bt;

Syn promoter, the transgene, WPRE(x), 3'UTR(globin), and pAGH-Hs;

CaMKIIa promoter, the transgene, WPRE(r), and pAGH-Hs;

CMV promoter, TPL-eMLP 5' enhancer, the transgene, WPRE(r), and pAGH-Hs;

HuBA promoter, the transgene, and pAGH-Hs;

CMV and TPL promoter, eMPL, the transgene, R2V17, 3'UTR(globin), and pAGH-Bt;

EF1α promoter, the transgene, WPRE(r), and pAGH-Bt;

Syn promoter, the transgene, R2V17, and pAGlobin-Oc;

CaMKIIa promoter, the transgene, R2V17, and pAGlobin-Oc;

CBA promoter, the transgene, WPRE(x), 3'UTR(globin), and pAGH-Hs;

CBA promoter, the transgene, 3'UTR(globin), and pAGlobin-Oc;

CaMKIIa promoter, the transgene, R2V17, and pAGH-Bt;

EF1α promoter, the transgene, R2V17, 3'UTR(globin), and pAGH-Hs;

CMV promoter, the transgene, R2V17, 3'UTR(globin), and pAGH-Hs; or

CMV promoter, the transgene, and pAGH-Hs, wherein the transgene encodes PARK2.

10. The vector of claim 1, wherein the vector is an adeno-associated virus (AAV) vector.

11. The vector of claim 10, wherein the AAV has serotype AAV1, AAV2, AAV5, AAV8, AAV9, AAVrh10, or AAVrh74.

12. A host cell in vitro, comprising the vector of claim 1.

* * * * *